US009463234B2

(12) United States Patent
Borca et al.

(10) Patent No.: US 9,463,234 B2
(45) Date of Patent: Oct. 11, 2016

(54) ATTENUATED AFRICAN SWINE FEVER VIRUS STRAIN INDUCES PROTECTION AGAINST CHALLENGE WITH HOMOLOGOUS VIRULENT PARENTAL VIRUS GEORGIA 2007 ISOLATE

(71) Applicants: The United States of America, as Represented by the Secretary of Agriculture, Washington, DC (US); The University of Connecticut, Storrs, CT (US)

(72) Inventors: Manuel V. Borca, Westbrook, CT (US); Lauren G. Holinka-Patterson, Deep River, CT (US); Douglas Gladue, Guildford, CT (US); Guillermo R. Risatti, Westbrook, CT (US); Vivian K. O'Donnell, Old Saybrook, CT (US)

(73) Assignees: The United States of America, as represented by the Secretary of Agriculture, Washington, DC (US); University of Connecticut, Farmington, CT (US)

( * ) Notice: Subject to any disclaimer, the term of this patent is extended or adjusted under 35 U.S.C. 154(b) by 0 days.

(21) Appl. No.: 14/495,540

(22) Filed: Sep. 24, 2014

(65) Prior Publication Data

US 2016/0082099 A1 Mar. 24, 2016

(51) Int. Cl.

| | |
|---|---|
| ***A61K 39/12*** | (2006.01) |
| ***C12Q 1/70*** | (2006.01) |
| ***G01N 33/569*** | (2006.01) |
| ***C12N 7/00*** | (2006.01) |
| *A61K 39/00* | (2006.01) |

(52) U.S. Cl.

CPC ................ *A61K 39/12* (2013.01); *C12N 7/00* (2013.01); *C12Q 1/701* (2013.01); *G01N 33/56983* (2013.01); *A61K 2039/552* (2013.01); *C12N 2710/12021* (2013.01); *C12N 2710/12034* (2013.01); *C12Q 2600/158* (2013.01); *G01N 2333/01* (2013.01)

(58) Field of Classification Search

None

See application file for complete search history.

(56) References Cited

PUBLICATIONS

Escribano et al. (Virus Research. Apr. 2013; 173 (1): 101-109).*

McKillen et al. (Journal of Virological Methods. Jun. 2010; 168: 141-146).*

Lewis, T., An African Swine Fever Virus ERV1-ALR Homologue, 9GL, Affects Virion Maturation and Viral Growth in Macrophages and Viral Virulence in Swine, J. Virol., 2000, 74(3.

Moore, D.M., The African Swine Fever Virus Thymidine Kinase Gene is Required for Efficient Replication in Swine Macrophages and for Virulence in Swine, J. Virol 98 72(12)10310.

Zsak, L., An African Swine Fever Virus Virulence-Associated Gene NL-S with Similarity to the Herpes Simplex Virus ICP34.5 Gene, J. Virol 1996 70(12), 8865.

Zsak, L., A Nonessential African Swine Fever Virus Gene UK is a Significant Virulence Determinant in Domestic Swine, J. Virol 1998, 72(2), 1028.

* cited by examiner

*Primary Examiner* — Shanon A Foley

(74) *Attorney, Agent, or Firm* — John D. Fado; Evelyn M. Rabin

(57) ABSTRACT

African swine fever virus (ASFV) is the etiological agent of a contagious and often lethal viral disease of domestic pigs that has significant economic consequences for swine breeding. Control of ASF has been hampered by the unavailability of vaccines. Recombinant viruses harboring engineered deletions of specific virulence-associated genes induce solid protection against the challenge with parental viruses. Here we report the construction of a recombinant Δ9GL virus derived from the highly virulent ASFV Georgia 2007 (ASFV-G) isolate. In vivo, ASFV-G Δ9GL administered intramuscularly (IM) to swine at relatively high doses ($10^4$ $HAD_{50}$) retains a virulent phenotype practically indistinguishable from the parental virus. Conversely, at low IM doses ($10^2$ or $10^3$ $HAD_{50}$), ASFV-G Δ9GL does not induce disease. Importantly, animals infected with $10^3$ $HAD_{50}$ are protected against the presentation of clinical disease when challenge at 28 days post infection with the virulent parental strain Georgia 2007.

4 Claims, 3 Drawing Sheets

```
                    SEQ
                    ID
                    NO:  ...|....| ....|....| ....|.... ....|....| ....|....| .... ....
                                 10         20         30         40         50         60

ASFV-G              2    MLHWGPKYWR [SLHLYAIFFS DAPSWKEKYE AIQWILNFIE SLPCTRCQHH AFSYLTKNPL

Malawi Lil-20/1     17   .......F.. T......... .T.G...... .......... .....M.R.. ..........
Pr4                 18   .......... A......... ...G...... .......... .......R.. ..........
Pr5                 18   .......... A......... ...G...... .......... .......R.. ..........
Killean3            19   .......F.. A......... ...N...... .......... .....M.R.. ..........
Cr1                 18   .......... A......... ...G...... .......... .......R.. ..........
Cr3                 18   .......... A......... ...G...... .......... .......R.. ..........
Tengani(62)         20   .......... A......... .T.G...... .......... .......... ..........
Fairfield/96/1      21   .......... A........ ...G...... .......... .......... ..........
Wildebeeslaagte     18   .......... A......... ...C...... .......... .......R.. ..........
Kimakia(64)         22   .......... .......... .......... .......... ........R. ..........
Victoria Falls      23   .......... .......... .......... ......S... .......... ..........
Zaire (67)          2    .......... .......... .......... .......... .......... ..........
Uganda(61)          2    .......... .......... .......... .......... .......... ..........
E70                 2    .......... .......... .......... .......... .......... ..........
E75                 2    .......... .......... .......... .......... .......... ..........
Haiti               2    .......... .......... .......... .......... .......... ..........
Spencer(51)         2    .......... .......... .......... .......... .......... ..........
La Granja(63)       2    .......... .......... .......... .......... .......... ..........
Lisbon(60)          2    .......... .......... .......... .......... .......... ..........
Lee(55)             2    .......... .......... .......... .......... .......... ..........

                         ....|....| ....|....| .... .... ....|....| ....|....| .... ....|
                                 70         80         90        100        110        120

ASFV-G              2    TLNNSEDF]QY WTFAFHNNVN NRLNKKIISW SEYKNIYEQS ILKTIEYGKT DFIGAWSSL*
Malawi Lil-20/1     17   .......... .......... K......... .......... ..N....... .........*
Pr4                 18   .......... .......... .......... .......... .......... .........*
Pr5                 18   .......... .......... .......... .......... .......... .........*
Killean3            19   .......... .......... K......... .......... .......... .........*
Cr1                 18   .......... .......... .......... .......... .......... .........*
Cr3                 18   .......... .......... .......... .......... .......... .........*
Tengani(62)         20   .......... .......... .......... .......... .......... .........*
Fairfield/96/1      21   .......... .......... .......... .......... .......... .........*
Wildebeeslaagte     18   .......... .......... .......... .......... .......... .........*
Kimakia(64)         22   .......... .......... .......... .......... .......... .........*
Victoria Falls      23   .......... .......... .......... .......... .......... .........*
Zaire (67)          2    .......... .......... .......... .......... .......... .........*
Uganda(61)          2    .......... .......... .......... .......... .......... .........*
E70                 2    .......... .......... .......... .......... .......... .........*
E75                 2    .......... .......... .......... .......... .......... .........*
Haiti               2    .......... .......... .......... .......... .......... .........*
Spencer(51)         2    .......... .......... .......... .......... .......... .........*
La Granja(63)       2    .......... .......... .......... .......... .......... .........*
Lisbon(60)          2    .......... .......... .......... .......... .......... .........*
Lee(55)             2    .......... .......... .......... .......... .......... .........*
```

Fig. 1

ATTENUATED AFRICAN SWINE FEVER VIRUS STRAIN INDUCES PROTECTION AGAINST CHALLENGE WITH HOMOLOGOUS VIRULENT PARENTAL VIRUS GEORGIA 2007 ISOLATE

BACKGROUND OF THE INVENTION

1. Field of the Invention

This invention relates to the construction of a recombinant African Swine Fever Virus (ASFV) live attenuated candidate strain vaccine for the highly virulent Georgia 2007 isolate ASFV-G. The vaccine comprises the ASFV-G Δ9GL, a recombinant ASFV-G modified by deleting a large portion of the 9GL gene.

2. Description of the Relevant Art

African Swine Fever (ASF) is a contagious viral disease of swine. The causative agent, ASF virus (ASFV), is a large enveloped virus containing a double-stranded DNA genome of approximately 190 kilobase pairs. ASFV shares aspects of genome structure and replication strategy with other large double-stranded DNA viruses, including the Poxviridae, Iridoviridae and Phycodnaviridae (Costard et al. 2009. *Phil. Trans. Royal Soc.* B 364:2683-2696). ASFV infections in domestic pigs are often fatal and are characterized by fever, hemorrhages, ataxia and severe depression. However, the course of infection varies, ranging from highly lethal to sub-clinical, depending on host characteristics and the particular virus strain (Tulman et al. 2009. *Curr. Top. Microbiol. Immunol.* 328:43-87).

Currently, the disease is endemic in more than twenty sub-Saharan African countries. In Europe, ASF is still endemic on the island of Sardinia (Italy) and new outbreaks have been declared in the Caucasus region since 2007, affecting Georgia, Armenia, Azerbaijan and Russia. Isolated outbreaks have been recently reported in Ukraine, Belarus, Lithuania, Latvia and Poland, posing the risk of further dissemination into neighbouring countries. The epidemic virus, ASFV Georgia 2007/1, is a highly virulent isolate belonging to the genotype II (Chapman et al. 2011. *Emerging Infect. Dis.* 17:599-605).

At present, there is no vaccine available for ASF and disease outbreaks are controlled by animal quarantine and slaughter. Attempts to vaccinate animals using infected cell extracts, supernatants of infected pig peripheral blood leukocytes, purified and inactivated virions, infected glutaraldehyde-fixed macrophages, or detergent-treated infected alveolar macrophages failed to induce protective immunity (Coggins, L. 1974. *Prog. Med. Virol.* 18:48-63; Forman et al. 1982. *Arch. Virol.* 74:91-100; Kihm et al. 1987. *In: African Swine Fever*, Becker, Y. (ed), Martinus Nijhoff, Boston, pp 127-144; Mebus, C. A. 1988. *Adv. Virus Res.* 35:251-269). Homologous protective immunity does develop in pigs surviving viral infection. Pigs surviving acute infection with moderately virulent or attenuated variants of ASFV develop long-term resistance to homologous, but rarely to heterologous, virus challenge (Hamdy and Dardiri. 1984. *Am. J. Vet. Res.* 45:711-714; Ruiz-Gonzalvo et al. 1981. In: *FAO/CEC Expert Consultation in ASF Research*, Wilkinson, P. J. (ed), Rome, pp 206-216). Pigs immunized with live attenuated ASF viruses containing engineered deletions of specific ASFV virulence-associated genes were protected when challenged with homologous parental virus. Specifically, individual deletion of UK (DP69R), 23-NL (DP71L), TK (A240L) or 9GL (B119L) genes from the genomes of pathogenic ASF viruses (Malawi Lil-20/1, Pretoriuskop/96/4, and E70) markedly attenuated the virus in swine and the animals immunized with these attenuated viruses were protected against challenge with homologous virus (Moore et al. 1998. *J. Virol.* 72:10310-10315; Lewis et al. 2000. *J. Virol.* 74:1275-1285; Zsak et al. 1996. *J. Virol.* 70:8865-8871; Zsak et al. 1998. *J. Virol.* 72:1028-1035). In particular, deletion of 9GL (B119L) in highly virulent ASFV isolates Malawi Lil-20/1 and Pretoriuskop/96/4 resulted in complete attenuation of these viruses in swine (Lewis et al., supra; Neilan et al. 2004. *Virol.* 319:337-342). Administration of Malawi Lil-20/1 or Pretoriuskop/96/4 Δ9GL mutants to pigs via IM injection at a relatively high virus dose ($10^4$ $HAD_{50}$ [50% hemadsorbing dose]) did not induce clinical signs, with all animals surviving the infection. Furthermore, IM inoculation of pigs with these viruses even at a relatively low dose ($10^2$ $HAD_{50}$) induced protection against challenge with virulent Malawi Lil-20/1 virus (Lewis et al., supra). These observations constitute the only experimental evidence describing the rational development of an effective live attenuated virus against ASFV.

Although a deletion within the 9GL (B119L) gene from ASF Malawi Lil-20/1 and Pretoriuskop/96/4 and E70 had resulted in attenuated viruses effective for protection from pathogenic parental ASFV, the modified viruses did not protect against heterologous ASFV strains. Thus, there is a need for an effective live attenuated vaccine for the highly virulent ASFV Georgia 2007 isolate, ASFV-G, for which there is no vaccine candidate.

SUMMARY OF THE INVENTION

We have developed the novel recombinant mutant ASFV-G Δ9GL virus, a modification of the ASFV-G (African Swine Fever Virus-Georgia 2007 isolate).

In accordance with this discovery, it is an object of the invention to provide the novel mutant ASFV-G Δ9GL virus, resulting from the deletion of a large portion of the 9GL gene of the parental ASFV-G. The nucleotide sequence of ASFV-G Δ9GL (SEQ ID NO:3) differs from the nucleotide sequence encoding the ASFV-G (SEQ ID NO:1). While the nucleotide sequence of ASFV-G (SEQ ID NO:1) encodes the wild-type 9GL (B119L) protein of 119 amino acids (SEQ ID NO:2), the nucleotide sequence of ASFV-G Δ9GL (SEQ ID NO:3) encodes a mutant 9GL polypeptide of 58 amino acids (SEQ ID NO:4) resulting from the deletion of amino acid #11 through amino acid #68 of the wild-type 9GL polypeptide (SEQ ID NO:2) of ASFV-G.

An added object of the invention is to provide immunogenic compositions comprising a viable ASFV-G Δ9GL virus.

An additional object of the invention is to provide a rationally designed live attenuated ASFV-G Δ9GL vaccine effective to protect an animal from clinical ASF disease when challenged with pathogenic ASFV-G.

A further object of the invention is to provide a genetic marker vaccine which can potentially distinguish between vaccinated animals and animals infected with ASFV-G.

Another object of the invention is to provide a method for protecting an animal against ASFV-G by administering an effective amount of rationally designed live attenuated ASFV-G Δ9GL vaccine.

An additional object of the invention is to provide a method for distinguishing animals infected with ASFV-G from animals vaccinated with said rationally designed live attenuated ASFV-G Δ9GL vaccine, comprising a genetic DIVA strategy for differentiating vaccinated animals from wild-type infected animals.

Other objects and advantages of this invention will become readily apparent from the ensuing description.

BRIEF DESCRIPTION OF THE DRAWINGS

FIG. 1 shows the sequence alignment of 9GL (B119L) gene encoded proteins by ASFV. The nucleotide sequence of ASFV-G (SEQ ID NO: 1) encodes the wild-type 9GL (B119L) protein of 119 amino acids (SEQ ID NO: 2, shown). Isolates of various temporal and geographic origins, including those from obtained from ticks and pig sources, were compared and are identified by SEQ ID Nos: 2 and 17-23. The partial deletion introduced into ASFV-G that yielded ASFV-G Δ9GL virus is shown between brackets.

FIG. 2A depicts an assessment of purity of the ASFV-G Δ9GL virus stock by PCR. Lane 1: ASFV-G Δ9GL; Lane 2: ASFV-G. FIG. 2*b* depicts identification of the presence of parental ASFV-G in viruses (V1-V4) isolated from animals infected with ASFV-G Δ9GL virus. Control (C) consists of a plasmid containing the respective target genes.

DETAILED DESCRIPTION OF THE INVENTION

Figure 2:
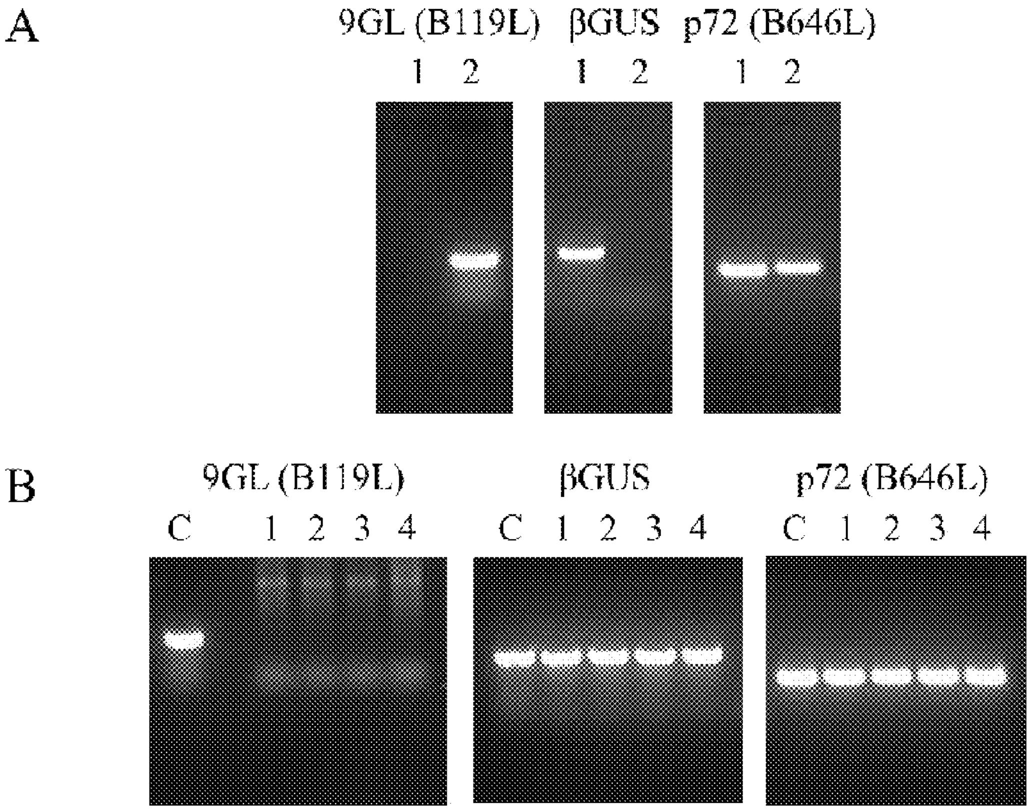
FIGS. 2A and 2B depict PCR analysis of ASFV-G Δ9GL virus DNA using specific primers targeting 9GL (B119L), p72 (B646L), or βGus genes.

We have developed an attenuated virus that can be used as a vaccine candidate through the approach of targeting 9GL (B119L) for genetic modifications. Here we report the construction of a recombinant Δ9GL virus of the highly virulent ASFV Georgia 2007 isolate (ASFV-G). In vitro, as observed with Δ9GL viruses Malawi Lil-20/1 and Pretoriuskop/96/4, ASFV-G Δ9GL has a decreased ability, relative to the parental virus, to replicate in swine macrophage primary cultures. ASFV-G Δ9GL administered intramuscularly (IM) to swine at relatively high doses ($10^4$ $HAD_{50}$) retains a virulent phenotype indistinguishable from the parental virus. Intramuscular inoculation of a low dose ($10^2$ or $10^3$ $HAD_{50}$) of ASFV-G Δ9GL does not induce disease. Animals infected with $10^3$ $HAD_{50}$ are protected against the presentation of clinical disease when challenge at 28 days post infection with the virulent parental strain Georgia 2007.

No vaccines are available to prevent ASFV infection. Only live attenuated virus strains have been useful in protecting pigs against challenge with homologous virulent isolates. These attenuated viruses have been regularly produced by sequential passages in cell cultures and, more recently, by genetic manipulation. Naturally occurring attenuated viruses have been used as live vaccine candidates. Attenuated viruses obtained by genetic manipulation involve the deletion of specific genes by a process of homologous recombination. Independent deletion of four different genes from ASFV has been shown to attenuate virulent viruses. Independent deletions of the NL (DP71 L) (Zsak et al. 1996, supra) or the UK (DP69R) (Zsak et al. 1998, supra) genes from ASFV E75, deletion of the TK (A240L) gene (Moore et al., supra) from ASFV adapted to Vero cells, Malawi Lil-20/1 and Haiti, and deletion of the 9GL (B119L) gene also from Malawi Lil-20/1 (Lewis et al., supra) and Pretoriuskop/96/4 (Neilan et al., supra) isolates rendered recombinant deletion mutant viruses with significantly reduced virulence in swine. In all these cases, animals inoculated with each of these genetically modified viruses survived the infection and became protected against ASFV when challenged with the corresponding virulent parental virus (homologous challenge) (Lewis et al., supra; Moore et al., supra; Neilan et al., supra; Zsak et al. 1996, supra; Zsak et al. 1998, supra). Those findings suggest that development of attenuated ASFV recombinant viruses by genetic manipulations of target genes is an effective approach for vaccine development.

The NL (DP71L) gene product exits in two different forms, a long (184 amino acids as in 23-NL) or a short form (70 to 72 amino acids) depending on the ASFV isolate (Zsak et al. 1996, supra). Although deletion of this gene in ASFV E70 isolate (short form) rendered an attenuated virus, the deletion of the NL (DP71L) gene from ASFV Malawi Lil-20/1 (long form) or Pretoriuskop/96/4 (short form) did not result in attenuation of the virus (Afonso et al. 1998. *J. Gen. Virol.* 79 (Pt. 10):2543-2547). Deletion of the TK (A240L) gene, a highly conserved gene among all ASFV isolates involved in DNA synthesis, has been introduced into pathogenic Vero cell-adapted Malawi Lil-20/1 and Haiti H811 viruses. The Malawi Lil-20/1 mutant virus was less virulent in vivo than the revertant virus (wild-type-like virus) but it was not completely attenuated (Moore et al., supra). The UK (DP69R) gene is located in the right variable region of certain ASFV isolates. Deletion of this gene from ASFV E70 isolates rendered a virus exhibiting reduced virulence (Zsak et al. 1998, supra). Although the UK (DP69R) gene is conserved, it is not present in every ASFV isolate (e.g. Malawi Lil-20/1), limiting its use as a candidate target gene for producing attenuated viruses.

The 9GL (B119L) gene is highly conserved among ASFV isolated and sequenced so far, including those from both tick and pig sources. The fact that deletion of the gene from virulent Malawi Lil-20/1 (Lewis et al., supra) and Pretoriuskop/96/4 (Neilan et al., supra) effectively reduced virulence in swine and induced protection makes 9GL (B119L) a strong candidate target gene for modification and production of attenuated virus that can confer effective protection against ASFV. Interestingly, here we observed that deletion of 9GL (B119L) from the ASFV-G isolate does not have the same effect in terms of attenuation and protection as reported for Malawi Lil-20/1 and Pretoriuskop/96/4. Only when ASFV-G Δ9GL was administrated at low dose to swine was it possible to observe a decrease in virus virulence. Data presented here indicate that the 9GL (B119L) gene is not required for ASFV-G virulence and that other virulence factors may be involved in the process. As observed with deletions of NL (DP71L) in E70, Malawi Lil-20/1 and Pretoriuskop/96/4 isolates that lead to different phenotypes (Zsak et al. 1996, supra; Afonso et al., supra), deletions of 9GL (B119L) have produced similar outcomes, suggesting that virulence of ASFV is the result of a multigene effect.

The NL proteins encoded by E70 (short form) and Malawi Lil-20/1 (long form) differ significantly and that may explain the phenotypic differences observed in swine inoculated with the respective deletion mutant viruses. However, protein identity matrixes indicate that the 9GL protein is highly similar among ASFV isolates where ASFV-G, Malawi Lil-20/1, and Pretoriuskop/96/4 share over 93% amino acid identity, making it unlikely that ASFV attenuation relies solely on protein divergence. Since the observed phenotypes are most likely mediated by the effect of multiple genes (Lewis et al., supra; Moore et al., supra; Neilan et al., supra; Zsak et al. 1996, supra; Zsak et al. 1998, supra), the evidence accumulated so far makes it difficult to speculate what is indeed the spectrum of genes mediating virulence in the ASFV Georgia 2007 isolate.

Nevertheless, a sub-lethal dose of ASFV-G Δ9GL is able to induce effective protection against the presentation of clinical disease after the challenge with homologous parental virus.

In summary, here we present evidence that deletion of 9GL (B119L), a gene that has been associated with virus virulence in Malawi Lil-20/1 and Pretoriuskop/96/4 isolates, does not drastically alter virulence of ASFV-G, i.e., inoculation of $10^4$ $HAD_{50}$ of ASFV-G Δ9GL caused disease. Although, when used at sub-lethal doses, ASFV-G Δ9GL entirely protects pigs against challenge with the virulent parental ASFV-G.

A vaccine is defined herein as a biological agent which is capable of providing a protective response in an animal to which the vaccine has been delivered and is incapable of causing severe disease. Administration of the vaccine results in immunity from a disease; the vaccine stimulates antibody production or cellular immunity against the pathogen causing the disease. Immunity is defined herein as the induction of a significant higher level of protection in a population of swine against mortality and clinical symptoms after vaccination compared to an unvaccinated group. In particular, the vaccine according to the invention protects a large proportion of vaccinated animals against the occurrence of clinical symptoms of the disease and mortality. The vaccine of the invention herein is a genetically engineered mutant virus vaccine. A genetic marker vaccine is defined as a vaccine that, in conjunction with a diagnostic test, enables genetic differentiation of vaccinated animals from infected animals. A deletion mutation can be used to differentiate infected from vaccinated animals as is observed in Example 7-Genetic DIVA Strategy—Real-Time RT-PCR. A mutation is understood to be a change in the genetic information of a "wild-type" or unmodified 9GL (B119L) gene of a parent ASFV-G strain which is able to express native 9GL proteins. Thus, the 9GL polypeptide expressed by the ASFV-G Δ9GL mutant virus is changed: the 9GL protein from ASFV-G Δ9GL has fewer amino acids than the wild-type 9GL, as amino acids #11 through #68 are deleted in the 9GL polypeptide of ASFV-G Δ9GL. The ASFV-G Δ9GL recombinant ASFV-G mutant comprising DNA encoding a mutation in the ASFV-G 9GL protein, wherein the mutation comprises a deletion of 58 amino acids, wherein said recombinant ASFV-G mutant (ASFV-G Δ9G) is a live attenuated ASFV-G vaccine when used at IM inoculation doses of $10^3$ $HAD_{50}$.

A vaccine against ASFV-G is provided that comprises a ASFV-G Δ9G virus mutant as defined above in a live form, and a pharmaceutically acceptable carrier or diluent. The vaccine according to the invention containing the live virus can be prepared and marketed in the form of a suspension or in a lyophilized form and additionally contains a pharmaceutically acceptable carrier or diluent customary used for such compositions. Carriers include stabilizers, preservatives and buffers. Suitable stabilizers are, for example SPGA (sucrose, phosphate, glutamate, and human. albumin), carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are well known in the art. Furthermore, nucleic acid sequences encoding polypeptides for pharmaceutical or diagnostic applications, in particular immunomodulators such as lymphokines, interferons or cytokines, may be incorporated into the vaccine.

A vaccine according to the invention can be prepared by conventional methods such as those commonly used for the commercially available live attenuated ASFV vaccines. Briefly, a susceptible substrate is inoculated with the ASFV-G Δ9GL mutant and propagated until the virus has replicated to a desired titer after which ASFV-G Δ9GL-containing material is harvested. Subsequently, the harvested material is formulated into a pharmaceutical preparation with immunizing properties.

Every substrate which is able to support the replication of ASFV-G Δ9GL viruses can be used in the present invention, including primary cultures of swine peripheral blood macrophages.

The vaccine may be administered by intramuscular, subcutaneous or intranasal inoculation or injection in an amount which is effective to protect the animal against challenge by a virulent strain of ASFV-G. This amount may vary according to the animal being inoculated, taking into consideration the size and weight of the animal. The vaccine according to the invention comprises an effective dosage of the ASFV-G Δ9GL mutant as the active component, i.e. an amount of immunizing ASFV-G Δ9GL material that will induce immunity in the vaccinated animals, swine, against challenge by a virulent ASFV-G. Immunity is defined herein as the induction of a significant higher level of protection in a population of swine against mortality and clinical symptoms after vaccination compared to an unvaccinated group. In particular, the vaccine according to the invention prevents a large proportion of vaccinated animals against the occurrence of clinical symptoms of the disease and mortality. Typically, the live vaccine can be administered in a dose of $10^3$ $HAD_{50}$. Effective amounts may be experimentally determined as necessary by those of skill in the art by following the guidance provided, for example, by Example 6.

In addition to the ASFV-G Δ9GL mutant, the invention can also include combination vaccines comprising a vaccine strain capable of inducing protection against another porcine pathogen.

The ASFV-G Δ9GL vaccine described above, in conjunction with a diagnostic method, has the potential of distinguishing between animals that are vaccinated with it and animals that are infected with naturally occurring ASFV-G strains or vaccinated with conventional ASFV-G vaccines.

The present invention also provides an invaluable tool to monitor ASFV-G control measures that may lead to eradication of ASFV-G if applied in large scale stamping out programs. This tool concerns a method for determining ASFV-G infection in swine comprising the step of examining a sample of the animal for the presence of nucleotides encoding the wild-type ASFV-G 9GL protein versus the polynucleotide encoding the shorter ASFV-G Δ9GL polypeptide due to deletions in the 9GL gene of ASFV-G Δ9GL. The sample of the animal used in this method may be any sample in which ASFV-G versus ASFV-G Δ9GL genetic differences allowing for differentiating of natural infection versus vaccination can be detected by genetic DIVA.

EXAMPLES

Having now generally described this invention, the same will be better understood by reference to certain specific examples, which are included herein only to further illustrate the invention and are not intended to limit the scope of the invention as defined by the claims.

Example 1

Cell Cultures and Viruses

Primary swine macrophage cell cultures were prepared from defibrinated swine blood as previously described by Zsak et al. (1996, supra). Briefly, heparin-treated swine blood was incubated at 37° C. for 1 hour to allow sedimentation of the erythrocyte fraction. Mononuclear leukocytes were separated by flotation over a Ficoll-Paque (Pharmacia, Piscataway, N.J.) density gradient (specific gravity, 1.079). The monocyte/macrophage cell fraction was cultured in plastic Primaria (Falcon; Becton Dickinson Labware, Franklin Lakes, N.J.) tissue culture flasks containing macrophage media, composed of RPMI 1640 Medium (Life Technologies, Grand Island, N.Y.) with 30% L929 supernatant and 20% fetal bovine serum (HI-FBS, Thermo Scientific, Waltham, Mass.) for 48 hours at 37° C. under 5% $CO_2$. Adherent cells were detached from the plastic by using 10 mM EDTA in phosphate buffered saline (PBS) and were then reseeded into Primaria T25, 6- or 96-well dishes at a density of $5\times10^6$ cells per ml for use in assays 24 hours later.

ASFV Georgia (ASFV-G) was a field isolate kindly provided by Dr. Nino Vepkhvadze, from the Laboratory of the Ministry of Agriculture (LMA) in Tbilisi, Republic of Georgia.

Comparative growth curves between ASFV-G and ASFV-G Δ9GL viruses were performed in primary swine macrophage cell cultures. Preformed monolayers were prepared in 24-well plates and infected at MOI of 0.01 (based on $HAD_{50}$ previously determined in primary swine macrophage cell cultures). After 1 hour of adsorption at 37° C. under 5% $CO_2$ the inoculum was removed and the cells were rinsed two times with PBS. The monolayers were then rinsed with macrophage media and incubated for 2, 24, 48, 72 and 96 hours at 37° C. under 5% $CO_2$. At appropriate times post-infection, the cells were frozen at −70° C. and the thawed lysates were used to determine titers by $HAID_{50}$/ml in primary swine macrophage cell cultures. All samples were run simultaneously to avoid inter-assay variability.

Virus titration was performed on primary swine macrophage cell cultures in 96-well plates. Virus dilutions and cultures were performed using macrophage medium. Presence of virus was assessed by hemadsorption (HA) and virus titers were calculated by the Reed and Muench method (1938. *Amer. J. Hygiene* 27:493-497).

Example 2

Construction of the Recombinant 9GL (B119L) Gene Deletion Mutant of ASFV-G Isolate ASFV-G Δ9GL was constructed from the highly pathogenic ASFV Georgia 2007 isolate (ASFV-G). Recombinant ASFVs were generated by homologous recombination between the parental ASFV genome and a recombination transfer vector following infection and transfection of swine macrophage cell cultures (Neilan et al., supra; Zsak et al. 1996, supra). Recombinant transfer vector (p72GUSΔ9GL) contained flanking genomic regions, which included portions of 9GL mapping to the left (1.2 kbp) and right (1.15 kbp) of the gene and a reporter gene cassette containing the β-glucuronidase (GUS) gene with the ASFV p72 late gene promoter, p72GUS (45). A 173-bp region, encompassing amino acid residues 11 to 68, within the 9GL (B119L) gene (FIG. 1) was deleted from ASFV-G virus and replaced with a cassette containing the p72GUS reporter gene cassette by the homologous recombination. Recombinant transfer vector p72GUSΔ9GL was obtained by DNA synthesis (GenScript, Piscataway, N.J., USA). Macrophage cell cultures were infected with ASFV-G and transfected with p72GUSΔ9GL. The recombinant virus was obtained after 11 successive plaque purification events on monolayers of primary swine macrophage cell cultures. The virus population obtained from the last round of plaque purification was amplified in primary swine macrophage cell cultures to obtain a virus stock.

The extent of purity of ASFV-G Δ9GL in the virus stock as well as in virus isolated from infected animals was assessed by PCR. To ensure the absence of parental ASFV-G, virus DNA was extracted from the virus stock and analyzed by PCR using primers targeting genes p72 (B646L), 9GL (B119L) and β-Gus. Detection of the 9GL (B119L) gene was performed using the following pair of primers: forward 5'TAGAGATGACCAGGCTCCAA3' (SEQ ID NO:5); reverse 5'GTTGCATTGGGGACCT AAATACT 3' (SEQ ID NO:6). Detection of the β-Gus gene was performed using the following pair of primers: forward 5'GACGGCCTGTGGGCATT3' (SEQ ID NO:7); reverse 5'GCGATGGATTCCGGCAT3' (SEQ ID NO:8). Detection of the p72 (B646L) gene was performed using the following pair of primers: forward 5'GTCTTATTGCTAAC GATGGGAAG3' (SEQ ID NO:9); reverse 5'CCAAAGG-TAAGCTTGTTTCCCAA3' (SEQ ID NO:10).

PCR products were sequenced using the dideoxynucleotide chain-termination method (Sanger et al. 1977. *Proc. Natl. Acad. Sci. USA* 74:5463-5467). Sequencing reactions were prepared with the Dye Terminator Cycle Sequencing Kit (Applied Biosystems, Foster City, Calif.). Reaction products were sequenced on a PRISM 3730xl automated DNA sequencer (Applied Biosystems). Sequence data were assembled with the Phrap software program (Retrieved from the Internet: phrap.org), with confirmatory assemblies performed using CAP3 (Huang and Madan. 1999. *Genome Res.* 9:868-877). The final DNA consensus sequence represented an average five-fold redundancy at each base position. Sequence comparisons were conducted using BioEdit software (Tom Hall, Ibis Biosciences Carlsbad, Calif., Copyright 1997-2013).

Only amplicons for p72 (B646L) and β-Gus genes were detected in DNA extracted from the virus stock; whereas no amplicons were generated with primers targeting the 9GL (B119L) gene (FIG. 2A) indicating the lack of contamination of the ASFV-G Δ9GL stock with ASFV-G.

Example 3

Full Genome Sequence Analysis: ASFV-G Δ9GL Relative to Parental ASFV-G

To evaluate the accuracy of the genetic modification and the integrity of the genome of the recombinant virus, full genome sequences of ASFV-G Δ9GL and parental ASFV-G were obtained using Next Generation Sequencing (NGS) and compared. First, a full-length genome comparison between parental ASFV-G and ASFV Georgia 2007/1 (Chapman et al., supra) was performed. ASFV DNA was obtained from the cytoplasm of infected cells using the Trizol method (Life Technologies, Grand Island, N.Y., USA). DNA concentration was determined using the Qubit® dsDNA HS assay kit (Life Technologies) and read on a Qubit® 2 Flourometer (Life Technologies). One microgram of virus DNA was enzymatically fragmented to obtain blunt end fragments in a length range of 200-300 bp using the Ion Shear™ Plus reagent kit (Life Technologies) and incubated at 37° C. in a Peltier Thermal Cycler DNA Engine Tetrad 2. After shearing, the fragmented DNA library was loaded onto a DNA chip (Agilent, Santa Clara, Calif., USA) and analyzed using a 2100 Bioanalyzer (Agilent) to assess DNA size distribution and size range. Fragmented DNA was ligated to Ion-compatible adapters and library barcodes, followed by nick-repair to complete the linkage between adapters and DNA inserts using the Ion Plus Fragment Library kit (Life Technologies). The adapter-ligated library was size-selected for optimum length on 2% Agarose Gel Cassettes (Sage Science, Beverly, Mass., USA) using the Pippin Prep™ instrument (Sage Science). Library concentration was normalized using the Ion Library Equalizer™ Kit (Life Technologies). Next, the DNA library was clonally amplified onto Ion Sphere™ Particles generating template-positive ISPs using the Ion PGM™ Template OneTouch™ 2 200 Kit (Life Technologies) with the Ion OneTouch™ 2 Instrument (Life Technologies). Before proceeding to enrichment, quality assessment of non-enriched template-positive ISPs was performed using the Ion Sphere™ Quality Control assay kit (Life Technologies) and a Qubit® 2 Flourometer instrument. The template-positive ISPs were then enriched using the Ion PGM™ Template OneTouch™ 2 200 Kit (Life Technologies) and Ion OneTouch™ ES instrument (Life Technologies) to eliminate template-negative ISPs and to denature DNA on template-positive ISPs. Using the Ion PGM™ 200 Sequencing v2 Kit (Life Technologies), enriched template ISPs were prepared for sequencing and loaded onto either Ion 314™ or Ion 316™ Chip v2 (Life Technologies) and run on the Ion PGM™ Sequencer (Life Technologies). Obtained sequences were then trimmed using Galaxy (https://usegalaxy.org/) NGS QC and Manipulation tools. Sequences were aligned and analyzed using Sequencher 5.2.2 (Genecodes) and CLC Genomics Workbench (CLCBio) software.

The following differences were observed between these two viruses (nucleotide positions are provided based on ASFV Georgia 2007/1, GenBank accession FR682468): (i) two nucleotide insertions, T at position 433 and A at position 441 in a non-coding segment of the genome; (ii) two nucleotide deletions, T at position 1602 and T at position 1603 in the MGF 360-1 L gene ORF resulting in a frameshift; (iii) a nucleotide deletion, T at position 1620 in the MGF 360-1 L gene ORF resulting in a frameshift; (iv) a nucleotide mutation, A to G at position 97391 resulting in a silent mutation in ORF B438L; (v) a nucleotide mutation, C to G at position 166192 resulting in a residue substitution (Ala to Pro) at residue position 85 in ORF E199L; and (vi) a nucleotide insertion, T at position 183303, a non-coding segment of the genome (Table 1). Second, a full-length genome comparison between ASFV Δ9GL and parental ASFV-G was performed. The DNA sequence assemblies of ASFV Δ9GL and ASFV-G revealed a deletion of 173 nucleotides in ORF B119L (9GL) corresponding with the introduced modification. The consensus sequence of the ASFV-G Δ9GL genome showed an insertion of 2324 nucleotides in ORF B119L corresponding to the p72-βGUS cassette sequence introduced to generate a 173 nucleotide deletion in the targeted gene. Besides the insertion of the cassette, only one additional difference was observed between ASFV-G Δ9GL and ASFV-G genomes, a G to C nucleotide mutation at position 36465 resulting in a residue substitution (Glu to Gln) at residue position 224 in ORF MGF 505-4R. In summary, ASFV-G Δ9GL virus did not accumulate any significant mutations during the process of homologous recombination and plaque purification.

TABLE 1

Summary of differences between the full-length genome sequence of ASFV-G Δ9GL and the parental ASFV-G compared with ASFV Georgia07/1*

| | | Virus | |
|---|---|---|---|
| NPN* | Type of Modification | ASFV-G | ASFV-G Δ9GL |
| 433 | T insertion | + | + |
| 411 | A insertion | + | + |
| 1602 | MGF 360-1L TT deletion FS@ | + | + |

TABLE 1-continued

Summary of differences between the full-length genome sequence of ASFV-G Δ9GL and the parental ASFV-G compared with ASFV Georgia07/1*

| | | Virus | |
|---|---|---|---|
| NPN* | Type of Modification | ASFV-G | ASFV-G Δ9GL |
| 1620 | MGF 360-1L T insertion FS | + | + |
| 36465 | MGF 505-4R G to C Glu224Gln | − | + |
| 97391 | B438L A to G SM# | + | + |
| 166192 | E199L C to G Ala85Pro | + | + |
| 183303 | T insertion in a NCR+ | + | + |

*Nucleotide Position Number (based on the sequence of ASFV Georgia 2007/1 isolate published by Chapman et al. 2011)
@Nucleotide modification causes frameshift in the corresponding ORF
#Nucleotide modification causes silent mutation
+Non-Coding Region Example 4

Replication of ASFV-G Δ9GL in Primary Swine Macrophages

Figure 3:
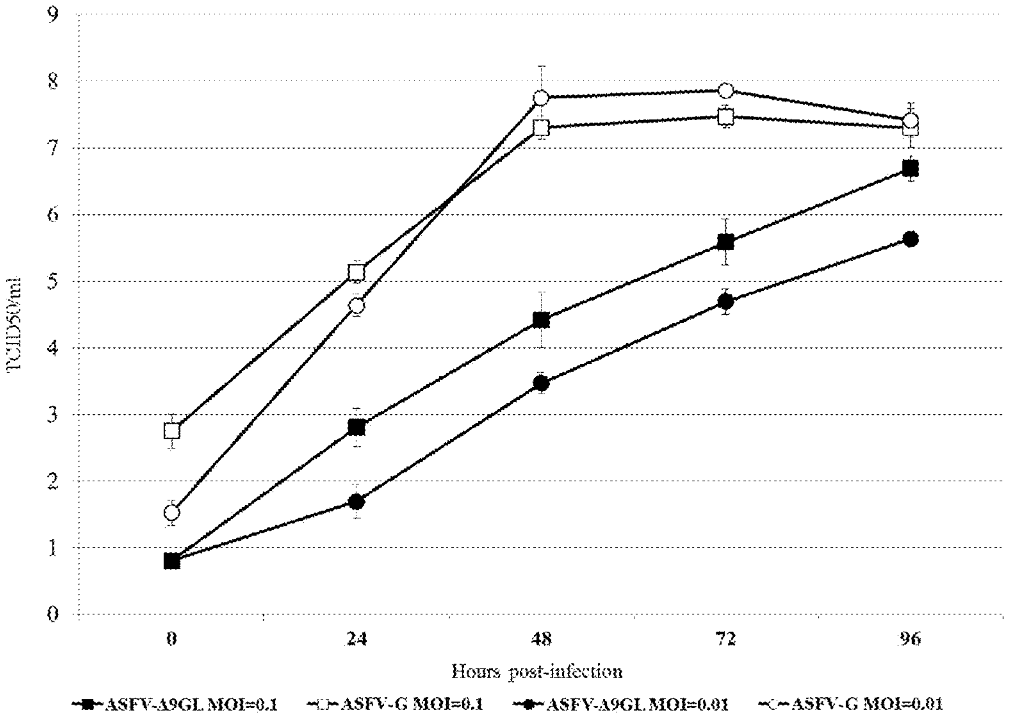
FIG. 3 shows the in vitro growth kinetics of ASFV-G Δ9GL and parental ASFV-G viruses. Primary swine macrophage cell cultures were infected (MOI=0.1 or 0.01) with either ASFV-G Δ9GL or parental ASFV-G viruses and virus yield obtained at the indicated times post-infection were titrated in primary swine macrophage cell cultures. Data represent means and standard deviations from two independent experiments. Sensitivity of virus detection: ≥1.8 $TCID_{50}$/ml.

In vitro growth characteristics of ASFV-G Δ9GL were evaluated in primary swine macrophage cell cultures, the primary cell targeted by ASFV during infection in swine, and compared relative to parental ASFV-G in a multistep growth curve (FIG. 3). Cell cultures were infected at a MOI of either 0.1 or 0.01 and samples were collected at 2, 24, 48, 72 and 96 hours post-infection (hpi). ASFV-G Δ9GL virus displayed a growth kinetic significantly slower than parental ASFV-G virus (FIG. 3). Depending on the time point and MOI utilized to infect macrophages, the recombinant virus exhibited titers 10- to 10,000-fold lower relative to the parental virus. Therefore, and as observed with ASFV Malawi Lil-20/1 Δ9GL virus, deletion of the 9GL (B119L) gene significantly affects the ability of the virus to replicate in vitro in primary swine macrophage cell cultures.

Example 5

Assessment of ASFV-G Δ9GL Virulence in Swine

Animal experiments were performed under biosafety level 3 conditions in the animal facilities at PIADC following a protocol approved by the Institutional Animal Care and Use Committee.

ASFV-G Δ9GL was assessed for its virulence phenotype relative to the virulent parental ASFV-G virus using 80-90 pound commercial breed swine. Six pigs were inoculated intramuscularly (IM) either with $10^2$ or $10^4$ HAD$_{50}$ of either ASFV-G Δ9GL or ASFV-G virus. Clinical signs (anorexia, depression, fever, purple skin discoloration, staggering gait, diarrhea and cough) and changes in body temperature were recorded daily throughout the experiment. In protection experiments animals were IM inoculated with $10^3$ HAD$_{50}$ and 28 days later IM challenged with $10^3$ HAD$_{50}$ of parental virulent ASFV Georgia 2007 strain. Presence of clinical signs associated with the disease was performed as described earlier.

Deletion of the 9GL (B119L) gene from the genomes of ASFV isolates Malawi Lil-20/1 and Pretoriuskop/96/4 has been shown to drastically reduce virulence in swine (Lewis et al., supra; Neilan et al. 2004, supra). In those reports, IM inoculation of either recombinant deletion mutant at doses as high as $10^4$ (Lewis et al., supra; Neilan et al. 2004, supra) or even $10^6$ TCID$_{50}$ (Lewis et al., supra) only induced a transient rise in body temperature. Furthermore, animals inoculated with either Malawi Lil-20/1 or Pretoriuskop/96/4 Δ9GL viruses remained clinically normal after challenge with the corresponding virulent parental viruses.

Here, 80-90 pounds pigs inoculated via IM with $10^4$ $HAD_{50}$ of ASFV-G exhibited increased body temperature (>104° F.) by 3 to 4 days post-infection. Pigs presented clinical signs associated with the disease including anorexia, depression, purple skin discoloration, staggering gait and diarrhea (Table 2). Signs of the disease aggravated progressively over time and animals either died or were euthanized in extremis by days 7 or 8 post-infection. Interestingly, animals inoculated via IM with $10^4$ $HAD_{50}$ of ASFV-G Δ9GL developed clinical disease practically indistinguishable from that observed in animals inoculated via IM with $10^4$ $HAD_{50}$ of parental ASFV-G being the only difference a slight delay in the appearance of fever. Animals inoculated IM with $10^2$ $HAD_{50}$ of ASFV-G develop a clinical disease comparable in severity to that observed in animals infected with $10^4$ $HAD_{50}$ with the exception that clinical signs appeared delayed in two days as well as the time of death was. Pigs inoculated via IM with $10^2$ $HAD_{50}$ of parental ASFV-G developed a slightly delayed clinical disease relative to pigs inoculated with $10^4$ $HAD_{50}$ of the same virus. Pigs presented a short period of fever starting by day 7 post-infection, with animals dying or euthanized in extremis around 8 to 9 days post-infection. Severity of the clinical signs observed in these animal were similar to those inoculated with the higher ($10^4$ $HAD_{50}$) dose. Conversely, pigs inoculated via IM with $10^2$ $HAD_{50}$ of mutant ASFV-G Δ9GL did not present any signs of the clinical disease during the entire observation period (21 days). Therefore, the degree of virulence of ASFV-G Δ9GL virus when experimentally IM-inoculated into swine appears to depend on the amount of infectious virus used in the experimental inoculation.

showed in FIG. 2A), viruses isolated from blood were tested by PCR using primers that target p72 (B646L), 9GL (B119L) and β-Gus genes. All four ASFV-G Δ9GL viruses isolated from blood of inoculated animals tested negative for parental ASFV-G. The 9GL (B119L) gene was not detected in these viruses, whereas amplification of p72 (B646L) and β-Gus genes was observed in all instances (FIG. 2B). Furthermore, PCR amplification followed by sequencing was conducted on blood-isolated viruses to assess the integrity of the p72-βGus cassette inserted in ASFV-G Δ9GL by homologous recombination. Obtained sequences revealed that the p72-βGus and both flanking regions were not modified in these viruses (data not shown). Since these data indicated the absence of contamination of the inoculum with parental ASFV-G, it was concluded that ASFV-G Δ9GL virus inoculated at high doses ($10^4$ $HAD_{50}$) is able to induce a clinical disease basically indistinguishable from that induced by the parental virus.

As previous studies with ASF Malawi Lil-20/1 and Pretoriuskop/96/4 and E70 had shown, a deletion within the 9GL (B119L) gene had resulted in attenuated ASF viruses (Δ9GL ASF Malawi Lil-20/1 and Δ9GL ASF Pretoriuskop/96/4 and E70) which did not cause disease at high doses ($10^4$ $HAD_{50}$) and were effective at $10^4$ $HAD_{50}$, $10^3$ $HAD_{50}$, and $10^2$ $HAD_{50}$ for protection from pathogenic parental Malawi Lil-20/1 and Pretoriuskop/96/4 and E70 ASFV. However, the modification of the 9GL (B119L) gene of the highly virulent ASFV Georgia 2007 isolate, of Δ9GL ASFV-G, of the present invention, differs from the deletion of that obtained in the prior studies, i.e., a larger number of amino acids have been deleted in the recombinant ASFV-G and the deletion in of Δ9GL ASFV-G covers an area of the targeted 9GL (B119L) region that is different from the modified of Δ9GL ASF Malawi Lil-20/1 and of Δ9GL ASF Pretoriuskop/96/4 and E70 as shown in Table 3. Further, unlike Δ9GL

TABLE 2

Effect of ASFV-G Δ9GL and ASFV-G infection on swine survival and fever.

| Virus | No. of Survivors/ Total | Mean Time to death (Days ± SD) | Fever: No. of Days to onset (Days ± SD) | Fever: Duration No. of Days (Days ± SD) | Fever: Maximum Daily Temp (F. ° ± SD) |
|---|---|---|---|---|---|
| ASFV-G $10^2$ $HAD_{50}$ | 0/5 | 9.4 (1.22) | 7 (0.0) | 1.2 (0.82) | 106.7 (0.58) |
| ASFV-G Δ9GL $10^2$ $HAD_{50}$ | 10/10 | — | — | — | 103.0 (0.17) |
| ASFV-G $10^4$ $HAD_{50}$ | 0/10 | 7.25 (0.7) | 3.5 (0.76) | 3.75 (0.71) | 107 (0.47) |
| ASFV-G Δ9GL $10^4$ $HAD_{50}$ | 0/5 | 8.25 (1.6) | 5.25 (1.91) | 3.25 (0.46) | 106.5 (0.46) |

Viremia in experimentally inoculated animals was quantified at day 7 post-infection. Pigs inoculated with either $10^2$ or $10^4$ $HAD_{50}$ of virulent parental ASFV-G had virus titers in blood averaging 7.92 (SD=0.17) and 8.28 (SD=0.09) $HAD_{50}$/ml, respectively. Pigs inoculated with $10^4$ $HAD_{50}$ of mutant ASFV-G Δ9GL had virus titers in blood averaging 2.44 (SD=0.2) $HAD_{50}$/ml, whereas pigs inoculated with $10^2$ $HAD_{50}$ of mutant ASFV-G Δ9GL presented barely detectable virus titers in blood, averaging 1.97 (SD=0.1) $HAD_{50}$/ml. Therefore, despite a low titer in blood that might indicate limited replication in vivo, ASFV-G Δ9GL induces disease in pigs without reaching the viremia levels observed in animals inoculated with parental ASFV-G.

To rule out that the disease observed in the animals inoculated via IM with $10^4$ $HAD_{50}$ of ASFV-G Δ9GL was caused due to contamination of the inoculum with remaining parental ASFV-G (undetectable by the PCR methodology ASF Malawi Lil-20/1 and Δ9GL ASF Pretoriuskop/96/4 and E70, inoculation of Δ9GL ASFV-G at $10^4$ $HAD_{50}$ causes disease and death; whereas, inoculation of Δ9GL ASFV-G at $10^3$ $HAD_{50}$ and $10^2$ $HAD_{50}$ does not.

TABLE 3

Comparison of 9GL deletions in ASFV-G and Malawi Lil 20/1.

| | ASFV-G | Malawi Lil 20/1 |
|---|---|---|
| Length of genome | 189,284 bp | 187,612 bp |

TABLE 3-continued

Comparison of 9GL deletions in ASFV-G and Malawi Lil 20/1.

| | Protein Length | | Deleted AA* | |
|---|---|---|---|---|
| | 9GL ASFV-G | 9GL Malawi Lil 20/1 | Δ9GL ASFV-G | Δ9GL Malawi Lil 20/1 |
| # of AA | 119 | 119 | 58 | 29 |
| Position: Deleted AA | — | — | 11-68 | 51-79 |

| | Gene Length | | Deleted Nucleotides | |
|---|---|---|---|---|
| | 9GL ASFV-G | 9GL Malawi Lil 20/1 | Δ9GL ASFV-G | Δ9GL Malawi Lil 20/1 |
| # Nucleotides | 357 | 357 | 172 | 82 |
| Position: Deleted Nucleotides | — | — | 32 to 204 | 154 to 236 |

*Amino Acids

Example 6

Protective Efficacy of ASFV-G Δ9GL Against Challenge with Parental ASFV-G

Since pigs inoculated via IM with $10^2$ $HAD_{50}$ of ASFV-G Δ9GL survived the infection without signs of the disease, a group of animals (n=5) were infected with a slightly higher dose ($10^3$ $HAD_{50}$) of ASFV-G Δ9GL and challenged via IM with $10^3$ $HAD_{50}$ of parental ASFV-G at day 28 post-inoculation (homologous challenge). Five naïve animals that were challenged using same route and dose served as non-inoculated/challenged control group. The five ASFV-G Δ9GL inoculated/challenged remained completely asymptomatic during all the observational period (21 days) with the exception of one animal showing a slight and transient rise in body temperature by day 8 pi. (Table 4). All the animals in the non-inoculated/challenged control group developed disease with a clinical course similar to that observed in animals inoculated with $10^2$ or $10^4$ $HAD_{50}$ of ASFV-G (see above). Therefore, sub-lethal doses of ASFV-G Δ9GL are able to induce protection against the presentation of clinical disease when challenged with the highly virulent parental virus.

TABLE 4

Swine survival and fever response in ASFV-G Δ9GL- infected animals challenged with parental ASFV-G viruses.*

| | | | Fever | | |
|---|---|---|---|---|---|
| Virus | No. of Survivors/ Total | Mean Time to death (Days ± SD) | No. of Days to onset (Days ± SD) | Duration No. of Days (Days ± SD) | Maximum Daily Temp (F. ° ± SD) |
| ASFV-G $10^3$ $HAD_{50}$ | 5/5 | — | — | — | 106.2 (0.87)# |
| Mock infected | 0/5 | 8.25 (0.6) | 3.5 (0.8) | 4.25 (0.9) | 106.1 (0.14) |

*The animals IM infected with $10^3$ $HAD_{50}$ of ASFV-G Δ9GL were IM challenged 21 days later with $10^3$ $HAD_{50}$ of ASFV-G virus.
#This temperature corresponds to the only animal to show a transient rise in temperature.

Example 7

Genetic DIVA Strategy—Real-Time RT-PCR

Total DNA was extracted from blood, serum and organ samples using the DNeasy mini kit (Qiagen), following the manufacturer's recommendations. Extracted DNA was subject to real time-PCR assay for detection and differentiation of ASFV-G and ASFV-GΔ9GL. The highly conserved full-length 9GL gene is present in the genome of wild-type ASFV-G and is detected in organs, blood and serum of infected pigs whereas the gene is not detected in pigs vaccinated with the vaccine comprising ASFV-GΔ9GL where a portion of the 9GL has been deleted.

ASFV-G DNA is detected by Sybr Green real time PCR using primer set: 9GL-For-191 5'GTAAGATACGAAAAGGCGTG3' (SEQ ID NO:11) and 9GL-Rev-297 5'GACGCTCCTAGCTGGAA3' (SEQ ID NO:12); ASFV-GΔ9GL is not detected. Modifications in ASFV-GΔ9GL DNA is detected by Sybr Green real time PCR using primer set: 9GL-For-127 5'GTTGTTATGGAACGCGAAG3' (SEQ ID NO:13) and GUS-Rev-366 5'GGGTTTCTACAGGACGTAACA3' (SEQ ID NO:14) or primer set: GUS-TT-For 5'CTGTTGAATTACGTTAAGCATG3' (SEQ ID NO:15) and 9GL-Rev-351 5'CATTG GGGACCTAAATACTG3' (SEQ ID NO:16); but wild type ASFV-G DNA is not detected by these primer sets. Assays were run in parallel.

Samples from vaccinated animals were analyzed for differentiation and confirmation using the set of primers by means of Sybr Green real time-PCR. Samples (n=5) from vaccinated animals tested positive only to ASFV-GΔ9GL and negative for wild type ASFV-G. After challenge, samples (n=5) from vaccinated pigs tested positive to ASFV-G by real time-PCR. Non vaccinated control pigs (n=5) tested positive to ASFV-G by real time-PCR but tested negative for ASFV-GΔ9GL.

Example 8

ASFV 9GL (B119L) Gene is Highly Conserved

Sequence analysis of the 9GL (B110L) genes from several ASFV isolates obtained from various temporal and geographic origins, including those from both tick and pig sources, reveals a high degree of conservancy (FIG. 1). Isolates compared include those from ticks: Malawi Lil-20/1 (1983), Crocodile/96/1 (1996), Crocodile/96/3 (1996), Pretoriuskop/96/5 (1996), Pretoriuskop/96/4 (1996), Fairfield/96/1, and Wildebeeslaagte/96/1; domestic pig isolates:

Georgia 2007/1 (2007), Killean 3, European-70 (1970), European-75 (1975), Kimakia (1964), Victoria Falls, La Granja (1963), Lisbon60 (1960), Spencer (1951), Tengani (1962), Zaire (1967) and Haiti 811 (1980); warthog isolate Uganda (1961); and bush pig isolate Lee (1955). Among these isolates amino acid identity for 9GL (B110L) ranges between 93 to 100%.

As a summary, results presented here demonstrated that genetic changes introduced in the 9GL gene of ASFV-G results in the ASFV-G Δ9GL mutated virus which in a vaccine induces a solid protection against the challenge in animals vaccinated 21 days earlier.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant ASFV-G (African Swine Fever Virus-Georgia 2007 isolate) mutant, the mutant ASFV-G Δ9GL virus, comprising cDNA (SEQ ID NO: 3) encoding a mutant ASFV-G Δ9GL protein wherein the mutant cDNA comprises a deletion of 172 nucleotides resulting in a mutant 9GL protein comprising 58 fewer amino acids than the non-mutated, wild-type 9GL protein of ASFV-G, amino acids #11 to #68 being deleted.

2. A vaccine composition against ASFV-G wherein said vaccine composition comprises the recombinant mutant ASFV-G Δ9GL virus according to claim 1.

3. A method for the protection of swine against African Swine Fever Virus-Georgia 2007 isolate (ASFV-G), comprising administering to swine a live attenuated ASFV-G Δ9GL vaccine comprising a recombinant mutant ASFV-G Δ9GL virus according to claim 1 in an amount effective to protect said swine from clinical ASF-G.

4. The method of claim 3 wherein the amount effective to protect said swine from clinical ASF-G is a vaccine comprising $10^3$ $HAD_{50}$ of ASFV-G Δ9GL virus.

* * * * *

UNITED STATES PATENT AND TRADEMARK OFFICE

CERTIFICATE OF CORRECTION

PATENT NO. : 9,463,234 B2
APPLICATION NO. : 14/495540
DATED : October 11, 2016
INVENTOR(S) : Manuel V. Borca et al.

It is certified that error appears in the above-identified patent and that said Letters Patent is hereby corrected as shown below:

In the Claims

In Claim 1, at Column 347, Line 52 change "(SEQ ID NO:3)" to --SEQ ID NO:3--; at Line 54 change "172" to --173--

Signed and Sealed this
Fourth Day of June, 2019

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 189346
<212> TYPE: DNA
<213> ORGANISM: African swine fever virus

<400> SEQUENCE: 1

gaatatacca tattattgct attgccatca atgagaatgc cacgtaggca taggtcatcc     60

tatggccgga ccaatccatg gctgcactta aaaatatcaa aaaagtttaa gttttgggcc    120

ggcgttaaaa tttaaacctt ttctggttga tctttagcca tgtatagctg cgatgtttgg    180

tgccttatct acatgctatt ggcattcctg atattcgcac taaagtgcta tgttacaacc    240

gtcttatgcg tgatttttat ccaccttatt ggccgaaggg ccgccttgta tttcctgtta    300

ggtggtttgg ccgtattcta ctggtggcaa gcagctatca ataaaattta atggctctca    360

cttaagatcc ttgctgtaag cgggcgttta catactttga tcaagaaaaa aattattttt    420

ggaccccccc ccatgtttta tacaaaaatc atataataaa gtggcgacaa tcaacatatt    480

aatcaaccac agcattttat gatgtgttaa tcaacatata ccatattaat caaccacagc    540

attttatgat gcgtcaatca acatattatt acggagagcg tcaatcaata taatattgag    600

aacagcgact tgataccgtg tatggtggtg gcggcggcat gttgtttgta acagcatttt    660

tcatcattcg aagcttacaa aagatatgta taagatagca tattaatgtt attaacagta    720

atatcaataa ggcgtagcta tagatcttca ctttggtaga ccaataatcc atggttgcgc    780

ttaaaaatac caaaaaaaac attaagtttt ggagggtaag attggttttt caccattggt    840

aaagattatt attctaaatg tttaccccat agatgtgaaa caatgattct tcatatatta    900

acatattttt tgacttatac ttttcttcat ctagtaaggc gttaattttt tccggatctg    960

tcgtttttat tgataaaaga gaagagtctg gactgtaatt tttaaataat aagatattta   1020

ttaatatcca attattcgtt tggctcgcta tttccatgct ctcttcgaaa gcatcagctc   1080

ctaaatctat acaaaggaat aagttacctt cacaaaaatt cattaccgag gtaatcattg   1140

cccgattaat gtcagccccc aacataaaac aataatatat agttgtataa ttacaatcat   1200

acatacaggc caactgcatc atttcatcaa tgtctatatt tgtcttctct ttgttataaa   1260

tttcatgaag gtcaaagacg ttgttataag caaccccaca tattaaccgc caatctttaa   1320

aatgactata tcgttgataa aaatattgga tggcttcagt aagcttatat agtatcgcca   1380

tactatacca atacctagtt agcatttcgt tgaatgaaat attatccaat gtaaagttaa   1440

ttgataatgt atctagttca ccaaaaattc ttaatttcag ttgagcatta tttaggaaaa   1500

ggggattatc agataataat tcatggcata gaataatatt actgctagtt ttaacatact   1560

gtacattata aaatatttct aaaattttat tttcactcaa agctttcctc gcacctaact   1620
```

```
tttggcatag gtcctggtgc actccatatt gacagtaacc aacccaaagc tgatgtctgc   1680
accccattcg gtaaacagct ctattaaacc atgattgttt tcctgtacag ccttcattaa   1740
tgcaacattt aatgttaaac catgtttaaa acttgctgtt tttattaata tttgttcatc   1800
tatacaagta tgataaatcg taattggggc ttcatgccac cacaaaccac aacgctctaa   1860
aatacaataa tcatctttta acacaggctg tgtagctagt actttttag taagtgcttg   1920
taaagtagat ggcatcttct atctgcaaaa taattatttc cgaaaaaaaa atcaaattaa   1980
aatactaaat tctatttttt tttttaataa agcctgtaaa ttatataata aatctcgccc   2040
accgtattat ttccggacac aactttttat acctcattat atttttagat ctatagtttt   2100
ttaacaaggc attaattttt tctggatctg tcgtttttaa agataaaaga gagacgtttg   2160
aactataata atctttaaat gataatattt ctactaatat atcatgattc ttttgttttg   2220
ctaattctaa gctctcttcg aaagcattag ctcctaaatc tatacaaaag aacaagttat   2280
tcatataaaa gtttttttacc gaggtaacca ttgcccgatt gatgtcagcc cccaatacaa   2340
aacaatagta aatggttaaa aaattgctat ctctcataca ggccagatat atcatttcat   2400
caatattcat atcaaccttt tttatatgat acatttcatg aagatcagac acgttattaa   2460
aagaaagccc acatattagc cgccaatctt taaaatgact atatcgttga taaaaatatt   2520
ggatggcttc agtaagctta catagtatcg ctatactata ccaatatcta gttagcattt   2580
cgttgaatgt tatttcattc aatataaagt tgatcgatat cttctctaga aaacaacaaa   2640
ttattacttt taattcctct atattctgga aaaggggatt attagataac aatttatggc   2700
ataaaataat attactacta gttttaatac gatgtatttt ataaaatatt tgtacaatat   2760
ccatttcatt caaaattttt gcgcctaact cccggcagaa attccaagta tgctccgtat   2820
tgacagtgac taagctagag ttgatgtctg caccccattc agtaaacaac tctattagat   2880
catagttgtt ttcctgcaca gttttcatta atgcgagatt taactctaaa ccatctttaa   2940
aaattgctga ttttatcatc aattgattat cctcattagt agaaagcata attggagctc   3000
catgccacca caaaccacaa tatttcaaaa taaagtagtg ttctttagat atgtgctgtg   3060
tggccagtat tttttagca agagcctgca gagaaattgg agtagacata tttttttttg   3120
caaaatggtt taagtttttc aagaatacag attggataaa ttaggttgtt gacttagtta   3180
caggaggtat taaatattat gtagacataa aaatgagatc ctccaaaaaa ataaacaaca   3240
aaaaaaatat gtttaatatt aaaatgacaa tttctacatt gcttattgct cttattatac   3300
tacttattat tattttagta gtgtttttat actataagaa acaacaacca ccgaaaaagg   3360
tctgtaaagt agataaagat tgtggtagtg gagagcattg tgttcgtgga tcatgtagct   3420
cattgagctg cttagatgcc gtaaaaatgg acaaacgaaa tattaagata gattctaaga   3480
tttcctcatg cgaattcact cccaattttt accgttttac ggatactgct gctgatgagc   3540
agcaagaatt tggaaaaaca cggcatccta taaaaataac tccatctcca agtgaatccc   3600
atagccccca agaggtgtgt gaaaaatatt gttcatgggg aaccgatgac tgtacaggtt   3660
gggaatatgt tggtgatgaa aaggagggaa catgttatgt atataataat ccacatcacc   3720
cggttcttaa atatggtaag gatcacatca tagccttacc tagaaatcat aaacatgcat   3780
aaataaatac attaggctca tcgtatcttt ttaaaatcca taaatattcg tttgatatat   3840
gctgaaattt ttataaaaaa aataactatt tcctataaat catctagaaa tagtcctcgt   3900
tttgatcggt ttatatctta taatattgtg catcgatgca caactgcttt ttttggtcct   3960
```

-continued

```
tctggaacat cattatattt tctttcatta atataccatt cagatgtaaa cgttgaataa   4020
tttttatggc aacaatctac cattgaatta tatttagtaa catctaatac atcgtttgtt   4080
ttatcaggct cagctctata atcttgataa tttttgttat cagcttctaa agctccatca   4140
ttatttttca aagaagtatc cataattatg tttggtaaaa atactttaag ttttaatgtg   4200
atatttaaaa tggttgttat ataaatttac cgcttacagg taatctttat tcagtgtcat   4260
aaactatact tttgatgatt cagtattttg tgaatcagta catttattat cattaatatt   4320
tttaggctgt ttttccaatg ttttattgtt gcaatgagcc tgctcctcct ttgacgagga   4380
agtgtctgtt ggagtcatct gtttaggaag agtatcatcc atatctatta tgaagaaaat   4440
atataaatat tgatatacaa tcaaaaatat ttttgatcac gtctttgtta tctatcgata   4500
ttgttgataa cgtcttgaat aacctacatc atttttttac ataaaaaaat agatataatt   4560
tttattatat ctcaattatt ttaaagataa ttatcaatac agcaaatatc ataagctaac   4620
atatttttcg aataatagtt ttttagtaaa gtattaatct tttcaggatt ggtttctttt   4680
gataataaga taggattcgc tttataaatt tttaaagata atatattcac aatgatagaa   4740
taaccgtata tatctgctaa tgtcttactg tgttcaataa cattagcccc taaatccata   4800
caaaagaaca tattttcaat acaaaagttt tttaccgaga ttaacattgc tcgattagcg   4860
ttggctccca atgcaaaaca gtagtaaatg gtcaaaaaat tattatcgcg catacaggcc   4920
agctccatca ttttattaat actcatatga attttcgttg tgttacatat ttcatgaagg   4980
tcaaacacat tgttgaaaga aagtgcacaa attaatcgcc attcatcaaa atgcctgtat   5040
tcttgacaaa aatattgaat agcttcttta agattatatt ttaccgctat gccataccaa   5100
tatttggtta gcatctcact aaatgagatc tcatttaaca tagaatttgt tgttaaatcc   5160
ttcaactccc aataaatgat catccttaaa tccaccatgt ttacattttg taaaaaaggg   5220
ttattagaaa ataattcatg acacaaaatg acattactac ttgttatttt acactttgtt   5280
tcaaagaaaa atcgtaaaat ttcacttgtc tcaagctctt ctttagctcc caattttcgg   5340
cataggtttc gagtatgctc gttattaata aaaagtaacc cataattaat atttgcaccc   5400
cattcagtaa acaacatgat tagatcatca ttgttttcct taactgccaa taccaatgca   5460
gtattaagcc ttataccctc tttaaagcat aatgtcctta tcattatttg attatcatca   5520
tctatataca ttgagatagg agcttcatgc caccataaac cataacgctc taaaatataa   5580
taatcatctt tagatacgtg ttgcgtggcc aatgcccttt tagcaagtgc ttgtaaagtc   5640
gatggctgca tgtttattct gttaaaaaaa atcaaattat cgggtaaaca taaggatcaa   5700
cccgtagtta atatttgcag tagtattttt taacaatgaa ttataataaa aaaataattc   5760
attactatct attataaaac ccatctttaa ctttaaagaa gaactagatc atcttttttt   5820
tgttgtgtca gaacttcttc aatttattac ccacatttta tctaaaaaaa taaaaactac   5880
atcatatctt gtttcttcat caaattatca taccatttat agggtgtagg ttgggaacat   5940
tccatcatgt ggtaatcagg gtatttatat atttttttgat agtaacatct atttggcaga   6000
tgtattgtcc aacaatcatg tctaataaaa tcattttcac ctatggggga atcatcttaa   6060
aaaccttatt cctacagatt ccattttgac agtcccagca aaagtcacaa tattttccat   6120
gagtacacca atgttcaagc tctctttcgg gaggaatgct gccaatttta tgttttttag   6180
cttctaactc tctgtacaac atcagttggg aaagcagaaa gaagattacc aggagaacca   6240
ttaaatatat aatagtctgc aaactacgtt tgcgaatgta atttgcaact aaaacacaac   6300
ccacaaggta aaatccataa gttaataact tttgccattt tcgtatgaca gcctcgtgcc   6360
```

-continued

```
attcatggtt gtgttgtggg cattctgttc ggtaaacttc atgaggcttt atagaagtta   6420
catagtaggt acagaattca ttgtgacgaa aaacactgca gttagctatg tagtcatttt   6480
caagaatggg agaatggttt tcaaagacct tattcttaca gatgccatct tgacagtccc   6540
aacagaacct acaatgattt gcataggtgc accagtattc aagctccttt tcaggagggg   6600
ttcttgttag atccaggagc tctagctcat atgtataaag aagagttgga atggatagta   6660
aagtaaatat ttgcagacca agcatggcta cttgtgaaca agtggctgct cgtcaacaaa   6720
tagctgttta tcagcaaata gctgtttatc agcaacaact aattatcagc aaatgctgct   6780
tgtgggtaag ccaataaata ggccataccc ttgaaaggag aattcagttt gataaaaaaa   6840
ataacgagtt ttctaataac ccggtcaagc atttaataaa tgaatagcat cacacgtctg   6900
catcgtgcat tctgcctgga aaatgggccc atctctaata tatttacact gacggtgaat   6960
catacagtgt tccatgggat agctatgctc ctgtacagga ggcatatctt ttagaacttt   7020
attcttacaa agaccatctt gacaagccca gcaaaaccga caatttttca catattgaca   7080
ccagtatcta agctcctctt ccaggggatt gtcggtcgaa aacccctgta gactagctag   7140
gccagctagc agcaagccga ggtaactaaa gaacctcatt gtagtgttat attacgaaaa   7200
aacatgttaa aatttggaaa aaaaagccct ttttatagat ctggaaaaaa attttcacaa   7260
atctaattaa aagccttaca gatcatcctt ttcataaatt ttcattaaca attggtgggg   7320
gcggttgtga ggtactggat cagaacaatc cataacatgg taatgtccat ttccttcacc   7380
atatgtacac tggttatacc agcgagaaac ctcacaagat gtcaaataac tgttctcaac   7440
aatcaatggc atgctcttat tcaccttgtt cttgcaaatt ccatgtgcac attcccagca   7500
aaacttgcag ttttccatgt aagtacacca gtatccaagt tcttcttgtg gaggattatc   7560
cgttgaacga agatgccctc ctgcctgagt aggtagtcct aagacctgat tggccagcag   7620
gccaagaatt tccaagaaga tcaccaacat tgctacggct ggctgaacag ctggcagata   7680
gctagctaat tagcaaacca agtgactcgc cctctctact cttaatatga gaatttaaga   7740
ttcggtccgg ctttttttccc atgttttaca gggaaaaggt atttttagcc tatgaatgta   7800
catggttccg cacattaaaa aaaataaaag aaattattta atattggctg ttattttctt   7860
tcaactagca acaagccagg taactaaaga acttcattgt agttttatat tacggaaaag   7920
gttaaatttt ggacaaaaaa atcatatcta attaaaaatc ctcacagatc tttcttttca   7980
taaattttca ttaacaattg gtaggggcgg ttgtgaggta ctggatcaga acaatccata   8040
acatggtaat gcccatttcc ttcaccatat gtacactggt tataccagcg agaaacctca   8100
catgttgtca agtagctgtt ttcaataatc aatggcatgc tattattcac cttgttcttg   8160
caaattccat gtgcacattc ccagcaaaac ttgcaccttt ccatgtaagt gcaccagtat   8220
ccaagttctt cttgtggagg attatccgtt gaacgaagat gccctcctgc ctgagtaggt   8280
agtcctacga cctgattggc cagcaggcca agaattccca agaagactac caacattgct   8340
acggctggct gaacagctgg cagatagcta gctaattagc aaaccaagtg actcaccctc   8400
tctactctta atatgagaat ttaagatccg gtccgacatt tttccgatat tttacaagaa   8460
aaagatattt ttagctacaa atacacttca tatatcccta aaaaaacaaa aatttattta   8520
attttaacta ttattttctt tccactctct ctttaagatt ttgtaaggat tccagggctt   8580
tggttcagaa caggccatta catggtgaat cccctgtcct agatcataca tacatttatt   8640
tagccagcgg gaaactatac atgattgcac atactcattt tcaagaattg ttgtattctc   8700
```

-continued

```
caatttgccc tcacaaaggc cattttgaca attccagcaa aacttgcagt tttctgtata   8760

agtgcaccag tattcaagtt cttcttgtgg aggattatcc gttggatgaa gttgtccagc   8820

tggttgatta ggtagcccta agacctggtt gcaattcatg gtatggtaga tacccttatc   8880

taaatcatac atacatttat ccagccaacg ggaaaccaga catgatttca catactcatt   8940

cttgtaaatt actgacccat ctattttgtt tatacaagtg ccgtcttggc agtcccagca   9000

aaattggcaa ctttccatgt aggcacacca gtattcgagt tcttcctctg gaggctcctc   9060

tgttggacga agttgtccaa cgagctgact tgaaacctgg ctggccagaa ggccaagaat   9120

tcccaagaag atcaccaaca ttgctacggc tggctgaaca gctgactgaa tagctagcca   9180

attagcaatc cactgtactt ttcataagat catttaagat tcggtcggca tttttttcaat   9240

agtttgctag gaaaaaattt ttaattttat agattcacac tacttcattc tcatgcttag   9300

gaaaaaaaca aactaaatct tacaatgtat ctggatctaa tgagaagcta gaattcatct   9360

tttttcaaat cctttctggg atgttcattc tttttccact ccttccttgc aattttataa   9420

ggattccagg gctttgggtc agaacagttc atgctatggt aaatgtgctc ctccacatca   9480

tatctacata ggtcacccca gcgggaaacc tcacaatatt ttacatagtc attctcaata   9540

atacttgtgg agttgtttcc ccaaaccctg ctggtacaaa tcccatcttc acaatcccag   9600

cagaaccgac agctttccac ataagtgcac cagtatccaa gttcattctc tgggggttca   9660

aatgttagag gaagatgtcc acctacccga gtagaagtgg aggatgaaac caggttgcta   9720

ctggccagca ggccaataat tcccaggata atcaccagca ttgtgctcaa ccagcaacgg   9780

ctagcaacga ctagcaactg actagcaata gctagaaatg gctagcaatc agtagtagct   9840

aacgctctac tctttataag aaaatttaaa attcgatcag atttttttag aattgagaat   9900

gagtaaaacg cttatattct ttttctagct agaaaaaaata agctagttta agataggatt   9960

tcccttacta acggtttaat ttttagcaaa ggtataggta aaatacactt gtacttagct  10020

gcaaaaaaat aagcttatgg cgtataagcc gccataagtt tatttaatta aaatgttaaa  10080

ctctgtgata agactggaat cttaggcagg tttgatgtgg agaacagcat gaaatacaag  10140

agtgcctgtt acacgaataa gttctctcaa accggggatg gtcatactca catctatgaa  10200

atcctggtct aggagattca tttgatgcat gatggccgca cccacactta tgagacactg  10260

aagaactaaa gggtttaatt ttgatctgaa tggtactata taggatgatg gcaatccata  10320

tcaagattag agcaatcaaa atcacctcct caagaagcat gatgtagcct taaatcttag  10380

actgctttaa accttaggcc ctcactatct ttaatgaagg agtttaaatt ttgatccctt  10440

tttcaagacc catttagaag aaaaaataaa gtttatatca atctaattca taagtcatct  10500

ctttcataaa tcttcatgta ttctctatgt ggataagtat gggatgttgg atttgcgcag  10560

tccatttgat gatctgtatg gtttttgggt ccttcataat aactacatat accattccag  10620

cgggaaaccg tgcaatttat aatccagtca ttttgatgaa taactggcca atctgtttga  10680

atcctgtttc ggcagatacc gtggacgcat tcccagcaaa agtcacattg gtttgcgtaa  10740

gtgcaccaat aaactagctc atgttcagga ggataacggg ttggtagtaa atcttctaat  10800

ttacgtatag gagcggcttg aaggacaacc acccccagta gtactagaat cagtaccttt  10860

atagtggcca ccctacacta gacctctaag ttgaagacaa agaactaaaa tttagagccg  10920

tttaattact actaataatt atattttttta ttgtctacaa taggattcta ttaaaaaata  10980

atgattttta ccaagaaata tttttataaa aaattaatat attttgtaat aaactttatt  11040

tccaatgact gttaaaataa ggaaactatc cttagttagt cgaggaagat ggttaggtta  11100
```

-continued

```
tttcgcaatc cgataaaatg tttattttat cgtaggtctc gtaaaatcca ggaaaaaaaa  11160
ttacggaaga gtttaaaaaa gctaaatttt taccaccctc cagaagattg ttgtcaaata  11220
tatcgtttgc tagaaaatgt tcctggagga acttacttta ttacagaaaa tatgacgaat  11280
gatttaatta tggtcgtaaa ggattcggtg gataaaaaaa ttaaaagcat taaattatat  11340
cttcatggaa gttatattaa gattcatcag cactattata ttaatattta tatgtatctt  11400
atgagatata cccaaattta taaatatccc ttaatttgtt ttaacaaata ttataacatc  11460
taagtaaata ttcttggaat ggattttctt atagaatggt tacaggatat gtcagcgaca  11520
ggcttaataa caaatttgtt aatatttttt tgttaaataa atgaacaggc caccatttaa  11580
tattacccgt tgcaaaataa gaaaaaaaaa caaacttata gttacaaatc atcttgatta  11640
atcacatgtc gttttaactc aatgaaccat tctaaatctt tgggttgtga acaattcatg  11700
ttatgttgat agtgtatcct aaagtgagct tcatacatac accggtcatg ccaccgggaa  11760
actgtacaat taacaatata atcattttgc gtaataatag ggtggtcact aaacacttta  11820
tttttacaca ttccatcttt acaggtccag cagaagtcac agtgttttgc ataggtgcac  11880
cagaacttga gatccctttc aggaggccta cgcatttgca tcggattatc tgtggaaaga  11940
ggtaggttca ttattatgtt cgtcatcaaa attcctaaaa gaacatagaa gccaagaaag  12000
ataagcagtc ttgtagcggc ttgcattcgc attcgtgagt attgtttgcg aacatagctt  12060
atgagagcaa tggtagctat catacaaaga caagtatgtt tgatattctc agtgtcaatg  12120
accctatcct cctttatttg cattaactca tcaaaccaat cataatatgt gggatttgta  12180
cagctcatga tgtgaaagcg gcgtatccta gagtctgtaa agtagctaca tctttcatta  12240
tagcgagaaa ccctacatat ttgtatgtaa tcattttttt tgatgagagg gtgtttttca  12300
aaaaccttat ttttacaaac cccgtgtcga caattccagc agaagtcaca cgattttgca  12360
taggtgcacc aatactcaag ctctctcttt ggaggtctcc gggtcattgg taactctcct  12420
gttcctggaa aagattggct ttgaatgacc ggctgcatga ccgccagtac caaaaggaac  12480
acaatcacct tcatggctgc aacttataag ttgcaactta tgggttgcaa tactgcaacg  12540
tataggttgc accttataga tcgcgactca aaaggtatga aaaccttacc ctcaatacag  12600
aatttaagtt ttaatcctga taatgtatct gtttatgaaa aaaaattttt tttactcatg  12660
tatgaattct tatacgaatc ataatatgta ggctgagaat aataattcat atacggtgtt  12720
gcgggctcaa taaaaatttt gttaccacaa aaaataaatg ctggattttt aagatatata  12780
tctattaatg actaaaccct ttatacgctg taggctgaaa acaatccata taatgaatat  12840
acggtgattt gggtttaata aaatacatac aacggtcaaa atagcgggca atactacatt  12900
gactaatata atcattttgt ttaataagag gcatatcatc ccacacttta tttttacaaa  12960
taccgttcct acattcccag cagaaatcac agtgttttcc atacgtgcac cagtattcaa  13020
gctctcttat aggaggcgta taagtccttg gtaaattttg tttcatataa aagatggaaa  13080
ggggtcgatt taaacccggc tgagatagcc aaatcaaaat acataaaaga gcaagtagtt  13140
tcatagtggt atttagatgt aaatttttat agtatgcaaa tacaatgtaa cctacaaata  13200
caatactaaa tacaaggtaa aaacaacaat gtcttataat gattggccaa taatcacccc  13260
cccccccccc atttttccat gaatatttca tttcctgtat agggtctagg atgtgaacac  13320
tccatgttat gatgattagg cattttaact gatatttcat aaaaacaccc ccaggaattg  13380
cgattaacta tacagtttac aatcgaattc atcgaattag actcatttgt tatcttattt  13440
```

-continued

```
ttacaaatgc cattttgaca atcccagcag aagtcacaat tctttacata cgtacaccaa  13500
tatggaagct cctccttagg aggatgctgg gttcttggta attctggtaa ttcatgtgca  13560
agaatgagga ctgagtagcc caacaaaagt cctagaacct tcatgttgtg tccaaatggc  13620
acctgtcatt ttaaaaaaga tttaaatttt gctaccgcaa aaaaaatcca gtatgtattt  13680
ttttaataca tataattatt gaagtcttat aagataaagc cgagaacact atattttgta  13740
tagatgatgt atccggtatt caaactctct tataagtaca tgtaggaaat ggtcaattat  13800
tcaagattgg ctgagataac aacaaaacca aaatactcaa aagcataagt aatttcatgg  13860
ttgtactcag tcgtagattt ttgcagatcg caaatgcaac gcaaccagca aatacaaagc  13920
taaatacaag gtaaaaacaa taatacctta taatgattgg ccaattctta tccctccatt  13980
tttccatgaa catttcatgt tcataaagtc taggatacga acaacatttc atgctatgat  14040
gattaggtat tttaagtgat atttcataaa aacaccacgg ggttgttggt gattgatagg  14100
taagaataag gatggttgaa taacctagta aaagtcctag aaaaaccttc atattgcgtt  14160
cataccacag atgttattta aaaaaaatat aaattttaca gtatgtgata tacacatacc  14220
acaaaaatgt tcttatatta actaaaatat gtgggcagag agcaattcat ataatgaata  14280
tatggtattt taggctcaat aaagtacata caacgatcaa taaaacgggt aatactacat  14340
ttactgatgt aatcattttg aacaataaga ggcatatcat ccaaaacctt atttttacaa  14400
ataccattct tacaatccca gcagaaatca cagtgttttc catacgtaca ccaatattca  14460
agttctctca taggaggcgt ataggtcctt ggtaaaattt gtttcgtata aaagatggaa  14520
aggggtcgat ttaaaactgg ctgtgctaac caaaccaaaa tactcaaaag aacgaaaagt  14580
ttcatggttg tactcagacg cagattctta caaagcgcac atacaaagca gcctgtatat  14640
gcaataccaa tgatgaaata gagacagtat tgctttatag ataattgttg atggtcaccc  14700
cccccccccc cccatgtttg catgaatatt tcatttcctg tatagggtct aggatgtaaa  14760
cattccatgc taaagtgatt aggcatttta gatgaaattt catataaaca ggattgagtc  14820
ttggaatcac ggaaaactct acagtttaca atagaatgat tggagtcaat gaaacgagat  14880
tccgttatct tatttttgca aatgccatct tgacagtccc aacagaaatc gcattgtggt  14940
acatacgtac accaatatga aagctcactc ttgggaggat gctgggttct tggtaagtct  15000
ggtaattcat gtgcgagaat gaggactgag tagcccaaca aaagtcccag aagaaccttc  15060
atgttgcgtc taaatgacac ctgcacttac aaaaaaaaat ttaaattttg aatataacac  15120
aaaaaaacca ccttaaaatt tcttatatta tttcttggat ctgccccgac gtcatacaat  15180
gtattaaaat tatagaccaa tcatcttttt gtatataggc taatcatctt tatatataga  15240
ttttagatgt ttgcttgttg tatcaactta actgctagcg aagaaaatgg ataaaaactt  15300
tctgtatttt tataggttga aatcatttta tgcacatcgc taggatctaa tattttattt  15360
tgaagaaccg aatgtgggct taaaattttt ttcttagaaa aaagtagaat cataatattg  15420
ctatgttttt gtttaatgat ttcttgtatc ttttttgtat acgggttggc acccaaacct  15480
atacaaaaat atacattact caaataacta ccttctatac ataatctttt ttccccacgt  15540
attttcctat ttatttccct atttatggaa ttaaaggata tcaatctctc taaggcacgg  15600
tcaaggtctg cgcctaaggc aaaacaataa tatataccta atttattccc agggcgtgca  15660
caggcaagaa acatcatgac gtttagccct aaacgtatat tttcctgaaa atacgcatga  15720
tgaacttcat caatattacc taagtatatg gccgtttgta aacgccaaag atctaaatga  15780
ggaaattttt tactaagata atgaataggt tttgtgagat taaaatctat ggcgaactta  15840
```

-continued

```
taccaaaatt ttaatacaag tgtatttctc gtcatttctt cttctttttc atctaaatat  15900
aagataaaac gattgtaaac aaagtctatc aataggtgaa aatcattgct attaaagctg  15960
tcgagaatca aaatattgtc ataataaatt tcgatcgcca gtaaaacctt ttttcgtttg  16020
acgagataaa caaacatatt atacaaccct acatctaaaa attctggatt ggctcctagt  16080
tggatacaca ggtctttagt ctgcttcgtt ttggcacaca tgatgccaaa attaatatca  16140
gcaccccata aaacaaataa cttgattaga tcagtctggt tttccttcac agcttttact  16200
aaggctctgt caagctcata gctgtcgaca tcagagcatg acatagagcc accggttacc  16260
attttacatt gcttacaaaa acctatgggt ccgttttccc accatagtcc aagctgttgt  16320
agaataaaaa tatcatcctc atgataattt gaaaaagcct tggtttctat caagactttt  16380
tttgtaagaa cctgtaaaga gttcatcgta ttattatgaa taacaggagt aaacgtaatc  16440
aattataaaa gtgatttttt cgaaaaaaac tttagatggt tgaaaatgat aatgtacatg  16500
ttcatacaaa aaatagatgc agtgatgtct aaaatcaaaa tttaattttc tatgtaaaaa  16560
gtacagactt acttatttgg gttaaattgt ttattttaaa ctttaattaa ccgtttgagt  16620
tagcgatgtt tgatttatct tccatactca tccggggggg gggggtcctt atagctctga  16680
cattattgtg gattattgaa tataatgaat acttcataga tgctaaacat tttaatagta  16740
gttctgaggc ttaattgtac tctataaatt tataaaaact ttttgatcaa aatttaattt  16800
cttataaaaa gagtacagac gtcgcttgtt taagcttcat catgtttcat tcattacttt  16860
ctacaattac gggggggggg agtcccctca tagctttagt attgctatgg tttactaatt  16920
attatgtaga atttatagaa gcatatgtac ctgaaagtat acctactcta taaaattaaa  16980
taatttcagt atattttttt tatgaataga acggaaatga tataaaaata atttaatatt  17040
gcaaaaaaaa ttcataatgt tggtatgtat tataaacata atagcatgtg taatttataa  17100
actgactcct ctatataatt attagatgag gtaccaacct acttatgata tgccgatgat  17160
agatattgta tactataaaa caaaattatt ttaaatgtat tcatggatac attataacat  17220
ttttaccgca aattgtctct cagcgaagaa aatgaatgaa acgtttctgt atattcatag  17280
gttgaaatta ttttacgcac ttcactaggt tctaatattt tcttatgaag tattgaatgg  17340
gggcttaaaa gtcctttctt aaaaagaagt ttcatcataa cattcttttc ttgtctaaga  17400
agagtttctt gtattttttt tgtataagga ttggcaccca aacttataca aaaatgtaca  17460
ttactccaaa taccataatt tgaaaagaaa gttatttccc tatttacttc atgattaatg  17520
aaacctatca acgtctctaa ggccgtattg atatttgcgc ctaaggcaaa acaatagtat  17580
atacccaatt tattttgagg gtacatacaa gcaagcgaca tcatgtcatt tggatctaaa  17640
cgtatatttt cctgaaaata tgcatgatgg atttcatcaa cattacctaa gtatacagcc  17700
gtttttaaac gccaataatc taggtgagga aatttcttac taagaaaacg aataggtttt  17760
ataagattaa actctatggc gatcttaaac caaaatttta atacatatgt atttttttatc  17820
atttttttctt tttcatctaa atttaagata aaacgattgt aaataaagtc tatcaacacg  17880
taaaaatcat ggctatcaaa actgtcgaga atcgaaatat tgtcataata aatatctata  17940
gctaataaga ccttttgttg tttaattaga tcaacaaaca tattatacaa ccctacatct  18000
aaaaattttg gatcagctcc tagttgaata cacagaactt tcgtcctttc cgtcttggca  18060
catatgatgc cataattaat gttggcaccc cataaaacaa ataacttgat tagatcagtc  18120
tggtttttct tcacagccct caccaaggct ctgtcaagct catagctgtc aacatcagaa  18180
```

-continued

```
catgacatag agccactggt taccatttta cattgtttac aaaaacctat gggtccgttt  18240
tcccaccata atccaagctg ctgtaaaata aaaatatcat cctcatgata atttgaaaaa  18300
gccttgtttt ctatcaagac tttttttgta agaacctgta aagaattcat cgtattatca  18360
tgaatgaaag cagtaaatgt aatcaattat aaaattgact tattgaagag aaatgttaaa  18420
tgagtgaaat cggtgtttat gatgatgtac atgatcatac gaagaaacac gttcactggt  18480
gtccatgatc aaaatttaat gttttacgta aaaagtacag atgttaactg tttagtttaa  18540
acataaattt aacctttagt ttaaacccta gttaatgatg tttaatattt cttctatact  18600
cattcaggga agtgtaatga ttctaatact gttgttatgg attattaatg aaaactttac  18660
agatgctgga gggaataatt ttaatcatac tgttttaatg tagctatata agctttcatc  18720
aaaatttaat ttttttttata aaaatacacg aattaaacta aagtctaaac tttagtttga  18780
ctatttgagt taatgatgct taacttatct tccatgctta tcaagggggg gtcctaatag  18840
ttttgatact attgttgtgg attgttgaat ataataaata ctttatagat gctgaaatgt  18900
ttgaaaataa tagtacatca atgttgtaag tttgatcaaa atttaatttc tcataaaaaa  18960
ggtacacatc aacattgctc atttaagttt catgatgttt gattcattac ttcctacaat  19020
tactgggggg gggggggggt ctttaatagc tttagcattg ttatggtttg ctgactatta  19080
tgtagaattc atagaagcac gtttagatag taatatcact gcagtgtaga ttatgaaata  19140
catactaaac taatttcagt atattttttt tgttcatata agttaaggta caaaaatgat  19200
taaacattgc aaaaaaagaa aatcacaatg ctattataca tagtgatcat agtggcttgt  19260
atcatttcta aactagttcc aaatgaatat tgggcaatac atctattttt tatcattatg  19320
atttttatgg tatatatgta tgaaaagtta gatatacatc aaaaatctca gttctggaat  19380
tataccatgt caggcttatc tggacataac gtacaggtaa catgtaagtg ttactaaata  19440
ctatgaagta tctatttttt ttgttgtaaa aaaaagaact tgatagtatt ttttaaaaaa  19500
taaaataatt aattgtacgt caacttcctt attttattct ttaaaaataa ctcgtaagta  19560
ttatttatct atttttgaa aaaatagatg taatcggttt catcatttag gtgtgtattt  19620
ctttttagca tctatcaaga attcattgtt tagtgatatg aaaacaatga atgatcatta  19680
tcttctattt aacaaccacc taaataaatg aacgtctttt tcatcttaac tgattaccaa  19740
aagttatttt gcgaaaaggc atacatatga tcaatatcag acctacaatg aatatttcca  19800
taatatccct ttattgtaat aattctattt ttgcattccg atatctcatc atctgtgcta  19860
ttatatgttt ccataactgt ttcatcatca aacataaatc ctgttaaata ggcaaaagac  19920
tttaatcccg gatagatttt taccattttc ctgagagccg tgtatagctt gtaataaatg  19980
gccaaaaata tgcaataaag cgtagaaaga gagtaatttt tggcataaaa gattttgaag  20040
gtttgatgaa tggctaaatc gcatataata taagatacga ttttaaagcg cacctgttca  20100
cgcagatttg ttgaaaaatt cgtggaaaga tttaacaaat aaaaggttat taatagttgc  20160
tcatcattcc ccttatacga catcgtcaga cgctctaata ttttactact aggcacatct  20220
gccacatgtt gaacatttaa agcctgttct tcttctgtgt tacggcaaaa gagccgtgcg  20280
tattcaggtg aagctcccca ggataacaac gtccttgcta cggctaaatt tttttgacg  20340
atgactttta tcagaaataa gtctttattt ttgcattgat cactatgcga atttgtatag  20400
ttgacgccgt tgcattgagt acattgatat aatgttttac aattccagcg tagccctaaa  20460
tggtataaaa gaactgtatt ttcgacataa gcatgctgat taacgatgtt tttgagacaa  20520
cacgtcgtta aggacaccat attgtctcca atttgttaga taaaagtctt tactaaaaaa  20580
```

-continued atagattttt agttttaaca atcgagattt tattatttgg atgcatcatc aaaaagattt 20640
ataagtataa gaggttgtat aagaaaaaaa tgatgttata ctatttatgt taaaatttaa 20700
tttatcatat aaaaagtaca gatttaatca gttggttaaa ctatttagtt aattaaacta 20760
aatagtttaa ccatttagtc agactacttg gttagcaatg tttgagcttt cttccattct 20820
tatccggggg ggggggtcct aatcgttcta atactattgt ggatagttga atataatgaa 20880
gactttatag atgctataat gatgaattct agtatgcctg tataaaataa ttaacctttt 20940
tgatcaaaat ttaatttttt tataaaaagc tacagagtag tgttttatta aacgtggctt 21000
atttaaaagt tacacaatgt taaaatctct acttacttta attctttgtg gggttttatt 21060
aactttatcc atattatggc ttactactta ccatgtagaa cttatagagg caatagatga 21120
tttctacgac tgaaatatag aatagtccat tttctatttg taaaataatg atttatattc 21180
tttcctaaaa atgatacttt atatggtttg aaaacaaata ttaacaactt gatttttttt 21240
tctataaata aactataaat gaaaatagta aaactcatag agtcttataa gtgaacatct 21300
tcataatgtt actcaaacgt tggactatta aaaaatattc cgtgtgcatt attgctttta 21360
atcagtatga ttactttata cgaagccgct attaaaacgc ttatcacaca ccgaaaacaa 21420
atttaaaaac accccgatag ccgtgaaatt ttactagctt tggggttgta ctgggataaa 21480
actcatattc ttgttaaatg tcgtgaatgt gggaatatga gtcttaccgg aaaacacagt 21540
acaaaatgta ttaacattaa ttgtctactt attcttgcca taaaaaaaag aataagcgta 21600
ttgttgatac cttgatagga atgggcgcgg atgtaacata tatacatctt ttaaagaata 21660
agataaaact gtcatacaac cagctgtcta tgcttaaaag caactcgcag atttcattga 21720
aggagcttca tgctatatgc tatcttttat atggtcggct tcccaaaaaa attaaacaag 21780
ggatgcgact gtgtaaaaca atggcgggac tatgtggtga acttttatgt gcatttttag 21840
ctccgtaaat gataatatgt atttaaaaca aacagatatt accaaaatat attctatgta 21900
cataatatct gggaaattat tttttttct catacccta aatataaaaa tattgggttt 21960
cttcactaaa ctttagaggt aaaaattttt ctttgttttg caccatcatg tatgggttta 22020
ggctgtccca gggattgttt atttgaatat ttcctaaata ggaacacaac gccatgatca 22080
tatatctttc attctggtaa gctttttgat acatcttcaa agatgccgta cctccgagtg 22140
tgtaacagca aacaaacgtc cgtacttttc catgggtcgc agcccattcc attccgtagc 22200
tcagcatctt ttgctgtatt tttttattcg ctttataaaa aaagtttttc atccattcca 22260
cgttctcata aaaacaggca cttaaaaaga gcactagggg tagtgtagtc ttattataga 22320
atgtaggaat gtatgtttta gttatttttt tcaacgcgtg ttccatacta tgttttaccg 22380
ccataaaaat acaaaaccaa taccaacttt ttctataaaa ggttttgctg tacacatata 22440
aacgagcaaa atatatttca aactctatat tctttttata aaaaaactcg agacagtcgt 22500
ttatgttacg actttttcta aatacctcaa aaacagtaat taattcactg tcgctgtgga 22560
aatgttcgta agctaactgt ttaatgtctt taggggtcaa ttcttttttt gggagcagtg 22620
gtttgagatt cggcaaaggt cgtctaaagt agtgagcgaa cttttcattc gctccccaac 22680
acaaaagccg ataagccagc atgtagttat cacgttttac cgcgtaaata agcaaatagt 22740
ttatattgat acatgtacca tgttgctgcc cgtttggaca tatgttgccg cattctgaac 22800
acttatgaat gagatcatag ttcttacaac ataaccccaa acgggttagt acttctttgt 22860
cacgttttaa aaactcgaca tgattcttta atgttaatgc tttgagcgca atgttaaata 22920

-continued

```
aactctgcat tttattaaaa tgaggttagt atcatgtttt agtataaaat ttagcggctg  22980
tttacataat gctaaataaa cttaacgttc ctactaaacc aaaaaaaatc aaattgacta  23040
agtcatagag aatttgacga tgttggtagg taatttttta acatggtata tatttttta   23100
gggtcggtta tattaggtaa taaaagagga cgtgccgtta aagtattttg cttaagatcc  23160
tttagatcct tacaaaaata tagattgttc gtctgatgat gccactgtgt tgcagtgatg  23220
gcttgatcaa tatcacctcc caagacaaaa cagtagtata tcgttaaaaa gttgtaatct  23280
ttcatacaag ccaactgcat cattttatcg atgtccatat gaacgatctt ttgctcgtat  23340
atttcatgaa ggtcaaatac attgttgaag taaatggcgc acatgagtcg ccacatacta  23400
aggtgcccat atgtttgata gaaaaaggag atagctcttt taagcttata ttttactgct  23460
atggcatagc agtatttaac gaatacgttc atgggtacat tatctaagat ataaaatatg  23520
aaaaacttta actctcgatg aatctcttcc cccatttcct gtacatttag agcttccaac  23580
ataggatttt tatcaaatat ttcatgacat aaaataatgt tattgctcgt tttatgacgc  23640
attaaaccgg tgaaaatttc cttattattt aaactatctt tagctcctaa ctttcgacac  23700
agctcctgag tttgttccgt cctagcacag gtcagcccat aataaatgtt tgctccccac  23760
tcggtgaaca gccttattac gtcatagtta ttttctttta tggccatgat taatgccaca  23820
tcaagatgaa gaagttcccc cttaaagggg gttgagctta aaataacgta attacagtag  23880
tgacataagc taatgggctt gttttgccac cataagccac aatattttaa aatataatga  23940
tactcctcag gcacgctctg tttggccaca gcctttttgg ccagggtttg caaggagagc  24000
atgataactt cttgaaaaaa aaactcaaat taagttccta cttttttaaa atattagtat  24060
ggacagatct accatcatat gaaggaattc tttcatcgtt aaacactgaa gagataatac  24120
tttcatcgta tagagaatat catgtcaatc catatattga atgttatata tcattaaacc  24180
catcattaat atagtgttta tgtgctatgg acaggttttt tgaatgataa tcttttaaca  24240
tacgttttat aacttcggga tcagtttctt ttaaagataa agaatcattc atgttataac  24300
aatttaatga taacatgctg gcaatgaacg agttgtcttt ttgatgcgct agagtctttc  24360
cctcctcaaa ggcattggcg cctaagtcta tacaaaagaa tatgtttccg atattataga  24420
actgaataga atgaaacatg gcctgattga tatcagcccc taagacgacg caacagtaat  24480
aaatcgttaa atagttatag ttcttgcgac aggcccactt tagcatttca ttcatgtcta  24540
tgcgaatcct ctccttttcg tacacttcgt gaagttcaaa cacattattg taaaaaaggg  24600
cgcacataag ccgccaccga tgtagatgag catatctctg ataaaaatag caaatcgcct  24660
ccttaaggtt acattctatt gccatcgcgt accaatattt agtaaacatc tcgcttaata  24720
tatcggtttc taccattaat ccctccagtt gttcataaat cattcccttt acttcaaaac  24780
gatttatggt atctaaaatg ggattattag aaaatacctc atggcagaaa atgatgttac  24840
tgctagttag atcacgtttc aatgtgtaaa aaaatcgtaa aatttcctgg tcatttaact  24900
gttctttggc acctagctgc ctgcacaggt ctcgggtgtg ctccgtgttg acagaaagca  24960
aaccgtagtt gatgtttgca ccccactcgg tgaacaattc tattagatcg tgattgtttt  25020
cctccacagc tttcaccaag gccgcgttaa gatttgtgcc gttcttaaaa tacggcgtcc  25080
atattttctt ttgatgatac atgatagggc cattatgcca ccatagaccg cagcacttca  25140
aaaaatgagg atggcatttg gccggatact ggctggccag cacctttttg gtgagagtct  25200
gcagagagag gaccatattt cttttttttg aaaaaatcaa attaaaaaaa tcatgcttgt  25260
ttagcataca tgtaatattg ttataattac gttataatta cgttataatt acgttataac  25320
```

-continued

```
tatattataa caatggtata acaatggtat aacaatgtta taacaatgtt ataacgatgt  25380
atcattgatg tcatcattca actaggccaa catacttttt aatttatagt tttttaatag  25440
atgatatatt ttgttaggat ctgcttcttt taacgttaat agcgaggagt ctgcactata  25500
aatgtctaat gataaatgat gagatatcaa atagtaattc cgttgctctg ctagggcctt  25560
tgcctcttca aaggcgtcgg ctcccagatc tatacaaaag aacaagttat ccatattata  25620
aaatcgtacg caggcaagca tagctgaatt aatattagct cctaagagaa aacaataata  25680
tatggttaaa aaattgttat cttttgtgca ggccatccgc atcatttcat ccacgtccat  25740
gcggatcttt tccttttcat acaaattatg taggtcaaac agcttattaa aacaaagagc  25800
acagattaac caccacgtat ttagatactt aaaatgttgg taaacataag aaatggcctc  25860
cctaagatta tcctgcaatg ccactataaa acagtatatc gttaacatat caccatccga  25920
catattactt aatatgtcgg tgtcttctac taacctttc aacttccaat atatggatga  25980
ccttatttcc cttataatga cataggctgg aaagggatta tcattaaaaa gtttaagaca  26040
taagataata ttactgctag tagtgccagg gtgtattaat ttaaagaaca tgtgcataat  26100
cttcttttta tccacgcggt acttggctcc taattcccag caaaattctc gaacaggcgg  26160
cgtattggcg caaattaacc catagttgat gtctgcgccc cattctgtaa acagttttat  26220
taactgatag ttgttttcct ttgtagccaa cattagtgcc gtattaaggt ccaagccgtc  26280
tgcaaagctt ggcagcttta tcagcatatg tttgcaatca agggaaattg gggccttata  26340
ccaccatagt ccgcagcgtt ctaagataac atggtactca atagatactt gctgtctggc  26400
tagtaccttt ttggcgaagg attgtaagga aggaaacatc ctgtttcttt tttttaaaa  26460
atcaattatc tttgttcata atcaagaaaa atccccatat ttattgagtg ataatttttt  26520
aacatgcaat ttattttttc agggtccgta acgatcgaca acagagaaat aaccggattg  26580
taatgcttta atgataaggc atgggctatc agataatttt ccttttgttc tgccaaagct  26640
ttgccctcct caaaggcatc ggcacccagg tctatacaaa agaacaggtt tccaagatta  26700
tagttttgta tggaaacaag catggcttga ttgatgttgg ctcccatgat aaaacagtag  26760
taaatggccg aatagctata atcttggatg caggctatgt gcatcatttc atcaatatcc  26820
atgcggaccc tttctatttc gtacagctcg tgaaggtcga acacgttgtt gtaaaaaagg  26880
gcgcacatga gccgccacct atgtagacgc gggtatttct ggtaaaagta gcggatagca  26940
tctttgaggt catagtccac cgctatcgcg taccagtatt tggttaaaac agtgctaaag  27000
ctatcatcat ggtccagcat gaaggttatc tccatgagcc ctcttaactc ccacatgatt  27060
tccccccca gatccagatt atctataatc cttaaattgg ggttattgga aaacacctcg  27120
tggcaaaaga taatattgct actggtttta tcgcgcgttg tatcaaagaa aatttttaaa  27180
atatactctc tttctaaata ttctttggct cccagctctt tgcacagatc acgggtattt  27240
tccgtgagag cacaaatcat tccatagtta atatctgcac cccattcagt aaacagcttt  27300
atcaagtcat gattattctc cttcacggct ttcatcagtc ctatgtttaa ctcgatacct  27360
tgactaaaac aggttgacct tataaataat ttattgcgtc gaatatgaag cataatgggg  27420
ccattatgcc accacaggcc acaacacttc aggacatgat attgatctac cggtatacac  27480
tgcccggcca gtactttctt cgtgagggat tgcagggaag gcaacatgcc tttccatcct  27540
ttgacggaaa tcaaattatc tactaataac tatcagtgtt tatattaagt atttagatat  27600
tatcccgggc tggatacgta gtatcgctat tcacatgtac ttccaactct agccggagcc  27660
```

-continued tgcagggtca tttattttta atattgattc ttttttgtat ttaatcattt agagaaggtc 27720
atcataggag ccagatgttc tctctccaga acttatgtcg aaaaacatta cctaaccgta 27780
aacttcctga attttttgac gaatatatat tacaactgct gggattatac tgggaaaacc 27840
atggaactat tcaacgagca ggaaacaact gtgtgcttat acagcaacat accctcattc 27900
ccgtaaatga agccctgaga acagcagcat ctgaagaaaa ttatgagatc gtgagccttt 27960
tattagcgtg ggaggggaac ctttactatg ctattatagg ggctctagag ggcaaccgcc 28020
acgacttaat tcgtaaatat gatgaccaaa tcaaggacca tcatgaaatt ctgccattca 28080
ttgacgatcc agtcatattt cacaaatgcc atatcatgcg gcaatgcttt tttgattgta 28140
ttttatatca agctgtaaaa tatagtaagt ttcgcgttct tctttacttt aaacatagat 28200
tagaggatga tttgcccttc actcatttac ttattgaaaa ggcatgtaaa gatcataatt 28260
atgaagttat taaatggata tatgaaaacc tacatatcta caatatgata gatacctttg 28320
aatgtgctat tgcccataag gatctacatc tatattgttt ggggtataga tttatatata 28380
acagaatcgt acccgataag tatcatcatt tagatattcg catgctttca agcctacaac 28440
tcctacataa ggtggcagcc aaaggatact tagattttat cctagaaacc ttaaagtatg 28500
atcataataa agataatata aatattattc taacacaagc tgcaacctat aaccatagaa 28560
aaattttaat ctatttcatt cctcaatcaa cccacgcaca gatagaacaa tgtttactag 28620
tggcgataaa agcaaaatct tccaggaaaa ccttgaactt actactgtct cacctaaacc 28680
tttccatcaa cctcatcaaa aaaataagcc attatgttgc cacttacaat tcaacaaata 28740
taataggcat tctgagtatg cggcggaaaa agaagatata tttagatatc atattgacaa 28800
aatttgtaaa aaaagctatt tttaataagt ttgtcgttcg atgtatggat acattttcta 28860
taaacccgga aagaatcctt aaaatagccg cgcgaataaa taggatgatg ttagtgaaaa 28920
aaatatctga acatgtttgg aaaaaatcatg cggttagact taaatacctt aaacatgcgg 28980
tacacacgat gaagcataaa gatgggaaaa atagactcat gaactttatc tatgatcgct 29040
gttattacca tatgcaaggg gaagaaatct ttagcctcgc aagattttat gcaatccatc 29100
atgcaccaaa gttgtttgac gttttttatg attgttgtat cctagatacg atacgattca 29160
aaagccttct tttagattgt tcacatatca taggtaaaaa cgctcatgat gctaccaata 29220
tcaacatcgt gaacaagtat atcggcaacc tgtttgttat gggagttctt agcaaaaaag 29280
aaatcttaca ggactatcca tccatttatt ctaaacaata catgccttag tttatttttt 29340
ttgcggccga aacattattc ttaccctaga aaacgcttat agtcatctta aatcataggt 29400
aaggaagatc atcatatttt ttgaaacgta attttttaac gcatgatcta tgatttcagg 29460
gtccgtgctt ttaggcaacg gggtggtggc cggactataa atctttaggg ataaaatgtt 29520
ctttataagc tcataccctt cccctaaagc tgtagtaccc tcttcgaaaa catcagcccc 29580
cagatctata caaaagaaca tgttttctat attatagtac tgtattgagc taagcatggc 29640
ttgattgatg ttggcgccca ggacatagca gtagtacatg gttgaaaggt tgtggtcttt 29700
gatgcaggcg atccgcatca tctcttctat gtccatatgg atcttgtcct tttcatacgc 29760
ctcatgaagg tcaaacacat tattaaaaca aagagcacat gttaaccgcc acgtattcag 29820
gtgtgtatat ttttggtaaa aatactgtat ggcctctttc aggttatagc gtatggctat 29880
agcgtaccag tatttgagta gtaatgtact gagcgaaaac tcattattta gcagatcggt 29940
ttttactatt aactccctta actcccagaa aatttctatc ctcattttta tattatttac 30000
tttttgtaat atcggattgt tggaaaacac ctcatggcat aaaataatgt tactactagt 30060

-continued

```
tttatgaaac tttagatcta taaaaatttg taaaatttct tcttcattca aggtttcctt  30120
ggcacctagc tctcgacaga ggtcccaggt gtgctccgtg ttgacagata ccagcccgta  30180
gttgatgtcc gccccccact ctgcaaacag ttttataagg ttgtagttgt tttcccttac  30240
agccttcact aacgccgtat ttaggtttaa gccctcttta atacctgctg attttatgag  30300
ccttaggtta tgatcaaacg tgatcggagc atcatgccac cataggtcat aacactttaa  30360
aagataatgt tggttcgtgg gcacgcattg tccagccaac acctttttgg tcagagattg  30420
cagggaaggc aacatgtctc ttcatctttt aaaaaaaaat caaattaatt agccgaataa  30480
atttttcttt cgagggcttt ttaaaagagc tctttaagag ctctttaaga gctttttaag  30540
agattaaaaa attattcttg ctggcattct gccaagtatg cggcattcct atcatctata  30600
gtatattatg agaatattcc caaatgatgg ataagttttt tgatttataa tcttttaata  30660
aactgcttat ttcttcgggg tcctttaagt ttagtggcaa ggaagcatct gagctgtaaa  30720
tatccaaagc caaactatgg ctcagaaaat tataaccttt ttgttccgct atggcacgac  30780
cctcttcaaa ggcattacca cccaaatcta tacagaaaaa tatattaccg atgttataat  30840
attgtactga agtaagcata gcttggttga tgttgccccc cagcgcgtaa cagtaatata  30900
ttgttaatgg attgttatcc ttggtagaag ccagacatat catgtcatgg acgtctattt  30960
ggatgttttc cttgtggtac atctcatgaa gctcatatat tttgttataa tacaggagac  31020
atttaatcg ccattcatta agatccgtat atttctcatc tagaaaacaa atggcgtcct  31080
tacaatcgta ttgtactgct ttggcgtacc aatacttcac tagtaaacca tttaactcgt  31140
ccgtttcttt tatttctatg agcccccata gtcttttata aattaagccc cttaattgta  31200
taacaaattt gttttctaaa ataggattat tcataaaaat ttcatggcac aaaataatac  31260
tgccgctggt tttattgtgc attatcctgg taaaaatacg gaaaatatcg ttgtcctcta  31320
gagtttcttt ggcgcctagc tgtctacaca actctcggat gtgcttcgta ttgatagaaa  31380
gcaaaccata gttgatattt gcgccccact ctgtaaagag ctttatcaga ctatagttgt  31440
tttccttaac agctattatt aatgccacac gaaggtctat atcttctcct aaaaatcctg  31500
attttatttg tattcggcca cgatccatac aaagcttgag aggagcatca tgccaccata  31560
ggccacaata tttcaaaatg cagtgttcat ctattgacaa acactggctg gctatcgtct  31620
ttttgacgag ggtctgcaga gagagcggca acgacatgtt tctttttcac caaaaaaaat  31680
caaatgttct cgtctttaaa ggttaattca tgttcttaaa atgttcattt catgatagtg  31740
attaataata tggtttaata acgctagaag gcttgtttat aagacagtca taagcagtct  31800
ataagacagt ctataagcag tctataagac agtctatgac ttagtctata actataattt  31860
ctggatgggc tgtaagatac tcttcggctc gtttcagatt ttttgaagta tatgtcttta  31920
gcatatcata tatttcctgg ggttcggtta catctaatac caaggtcaca tcacggctga  31980
aaagctgctt tactaagaaa atgttgctca agttatacat ataagctttg tgcgcaatga  32040
gttgtgccct atcaaaatcg gcagccccca aatcaataca gaaaaacatg tttaaagtat  32100
tattgttata gatagaaaga ttcatgccat aatcgagact agcccccaac ctatgacagt  32160
aataaatggc cgcgtaattt ttttcccgca agcaagcaaa tttcatcatc agattagggc  32220
tgatgcaaat ctctttttca cgacacaact cgtgtatgtc aaaaatgtta ttaaaataaa  32280
ggctacaagc tacccgccaa tagaggtgat ttttatgcct tttatagaaa tagtgaatag  32340
cctttgtaaa attatgtcgt aatgccaggg caaaccaaaa ctttgttaat aggtggtgcg  32400
```

-continued

```
ccgtatcccc cgtcaacgga atgtttgaac aggtgtacgt aactgtgtct aaagtggttc  32460
tagttacggt ttccaagagt ggattatgac aaaacatgtc ataacccagc agaactcctg  32520
cacaggattt tagcctggcc acttctttta aaatttccag aagacggggt tcggatacag  32580
gcgttaagcc tcccagttcc gcacacagcc gctttagata cacggcagga acacgtataa  32640
gcccatattc aggatttgcg ccccaatcca caaataaacg tataagttca agattatcgc  32700
tcttcacggc ctttactagc gccgcttcga gacaaagatc atcctcagaa aaacactgta  32760
aatgtttata cgaaaaaact tgcttacaat tgttacatag gtgaatagga cctaaatccc  32820
accacaaacc aaaacgctgc aacgtataat catagtcact tgaaagataa ttgcatgcca  32880
caactttttt ggccaacgtt tgtaaagaca acatactaag tttaaaacat cttaaatcta  32940
agctagctaa ctttcaagaa aaccctctat ccctaagaat atatcttata actagactta  33000
tagcagtaaa aatcaacttt ggttattctt tttaatataa aacgtctaat tacttgcaaa  33060
ggactataaa gcccattttc ctcagctaga atttttattt tttaatgaag taggggggata  33120
tgttttccct tcaagacctt tgccgaaagc atctttttat tcttcccgat gtttttggcg  33180
agcatgtact acaacgatta ggactgtatt ggagatgtca cggctccctt caacgcatag  33240
gagacgacca catactcata cgacgggatc tcatcctttc caccaacgag gccttaagaa  33300
tggcgggaga ggaaggaaac aatgaagtag taaagctctt gttactgtgg aagggaaatc  33360
ttcattacgc cgtcatagga gccttgcagg gtgatcaata tgacctgatc cataagtatg  33420
aaaaccaaat cggcgacttt cattttatct taccattgat tcaagacgcg aatacgtttg  33480
aaaaatgcca cgctttagaa cgtttttgtg gtgtttcatg tctgctaaaa catgctacaa  33540
aatacaacat gctccctatt ctccaaaaat accaagaaga gctgtctatg agagcgtatc  33600
ttcacgaaac cctatttgaa ctagcatgcc tatggcagag gtatgatgtc cttaaatgga  33660
tagagcaaac catacatgtt tacgacctaa agattatgtt taatattgcc atctccaaga  33720
gggatctgac tatgtactcc ttaggatata ttttcctttt tgatagaggg aacaccgaag  33780
ctacgttgct aacgcaacat ctcaagaaga cagcggccaa agggctcctc cactttgtgc  33840
tagaaacgtt aaaatacggc ggcaacatag ataccgtcct gacccaagcc gtaaagtaca  33900
atcatagaaa acttttagat tattttctgc gtcaactacc tcgtaaacat attgaaaaac  33960
ttttgttgct ggccgtgcag gaaaaggctt ctaaaaaaac attgaactta ctgttgtcac  34020
atttaaacta ctccgtgaaa cgcatcaaaa aactaccgcg ctatgtgata gagtacgagt  34080
ccaccttggt gataaagatt ttattaaaaa aaagagtgaa cctgatagat gccatgttgg  34140
aaaagatggt aagatatttt tctgcgacga aagtgaggac gatcatggat gagctttcga  34200
ttagtccgga aagagtcatt aagatggcta tacagaaaat gagaacggat atcgtaatcc  34260
atacttctta tgtttgggag gatgatctag aacgtcttac tcgtcttaaa aatatggtat  34320
acaccataaa gtacgaacat gggaaaaaaa tgttaattaa agtcatgcac ggcatataca  34380
aaaacttatt atacggcgaa agggaaaaag tcatgtttta tttagccaag ctctatgttg  34440
ctcaaaacgc ggccacccaa ttcagagaca tttgtaagga ctgttacaaa ctggatgtgg  34500
cacggtttaa accgcggttt aagcaactaa tattagactg tttagaaatt attactaaaa  34560
aatcttgcta tagtatcctg gaaatcttag aaaaacatat tatttccctg tttactatga  34620
aagttatgac tgaagaagaa aaaaacctat gtttagaaat attatataaa gtaattcatt  34680
ataaaacaat acaatgttaa aattcaatag atatccatca ttaatattga ttatattttc  34740
gaatattatc ttctatggtg caagataatc atctagcgcg tgaaacatgt cctcttctct  34800
```

-continued

```
tcaggaactt tgtcgaaaaa agctgcctga ctgcatactt ccagagtttt ttgacgacta  34860
tgtattgcaa ctgttaggac tgcactggca agatcatggt tcccttcagc gtatcgagaa  34920
gaaccagata cttgttcaac aggaacccat ccatatcaat gaagcactca aagtagcagc  34980
atcggaaggg aactatgaaa tcgtagagct gttgttgtca tgggaggcag atccccgcta  35040
cgccgtcgta ggagccctag aaagcaaata ctatgacctg gtttacaaat actatgacca  35100
agttaaagac tgccatgata tcttgccgct gattcaaaat ccggaaacat tcgaaagatg  35160
tcatgagtta aacagcacct gttcactgaa atgcttattc aagcatgctg tgataaatga  35220
catgctgccg attcttcaaa aatatacaga ctatctggat aggtgggagt attgcagcca  35280
gatgctgttc gaactggcat gtagtaaaaa aaaatatgag atggttgtgt ggatagaggg  35340
agttctaggc gtcggcaaag ttacatctct tttcaccatt gcgattagca acagagacct  35400
acagctgtat tctctgggct actcaattat ccttgagaat ttgtactcct gtggacagga  35460
ccccaagttt ttactaaatc atttcctgcg agacgtttca ataaaagggc ttctaccctt  35520
tgtaatcaaa accatagaat atggtggaag caaggagata gccataactc tggctaaaaa  35580
atatcagcat aaacatattt tgaaatactt cgaaacctgg gaaagctagg ttcagtatgg  35640
tgtactcact attgtagtga atcgtatcct gtaaattttg taaaaaagct taaacttttg  35700
accacatcat attgttttag aaatctcaaa ccagtgaaca acagtcttat catacattaa  35760
aattccagta aaatttatat tttttttggt aaacaaatgt tttctcttca agacatctgt  35820
cggaaacatc tttttcaact tcctgacgct tttgatgaat atatattaca agcgctagga  35880
ctatactggg aaaaacacgg atctcttcaa cgaataagaa aggacgctgt gtttgtacag  35940
cgaaacatcg tcctttctac caatgaggcc ctgagaatcg cagcctcaga gggaaacgaa  36000
agggtaataa aacttctgtt atcatgggag ggaaattttc attatgtgat cataggagct  36060
ctagagggtg accaatatga cctaattcat aagtatgata gtcaaattaa agactaccac  36120
atgattttat cattgatcca aaatgcaaat acctttgaaa agtgtcatca gttatccaat  36180
agtaatatgt ggtgtcttat acagaatgct ataaaatata atatgctccc tattctccaa  36240
aaacacagaa atattctgac acatgaggga gagaatcagg aattgtttga gatggcatgt  36300
gaggaacaga aatatgacat agttttatgg ataggacaaa ccctaatgtt aaatgagccg  36360
gagtttattt ttgatatcgc cttcgaacgg atagattttt ctttattaac aatgggttat  36420
agccttcttt ttgataacaa gatgagtagt atagacattc atgatgaaga agatcttact  36480
tcattaccaa cagaacacct cgaaaaagca gccactaagg gatgtttctt ctttatgcta  36540
gaaactttaa aacatggtgg aaatgtaaat atggcagtct tatctaaagc tgttgagtat  36600
aatcatagaa aaattttaga ccattttatt cggcggcaaa aatgtttatc acgtgaagag  36660
attgaaaacc tattattaac cgccataacc aattgtgcat ccataaaaac gttaaactta  36720
ctcttgtctt acctaaacta ttccgtaaaa aatatcattg gaaaaatagt acaacatgtc  36780
ataaaagatg gtgattatac catcatatta cttttaaaaa aaaagaaaat aaacctagtg  36840
gaacctgttt taacaggttt tatagattat tactatagct attgttttat aaaacatttt  36900
atccaagagt ttgctattcg tccggaaaaa ctgattaaaa tggccgcgcg aaaaggtaaa  36960
ctaaatatga ttatcgaatt ccttaacgaa aaatatgttc ataaagatga tcttggaact  37020
atatttaaat atctcaaaac cctagtatgt accatgaaac ataaaaaagg aaaagagaca  37080
ttaattgttc ttattcataa aatatatcaa gatattcatc tggagactaa agaaaaattt  37140
```

-continued

```
aaattattaa gattttatgt catgcatgat gcaactatcc aatttctatc tatgtgcaaa  37200
gactgtttta atttagccgg ttttaaacca tttgttttag aatgtttgga tattgctatt  37260
aaaaaaaatt accctgatat gatacaatat atagaaattc tatcgaaatc tgagtaaaat  37320
ttattttttt gatcagagta agaaaatgtt ctccctccag gagatctgtc gaaagaacat  37380
ctactttcta cctgactggc tcggtgagca tgtgattcag cgactaggtc tgtactggga  37440
aaaacatggt tctcttcagc gaatcggaga caactatgta cttatacaac aggacctcat  37500
catccccatc aatgaagccc taagaatggc aggggaggag gggaatgatg aggtggtaca  37560
actcctatta ctatgggagg gaaacattca ttatgccatc ataggagctt tggagagtga  37620
ccattatagc ctaatacgta agctctatga ccaaatcgaa gactgtcacg acatccttcc  37680
cttgattcaa gacccaaaac tctttgaaaa atgccatgaa ttagataaat cttgtaacat  37740
tttatgtctc gtattacacg ccgtaaaaaa cgatatgctt tgcattcttc aagagtataa  37800
aatgcatcta agtggagagg atattcaagt ggtgtttgaa acagcatgcc gttcacaaaa  37860
aaacgatatt gtgtcatgga tggacaaaa tattgcaata tacaaccccg aagttatttt  37920
tgatattgcc tttgataaga tgaatgtgtc cttattatct atagggtata cgcttctttt  37980
caatcatcat ataaataata cgaacgaaaa tattaattct ttattgacac aacatcttga  38040
atgggctgcc ggcatgggcc ttcttcattt tatgctggaa actttaaagt atggcgggga  38100
tgtaacgata atagtcttgt ctgaggccgt aaaatatgac cacagaaaga ttttagatta  38160
ttttctccgt cgaaaaaact tgtaccaaga agatcttgaa gaactattat tgttggcgat  38220
acgtgcagat tgttctaaaa agaccttaaa cttgttatta tcttacttaa actattccat  38280
aaacaatatc cgtaaaaaaa tattacaatg tgtaaaagaa tatgaaacga ccgttattat  38340
aaaaatttta cggaaaagaa agataaatct gatagagccc attttggcag actttatagg  38400
atatcatagc tatacctata tggtagattt tatgcgtgag ttttccatcc atccggaaaa  38460
aatgatcaaa atggctgcac gagaatcgag ggaggacttg atcataaaat tttccaaaaa  38520
agtttgcaaa gagcctaaag atagacttca ctatctcaaa agcttagtgt atactatgcg  38580
acataaagaa ggcaaacaac tgttaattta tacaatccat aacttataca aagcttgtca  38640
tctagagagt aaagaaatgt ttaatttggc acgattttat gcacggcata atgcagtgat  38700
ccagttcaaa tcgatttgcc acgatctctc caagctcaat attaatatca aaaacttgtt  38760
gttagaatgt ttaggtattg ctattaaaaa aaattacttt caacttatca aaacaataga  38820
aacggatatg cgttatgagt aacattttta gatgagggaa gattctacca aactaactaa  38880
gacctttcgc tagaatgtat cttattgtta atatagatga gatatgtcat tgtgaaaaaa  38940
tagattaggt aggttgtgaa aaacagatta aacttaaaat tatgtgtatt atgtaaaatt  39000
ttagaaataa aaatttattt tttttattga gggtacggaa aatgttctcc ctacaggacc  39060
tctgtcggaa gaacattttc ttccttccaa atgattttag caagcatacc ctacaatggc  39120
tgggattata ttggaaagag catggatccg tccatcgagc agaaaaagac agcataatga  39180
tacagaatga attggttctt tctatcaatg atgctttaca gcttgcagga gaggaggggg  39240
acacagatgt agtacagctc ttgttattat gggagggaaa tctgcattat gccatcatag  39300
gagccttgaa gactgaaaaa tataacctaa tatgtgagta tcatagccaa attcaggact  39360
ggcatattct cctacccatg attcaagatc cagaaacatt cgaaaaatgt catgatttaa  39420
gccttggatg tgactttatt tgccttctcc aacatgctgt aaaatacaac atgctttcta  39480
ttcttgtcaa atataaggag gatctactaa atgcaaggat taggcatcgt atccaatccc  39540
```

-continued

```
tgtttgtttt ggcatgcgaa aatcggagaa ttgaaattat tgattggata ggccaaaatc  39600
tgccaattcc tgaacctgat gccattttta gcattgctgt tgctacaaga gatttagaac  39660
tgttttcctt agggtacaag attatttttg attacatgca aagacaggga atcattcaat  39720
taaccaatgg agttcgcatg gttgtgctaa atcgtcacat tagcatggca atagataatg  39780
gtcttttacc ttttgttctg gaaactttaa aacatggtgg gaatatacat agagccttat  39840
cttatgcagt aacacacaat agaagaaaaa ttctggatta tcttattcgc cagaaaaata  39900
tagcccctaa tacaattgaa agacttttat atctggccgt gaaaaatcaa tcttccagga  39960
aaactttgaa cttgttgcta tcttacataa attacaaggt gaaaaatgtt aaaaagctgg  40020
tagagcatgt agtaaatgag aaatccactc ttgtgttaaa aattttatta gaaaaaaagg  40080
aaaatctagt ggatgctgtt ttaacaagac ttgtaaaaca ttctacatat ttccaggtga  40140
gagaatttat ccaggagttt tccatcagcc cagaaaaatt cattaaaata gctgtgcggg  40200
aaaagaaaaa tgtgttaatc gaggctattt ctgaagatat ttgggaaaat cccacagaaa  40260
gaattactta tctcaaacag atagtgcaca ccataaaata tgaaagtgga aggcgatttt  40320
tggtagacat cattcacagc atttaccaaa gttactcact aaaacacgaa gatattctta  40380
aactggcaac attttatgtc aaacacaatg caatcaccca ttttaaagac ctctgcaaat  40440
atctttggct gaacagagga acagaaagta agaaactgtt tttagagtgt ttagaaattg  40500
ctgatgagaa ggagtttcct gatattaaaa gtattgtgag tgaatatatt aactacttgt  40560
ttactgcagg agctattacc aaggaagaaa tcatgcaagc ctatgatgct ttagagtagc  40620
catgtattaa cattctgaaa gtagaataaa atatactata tactaaaaac caaattagcc  40680
atttttaact atcttcttct taaaaactct ggataaaaat ttattttttt taatttgggt  40740
agggaaaatg ttctcccttc aggacctctg tcggaagaac accttcttcc ttccaagtga  40800
ttttagcaag cataccctgc atttgctggg gttatactgg aaggggcatg gatctatcca  40860
aaggataaag aatgatggtg tgcttataga gcatgatctt actctttcca tcaatgaagc  40920
cttaattctt gcaggagaag agggaaacaa tgaagtagta aagctcttgt tactatggga  40980
aggaaatctt cattatgcca tcataggagc tttgaggact gagaactata acctagtatg  41040
tgagtaccat agtcaaattc aggactggca tgttctcctc cctttgattc aagatccaga  41100
aacattcgaa aaatgtcatg atttaagcct tgaatgtgat ctttcatgcc ttctccaaca  41160
tgctgtaaaa tataacatgc tttcgattct tgttaaatat aaagaggatc tactaaatgt  41220
actatttagg caacaaattc aaggactatt tattttagca tgtgaaaatc ggaagcttga  41280
gattcttacg tggatgggtc aaaatctgcc aattcctgat cctgagccta tttttagcat  41340
tgctgttgtc acaaaagatt tagaaatgtt ttccttaggg tacaagattg tttttgaata  41400
catggaaaac caaggacttc atttaaccca ggtagttcgt atggttatgc taaatcatca  41460
ctttggcatg gtaataaata aaggactttt accctttgtg ctggaaattt taaattatgg  41520
tgggaatgta aatagagcct tatcttatgc tgtcacacaa aataaaagaa agattttaga  41580
ccatgttgtt cgccaaaaga atatacccca taaaaccatt gaaagaatgt tgcatctggc  41640
tgtaaaaaag catgctccca ggaaaactct gaacttgtta ctatcttaca taaattacaa  41700
ggtgaaaaat gttaaaaagt tgttagaaca tgtagtgaaa tacaactcta ctcttgtgat  41760
aagactcttg ttagaaaaaa agaaaaacct gctggatgct actttgacaa gatatgtcaa  41820
agattctaca tactttcagg tgaaagaatt tatgcaagac ttctccatca gcccagaaaa  41880
```

-continued

```
attcattaaa atagctgtgc gggaaaagag aaatgtgttg atcaagggta tttctgaaga  41940
tatttgggaa aatcccgcgg aaagaatcag gaatcttaag cagatagtgt gtaccataaa  42000
atatgaaagt ggaagacaat tcctgataaa tatcattcac accatttacc agagttattc  42060
tttgaaacct gaagaaattc ttaaattggc aacattttat gtcaaacaca atgcaaccac  42120
ccattttaaa gatctctgca aatatctttg gctgaacaga agaacagaaa gtaagaaact  42180
gtttttagag tgcttggaaa ttgctgataa gaaggagttt cctgatatta aaagtattgt  42240
gagtgaatac attaactatt tgtttactgc aggagctatt accaaggaag aaatcatgca  42300
agcctatgct ttggagtatg ccatgtatta aatttctgaa tcagtaagca atagatagat  42360
tttagaatat gctgtattaa gttagtttct gaataagtaa ttaatagata gattttagtt  42420
tatgtaaaaa tgttaacatt tgttcataag ttttagatac cattttagag ttactttttt  42480
agatattact attttagcca ttattatctt aaataatcac tattttagat aggtccccgt  42540
attaaaaacc aaattaacca ttatctatgt ttttaataat actttttaaa aaccctccat  42600
aaaaatttat tttttttcat aaaagtagag aaaatgttct ccctacagga tctctgtcgg  42660
aagaaccttt ttcttccact tgagccctta ggcaagcatg tggttcaacg gctgggatta  42720
tactgggaag gccatggttc agttaaacga gtgggtgatt gctttatatg tgtagaccag  42780
atttggatgc tatcaatcca taaggctata caaattgcag cctcggaagg aaatgagaac  42840
attgtcaagc ttttcttact atggaagggg agtctacaat atgccatcat aggagcctta  42900
gagggcaggc aatatgatct gattcaaaaa tattacaacc aaattgggga ctgccatcag  42960
attctaccac tgattcaaga tccagaaatt tacgaaagat gtcatgaatt aaatgttaca  43020
tgtacctttc aatgcttatt tcaacatgct ataagagata acatgctgcc catttttcaa  43080
aaatatggag aagatctgaa tggaaacagg agaatggttc aacttctgta tgagatggca  43140
tgccgattac aaaattatga tatcatcaaa tggataggat ctaacctgca tgtttataac  43200
ttggaagcca tttttagcat tgcttttgtt agaaaggatt taactttgta ttctttaggc  43260
tacatgcttc ttctgggtag aatgagtact gaagatagaa actttatctc aatcataaca  43320
cgccatcttg aatacgcatc aaaaaaggga ctttttgact ttgtactaga atctttgaaa  43380
tatggaggtc aagtggatac agtgttgttt caggctgtaa aatacaacca taggaaaatt  43440
ttggcccatt ttattcatga aattccccgt gaaacggttg aaaagctgat actccatgct  43500
gtggagtcac gggcctccag aaaaacattc aacctgcttt tatcttccat aaactactgt  43560
gtgaaccctt ttgtcaaaaa actactgcac gctgtggtga aacacaagta catgcttatc  43620
ataaagcttt tgctcgagcg gcccaaaaag aagataaacc tggtagatgc tgctctattc  43680
aaacttgtaa aatactctac ttatacagaa atagtaaaat acatgggtga gttttctgtg  43740
gacccaaaaa gggtggtcaa aatggcagca cgactcatga gagtggacct gattaaaaag  43800
atttctaatg atgcatggga agataaacta gagagaatca agcaccttaa acagatggta  43860
aataccatga accacagaaa tggaaaaaat ctattgatgt acaatattca caatattact  43920
ggatatacct atctgaacac caaagaagca tttaacttaa caagatttta tgctgtccac  43980
aatgcaacat gtttgtttaa agaaatgtgt aaaagctgtt ttgtacatga taaaatacag  44040
ctcagagaat tgcttgaaga ttgtttacat attgctaata ggcatgatta tatccagatt  44100
gcagaaaccg cagatgaatg tatcaaatat atagatctta ttacatttaa gtaaaccatg  44160
tatatatcaa gtaaatccag attaaatcag gctaattgta aatagttgta gataccatat  44220
aatgaatgtt ttattaggat agtagttcag ttaagatagt agtttagtta agatagtagt  44280
```

-continued

```
ttagttaaga tagtagttat gttaagatag tagttctgtt aagataatag tttagttaaa  44340
actagttcat gttaagttaa tagttttgtt aagacaatag ttcatttaag tcaatagttc  44400
agttaagtca atagttttgt taagtcaata gtttagttaa gtcaatagtt tagttaagtc  44460
aatagtttag ttaagtcaat agttatatta agacattagt tctgctaata cattagtttt  44520
gttaagataa taaaaattta tttttttca tcagggtaga gaaaatgttc tccctacagg  44580
agctctgccg gaagaacatt tacattcttc cttacccctt ggctaagcat gtacttcaac  44640
aactagggct gtactggaag ggacatggat ctcttcaacg aatcggagat gaccatgtac  44700
tcttacagca ggacctgatc ttttccatca acgaggcctt aagaatggca ggagaggaag  44760
gaaacaatga agtagtaaag ctcttgttac tatgggaggg aaaccttcat tatgccatca  44820
taggagcttt agagggcgac cgatatgacc ttatccataa atattatgat caaattgggg  44880
actgccacaa gattcttcct ttaatccaag acccgcaaat ctttgaaaaa tgccatgaat  44940
tgagtaactc ctgtaatatt cgatgccttt tagaacatgc agtaaaacac gacatgcttt  45000
ctattcttca aaaacacaag gagcaaataa gattacacat ggcattaacc caaatactat  45060
ttgaattggc gtgtcatgaa cgtaaaaatg acatcattag atggatcggt tattccctgc  45120
acatacacca tctagagact atttttgatg ttgcattcgc ccataaaaat ttatccttat  45180
acgttttagg gtatgaactt ctcatgcaca aagtaaatac agaggctgca tatatagaat  45240
tacccaattt gctatcatat caccttcgaa ctgcggcggc aggaggtctt cttaacttta  45300
tgttagaaac aataaagcat ggtggatatc tggataaaac ggttttatcc gcggctatca  45360
ggtacaagca taggaaaatt gtggctcatt ttattcatca ggttccccgt aaaaccgtta  45420
aaaaactgtt actctatgct gtgcaggctc gggcccccaa aaaaacactg aacctacttt  45480
tatcttcctt aaactactcc gtgcacacca tcaccaaaca actcgtacac aatgtcgtca  45540
tctacagttc cacgcttatc gtaaagcttt tactcatgcg gcgaaaaaac aagttaaacc  45600
tagtagatgc cgttttagcc agacttgtaa aatattccac ctatacagac attgtacaat  45660
tcatgggtga gttttctgtg agcccagaaa gggtgatcaa aatggctgca cgggaatcca  45720
ggacctttct gattgaaatg atctccaaag ctgcttgggg aaatcaccca cagacgttga  45780
ttcatcatct caaacaacta accaatacca tgaagcctca atctggaaaa gaccacatca  45840
tatataccat ccactatatt tatctaaact ctaatatgct ggtagcggag gaggaaaaaa  45900
atattttaa attagcaaaa ttttatgcga atcataatgc ggtaaacagg tttaaacaaa  45960
tttgtgaaga ctattatata ttagatgcac gatttaaaac acttatttta gaatgttttg  46020
aaattgccgt ccagaaaaac tatcctagaa ttgcaaatat tgtggatgac tatattcgat  46080
tcctttttta caggggaaat ataaccgagg aagaaattcg tgaagcctat tctttaaaag  46140
atgctgaggt ttatgtagat ttaaaatggt tacaacaagg agaaatggtt taaaccaaat  46200
ccggtttaaa ctaaatccaa tttaaactac atttggttta tcattagtca ttgaaaccat  46260
cgaaaaaaaa gctatttgtt tatccccata aactcatctt ttttttgtct caaagtttga  46320
cactaaaatt cagtgtttta tagtgtttat aattaagtgt tttgcatgca ttgcagaaat  46380
tttcatcttt tttaattggt tcaataccac atgtcataca atatgttgtt tgattatcaa  46440
gattaacttt atgaaaggaa agtaagtgag ccgcaaattt aaaagtaaaa tatctttcat  46500
ttaaaatgat cttatgaatg tattttcgat aaggaggaat gaaagcattt gccaaaataa  46560
atcgcataaa aggcttggaa aaacccatat cttctaatct tttgtgggta taaaccctat  46620
```

-continued

```
tttggtgttt tacaaaaact tcattgttat aatagtcgtt atagctatca atcatttttt  46680
taagtcctat aatgcccaag gttgcacgca taaagccaca gtttctgctc caaaaagcat  46740
gcacctgtaa agggtgcttt tcatataacc aattacaaaa tttcattccg caacagtagc  46800
atgttatttc agtgggggat gtatagaata atccggcatt cgaaaatttt tcataatttt  46860
ttatgtcatg gattgcgaag ctttgatttc gtgcatctat ggagctatag cctacatatt  46920
taggttttac ttcaaataat cgcaaagaga tgtatggatc tatcgtattt attttaggaa  46980
acatttcata attttaaatt cttatatata atataaaaaa aattacaaac atttgtaatg  47040
atcatcctca attgaaggct gagttgtagg ctttattttt ctaattatac gaagaaggta  47100
ggttctcata aagccttcaa gatgactatt gatgtttcca atacattttc tcaatgagtt  47160
cataaaccca gacattttgc taatggcttg gcaaagtgcc aacaagttgt ccacaaagta  47220
ctggtagatt gccactagct atagctagct atagtgagcc aacctctctg tatgtatttt  47280
atatatttca ttttttaata gatttaatat ttttataaaa aatatttagt tttttataca  47340
agaatgtcga caaaaaaaaa gcccacaatt accaagcaag agctttactc cttagtagcg  47400
gcagataccc agttaaataa agcattgatt gaaagaatct ttacaagtca gcaaaaaata  47460
atacaaaatg ctttaaagca caatcaagaa gttattatac cacccggaat caagttcacc  47520
gtcgttacgg tgaaagctaa acctgctcgc cagggccata atcccgccac aggagagcct  47580
attcaaatta aagctaaacc tgaacataaa gccgtaaaga tacgagcatt gaaacctgtc  47640
catgatatgt taaactaaac tataaagtca tattcttctt tatcgttatt atcttcaata  47700
tatttttgcc aatcgaaatc gaataaattc agatcctgga catttaaata cttatcatcg  47760
tacattttaa tataatttaa acatgagttg ttgtcaaaaa cttttagcgt ttttgttaaa  47820
attatcatat gaataatttc cttattaaga gttgccggaa taatacaaaa cctattttta  47880
ggtacatcat ccatgataat agtaaaatta gtaaaaattg tttcttgttt ttcttttgtt  47940
tcaaataaac gttgtaaggt taaaggtttc tcgttcaatg gtttctttga agataaaaag  48000
aatgtataat ctggtttaaa ggtatttttg gtttcaatcg tgattccatc tgcttgagca  48060
tatactaaac cagaccaaat ataacggtcc actattacaa tataatttag cttaagtagc  48120
actgcaattt ctgcgataaa ttcactacga tgttttgtaa ataatttatg taattgttcc  48180
gatgacattt ctatggtttt atttaacacc tgcaatataa gatcaccggt ggtcgtgtct  48240
ggattaggaa aatgtataca tatagcatta taatccatgc attccaatgt ttcttttaat  48300
ttcattgcct gtgtgctttt tcccacacca ttgattccct cgatggcaat gagtattcca  48360
cgcatgatta ataaaaggaa aaaaagaatt cagtttttaa catttcttac aaatcttttt  48420
ttatacaaca ttgtacaaca ctgcattagc ggtatatgat gttatagctt cattaaatat  48480
ttgcttttat ataatcttta ccaacctata tttggtagat cactgcagat ggtcataaat  48540
aggccataac taagataaaa attatttcag acgctactac ggtagtatta ttaaaatcat  48600
gtgtggcaat gtatgacgtc ttaatagata aaacatttaa ggaaaacaaa tttgaataaa  48660
aaaataattg ttatgatggc gttgttacac aaagaaaagc ttatagagtg catctatcat  48720
gagctagaaa atggcgggac aatattgctt ctaacaaaaa atattgttgt gtcagaaatt  48780
tcatacattg gcaatactta taaatatttt acctttaatg acaatcatga tctgataagc  48840
aaagaagatc ttaaaggagc aacatccaaa aacattgcta aaatgattta taattggatt  48900
ataaaaaatc ctcaaaataa taagatttgg agtggtgagc cgcgtactca aatttatttt  48960
gaaaatgatt tatatcatac aaattacaat cataaatgta taaaagattt ttggaatgtt  49020
```

-continued

```
tcaacttcag tcggtcctca tatctttaat gatcgtagca tttggtgtac taaatgcaca  49080
tcctttacc catttaccaa cattatgtcg cccaatatat tccaataaat tagatatctt  49140
tgctattaaa atagttaaaa accttatagg ataattaggt actttattac gataaattat  49200
gatattttat aattagttac tttattataa ttaatctctt tattaatgaa ttatcataag  49260
ataactaatt attttttcc atatatcaga taataaatct gatatgggct aaaagtatgt  49320
ttcaaactat ttacaataga atttctgtta agaaaacata cataatttga ataaaatttt  49380
tttaaatatc accgaaacaa tcaacatggt gttaatagag tttttaacag gtttcttcta  49440
tttatatgga aagagactgt tttccattag taaagtcatg gacatgatat gtctagacta  49500
ttataccatt attcctgctc ctctggcgat gatgttagcg gcaagactaa aaaactatga  49560
cctcatgaaa cgactgcacg aatgggaaat ctctattgac tacgctctac ttgtagtaga  49620
tgatgtgccg tctattgact attgcttaag tcttggcgct agatccccga ctagagcaca  49680
aaaaagagaa ctgctgaggg acaacacgtt taatcccgtg tataagtatc ttatgaactg  49740
ttccggcttc ccaacaaaga gagaaaaaaa cattccttgt gatgttcaat gcgaaagact  49800
gcaaaaaaac attataaaag aactggtatt taactgctct gtactgcttg aaatggtact  49860
gcacacagaa agagaatatg catacgccct acactgtgct gcaaaacata accaattgcc  49920
catcctcatg tattgttggc aacaatccac agacgcggaa tctattttgt tgaaaacctg  49980
ctgttctgat aagaacatca attgttttaa ctattgtatt ctatatggcg gcgcccaaaa  50040
tttggatgct gcaatggtgg aagcggcaaa gcacgatgcc cggatgctga taaactactg  50100
tgtcatgctt ggtggaagat ccttaaacga agcaaaagaa acggctgcca tgtttggaca  50160
cattgaatgc gcacaacact gttttaaact gcagtcttac gtcgtggaca catcgaatac  50220
agacgacact gattaaagcg acaatcttac gtcatgaacg actgtctttt gagtatctat  50280
acttacatta tattttttta tgaaaaaaat ataaaggttg tatacaaacc tttgtataca  50340
agaaatttgg atcattaaac aataattaat ttggacacag gaaacgatct agatcgatca  50400
aaaagctatt ttttttgcac acagaacatt tagataattg agagattact ttccatactt  50460
gttaagcttt tttacacaca ggaactttgg attctgttca ggaagttttt catagacatt  50520
atgtttacag ccagtaataa taattttggg ctttttctta aaccaccggt ggaaaacatc  50580
cagcttgtaa agagggaaat gcatgtagag aggttttggt agtcatggtt aagagatttg  50640
actaactcca tgtttcctgt aaagactgcc cagtcccaag cagtaaaacc tctatgatag  50700
tctttttgag tcggatctgc tccaaatttt atgagagaaa gcatatttaa agaacggccc  50760
cgtattgcgg ccttcatcac aggagtcatc ccattaaaat tcggtaaaca aattctggtc  50820
ccattttttc cgaaatagcc caacacccct tccaggatta aatgattttt tttctcagct  50880
aaataatgta aagcagagtt tccatcttta tccctcctat gagggttaat tatttctcca  50940
ggataagatt cttgttcaaa aagaaatttt aaaaagtcta tacgtccgta gatgcatatc  51000
cacatgaata ccgaggatcc atttttatcg catctattga caatccacgg atctgtttta  51060
aaaaattcct caaatagtgt aagattccca tttctaatat gttttttaat ccatttaaca  51120
aacaagtttt ctatctccct ttctggaaac atgtgttcca ttttgaatgt cgcccctact  51180
ccactatatg attttactcc tttaattttt aatgtccttt tttttcggac ttctttggat  51240
aagctgttta ttaccatctt taaatgcctt atagcgggga ggagccaggc ccttttccca  51300
tatgtgcggt aattcttggt gtttatgctt gcctttggca taaccaggcc agtattttc  51360
```

```
gatatattca gggtttgttt ttacgtattc tttaaaggtc cgataggctt cttgaataca  51420
ggtaggctca ccggtataat ttccatgttc atcttccttt aaaaagccat taaccctgtc  51480
ctttctccac ttaagattgt gctttccaaa aatgcgatca agatcttgcg cctgctgggg  51540
tggaatcata aatccctttt taggtcgaag ctttttattt tttccatagc ttcggccatc  51600
gcgttgcgaa acagtggtta ggacgcctga tagtctttcc atgggcgtcg catctaatcc  51660
tatccatcca ccctgatgaa tatcaatggc aacaagctct cctttatttt gggcaagcca  51720
agtttccaag aatgccatgc tttcttccca gggataaggc ccgccaacac cacgggttgt  51780
ccaatcttgc aaggactcca ggtccgacac ctggtaaggc tctaaagaag acggttcctt  51840
gtttttgtac tgcaaataag atttaatgac ccatttatac catgtgtcga accgcagcgt  51900
ggcgcctcca aagtgaaagc cgtcgttgat tttaggatat ctgcaacata tttcaaccgt  51960
acgtttgagt tctgcaaaag cggccttcca aggaagtctt tcgctgcggg taagacggtc  52020
tattttgccc tgcgtgccat agcgtatggc atgtcgtgcc aattgcaaca attctgacac  52080
cgatccgtgg gccccgatcc agtttatcgg ataggcaacc tccgaagggt ttaaaagatg  52140
ctcgtaaaag cgtggatctt cagatgccaa ggcgtctgca aaggggataa tgctagaaaa  52200
cctgtctaga catacgtttt ctgtgtttac ttctaaaggt agaaaaatgg ttgcgtgagg  52260
cttttgaacc tgcttgttca gcggtctgca tatgctttga ataatgtctc taggactatg  52320
tcgcggcgct gcaaaaaata ccgcgtttag ttctggaacc tctacgccct cttgaaagag  52380
tcgacagttt aataaaataa cgggttcctt tgaggaacaa aattctgtaa atgttttgag  52440
gataacctgt cgcggcaggg ttgagtgagc tatcagggca tagacccctt ggtctaccaa  52500
cgccgcgtat agctccttgg cctgtttaat atcacgggta aataccagca ttttaggagc  52560
cggtatattg gtttttaaat aggctaaggc cattataatt tgctttacta tgatctgttt  52620
cgtggtctcc tctttggtac tcggttggtg ggccaattta ggcgcggcta ccatctgcaa  52680
ttcaaaatca tttacatagc cggcctctat gccttctcgc agatagtagc gaaaggcaac  52740
gccgccaaaa agttcacgat ttttcatgga aagcggggtg tcgtacctgg gcgttgccgt  52800
taaaaaaagt cggtgccctt ttttaaagtt gagcaacacg tgggtaaagg gccgtgtctc  52860
ccattcgccg caaatccggt gacattcatc gctaataata agatcgaaat catccaccag  52920
tagcgtggag gattggtagg tggcaatcac aagaagagaa ggggcctccc gtatccgttt  52980
tgcaataaag acaggattgg tggtcatttc tatattgtcg tgatttagca caatgcgggt  53040
ctggtcagac cccacaagca aaacgttctt caaagaaatt ccatactgat agagtttttc  53100
cagagtctgc cgtagtaggg acaggcccgg caccaggtac aaaacttttc cttgaagata  53160
attggagagg ataagatagg cgacgcgagt tttgccgcat cggcaggcca tctgcagaat  53220
ggccctccca cttcgccgca gctcctgata gcccatattg gccgcctcct tctgataaag  53280
tcgatcctcg attgcagtcc gtgtctcatc tgtagaaaaa aataatacgt catctgcgaa  53340
atgttcatct tccacaggag ttatcaccag gtgtctcagt ttctccttgc ttatcagcgg  53400
atcagagggc aaagatggct caaccactat cgtggaatca ttcatctcat aggcgggaga  53460
atcacacaaa gtatagctta tgtccagaca gtttgcaaca tcctcagcca attgttttat  53520
tttttcgggt aaaagacata cgagttcttt gtttttgacg cgaaaaaaact gtgcacaata  53580
taacacccct gcttcaattt tttgcgcatc cttctttgta gatgtttcca atgtgaaaca  53640
atacttccat tcatccgtaa aacaggttgt ataagatcca tcatgaagcc tagcggccaa  53700
gtttcctgtg tgcccaactt tatgtaagga ttgggcctcc agccagggat gaaccgccac  53760
```

-continued

```
gtaaaatcct gcgcacatgc tatatcaaat tgcagtttct taataactgt acacaggatc  53820
tgaaaaacat gtgattacaa aatttagata agaaatattt aatattaaaa atcacagaat  53880
acatgtcact gtgtagagag aaagccaaaa actcctcttg accgccgtgg gaaatcatcc  53940
agggtagtag gttgtgtttc ataaagttgt atgccgtagt gatcaccgtg gactccagat  54000
ggttattggc atctttgcaa tactttgcca tcttggcaga aaagacgata aatccacaaa  54060
ttctacccca gttgataaga tccttaaaca gctcagtcac aaccccagta aactgggttt  54120
taatttcttg aacactcgta agagaaaagg taattgtaac ctgtttgttc aaacactcat  54180
cataataggt taaaattttt tttatttgtt gttgatatgg gctaagctca tgctctgaaa  54240
tatcattaat gtaatattta atatatccca ctagtatttc attaatgata ttatgatata  54300
ttaactcttc tccctccata gcggcaccct atattttttt atttaggttt caatgttatc  54360
acaattgcga tacaattgtg atacaattgt gacacaactg tgttgtatac aacaaatgtt  54420
aggccacgta tagcaaccta tatgttaaga aatattttta tcccaacatt agttggaaac  54480
gagcagccgc aaagaagtca tttaaaataa gccatttaaa gatttagaat ttatatgtat  54540
acaactgtac aatggaagca gttcttacca aactcgacca ggaggaaaaa aaggctctcc  54600
aaaattttca tcgttgtgct tgggaagaaa ctaaaaatat tataaacgat tttcttgaaa  54660
tccctgagga acgatgcacc tataaattca actcatacac aaaaaaaatg gagcttttat  54720
ttacccctga attccacacc gcctggcatg aagttcctga gtgcagagag ttcatattaa  54780
actttttgag actcatttcg ggacatcgag tggtattaaa aggccctaca tttgttttta  54840
caaaagagat caagaatctg ggcattccta gtaccatcaa tgttgacttt caggccaaca  54900
ttgaaaatat ggatgatcta cagaagggaa atctcatcgg caagatgaat atcaaagaag  54960
gctaaataaa acaactaaca tcaaaaaaca ttaaaggcta tgttgtggac gatgcctttg  55020
tctcaatagt ttcgaggtca tccaataact catgtaacgt aaaaaagttg gtccattttt  55080
ttgaaaacat taaaagacgt tcgtcttcat aaataaaaaa gtcattcgaa ggaaaaatga  55140
tatactcaat accatagtct tgtaatattt tttttaggtc tctcagggtc cagggattta  55200
ccaggcttct acgcgaagtg agcatcataa aaatatctaa tattttttgc gccataagcc  55260
agcgcggatt ctcattggcc cacaaatcaa caataattct cttatcaacc gtgagcattc  55320
ctacttgatt cgaagaaatg attagatgcc cagcagtcca ccccatgagt agataacgca  55380
gcgttgtaga aatgtcacat atggaaggca ttcctccaca acatgaaccc aaattaggat  55440
gcgtgtgaaa cacaaacata gcaggcttgt tggccaccct gctataaata tcagcaggca  55500
tcatagcctc gctgccaaaa taaatgttct ctcctgccct ataggggctt ggaatgattt  55560
ccactatctc gggtacaccg tttatcatat taatgcggcc gcaccattca cggtcatcgt  55620
ccaaaaattt tttgatggca ccccgaacat tgtcccagtt aagcaacaga gtattcacaa  55680
tctcattacg ctccgcccag tattccttaa aacttctttt agacttgctg agctgttccc  55740
aggattcgaa ctcagtccaa tgtttttttt cttttgggga agacttccct tttgaaacat  55800
tttttgcggc tccaccatct acactatgat tttccaaaat aatctccttc atcgtttgag  55860
ttatatgggc attgctaagc accttagtgg taacctgttt acctatgtga tttagcagaa  55920
aaccaagttt gtccatttgt gtctcaacca tttattctta acaaaacaaa aaaaattaaa  55980
aatcatcgtc gtttaaaaag agtttgaagg caaacgcatc atccttaaca cagttctgat  56040
actgcgtagg tcttaactcg aaaaagttgg ttttttctac ttcattaaga aagaatttag  56100
```

-continued

```
tcatctgagg aaaagggttt cccaccttat aaatgctttt gcactgcatc atgaagcaca  56160
aattatctgt aaagtagcgt atatattgaa atagcatttc ttttgaaaaa ccgggaactc  56220
ttcctcttgc cttgtcaaag gcatagttaa taaactcatc caccaactcc acagcctcct  56280
tcaaaatttt gtgaatgatc ttttcctcgg gaatgttata cacgtaattt gagataagaa  56340
aacacgcaaa actacagtgc atcccttcat cacgtgagat aaactcatta tagcttacaa  56400
gccccggcat aatattctgt tccttaagaa actggatcgc cacaaagtgg ttttgaaata  56460
aaatgccttc tacggcggcg aagcccacca gccgctcacc tagagtgttc ctgtcggggt  56520
ccatccactg ccgcacccac tgcgccattt tttttatgat agggtgtttt tcaatgccgc  56580
taaagatgcg ctgttgttcc ttctcatccg ggatcagcgt ttttacctgt attgagtagg  56640
cttcgctatg aacgcactct tgggcagcct gcattgtata aaagtataac acttccttta  56700
ctttaatttc gcgcataaaa ttggttaaaa ggttttcgat aacaatttcg tcggcaacaa  56760
caaagaaggc taaaatttgt ttataaaatt cgcgctgtgg ctttggcatg gcttcccaat  56820
catcaatgtc cttacacatg tccacctcct gcgccgtcca cgtcaaactt tctaattttt  56880
tataccagtt ccaacattcg gggtgctgaa taggaaaaat agtgaaacgt tgggaatttt  56940
caattagtaa ttcctccata tttgaaataa atattaacat cttcaaattt attggctgcc  57000
atggagacgt tttttattga gacgttggca tctgatgtgt atggaaaggc gttaaatgtt  57060
gatttagata gactatcgca ggcgcaggtt aaatataccc ttcaagagct tatttcctac  57120
tgcagcgctc taaccatttt acattatgac tattcaaccc ttgcggcgcg tctttcggtg  57180
taccagctgc accagtcaac ggcctcctcc ttctcaaagg cggtgaggct gcaggccgca  57240
caatcctgct cacgcctgtc cccccagttt gtggacgtcg tttacaagta caaagccatt  57300
tttgacagct acattgacta tagcagagat tacaagctgt ccctcctggg gatagaaacc  57360
atgaaaaatt cttatttgtt aaaaaataaa gatggggtca tcatggaacg cccgcaggat  57420
gcttatatgc gggttgccat catgatctat gggatgggaa gagtggtcaa tatgaaaatg  57480
attctgctaa cctatgacct gctttcccag cacgtcatca cacacgcgtc gcccaccatg  57540
ttcaatgcag gcaccaaaaa gccacaactc tccagctgtt tcctgctaaa tgtaaatgat  57600
aatttagaaa atttatatga tatggtcaaa acggccggca tcatttcagg cggcggcggt  57660
ggaatagggc tgtgcttgtc aggaatacgg gcaaagaata gttttatttc tggtagtggt  57720
cttaaaagta acggcataca gaattatatt gtgctgcaaa atgcttcaca atgctacgcg  57780
aaccagggag gcctacgtcc cggagcctac gccgtctact tagagctgtg gcaccaagac  57840
atctttacat ttttacaaat gcctcgccta aaaggacaaa tggctgaaca acggcttaat  57900
gcccctaatc tcaagtacgg cctatgggtc cccgacctat tcatggaaat acttgaagac  57960
caaatacaca acagaggcga cggcaaatgg tacctctttt cgccggatca ggcccccaat  58020
ctacataagg tctttgattt ggaacggtcg cagcacgaaa acgcacaccg cgaatttaaa  58080
aagctttact atcagtatgt tgctgaaaaa aggtacaccg gcgtcacaac ggccaaagag  58140
attatcaaag agtggttcaa aacagttgtt caagtaggga atccctatat cgggtttaaa  58200
gatgccataa atcgtaaaag taatctttca catgtaggca ctatcacgaa ctccaatctt  58260
tgtattgaag tcacaatccc ctgctgggag ggtgataagg ctgaacaagg tgtttgtaat  58320
ctggccgcag taaatctagc cgcctttata cgtgaaaatg gctacgacta ccgtgggctc  58380
atagaagcat caggcaatgt cacagaaaat ttagataata ttatagataa tggctactac  58440
cccacagaag ccacgcggag aagcaatatg cgtcaccgac ctattggcat cggggtcttt  58500
```

ggcctagccg acgtgtttgc gtctttaaaa atgaaatttg gttcacccga ggccattgcc 58560
atggatgagg ccatccatgc ggccctatac tacggggcca tgcgacgatc catagaactt 58620
gcaaaagaaa aaggaagtca tcccagcttt ccggggtctg cggcctcaaa gggtctactg 58680
cagcccgacc tatgggttcg ctgtggtgat ttagtttcct cctgggaaga acgcgtggca 58740
cagacgacgc agggtgtgtt gacgccgaaa aggtggtcgc agctacgcct ggcggctatg 58800
cagggacttc gaaatggata tgtcacagct cttatgccca ccgcaacctc ctcaaattct 58860
acaggaaaaa acgaatgttt tgagcccttt acatccaatc tatatacacg tagaacgtta 58920
agcggggagt ttattgtttt aaataagtat ttaatagacg atttaaaaga aattaatctt 58980
tggacagaag ccattcaaca gcagctacta aatgcgggag gtagcattca gcacattttg 59040
gatataccgg ccgagatccg cgatcggtat aaaacctcca gggaaatgaa tcaaaaaatt 59100
ttaacaaaac acgcggccgc acgaaacccc tttgtatccc aaagtatgtc cttgaactat 59160
tacttttatg aacctgaact aagccaggta cttacagtgc tcgtcctagg ctggaaaaaa 59220
ggtttaacta ccggttccta ttactgtcat tttagccctg gagcgggtac ccaaaaaaag 59280
attataagaa actctgagaa agcgtgtaat gcggactgcg aggcgtgtct tctgtaggtg 59340
tctcgcggta aaagagcagc ggggaccata tggtaaaccc caacaagagg ataatgaata 59400
aaaaaagtaa acaggcatcc attagttcca tattaaattt ttttttcttc tatataatgg 59460
aatattttgt tgcggtagac aatgaaacct ccttgggggt ttttacttct atagagcaat 59520
gtgaagaaac gatgaaacaa taccccggcc tccattatgt cgtttttaag tatatgtgtc 59580
cggcggatgc agaaaataca gatgttgtat atttaatacc ctcgttaacc ttgcataccc 59640
ccatgtttgt agaccactgt ccaaatcgta ccaaacaagc acgacacgta ttgaaaaaaa 59700
taaacttagt gttcgaggaa gagtctattg aaaattggaa ggtttcagta aatactgtgt 59760
tcccccatgt tcacaacaga ttatctgcgc cgaaactttc catcgacgag gctaatgaag 59820
ccgtagaaaa gtttttgata caagcaggac gactcatgtc tctgtaaatg tctcttcctt 59880
tatgggtgac gtctcttcct ttgccgagga agtctctgtt atgggcaaga ggtttgaaac 59940
aacgcaagga ctctgcttaa tctgctgtct cacaaaggga atcaaactac ctgctttcgt 60000
atttttaatg tagtaattac ccttgttgtg atgaatttta agaccatagc gtagtcccag 60060
tactttatta atgaatttta aaattgtttg agggtccgtt ttattgggct ttttaagctt 60120
aaactcaaag ctgatcgcgc ttaaatcata ctgaacaaat tcatcaacga gtttcgtcat 60180
taattgttca ttggtcaata tattagggtc ctgaacgcat ttaaagccgc acttagttaa 60240
tagcataata gcgtacatat gagattgaaa actataatta aattgtagat catgatgctc 60300
tgcgtgttgc atggcccatt gatgaaagtt taattcctga gtttgtaaca tagtgagcga 60360
ctcgtatact gtctttccgc ggcttatttg gacacggcca gtatagttct gttttgtcat 60420
aaaactattg tattgttcaa caaatttggg agtaatttta tgaccgtgcc atgcataaaa 60480
ttcgagtagt ttatactttt catacgcaaa taggtcttgc tggtctactg tgatgccttc 60540
ctttaagttt tgtttaattt gtaaagcttt attggcatca atggtttcag ccgaggcaat 60600
gtttacatag tcctggtgtt taatttccat tttaatgctt gtatattgtt tgactgtctc 60660
cagcttttca cccgtcagta taaacacctt agcgccggtg tcggcgatct ggttaataaa 60720
tcgggttata aagtgatttt ttgatagatg ttgtatccgc attgtttcga gccatagatg 60780
gtagtatgga gttttataat atatcggcct acctgtttcc ttactatacg tgaaggaaag 60840

-continued

```
ctggtgattg cttatggtct gaaaaagggt gtcacgtttt tgtaacgtaa acatttcaat  60900
gtcttcgatg gtttctggat agtaattttg tttcccctgt aagcagattt tataacactt  60960
actttttaat tcacgcacgc ggcccaacat ttggcaacat gtttctacgt cacacgacat  61020
attgttaaaa aagccgtata aaacatcaaa tctcttatct tcgtatgaaa cacccgctga  61080
aatcgtgggc gtatagataa ggatatcaac gagcccccaa taatacgata cattattaaa  61140
atgggattcc cgttcatgag cagtgctttt agaactataa aacccaattt ttttttccgg  61200
aaactttttt tggataaatg attgcaacag ccgggcctcc attaatgaat ttgtagggat  61260
aacaattttt ttgtcttcta gcaaatcctt taaaaggtta tttaaccaag tttctcgtga  61320
agaggtaaaa taatacgtgt catgctgggc ccttttatat tgattccagt gaaagaagat  61380
agggacatcc ccgcgaaaac gctgtagaat attatacgtt cgatttccta ggtttgcgtc  61440
caagcatata acataatttg ccgtttcgag catccacatg aaaatggcaa aagagggagc  61500
aaagtatttg tgcaggccgc tattgaattg attaaaaatc gattctacct catccaaaat  61560
aagtaggtct acaggctcgg ctgtggaggt tagccggaaa agtgattcta cctgaatgat  61620
gactctttcg tagctgtcca aatctccagt tacttcgctg tacaatgtga aattcggtag  61680
ccgggattgt atattttttg agaagatctg tcgaaacgtc acaaaccgta tggtttgttg  61740
ttttgaaata gaattattgc cgtagtattt ttgcaaatag ttgcgcagtt ggacggtttt  61800
acctattttc atttgagcct ttacaacaag cgtagggact cgttcatatt ctcgcatact  61860
actttcatca tagatgtgtt tttgagtatc aggcagttct tcaaagagaa tggactcatg  61920
aacctctatg ctctttgtca tcacttggtc cacatatgtt tccacaaaat tatttgtgcc  61980
ggaaaggctg cccatgagaa ggctatgttt attgtcatgg cgacagtgtt gatacacttt  62040
gtttcccgtg actcttaaaa ttagggtatt gtccttatca tgcatacgct tacatatttc  62100
gcagtaactt ggacttgtac gtttaaacaa tactaaattt ttatgaacac ggaggaagca  62160
atgattttta catagtgttc ctgcaaattt taatacctct tcaagttcac tttgttggat  62220
agtatcgcag gaactcggtg ttgtttcttt tacatttgtg aagatacaag gtaaacacgt  62280
cgtttcaaag gggttgcta taagggtatc actctttttc gtggttgtac tggtctcaaa  62340
cacctctgca agctcctcat taaacatttt aacacgcatg ctaccttttt tatgagaccc  62400
tatgatgcga aaattttgaa tacttttgtt gacctggggg tcaacaaaag gataaacgtg  62460
tttgggaaga ttttctaaca ctttggatgt aaagactttg gcctcattat tgtttaatac  62520
tgagtatgta taaagtatga tatgaaagga gtatttaagt tctcgctttt tatttaatcc  62580
gatagaatct gttagcaaaa tttgttcacg cgttagattg atgttataag gtaaagaata  62640
tgtctcgtaa aatacatcca tgatgacgtt aattatcatg tcaaggatgt catagacatt  62700
gtcttcgaca ttatcattgt catcaacatt gtcatcagag tatgacttat ttaccggaaa  62760
gtcgatgtca aattttaagc gctgaggcaa aaacccaaat accacttcgt ggaaacactt  62820
ctgctcaaag ggctgagccg cctcccactc ccaaaagtca tcacgacttg aaaaaactct  62880
aaaaagatta ttatattcat ctcgcaccac gaagtgattc tttaaggttt cgagagaata  62940
tttatcctct acggcttctc cttgggagtt acagcgaaga aacttgaatg tttcttgcat  63000
tttgatattt aaaattaaat caattatgat gcggccgcta atgcggcggt tgacgcggcc  63060
gcgccgctga cgcagccatc atacataaag cggcatggcc gttttataac gactagtcgg  63120
ccgttatatg acgaactata taaaaatgaa ttcttttaat tagagttaag tattgttgat  63180
tgtataatcc atcatggttg agccacgcga acagtttttt caagatctgc tttcagcagt  63240
```

ggatcaacaa atggacactg taaaaaatga cataaaagac attatgaaag aaaaaacgtc 63300
ttttatggta tcattcgaaa actttataga acgttacgat accatggaaa aaaatattca 63360
agaccttcag aataagtacg aagaaatggc ggccaacctt atgaccgtca tgacggatac 63420
aaaaattcag cttggagcca ttatcgccca acttgagatt ctaatgataa atggcactcc 63480
acttccggca aaaaagacaa caattaagga ggctatgccc ttaccttcat caaacacgaa 63540
taatgaacaa acgagtcctc ccgcctcagg caaaacaagt gaaacaccta aaaaaaatcc 63600
cacgaatgcg atgttcttca cgcgtagcga atgggcatcc tcgaatactt ttcgagaaaa 63660
gtttttaaca ccagaaattc aagccatatt ggatgagcag tttgcaaaca agaccgggat 63720
cgaaagattg catgccgagg gtctttacat gtggagaacc caattctctg acgaacagaa 63780
gaaaatggtc aaagagatga tgaagaagta atatttttgg taaaaatatt tttatcaaaa 63840
tttttacca aataataaaa atatttttac tttttttctt cataatatac atagaatgcc 63900
tacaaaagct ggcacaaaaa gtaccgcaaa taaaaaaaca acgaagggct cctccaaatc 63960
tggttcttcc agaggccaca ccggcaaaac ccatgcttct tcgtccatgc attccgggat 64020
gctctataaa gatatggtaa atattgctag atctagaggc attccgattt accagaatgg 64080
atcgcgtctt actaaaagtg aattggagaa aaaaattaaa cggtcaaaat gaatataatc 64140
aggaaactta agcctggaac aattagcctt gtgctgggac ccatgtttgc cggcaaaact 64200
acgtttctta ttcattgcat ttacatgctc gaacgtttgg aaaaaaaagt agtcttcata 64260
aaatctacca aaaacacccg agacaaaact attaaaacac actccggtat acagctacga 64320
cccaaacaat gtaaaatcat agaaagcaca cagttatctg acgtgggttc tctcaccgat 64380
atccatgcag ttgtcgtaga tgaagcgcat ttttttgacg atttaatcac atgccgcact 64440
tgggcagagg aagaaaaaat tattattctt gcgggactca atgcttcctt cgagcagaaa 64500
atgtttccgc ccatcgttcg tatttttcct tactgcagct gggttaagta tattggccgc 64560
acctgtatga aatgtaacca acataatgca tgctttaatg tgcgtaagaa cgcagacaag 64620
acgcttatcc ttgcgggagg aagtgaactg tacgtaacat gttgtaacaa ctgtctaaaa 64680
aatacattta ttaagcagtt gcaacctatt aaatattaaa aatcttatac aataatggat 64740
cattatctta aaaaattaca agatatttat acgaagctcg agggtcatcc ctttcttttt 64800
agcccgtcga aaccaatga aaaagagttt attactctgc taaaccaggc cttggcctca 64860
acgcagcttt accgcagcat acaacagctg tttttaacga tgtataagct agatcccatt 64920
gggtttatta actatattaa aacgagtaaa caagagtatt tatgcctgtt aattaatcct 64980
aaactcgtta ctaagttttt aaaaataacg agctttaaaa tttacattaa tttcaggctg 65040
aaaacttttt atataagtcc taataagtat aataattttt acaccgctcc ctctgaagaa 65100
aagactaacc atcttctaaa agaagaaaaa acttgggcaa agattgttga agaaggagga 65160
gaagaatcct aagtcgctta catttttttt tgctattttt atagaatgta cacgcatgtt 65220
gatgttgtcg gaatagctga agcctcagcg gccctctacg tgcaaaaaga tagggatcgc 65280
tacttagacg tgctaacaac cattgaaaac tttatttacc aacacaaatg catcataaca 65340
ggggaaagcg cccacctact ctttttaaaa aaaaatattt atctttacga attttactcc 65400
aacaatgtgg cggagcacag caaggctttg gcgaccctgc tttataaact tgatccggaa 65460
tacctcactc gttacacagt actcattacc aaaattccca accattggta tgtgattaac 65520
gtagatcagc gagaatttgt gcgcctatat gccatcccgg cagttaaaca acacttaccg 65580

-continued

```
attcccattt tacccttcta ttgcaccagc gcactcaccc agcaagaatt gttttgttta  65640
ggacctgaac tgcagttaat acaaatatat tccaagctct gtaaccccaa ctttgtcgag  65700
gaatggccta cgttgctcga ctacgaaaaa agcatgcgga tgttattttt agaacagttt  65760
ccgcaaagat tggaaatgac gggcgggaag aaggaggaga aggaaaagca tgaaagtatc  65820
attaaaaaaa taatactaga aatggtctct acccgtcagc gaatcgttgt tgggggttac  65880
atacaaaaaa acctgtacaa ccatgtactc aagaatagaa atcgtttaca gcttattacg  65940
agcttaaata tttatgaaga aaaagatatc atccagcaat tttgtgattc aaatggactg  66000
aagatcaaaa tacgtatcaa caatccgctc ttgcctacaa atccggaatt acggcgtttg  66060
actatttatt ttaatcataa taatgatgat gatcagtcat atctaatagt agatatgtac  66120
aacacgggaa gctatgagct agtgcctaca aatcagataa acacgcttga tggcagcttt  66180
ttaataggaa cacccttcgt gcaagcgcga tttttgttgg tagagatctg ggtgcttatg  66240
cttattgcgc agcaaactaa aaaggacacc aaaaaaataa tacaattttt tataaatcaa  66300
tatgaaatgc ttatgaatag tccttggccc agtatggagg cccttttttcc ctcaagcagt  66360
aaaagatatt taggcaacta tgtagaccct aacgcgctca taaagtgggc acaactcaaa  66420
ttaaaaagaa taccgccttt ttatcctgga aagccggatg aagaatcatg ttaagccgat  66480
taaaaaatca tgttaagctg gttgaaaaat catgttaagc tggttgaaaa actcttggtg  66540
aaagcacgga tgtaatatta acattggccg ctcgcatttc gtgttgaaat acgatggaag  66600
agcgacggct atctaccatg ccgatatcgg cctggacatc acagttcatg cacttgtaga  66660
tgggatgact cgcgttatag atggcaggct cgccacagtt tctacagatg taggagatgc  66720
agccatccga gtcgtcgtgc gatttttcta tgatggtttg catggcgccc tgcgccgtaa  66780
gcacccaatg ctccatttct cccagacgaa gacctccgtg cgatcgtttg ccgtccaacg  66840
gctggcctgt gagggcatcc gtgggcccat agcttgcaac ggcgtatcgg tcatccagca  66900
caaatttttg caggcgctgg tgataggtcg gtcctatgaa gatggccgca tcaaagtact  66960
cgccggtctg gccgttgaac attttttggc atccattgaa gcgtagacct tcttgcgcca  67020
gtctttctga aagaagctgc acattaatag gcaggaatgc ggtgccgtct gttaccaccc  67080
cctgtagggc atttgctaga ccaaccgtgg tttctatcat ttgaccgttg gtcattcggg  67140
agggatgtga gtgggggttt acaatgaggt cgggctgcaa tccgtcctct gtgaagggca  67200
tgtctgaagt gggcagggcc agcgccgcaa tgcccttgtt cccgctgcga gaactcattt  67260
tgtcgcctat attgagattt ctttcatagc gcaggcgcat gaggccaaag atctcgtcat  67320
taggcccatg ggacgcatcc acagcatcca cgacggccgg ctcatcgaag ccgtacatga  67380
cagaccggtc gatgtatttg ttgagttcgt ctttttcgcc ccgtattttg gccacttttc  67440
ctataatgat gtcgcccttt ttgaccaccg ttcctacggg cacgaatcca tctacaagct  67500
tttcgtaatt agcaccaggc ttaagatttt tggtgattaa agggtcgggc ttcccaaacg  67560
actctatatc gctttctaat tctacttttt cttctcggta gaaggtgccg gcaaagccgc  67620
ccctgtcaat aaaggactgc gacacgatca cagagtcctc ctgattgtag ccgccgtaga  67680
tcatataagc cacaatggta ttaagcccgt tgggtatgac atagttatgt gctatggtct  67740
ttacaagcgg catttcattg taaaactgga agaagcggtt catgtcgaca cgatatggcc  67800
agctaaagca ataccagccc cccgtttgcc ggccttggtt tgtttcatag gtaacacgcg  67860
caggttgggt acagtttgcg tagggggaca ctagggcggc aaggcccaaa atagcttggg  67920
gcacgtccac gtgtgtgaaa cgacgcgtta catcatgttt atgtttgcgt agctcgatga  67980
```

tggagaaggc aacaagacag ttttccgcct cctcgggggt aatgaactca cagatgccct 68040
gtgctacgag atcttcaagt gtaagcgttc cggctaaaat gtcttttgcc atttgaggcg 68100
taaatcgcgt attttgaatg aaagggattt tatgtttttc ccagtcttta tcgccttttt 68160
ttctggcctc tgcggccttg tagcaggctt gattgtattt ttcaatatta ttatctacaa 68220
tgagtagggg gcgggtcagc ctaccgacgt ccaaccaaaa ttctacttcg tctaccatgc 68280
tatcccagta gatggtggta tggggatgca caaccttgcc ctcacggcga agcattctat 68340
accgctgagc aagctcaaag gcattggtgc agcagccgat ccattctccg ttgataaata 68400
cgcgcgctag gccctttcgt acaatgtcct tgttggaaac atcggctaac tgttgaatgg 68460
ccggatctga tagaaggcgt tgttttaacg aaagtacttc tccggcggtg cagacattgg 68520
cagtgatggc taactgttta gacatgccta ctttttcacc agtatcggct gactgggcta 68580
cgcagatgta tccaggatag gatgcgtgca cgcgacgcat catgtcagcc ctttctgttt 68640
gtttggatgc gttggtggtg ttatgagtat ttaccgtacg caatgctgaa atggtattta 68700
ataaattttt tctttccaaa ctttgagtag atactctgtt tacaatgggg cgctgtcgca 68760
ccatgatggt tttatttcct gaaatgatag actgttccat actgcgatta agatcggagg 68820
cggtattttt tgataaagcg gcagaaaatg cctcgataat gtttcgctga gtaagctcct 68880
caaaggctgt ttgtttaaga agttctttga acccattgat gatgggtgct atcacggaag 68940
tattaaaaat agccttaaag gccttggcga gtgagacccc tgagccgtgc acccgcttgg 69000
tgcggtagct atcacggtcc gtgggtggaa acacattcat aatgacaaga agtattttat 69060
gaataagcag gcctaaaaag cgcagctttc gtacacgtgt atctgcggtt tggcccatgt 69120
gtggcagcaa tattttgtct aaaatagtaa gttgtctttc atttaagtat tgtaccgcat 69180
tttcatcgct tttgtaagca gatgggtttg agacaaattt ggaaaccttc tcggataaaa 69240
actggataat tttttctcgg ttcagctcgt gttggaccgg ttgaaatatg gggtctaaaa 69300
catgaatgga tttttccaga atttctatca tgaaggtatt cacaagggag ttggattcta 69360
gatcaaatac cacttgctca atgatgctgt catcgcctgt cattccaaac atgcgaaaga 69420
tgagatacca aggtatgcga agttttgaga acttggtgct attgatttca atggtaatgg 69480
cgccggtggt catgtagcgt ataataattt gagagctatt ttcgaaggca cctcccggtt 69540
gggagataaa ctcgccgcga atgatttcat tattcccttg ttgcatggta tggtaatgga 69600
tgtgaagcgt gttaaagcgg atgttttcta agaggtctac gacccattcc ccgcctcggg 69660
ctataaagta gccgccgggt tcattagggt cttctcctat ttcttttttt gcggtttttg 69720
ataggtgatg agtgtggcag cggttgctgc cccgcatgat gggaaatgta gatacctgaa 69780
aaggaggaat acttgctcgt tttacctcct gccgaccatt gctgtagtgc gccgttaaaa 69840
taacctcggc ggctagatta accgggcccg aataggaaag gccacacagg cgtgccttat 69900
tgggtagtaa atttatcttg tttccctgtg aatagtttcg atgttgcggg cgttcaatgt 69960
tcacatctgt aaagttaaat tggatctgaa ctgattcccg aagcttatct atttcagtat 70020
ggtcgcgttg gtctttataa gtaatatcca cgttaaacat ttgttttaca atttgcggaa 70080
ttccattgtc cataagatcg tcgaagcttt tgatgttata ccctatcaat cctgtagagt 70140
ttactgcagc ggagataaag ctcagcatat cagcctctgt aagctcctca ttatccacgg 70200
tttcaatggg gccgtaggtt atttgcggcc gcaagggttc catgattatg aagtactaca 70260
ttaatattca gttattcttt aaaataaatc tttatttata aatcttattt ataatataag 70320

```
aatgccttat gcaagagaca tcacaaagtt tattacggca acggaaccag aggtgggtct  70380
tcccctgttg gcgctgcagc gctccaaatc catcataggg gttattcttc ttgtaataag  70440
tttgttattt attttcattg gcattattat attatcagtg agtagtggtc ataccacagc  70500
agcctctata tttatcgtat tgagtcttat cctaggtggc ggtggttttt ttcttattta  70560
taaagataat tcttaaccca cataaaattt gaaaaaatat agagtaagaa aatgtccaat  70620
tactattatt actatggcgg ggggagatat gattggttaa aaacagtaga acccactaat  70680
tttttaaaaa tcgggttgcc ttaccaggca cacccattac atcttcaaca tcaggcaact  70740
actcccccat ctatcttaga aaaatttaaa cgagcagaca ttcttcttaa tgaggtgaag  70800
gccgaaatgg acccactcat gttacaacca gaaaccgaaa aaaaactatt ccagatattg  70860
agtagtattg atatgttcaa aggtctgcga aaaaaagtag aattcacgta caatgctcaa  70920
attgttacga atgcttggct taaaatgtat gagctgctaa ataccatgaa ttttaataat  70980
acatctcagg cattttgcaa ttgtgagctt ccaggagggt ttataagtgc aattaaccat  71040
tttaattata caatgatgca ttaccctact tttaactggg tagcttcctc cctttacccc  71100
agttcggaaa cagatgccct ggaagatcac tatggtcttt atcagtgcaa tccggataac  71160
tggttgatgc aatctccttt actgaaaaaa aatatagatt ataataacgg ggacgtaacc  71220
atcgctagca atgtaaaaaa cctagcgctt agagccacac aaaggctgac gcccatccat  71280
ctatatacgg ctgatggggg tattaatgta ggacatgact acaataaaca ggaagaatta  71340
aatcttaagc ttcactttgg tcaagccctt acgggtttgt tgagtcttag caaaggcgga  71400
aacatgatac tcaaacacta taccttaaat catgcattta ctctttcttt aatatgtgta  71460
ttttctcact tttttgagga actatacatt accaaaccta cctcctctcg gcccacaaac  71520
tctgaaacct atattgtggg taaaaacaga ttacgcttat ttacccccaa ggaagaacaa  71580
gtccttctaa aacggctaga attttttaat gatacgcccc tcgtagacct aagtctttac  71640
caaaatttac ttgaaagcgt ttactttgcc gtagaaacaa tacatctaaa acaacaaata  71700
gaatttctaa acttcggaat gaaatgttat cgacattttt ataacaagat taaactactt  71760
aacgattatt tagctccgaa aaaaaagatt tttcaggata ggtggcgtgt gcttaataag  71820
ctttatgttc ttgaaaaaaa gcataaactt aagctttgtg cctcctaggg atctgttgct  71880
taatttaaca gatgcaatct taacagatgt aaactaaaaa gtgtgttcat acaaggattg  71940
tatttatgaa tatttattaa catataaggt tgtgatgtaa cactgtataa cctatataac  72000
tacactatga agcacggcgt ataataattt atattgaaca cgatgttgac tcatttattt  72060
gcaaacaaat atttgtttgc aagacgtttg catgcattta ctaatatgtt gttgactagt  72120
ttatttgcaa actagatgtt tgattgcaaa ctagatgttt gcacgtattt atttgaacta  72180
atatacactc cttgttttat ttgttatata cacagcatac ataagtgtat attgtttaca  72240
cttatgttta taactcgacg taataacatt ttacacgctt ttttttgca aatcttaata  72300
atattgtatg ataaatcaaa caatgtctta tatatgtggt ttattatttt aggcgccgca  72360
agatgtactc cattctcatt gcatgcttgg tgttattact ctgtctagtt atatatgtcg  72420
gtcatcgtgc cgatcatgca cgaaaatatt tagaaggaat gtggcatgga gatccggttt  72480
ttctaaaaca gtcggggcta caatcctttt atctctacat acaacctgac catacatgtt  72540
tttttagcat tgtgaataaa aatggtgaaa agctgatgga aaccaaaata ccttgtacga  72600
taacaaataa aatatatatg ttttttaaac ctatttttga atttcatgtt gtgatggaag  72660
acatacatag ctacttccct aagcagttta actttctgtt agatagtaca gaaggtaaac  72720
```

ttattttaga aaacaatcac gttatttatg ctgtattgta taaggataat ttcgccaccg 72780
cactaggaaa aacggttgaa aaatatataa cacaaaatta atcatgtttt ctaacaaaaa 72840
gtacatcggt cttatcaata agaaggaggg tttgaaaaaa aaaatagatg attatagtat 72900
attaataatt ggaatattaa ttggaactaa catcttaagc cttattataa atataatagg 72960
agagattaat aaaccaatat gttaccaaaa tgatgataag atattttatt gccctaaaga 73020
ttgggttgga tataataatg tttgttatta ttttggcaat gaagaaaaaa attataataa 73080
tgcaagtaat tattgtaagc aattaaatag tacgcttact aataataata ctattttagt 73140
aaatcttact aaaacattaa atcttactaa aacatataat cacgaatcta attattgggt 73200
taattattct ttaattaaaa atgagtcagt actattacgt gatagtggat attacaaaaa 73260
acaaaaacat gtaagtttat tatatatttg tagtaaataa tatttttaat tacttaaaat 73320
ttttatatat aagtttttga tactatatta taaaacatat gttcataaaa tgataatact 73380 tatttttta atattttcta acatagtttt aagtattgat tattgggtta gttttaataa 73440
aacaataatt ttagatagta atattactaa tgataataat gatataaatg gagtatcatg 73500
gaattttttt aataattctt ttaatacact agctacatgt ggaaaagcag gtaacttttg 73560
tgaatgttct aattatagta catcaatata taatataaca aataattgta gcttaactat 73620
ttttcctcat aatgatgtat ttgatacaac atatcaagta gtatggaatc aaataattaa 73680
ttatacaata aaattattaa cacctgctac tcccccaaat atcacatata attgtactaa 73740 tttttaata acatgtaaaa aaaataatgg aacaaacact aatatatatt taaatataaa 73800
tgatactttt gttaaatata ctaatgaaag tatacttgaa tataactgga ataatagtaa 73860
cattaacaat tttacagcta catgtataat taataataca attagtacat ctaatgaaac 73920
aacacttata aattgtactt atttaacatt gtcatctaac tatttttata cttttttaa 73980 attatattat attccattaa gcatcataat tgggataaca ataagtattc ttcttatatc 74040
catcataact tttttatctt tacgaaaaag aaaaaaacat gttgaagaaa tagaaagtcc 74100
accacctgaa tctaatgaag aagaacaatg tcagcatgat gacaccactt ccatacatga 74160
accatctccc agagaaccat tacttcctaa gccttacagt cgttatcagt ataatacacc 74220
tatttactac atgcgtccct caacacaacc actcaaccca tttcccttac ctaaaccgtg 74280
tcctccaccc aaaccatgtc cgccacccaa accatgtcct ccacctaaac catgtccttc 74340
agctgaatcc tattctccac ccaaaccact acctagtatc ccgctactac ccaatatccc 74400
gccattatct acccaaaata tttcgcttat tcacgtagat agaattattt aatatgtact 74460
atatattaat tatttaacct ttcaagctgg tcttcattta aatttaaaat ccactaataa 74520
aatgtatttt ctagtagcag atcatcgaga acatcatgtg attccttttc ttaaaaccga 74580
tttccatcac atgcatcaaa atcctataca aaaaaatcaa gctctcctag aaatcaaaca 74640
gctttttact ggagattatc tcatctgcaa aagcccttct accattctgg cctgtattga 74700
acgaaaaacc tacaaagact ttgcggcttc tttgaaagat ggacgttata aaaatcgcca 74760
aaaaatgctg tcgctgcgag aacaaaccaa ctgtcaactt tattttttg tagaaggccc 74820 ggcatttcct aaccctcaaa aaaaaattaa tcacgttgcc tatgcaagca ttattactgc 74880
tatgacgcat cttatggtta gagatcatat ttttgtcatt caaacgaaaa atgaggccca 74940
cagttcccaa aagcttgtgc agcttttta tgccttttct aaggaaatgg tgtgcgtcgt 75000
tcccacctcc ctcacccca cggatgaaga gctatgcatc aagctatggt cttctcttc 75060

-continued tggtatttca ggcgtgatag gtaaaatctt ggcaaacact tgttccgtag ctcatttggt 75120
tcatggaaag ctttcatcgc agaatattga tcagttaaaa actccctcca accgaccatt 75180
ccccaaaaaa gtaaaacgta tgcttataag cattagcaaa ggaaataagg agttagaaat 75240
aaaattgctc tcgggggttc ccaatatcgg gaaaaaatta gctgccgaaa ttttaaaaga 75300
tcatgcgctt cttttttttc taaatcagcc cgtagaatgc ttggcaaata tacaaatcgt 75360
tcaaaaaacc cgtacgatta agttgggaat gaagcgagcc gaagcgattc attatttttt 75420
aaactggtgt ggctctgccc atgtaaccga tgatagccaa aatatcacag aggcgtcgcg 75480
gtccacaatg caggtcgcga cgcagtccgc cgcaatacag cccgctgcaa cgcagccatt 75540
gcacgaagta tcagatgatg catcatcaga tgcttcatca cccgtagggt atcaaacatt 75600
atctaaagaa atgttattga acacagcctg atgttaataa ttcactacat ctaaagaaat 75660
gttaacctcg atactaaaaa gtcattgaac acaactactg gggcgctaag ttgtccaaca 75720
catctaaaga aatgtcaaca tcctcgatgc taaaagggtc atcgagccgg tcaataatgt 75780
cttccccaaa aagtccggga gaactgtagg ccgagatgtc gtccatggag ctatcttccc 75840
cagagcacac aaagtcctct ccaaaaatca taaagttaaa tgcaccgggc ttacttaaca 75900
gcttttcgct ttgaataata gtgttgagtt ctgtcagcgc aaactctctc acaatattca 75960
caacccagga gggctcttta atttcataca gcgttaagaa acttatacat aaaaattcta 76020
tagagtaaag caaggcgctg gcaggatctg ttacccgtag gtgtttaaat gtagtgtgat 76080
attcattcac aacgttaggc agcacctttt ccaaatcctc cttttcctcg tacgacaggt 76140
gctttacaag cctttcaaca tgtataggag gcttgttaaa tgtactaacg tgccgcaaac 76200
agttataatt atataagaaa atacgtacgg cagagtcgac cgccatgagc cttggatcat 76260
ccattgaggt aggtggtggc ggggcaccct ggccttccct gatgtctgcg taggagcgcc 76320
cctccatggc ccctatggcc tctatcacag caggactgat atccaaaatc ttggccgtct 76380
tgattatttt tccgtaatcg aaagtccatg gctcctgtgg aggcttgggt tgtgtttcgg 76440
tggagggcgt ggtcatatct ttctttattt gaatagaacg gatcgacatc ttttccttat 76500
cgtactggtc tttataatta ttataatagt catgaactaa ttcgggttga gaaagatgat 76560
cgtatataat ataggtaaaa agtccgcact tgacacattt tttatcctgg aagtcgtgta 76620
atcctccctt ggggcagcgt gactcgtaga aggcataaaa ggtgttaaat tctaagctcg 76680
cctttagggc tgtttggacc ttttttatgt ttaattgccc cacctcatgt tgtagcacgt 76740
ggcatacaga acagcgtaga tcggcaagtg cataatggtt gtcaattttt tttatgacgt 76800
ctttgcgtgt tacttcaatc tcggcgggtt tctgcgaact gtctacggcc ttgtaaacgt 76860
aaatggtcca cttatgagga agcccccttt catcgtatag ggttgaaatg ggaagccttt 76920
tatactcaaa cagccgagtc cgttggtcgg ctcttcctgt gttaggatca aatatgttat 76980
aaaatccttg ctgagcaagc agggcctttt gctcgccata agcattttcg tacgttttga 77040
attctgcaag ttcggagtta aaattaggtg cattttgtaa atacttaaga aataattcat 77100
aggctctaag gtaaatgaga gttgaggttt tttcctcatc ccgtcctccc caccacaccc 77160
gcaggctttc ttcttgaaaa tagatgtcat tcagacgcgt caactgcgta aaatcaggcc 77220
gatatttaga ggtataaatt ttatcataaa attctttttg cgataatagc tcggccgggg 77280
tacgtcctat cacggtttta aactcatatt cagcctcctt gggagtccgt ggtttgtgca 77340
tagggatgct gccgtcaata cgggccactg tggcagcata atcatacatg gggtccagca 77400
gaatctctgt caaaagtacc ttggtgtcgt cctgcacgct aagcccttgt agcccatttt 77460
ggtggataat ttttttgaaa gcctcccgaa aattattagc aatccactga tccgtaatct 77520
cagatagctg atttattata ccgctatatt gctgcatcat tttctccaaa agaaaggtca 77580
cgtatgcatt caaagagcta tccgccttca ttccatgaat ggtaatcgta agaaattctt 77640
tatttttttg cgagctataa atgagattca aaatataggc atagatgtag atcacagcat 77700
acagctgcgt taaaggatcg taatcctctt cctttttaat attttcgatg ctatacacga 77760
gcggcaggca gacatttacg gctatattgg caaactgttt cacgtctaca agctttccaa 77820
agtggataaa cgtgcaggcc ttcatggttt cctgccaaat aaaaacacgg agcttactat 77880
taagatcgcc gatgatgccc acatctgccg tacgatcctc ttgaataaaa tgggccagct 77940
cttcgccaca aattttgcaa aagtaggagt aaataagccc ctggttgttt tctttctcct 78000
tgtttattcc tgaaaatttc attagcttgg ttcgcatggt gtcgtaggac gcttctgccg 78060
cttgaagctg tataagcatg tccacatggg gacaaagcag cttaaacccg caggctttgc 78120
atagattcca attggtggta ttgttttttt ccttgtagag tacacgaata ctttctaata 78180
cttttaataa ctccgcgtat tgaagacccg aacgcaactg ttttaccagc ttgagatgag 78240
cacatgcatt tttttcttgg agttcccact gtttttttaat gtttaggtat tctgttgtaa 78300
taagttctgc ctcctgtttc ccacaggctt taatgacttc ttgaaggatg ctgttagggt 78360
catccacttt accctccatt gtaagaattt cacgtatagc atccgactgc accctaccta 78420
ttttttcttc cataatttta aaatactgtc tcgcctgggt aatgacctct gtgagcttca 78480
tgtccacctg ctgcagaatc atttgctcct tttcacgctg ttcagcatgt tgtaaaaact 78540
tttgttctac agggttccaa agcacctcca aatagcctgc tctatatagg tcataaagca 78600
agggcatgta tcccgatgta aaaaccgggg acaccgagta catcgtagac aactctttta 78660
aaaaaaatat cacgcgctta atgttctcct ccggttcaat ctcctcggtt tcaacgatat 78720
tagatatatg actgccctga tcctcacggt ctagctttcg gtgtaccatc tcctctgcta 78780
gccgattaat gagccagcta tgcccgccgc tccgcaaaaa cttataaagt tcgatatact 78840
ggtgcgtaaa ctggatgatg ttttccttgg tggttacgac aaccccttct ccgttttttt 78900
tccaggtttc ttgatccacg catttcataa atactcgaat aaaattggtc aaattggctc 78960
ctgaggcgac gtagcccaag gtttcaggcg agaaggagcc tatctcagcc atacgcataa 79020
aacactgcgg ggaaaaagtt tttagccgca acttaagtcc atagatttca atgggggctt 79080
ctgcgggaac ggccaggtgc gtcccattaa ttaaaaaaat ttctttgcgt gtgctagggc 79140
gaacacgtaa ttcctttttt ttttcactca cgatggggac cacatcgggg tctaccagca 79200
gttgacgtat gtaggcctct atgggcatgg atagatcggg cagctttgac tgctcggcgc 79260
gaacatggtt cacaaaatct tttagagtga aaagaaagtc tattaaacgt atgtttttta 79320
tatcattaga ccctttaagg gtagagtaga tttcatccac tagtgcctcg atttcctcat 79380
tattgagcga taagatatct gtgccacggt ggactatttg cgcgatcgta attacttcct 79440
ccattagata gaaactgaat attatattta aaataaatac aaaatgtcaa atgaaagttt 79500
tcccgaaacg ttggaaaact tactttcaat gttacagacc aaacagcaaa acgcaattca 79560
gtcagaggtg attgaatggc tgcacagctt ttgtgaaacc tttcacttaa aaatacactg 79620
ccataaacag tttattccta gcggggaaaa aaaacgagct aaaataccg ctcaagaaac 79680 acagggaaac acgcagccct cccaccatgt gtaccgggtt gttctctcca gagcacagcc 79740
agtcaaagca caggaatctc tgctaacaac catgtgcaac ggactggtgc tagatgcaaa 79800

-continued

```
cacatggaca tgcctagcca ttcctccgcc tgcgcccttt caacaggcga cccgccaggt  79860
ccaacacttt taccgtaaca atttctacga agtggttccc atccaggatg gcacccttct  79920
cacaatctac cactgggatg accctgaata tggcccctcc tggtgcctag caagtaccca  79980
cggatatgat gtgagtaact actgttggat aggcgacaaa accttcgccg agcttgtata  80040
cgaattgctg cagcagcact ctacctgcga cgtcaccctg gaaaaaaata aaacgcgggg  80100
aacgcgtctt ttctttgata acttaaatcc cgattactgc tatacgattg gaatccggca  80160
ccataattta cagccgctca tctatgaccc tcaaaatatt tgggcgattc aatctacaaa  80220
cctaaaaacg cttaaaacgg tatatccaga atactacggc tatataggca ttccaggaat  80280
tcagagtcaa gttcctgagc ttccccagta tgatttacct tatctaatac gatcttataa  80340
aactgctatg aatcaagcca aaaatgctat aaaaaatggc aaaaaagaca agggatactt  80400
taattatggc tatttactca tttcgcgagc gcctgccatt actaaaagta cttctaatgt  80460
tttgttaaaa tcgcctctgc tggtattttt acaaaaaagt gtgtaccaga aaaaacacaa  80520
tatctctaac agccagcgac tagaatttat tatactgcaa aactacttga tgcagcattt  80580
tcgagatcat ttcattgctc tatttccgca gtacatatcc tattatacga aataccaaaa  80640
catgttgaat atgattatcc atagtattgc aactaaagat aaagatcatc cctttgcagg  80700
agccgtggta aaaaaagtgt tggaagatat tgaaaacgcc gaaaacatta ttgatcatac  80760
aaccattcaa aactatgccc atcaaagcaa gtacgccatg ctttacttgt caattatttc  80820
ccatttttaa tctaatacgg ccaaagccgc gggtttttta ataaactaac atttaaaaaa  80880
actgttttat taaaaattat aatactttta ttatatatgg aacatccatc tacaaactat  80940
actcccgaac agcaacacga aaaattaaaa cattatgttt taatccctaa acacctttgg  81000
tcttatatta aatacggaac gcatgtccgg tactacacca cacaaaatgt tttccgagtc  81060
ggtggctttg tgcttcaaaa tccctacgaa gccgttataa aaaatgaggt aaaaacagca  81120
ataagactgc aaaatagttt taacacaaaa gcgaaagggc atgtaacgtg ggccgtccca  81180
tatgataata ttagcaagct atatgccaaa ccagatgcaa ttatgcttac catacaagaa  81240
aatgttgaaa aagctcttca tgctttaaac caaaacgtac tgacgctcgc atcaaaaata  81300
cgttaaatat aatttttgta gaggataaaa agctatttta gctaaaaaat aattcatata  81360
cgtttatgca gaggaagaac ggtggctttc aaattcagat tgcatccacg tagaccgtag  81420
cgtttttttt gcttctggtt tatatcgtaa accgtaataa acatcatcat ttgtatccgt  81480
tggatctttt tcccactccg gataaaaaat cggttttctt ttttttggtc gttttttgca  81540
gtaagctgta aattaaggga atatagctta tcgaaaagtt gttcctgatc catataaata  81600
gcagcatata ttaaaaaaaa taaaaaaaga cgcttcaacg agtcagtacc actgcttgcc  81660
aacgatttac gttggttggt gcattatggt gatatagtaa tgagtgcctg cacaagtgct  81720
tgcacaagtg cctgcacaag tgcttgcaca agtgcttgca caagtgctta cacaagtgct  81780
tgcacaagtg cctgtacaca ttactgcatc gccaaagcac ctgcaatgcc tacttcctca  81840
acagagtacg ataactaaat gcttttaagc accgcttgcg tcgatgtgtc cttcggggca  81900
atcgggttca attggatcca atattattag tcataattac ctaatactta ttcaatttta  81960
tctttttttac cttgtaagat ttaaacagcg ttttagcttg tttaaagcaa cgtttaaaac  82020
aagctaaaat gctgtttaaa acaacgtttt aaacaagtta aaacaaataa gcttataaat  82080
ataccatgac aaaattagcc caatggatgt ttgagcagta tgtcaaagat ttaaacctaa  82140
aaaatcgagg gtccccctcg ttccgcaaat ggctcacatt gcaaccctca ctgctgcgct  82200
```

attcgggtgt gatgcgtgct aacgcctttg acatcctaaa atatggctat cctatgcagc 82260
agtcaggtta tacggttgct acgcttgaaa tccactttaa aaatattagg tcttcctttg 82320
ccaacattta ctggaaccgt gatagcgagg agcctgagta cgtctgctgt tgtgccacct 82380
atcaatcgca cgatggcgaa taccggtatc gatttgtttg gtaccaaccc ttcatagagg 82440
cttataatgc catagaggcg gccctggatc ccctggaaac cattatcctg aacctcattg 82500
cggcacgaga tctagacttc gttgttcaca tatttcctta taataagggc catgaagact 82560
atttggcctc cacgcaactt attctcaaaa tctttattgc gacgctttta atggacattt 82620
taagaattaa agacaacacg ttggacgttc acttaaattc cgactatatt attgtgatgg 82680
agcggctttg gcctcacata aaggatgcca tagaacactt ttttgaagcc cataaggact 82740
tactagggta cttaattgcc tttcgcaatg gggggaactt tgcaggaagt cttagaccct 82800
cctgtgggca aaagattgtt cccctaacga ttcgagaggt cctacaaatg aatgatatta 82860
atttagccgt atggcgggag gtgtttatta tgcaggaatg ttccgactta gtcatcaatg 82920
ggatagcgcc ctgtttcccc atttttaaca cgtggacgta tttgcaaggt attaaccaga 82980
ttttttttga aaacacgtct ttgcaggaga aatttaaaaa agattttatt gcccgagagc 83040
tttccaaaga aattatcaag ggccaaaaaa cgttgaatga caaggagttt aaaaagttaa 83100
gcctacatca aatccagtac atggaatcct ttctacttat gtcggatgtt gccattatga 83160
ttaccacaga gtatgttggc tataccettc aatccctgcc gggtattatt tcgcgatcca 83220
gctatttatc ccccatcgtg aaaaacattt tgatggacga agactctttt atgtccctac 83280
tatttgacct atgctatggc gcctacgtgt tgcataaaaa agaaaatgtg attcacgcgg 83340
atttgcacct gaataacatg acctactacc atttcaaccc aaccagtttt acagatcgca 83400
acaaaccagg aaaatacacc ttaaaggtca agaatcctgt gattgccttt ataaccgggc 83460
ccaaagtcga aaccgaaacg tacgtgttca agcacataga tgggttcggc tgcatcattg 83520
actttagcag agccattatg ggccaaaacc atgcaatcaa gcttgagcgg cagtacggcc 83580
tcgcttttgt aaacaccttt taccgcaatc aaagtgagca tattttaaag gtattacggt 83640
actattttcc tgaaatgcta accaatcgcg aaaacgaaat acagggggtg attttatcaa 83700
actttaattt ctttttcaat agcattactg ccattgattt ttacgccatt gctagaaacc 83760
tacgtagtat gctttctttg gactatttac acacctctga ggtgaaacga aacgtagaaa 83820
tttcgcaaac atttttggat acatgtcaat ttttggagga aaaggccgtg gaatttttgt 83880
ttaaaaatct tcatactgtc ttatctggca agccggtcga aaaaacggcc ggggatgtgc 83940
ttttacccat cgtatttaaa aaatttttat acccaaatat tcctaaaaat atattacggt 84000
cttttaccgt aatagatgta tacaattata ataatataaa gcgttattct gggaaagcta 84060
tacaaacgtt tccaccctgg gctcaaacca aagaaatctt gacgcacgcc gagggtcgta 84120
catttgaaga tatttttcct agaggagaat tagtttttaa aaaggcttac gcagaaaaca 84180
accatttgga caaaatttta cagcgtattc gtgagcagct tgctaatgaa aatttgtaag 84240
gcttgcagtt cttgtatggt cagaacctat gtcgatggaa acattatttt tcgctgcagc 84300
tgcggcgaaa gcgttcaagg ggatagtcag aacttgctcg tctctagcaa ggtgtaccac 84360
accggggaaa tggaagataa gtacaagatt tttattaaaa atgcaccctt tgaccccacg 84420
aattgccaaa taaaaaagga ttgcccaaat tgtcatttag actatttgac acaaatctgt 84480
attggaagcc aaaaaatcat tatattggtg tgccgctgtg gctatatgag caacagagga 84540

-continued

```
taaaccatat catcccaccg aattatgaca ttcctttaaa accgtccgcc taaatagttt  84600
tcacaccttt ggtggcagac tattttataa aaagtaatgt tggttcatga agataaagtg  84660
tgccaaagaa acttttataa acaaatgatt aatgtaggtg ctagtcgtgt gtacttaaac  84720
agggtattct atagccaagt attttctata gccaagtatt ttctatagcc agtattagtc  84780
aagtatttag atgtcagggt atttttatag ccagtatttt tctatatgta caaactattc  84840
cagtaaacat atgtgtgttc tttattgagc agcatcatgg cattaacaag tttattaaac  84900
tgctctaatg ggcattaaat gacaactcgg tgcttagcaa aagtgcctat accttttaac  84960
aattagggcc gggaggcatt cccagctttt ttctataatc agccatacag taccccctgag  85020
cctcatacac gggaataagg tccttccatt ccttgttggg atcggcgggc cagctctcaa  85080
atgaggtgtg aatgtaaggg tcctgttctt tttccttaat gaagcgttta atctccattt  85140
gatgttgttt actttttgt ttgcggcgga gcgtgttccg caccaatacg taaaaaatac  85200
caagaatcac acataaaaga attattaaaa aaaatatcat catcgcgggg tttaaaaaac  85260
gatcccatgc aacaggaatc gttcttaaaa ccttgtctgg cagggctgta aacatgaagt  85320
ctcctcctat aatcggggtg ggactgtagc ctaacagttc aaggtcctgt cgttctagat  85380
acttattggc gaactgccca ccctttgccc ccgttttttt attaatcaag cagcgctgca  85440
ttttccacca ttctaaatct tcaggagaaa gctcaatgcc atatatcaac tttaacgtta  85500
ttgcatcttt ttcaatatcc ttatcaattt ggctgagctt ttgagcttta agcgggtcta  85560
gtgtgtactt ccatttaaac ttagtgtcct gtagtttggc tacatgaaat acggaacatt  85620
tcggcggggc ctttgtgacg cccttacact gcggaagttt atcattagga caggcgcata  85680
gatgagactg cgccacagca tcgcgaacta catcgcagac ggagtacatt ttcctcctat  85740
gttaaacaat aaattttttt catagctgaa atttgtgggc ctatcttttc ccttgcccgg  85800
ataataatta taagggagtg ttgaaacatc tgggagagaa ttgcttaaaa aatgggtttt  85860
tgggaggggt aactgcgact gttgtacgtc gttggccagg gagattctat atgccgggct  85920
aaaggtgcaa cgttcctgtg aacaacttag tacgcgcgtt gttaatacaa atggactggt  85980
attagcaaac ctcgtaaact cttccggact tgtttgtttt tgtatgatgt ttagcaggga  86040
gtctgccttt tcgagaatcc aaagcgtcgc attgtagtaa aataaaaata gcgacttatc  86100
ggcaggcgtt gcaaaagcgc cgtatagaaa ataaagcagt aagtactggg gagacaccac  86160
aataaggtta tcttgaatga tagatatcgc tagctcttta aacatagtgc taaaaaaatg  86220
tatgtcgttc gtcttgaata tagggggact atagtccatg tagggctcac atatctcagt  86280
caggtgaagg cccatttctt ttatgacttc ttccgggttg tacgtcgcta acaccagcgc  86340
gggataggct ttgggcatat ccacggtaag tgttatgttt ttatcattct tatggtagga  86400
gtaagatggt tgtggaaatt ctgttttcca ctccgggact ttgcaggtaa ttctcagctc  86460
atttagagtc tggtacagga gggcgtatgc cgcaaagccg tgtatggcca cttgtttaaa  86520
gggaattgaa aacgttttac tttcgtatgt cgacttcaca ggaacaacgg gaatggggta  86580
atatttttct atgaggttat accgctgcaa atccttttta aacctgctaa aaacatcttc  86640
ccttggtggg ttatcaaaag gaaagcaaaa tgctaggtgt agcccggccc gctggtaatc  86700
ggggtgaatg attttaaggt ttttatacgt taatgtgggt atggtgttaa agatattggg  86760
gggcatatat gaaagatcag caacccacac aaagtccgtg cgcacccgca tggtctgcac  86820
atggatggcg cgcaccgtgc ccacctgctt gaagcccttt tcatacaaaa tgtcagcaag  86880
ttcgtaggcg tcctcaacgt ggttggggga aaacatatca aagtcgggtc tttctccctc  86940
```

-continued

```
gggataaatt gagctgcctt taagatgcag ggcataatca atggcaatcc ccccgtacaa  87000
aataagcttt ttctttatga taaattcgcg gaccacctcc aaagccgcct caatctccac  87060
ggcatttgcc tcacgttttt gagcaatgag ccggtactta gaaacattaa aatcagtctt  87120
tagtaaagac gtcataaata gtgtttaata tatattaaag gtttgaataa aatactaaat  87180
agtaaaaatg gatgccctat taaaggaaat agaaaagtta tcgcagccat ccttgcagaa  87240
agaaaacaat gatgtatgcg atctctgttt tatgcaaatg aaaaaaattt ctaactatca  87300
gcttttatgc gaagagtgcg gtcagctgaa ggactggttt gaacctgaat ataatgaaaa  87360
attcacggta tattctcgtc taaagatcgt gggtgccaat agttcctatc accagcgcga  87420
tttggacaag gccaactcaa gtgactatag ctccttgcaa tttcatcaca ttttagagga  87480
gctcaaatcc ctaaatgtta agtatatgga tgcggggcaa aagccctttc ctattcaggt  87540
gttaaaagaa actgctcaca gttataacca agtacaacaa catcgggtca tacgcagcat  87600
tacaaagctt cagatcttag ccagtattct acgtagcatt tgtttaaaat taaacattgc  87660
ttgtacggtg gcagacgccg cgaggtttac tcaacttaat accaaaggga tctcaagggg  87720
catggatctt ctgcgctccc tatttgtaga caataaaatt actttaaacg ttgatttaaa  87780
ccctatagac agctttatta atagtaccta cagtgcctta caaattaaac aaatccacca  87840
agaactgcag gaggaaaatg tttataattt aaaagaaatt gttaagagct ttatattata  87900
cgcggatgag aagaacatcg gcgtcgatct taacaggaga accgttgtga ttgctacgat  87960
gtataatgtt ttacgccgtg cctactaccc catagaaatt gatacggtgg tgtatcaatg  88020
taaaatacga aaaaatacaa ttacacgtgc tcttaaaatg tatgaggatt actactccca  88080
ctttaagtct ctttatgagc agtatcattt aaacgcggca aaaaaattaa tttaaactaa  88140
acgtttaaac taaatgttta aactaaacgt taaaactaaa catttcgact aaagtttaaa  88200
acctagtcta acagcgggat gcccatttcc ctggggttcc atatttcaac aattttttga  88260
ccttcgggtg ttaccttgat gcagcgcatg acgagcagtg gaattttcct attaaagagt  88320
tcttgcttag ctatatcaat aggactgcta tattttttttt taagcattgt agatccatta  88380
attgccaatt gttgcgctct aacggcgacc aaccttgtgg cctcaaaggt ggttaaaacg  88440
ttggaggtaa tgcgctcgtt atcgggtata atgaccaatg tttgcgacga ggcctgcaca  88500
aagccctcgc agatggacgg agactccacg atctcgtcct tgtcctcgga ctcctcctca  88560
ctgtcgacga ggttctcctc ttccgtttcc acatattcct ccacgaggtc atccatgata  88620
agatcctcgt tgtcattatc agccatatta cactgttatc aaatgtactg tttaatacgc  88680
aaatggattt actacgtttt aattgtatgt cttcatgtgc aggctctagt ggaaagtaat  88740
tttctcacaa tttttggcac cgttacactt gtgcccacaa aaacccgcga ttttttttatt  88800
ttatattact tttggaagta cgagtttaac cagtcgcttt caaaccttat gcgtctatct  88860
cgccaaaaaa cgctcacagc ggtgttggat attaccttta aaaaaataac attaattttt  88920
accacagagg gcgtattgcg tatggattct acgaataagc caggcgtgcc actcgatata  88980
gacccccagt tcattgacct tgatagtatt ttaatggaac tggatcatta ggacctctcc  89040
cgcccattta aatttttagt ttctacaata ataaaatgcg cgaggaatca tgggaagacc  89100
acgataccat tcagctcacc gctcagcgca aatacctcgc cgaggtgcaa gctctagaga  89160
ccctttttgac tcgagagctt tcagtctttc tcacagagcc aggcagcaaa aaaacaaata  89220
ttattaatag aatcacagga aaaacctacg cacttcccag cacagagcta ctaagactct  89280
```

-continued

```
acgagcatct cgagcaatgt cgcaagcaag gcgccctcat gtattttttg gaaagacagg  89340
ggacctactc gggtctcatg ttggactatg accttaaact caatacaaat gctgttcccc  89400
cgctggaacc ccccgcgcta tcacggcttt gccatcgaat atttgtgcat ataaaaaaca  89460
gcagtgtgct gcctgagggc agccataaaa tccacttctt ttttacatta aaacctgaag  89520
tggttcaggg caaatatggg ttccatgtgc tcattcctgg tctcaagctg gcggcttcta  89580
ccaaaaaaag cattatagga tccctacagc acgatgccac cgtacaaaaa attctacacg  89640
agcagggcgt tacaaatcct gagtcctgtc tggaccccca ctccgcctcc gttccctcgc  89700
tcctctacgg ctcctccaaa ctaaaccaca agccctacca actgaaaacc ggctttgagt  89760
tagtctttga tagctctgat cccgactaca ttcccattca tcaaataaaa aatttagaat  89820
cttataattt agtttctgag ttgagcctta cgaatgaaca gggaagcctt gtaagacctg  89880
tctattgcgc ggcagacatt gccgctgaga aggaggaaga gatcccgacc gaggatcact  89940
cgctctccat attaatgcta catgatcccg aagcccggta tttacataaa attttaaatc  90000
tgcttcctcc ggagtattat gtagagtacc ccctatggag caacgtcgta ttcgctttgg  90060
ccaatacatc cgctaactat cggcccctcg ccgaatggtt ttcgcaaaaa tgccctgaaa  90120
aatggaatac gggaggaaaa gagaaactag aaaaactttg gaatgatgcc tcgcaccaca  90180
ctgaaaagaa aatcaccaag cggtccatta tgtactgggc ccacaaacat gcccccccagc  90240
aatacaaaga aattgtagaa caaggctact tttccattct cgctgaatat gtgtatagct  90300
ataacggcat gcttgagcac tacatgatcg ccaaagtcat ctatgctatg atgggcaaca  90360
agtttgtagt ggacgtggat tcaaacggga agtacgtttg gttcgaattt gtgctaccgg  90420
gccagccaat gaatcaggga gaaatatgga agtggcgcaa ggaggtaaac ccggatgagc  90480
tgcacatcta tatttccgaa aacttttcaa gggtgatgga ccgaatcacg gagcacatca  90540
aataccacct cagtcaaccc catgaaagca atattttaaa ttattataaa aaactattaa  90600
aagcctttga acgctctaaa agtaaaatct ttaatgacag ctttaaaaag ggagttatca  90660
ggcaagctga gtttttattt cgccaaagaa gctttattca aactctggat accaatcccc  90720
acctactggg ggttggcaac ggggttctct ccattgagac catcccggct aagctcatta  90780
atcattttca cgagcatccc attcatcagt acacacacat atgttatgtg ccctttaatc  90840
ccgaaaaccc ctggacaaaa ctattattga atgcactcca agacatcatc ccagaacttg  90900
atgctaggct gtggatcatg ttctacctaa gcacggccat atttcgcggc ctgaaggagg  90960
ctctgatgct tttgtggctt ggaggcggct gcaatggaaa aactttttcta atgcgacttg  91020
tggccatggt attgggcgat cactatgcct ccaagctcaa catcagcctt cttacaagct  91080
gcagagaaac cgcggaaaaa cccaacagtg cctttatgcg gcttaagggg cggggatatg  91140
ggtactttga ggaaaccaac aaaagcgagg ttctaaatac gtcgcggctg aaggaaatgg  91200
taaatccggg cgatgtcacc gctcgagagc ttaatcaaaa acaggaaagc tttcagatga  91260
cggccaccat ggtcgccgcg tccaactata acttcatcat tgacacgacg gaccacggca  91320
catggagaag actgcggcat tatcggtcaa aggtgaaatt ctgccataac cccgacccca  91380
gtaaccccta cgagaaaaag gaagatcctc gctttattca cgagtacatc atggatccag  91440
actgccaaaa cgcattcttc agcatactcg tctatttttg ggagaagcta cagaaggaat  91500
acaacgggca gattaaaaaa gtgttttgtc ccaccattga gagcgaaacg gaggcgtaca  91560
gaaagtcaca agatacgcta cataggttta tcacagaaag agtcgtggag tcgccctccg  91620
cagaaactgt gtacaaccta tccgaggtcg tgacggccta cgcggaatgg tacaacacca  91680
```

acattaacgt aaagcgccat attgccctcg agctatccca ggagttagaa aactctgtgc 91740
tagaaaaata ccttcagtgg tctcccaaca aaacgcgaat tctaaagggt tgccgtattt 91800
tgcataaatt tgaaacgctg cagcccggcg aatcctacat tggggtgtcc acggccggca 91860
cactcctaaa cacacccata tgcgagccaa aaaataaatg gtgggaatgg tcccctaatc 91920
cctctgcccc tcctgagaaa gaagcgtctg caccaactcc ttagggaata tccttagaag 91980
catgtctttc ggcagagcca ttaccggtag caaaaaagca acattgagta tattatatgc 92040
cttagcctgc tcataagcgt ccttttttt catggtattt tatgtttta aatattttta 92100
attatttttt aaatacgatg aacagttcgt gctccgaagg ctgtttacta aaaatcggtg 92160
tgaatccgca ttctttaaat atggtttccc attcggggat ggtatggaaa tccatgtctc 92220
tacgaatagt atggtgccca agtgcgtcct gcaggctgtg aagccagaag gcctcctgac 92280
cttgatgaag gtcgtacatg ataagaaaac catcaggttt caacagatgg taaagcttgt 92340
taaaatcgtt tatcgtaaga tgatgcgccg ccataggtaa ccctatgagc tccacagagt 92400
tttcatgctg gacatcgtcc atatcggtat aaaacgtttc acagtaaatg agacgcttaa 92460
acgagtatcg atgacaaaca tttatttcca agtaggtttg cactacgttt ttaggtatat 92520
cgggaatcat gttgattaag gttgtttcgg gaaacttaat catctgacta ggcttcattt 92580
tcaactcttt aaaggatttc ccggagaagt gaaaatgggt ctttacgtat ttatgtaaaa 92640
atacctgaat gggcagaggg ggctcctcct cttcgttctc gacgcctccc aaaatatttg 92700
gaatttcctg acgtggcaaa agaaagttta tgtccacgtt tacgaatcca tcgaggacgg 92760
acacaaagct tggctctaat ctccattcca tatactgttt agaaacggga gatagcataa 92820
tcctaggcgt cacaatgcac gaagggtttt taatcaccgc atcgtggtaa gaaaagtgta 92880
ttccatttct tccagtataa agaagcctat gttcgtcgta gcagaaacaa ttaaggcggt 92940
atgcctcata catacactgt ttcaaagtac aaacacgttt taaaaaggtt tctgcattgg 93000
cggaggccaa gcggttttgc cattggtgga aggggttcaa tcctacaatg gccagctcgt 93060
ttaaaatatc ttcgcggcgc gctaaaatct gcaccataga agaatacttt agcatttttt 93120
tttcgcacca ttcgcgaaga tgtttagcta cattattaac cttattattg ataaagtata 93180
cgatggcatg ttggaagcct tcaaaaataa agagcccctc caaaagatca tctgccaata 93240
gaagatggat gttggtgtaa gcattgtcaa tattttgtag aaacggcgga atgcctgcca 93300
aaaccgcttc agcaagcata gctccgttcc gttgtttact gtccaataga ttcgtaagtt 93360
ttttgtccgc aacagacacg acggctagga tggttgcaat gtcagaaatg gcggcttgcc 93420
agaaataacc cgaaaagcac atgcgcgctt cttctataga taaaaacgaa aagcgagagg 93480
caatgtctcc gagctgcgtg agttgaagac ctttttctcc tctggttaaa aggcctgcca 93540
caatggcccg ctcaatggct gatgccagcg catccgtggg gggaggatcc agcatatcaa 93600
tctcctctgc cttaaacacg ccttccttat ttttttaat cgtttctacg acaatgctaa 93660
gaaaaatggc cccagggcct tccgtaatga tttcaggata ctgctgcact ggtatttgct 93720
caaagacgtg ttttgtgtaa agcgggtaaa agtgcccagg aaatactctc cctacacgcc 93780
cctttctttg ctcgatacgg ctttgagccg cggggcgcgt aataagccct cccgcccatt 93840
cgggatagta ggtttcaatg cttctgttcc acccgggatc tatgacgtac ttcagcgttt 93900
caatggtaag gcccgtttcc gcaacaaccg tggaaacaat gacccttctt aaaggttttt 93960
ccactttagc ggttaaggga tttttcaccc acagattctt aatttccgct ttcaggccaa 94020
ggtaggcctc attttcctgc gcaatcgcct cactatcgat cggcaaaatc aacattaacg 94080
gcagcttttc tttggcaagg tccatatttg cattattcag caacatcgaa aggaagcgta 94140
tttcagccat accgggcatg aaaattaaaa tatctgcttc cgtgggacga tcatgaatgt 94200
tttctttatg aatagtgaga gccgtttcgc aggcggtctt aatgtagttg ttggtgttat 94260
acagcggcca gtgggtttcc acaccgtact gtcgtccttc caccaaaata atgttttctt 94320
ttccgatacc aaaataggtt gagtatttat gggtatcaat ggtggcggag gttaaaatta 94380
caaagggaat acgcagcgcc cctatgcttc ctctttgcaa catgcgctga agcatacttt 94440
taatatacat gagcataagg tcgatgccta gggctcgctc atgggcctca tctataatca 94500
taaaggcata gcgggaagct atctcatcat ccgtcattgt atgtagctgc gccaacagaa 94560
cccccgcggt tgcataaata aggccccgat tgggtttttc cgtcagaggc ttcgtttggt 94620
agcccactgt ttggcctaat atcatgtcgg ggtagtgggt tgaggcgccg atgtctttgg 94680
cgagggtcac cgcggttagg actcttggct gggtacaaat aaccgagcgt cccaagtatt 94740
tttggaaaga atgcgtgttt tcatttctca gaattctgaa cacgtgtacg ggtaaggccg 94800
tggattttcc ggaaccagtg cgtgacttta taatgagcac ccggtctgcg agggaggttg 94860
gaatggcccc tccaaactcc gggagacgtt gttttatcca agtgatgatg taatgaatag 94920
gaacatcatt cttgtgctca gcgggcacgt tatagagatg accaggctcc aataaagtcg 94980
gttttcccat attctattgt tttaaggatt gattgttcat aaatattttt atactctgac 95040
caagaaatta tttttttatt aagccggtta tttacgttgt tatggaacgc gaaggtccag 95100
tactgaaagt cctccgagtt gtttaatgtc aagggatttt ttgtaagata cgaaaaggcg 95160
tggtgctggc acctggtgca tggcagagac tcgataaagt tcagtatcca ttggatggct 95220
tcatattttt ctttccagct aggagcgtct gaaaaaaaga tagcatatag atgcaaggat 95280
cgccagtatt taggtcccca atgcaacatt tataaccttt tgaaaaatct cattccatat 95340
agaggtaaat atttttttc catggagaat ttttttgcac tcttgaaggg attgcgccac 95400
atcgtcaaat gtttttttgtt ttccatgtat tttggcgtaa ttccagccag tatctgtgtc 95460
atggtcctta atgtcatccg ctaactgaaa ggcatgtcca aaacaatggg cagccctttc 95520
aatcatccca atgtcttcaa cggatccagt tcctaaaacc cagcccataa taaacgcgat 95580
cttaaaaaag ggaatggttt tttctggagt gtctactaac tgaccggaac ccgcgctgtt 95640
tagagagtgg cttacaaagg tacacagcag cgctcccagt tggttgggat ccggaaacct 95700
tggacagtgt tccttaatcc agtcgatttg ccggcaaata ttttgaaatc cttgcatggt 95760
tagcgccaga gcgctcatct gcgccttggc tacgccaaag cgggcccaca ctgtatcttt 95820
atttcgccgc ttcacatcgt tgtcaaagga gggcatatca tcgataatca aagaagctac 95880
gtgaaagtac tccgctgcta gggcggcctc tgccggataa ataggcgccc caaaggaatg 95940
ttgcaactga caggcccgaa caatttccat caggataatg ggacggatat acttcccacc 96000
tcttagagcg taagagcaag gctctgttag ttgtccctta aagtccccat cttcaatagc 96060
attatttaag atggtctcaa actcttcact aaaggtttta taatttttag gattcagtgg 96120
atgtattcca tgaaaaagcg cgacactacg cggtgctgtg attctaaaat acttaggttt 96180
gcgcgtatag gatattaaaa taataataag aactacaatg atggagatat agatgagatg 96240
caacatgctg agttgtctcc ccgcagggaa tggtcctttt ccgcgcttgt taacggtacc 96300
gaggaggcgt tgaaatcttt aggaaaggtg ctgtctagtt tggaatctcc aattcctccc 96360
gtatatttag gtatataatt attgtgtcta gaaattgttt gctttgaggt atcaaaatat 96420

-continued

```
tcagcctgac cgctatttct tttagaataa ttcggtatag ggcttgagta gttggcaata  96480
ctcttaaacc ggggcaccaa ggtaacaata ttttccatat aatgggtttg atacgctttg  96540
tttaaaaatg ggcttaccgg ctttatgctt gttagttgtg cattgagtac cggtatgtct  96600
tctaggattt gtggctttat agaatgatta gcaaacacag aatgtagtat attagatact  96660
tgtagcatat gtctatttgc ggaaaattcc tggtattctc tgccgtgttg cgaatctttg  96720
ggcggaaggg gaccaagcat cggcacgtcc gtgtaggtac tggtggattt tatgagttcc  96780
tgctctatgt tcggtttgac atgtggattt cctaaaggaa tacctctacc tgcaatccct  96840
ttttctaccg acgcaggtag attgtgcgct aaacacaaaa tattgtacac gtctttgtgc  96900
ggaatatatc cgttatagtg ctggcccggc atctgatcgc caaggtgctg ctcatgctta  96960
atggtaccct ttgttctgag tttaggaaga tcctcgtacg aaaaaaattt tgtgtgctcg  97020
ctgaacctcg tagaaggaac cgaactattt tttgggtttt ttaaggaagg caatgaggaa  97080
ggctgggtca gacaattttt ctgtgtgccc tttaagctag ccacctgcgg aaatgttttt  97140
ttttccgtac gaacaacatt gcgcctaatt aggttttccg tatgggttga aaaagcagga  97200
cgatgatttt taaaatgatt aaaaagttta tttttggaa tggagctgta cggctccaga  97260
tcttgcgcat cgccgtaacc aatgtttttg tgctgagggt tcagcataaa agaaaagtta  97320
cgtagatcac tgagttgcaa tccctttca gcctttcag gactattagt gtattcattg  97380
tatacaggcg cggctccatt tttgttgccg cagtaccggg aatttagtat attatcagaa  97440
taccggttat gacgcggcaa atcgctttcc caaagaggtg gatctgacct ataatcggct  97500
aacagctttg aagcataatc atgatacatt gtatataaaa gttaattatt atattgagaa  97560
ggcataatta cttcttgtag gggtacaaga ggctttgaat caggcaaact gacgggtttt  97620
gaatcggccg gctttggacc ggcaggtatc tttttaggtt gatcttcttc tagctcatta  97680
gacacggatg ggggagaaat aggaggaata atttcatctc cgcccttata tttgtcatgg  97740
atagaagaaa caattacatc catgtttgat ttattataaa tgtcgtttaa ctggtgattt  97800
aaaacataat aatgcaaaaa taatagggct acaatgcata tatatacgta aatagccgtc  97860
ttcgtttttc gtttttatc caccggcgga ttacaaattg caaaaaatac aactaatacc  97920
accgctgtaa tgattaaggc cacaatgaaa ggattttgaa aggatgtttt gaacggttcg  97980
cacgtataaa tttttctcc taaattattg atacccgcaa taaaatctac attcatttta  98040
tatatttata aattatgaaa aatttagagt tacatctccg ccggaccaat cattgctaaa  98100
atttgaagat tcttcaaaaa ggcccgactg gttgaatgtc ttctgctcag gtttccaaaa  98160
attttccaag aatggatttt gaacaatagg ctcatcttga ttttcttctt caaggatatt  98220
ttctttgata tcaagaacag cttctttaaa ctcaggtgta tcttgattaa actcaggttt  98280
atcctgatca atcgcaaaaa tattatcttc ttcagatata tcctgtttaa tcgcaagaat  98340
agtttcttcc tcaggtttat cctgatcaat cgcaagaata ttttcttctt caggtttatc  98400
ctgaccaaac tcaacaatat ctttctcgct aaatccgttt ttagtgtgaa gctcttggtt  98460
ttgaagagaa ttatcaaaat ctattttagt tgttgtccta gaccgtggca cgggatagtt  98520
atctaatggt ttacttacta tagtcctcga atgtggcacg ggataattgt ttggtgactt  98580
gctggttagc tcttggcttg ttaatagttc ttgttttctc aataattcca tctctactac  98640
ttctttttga tccgctggtg tctcttttg gtattcttca ttagaaaaat gttcagaggg  98700
taatgtttca ataaactttg tgagtggata gctgctcttt gatgtagaag agcgttgaat  98760
```

```
ttgctgataa aggagttgaa caagtcgccg gtattcactc tgtctttttt catatttttt  98820
acgtagcgtg gagagatctg ctaagagcga cttgttttca gatgttaatt cttcaatttg  98880
atgaagaagg ctgcgattgt atgaactaag tcttgcatac gtttcttcta attctgtctc  98940
cggctccaca taggcctgtt ttcgcagaaa tttattgtat agttccattc tttttttgag  99000
cagaaaggta agactataat cttgcatttc tttcgtaact ttatggtagt tttctttccg  99060
gtttttgata ataaagggca gcattttttc tgttgtgata aaggtgccca gattgctaat  99120
gtagtcgcac agtagcaatt ccaagataga ttctttcttt tcaaggctta tagattggct  99180
gtattcttta ggtatgaaag aatcaacaat cgttgttacg aagtttgaaa agtttaatgt  99240
tttgctgtta atttgggtaa tgttacaaaa atatttgtaa aaactatcta gcatttttttc  99300
ataaagtttt ttattttgtt taacccctaa aatatagccc tttacttgat actgatattc  99360
cgtaacaatg gaatgttttt tgtatagtgc atttttgtat aaaaagttat aaaaaatgtt  99420
gataaaatac gcaccaaggg tttcaaaaat acttataacg tgggattctt cctgatccat  99480
tatatcatat gtaatattat tttaataaaa aattactgac gaataacatg caaaaaaaat  99540
atgtttaaac ttattttaag ctagcactta tttaaaagtg ttttaaacac gttttaaatt  99600
gtatgttaat acacttaaaa attaagccga aatttgctcc aataaggatt acttttatca  99660
atgaccacct ctttactata aacggcttta cataatttta ataatgcttt agagccaaag  99720
ctgaaggcag tgggaagcgg cactgtacta tggtaaaaat gttgccgatg ttcatcctcg  99780
cggatgtaca caagtttcct atatccttta aacacaatat ggctaatttc ttccacatac  99840
tccttatcct gtttggaata gcggttgctt tgacgggaaa aattcgacat acaaatagag  99900
gcatttgtaa aaatggaaac aaatgcgttt ttacgaagat tggcgggtaa atcggtatca  99960
tcttggcagc aaataatcat cgaaataaaa cagtgacgat tttggtaaaa aaactttttta 100020
aaaatttctt ttgtaaataa tgggtgcagt tcggccgcgc agtcgtctaa tattaaaagt 100080
aaacgaggat taagattgat atagtttaac gtaaactttt catcctctgt aaggcataag 100140
tttttataca tatgaatgtt ctgtataata atttttttta aaagttgctg ataaagcgat 100200
gtaatctttt cttctttttt ttggtccgtt tgttcagcct ttaagcactc cacttttgca 100260
atatttttgt tttccttttg ctgtatatcg atcggaagtt tatgatacaa tgtttttagc 100320
atatcgatgt tgtttactcg actgtagatg gaggacatca tagtttgccg ctgccagatg 100380
gcctccaaaa agcgttcagc gcccttgttg tcattttttt tttgcttatc ggcgagccac 100440
aagcggtagt gtattagagt tggatgtaca aaaccctcat atgaacgatt tgagggttcc 100500
gagggggcaa ccactaaaat ttgttcaata tggggttgca ggattttcat aatatgttta 100560
acgtacacgg ttttgcctgt ttttgagggg ccatatagca cagttgtttt atctataaaa 100620
tgatgtgctt tgaactgtag ttcaggaatt agcttccctg aatgggtcgt tagggccatc 100680
tctatattat tacaattctg cttttgtata taaaatttct ttttcgagtt tattattatt 100740
gttgacccac atatctaccc gtatcgtatc atcaggcaca ttgagcattt caagcgcatt 100800
atctaactgt ttttttgttt ttatcagctc gctttcttca tcgggggtta aattttcttt 100860
actaagcagt tgcttaattt tttcttcgca gtcgtctata aaatcatact ctcgagcttt 100920
tttgatattt ccagatgctt tttctaggtt ttttagctcc ttaaaggaaa gcagtccctt 100980
aatcccgcta tccgtgtgaa aggttgaatt atagatggag agccccggag catccgggcc 101040
agtttcttgt atatttttttg ctttttttgtg gtaaatagta tttcgtaaaa tctcttttcc 101100
tatctttagg tcttcctcat gacggtccaa aatccgtttt attatttcat tattttgatt 101160
```

aaaataattg tagcgctctc tgttggcctt aaagcttccc aggagtgtcc agttgcctaa 101220
ttgaatggat gaaacctctg agaaaatctg gtctttatat ttataataaa attcatcaac 101280
cttttgttgg ttgctgctat ccaccacatc ataaataatg aaggcaaact ctaggtcggg 101340
tttttctggg tagatgcttt ccgtagcggc ccgcaactct tcgtaattat cctcaatgta 101400
ataattccac ttataaaaag tatcctgagg tggaatatgc tgcgaaagat atctagtaat 101460
ttttgtgtta aagagaatgg gtttaaacgc cctcggattt tcaagcatat gtttaatgct 101520
ttggtgaagt tctatatttt gtaatatgtg ggctgctgcc ctatagccct gtggggtttg 101580
ggtgattgca tcaatatcgg cctgaagctc attaggcaca tttaatgttt tttgcatgat 101640
gtgtaaaggg atgcgctcag gatctgctaa atcggtgtat tctgtgcttg tacaagtgct 101700
tgcacaggta tctacattgg tatctgcaca catgcttgca caggtgtcta cattggtatc 101760
tgcacacatg cttgcacaag tgtctacatt ggtatctgca caagtatacg cactttgagc 101820
atgaagatta ggatcaaaca caaaatgttc tcgtaaaaag ctatcgatcg ttgttttagc 101880
ttccttgctt ttctgcgtct gggttttgca gctatctgct atagataaaa ttgtatttac 101940
taccgattca gagggaacat cattagtttc ctgtttcaaa gtatcaacta acgttattag 102000
ctcactgaga agagttttgg tcgtgtgggt aggttttgaa taggaaggca tccattcctg 102060
cagagctttg aagacatatc caataaagct agtcattata agacgtcgaa tatactgctc 102120
ccgcaaattt gtaaaagagc aaaaggccac cctgctatca tttttgaact gtttgtaagg 102180
gttcgtcctt tggtaaagct gtttaagcgt ttcttcggat atttcagtag agggatcctc 102240
caatacgttt ttgagaagct catcaatatt aaattctgcc atatcttaga gtttattata 102300
tacatattaa agctttaata taaggggggt ataacaatgg acgaaatcat caataaatac 102360
caagctgttg aaaaactttt taaggaaatt cagcaaggat tggccgcgta tgatcaatac 102420
aagaccttaa ttagtgaaat gatgcactat aataatcata tcaagcagga gtattttaac 102480
tttttaatga ttatttcacc ttatcttatt agggcgcata gcggagaaac gctgcgaaac 102540
aaagtaaata atgaaattaa acgtcttatt ttggttgaaa atatcaatac caaaatatct 102600
aaaacgctgg taagtgttaa ttttttacta cagaaaaaac tttcaacgga cggggtgaaa 102660
acgaaaaaca tgtggtgcac caataatccc atgctgcagg taaaaacagc ccacaacctt 102720
tttaagcaac tatgcgacac acagtccaaa actcaatggg tacaaacttt aaaatataag 102780
gaatgcaagt attgtcatac cgacatggtg tttaacacca cgcagtttgg gctgcaatgt 102840
cctaactgcg gttgtattca agaattgatg ggaaccattt ttgatgaaac acatttttac 102900
aaccatgatg ggcagaaagc aaagtcaggt atctttaacc ctaaccgtca ctatcggttt 102960
tggatagaac atattcttgg tagaaatcca gaacaagagt tggggaccaa acaagatccc 103020
tgcggaacca aggtgttgca acaactaaaa aaaattatta agcgcgataa taaatgcatc 103080
gcgcttttga cggtcgaaaa tattcgaaaa atgttaaaag agataaaccg cacagactta 103140
aataattgtg tttctcttat attgcgtaaa cttaccggag tagggccgcc tcaaatatca 103200
gagtcgattt tactacgagg cgaatacata tttacagagg caattaagat acgggaaaaa 103260
gtgtgtaaaa aagggcgtat taataggaat tattatccgt attatatata taaaattttt 103320
gacgccattt tgcctccaaa tgataccacg aatcgacgca ttttacaata tattcatttg 103380
caaggaaatg atacgctagc taataatgat agtgagtggg aatctatctg tatggagctc 103440
cctgaaataa aatggaagcc cacagatcga acccattgtg ttcatttttt ttaaagatga 103500

-continued agatttttta gatgattttt tttagttttt taaaagacga aaaaattttt taaaagatga 103560
atattcttaa accccgcaaa ttactttttt ttaggtactg taacgcagca cagctgaacc 103620
gttctgaaga agaagaaagt taatagcaga tgccgatacc acaagatcag ccgtagtgat 103680
agaccccacg taatccgtgt cccaactaat ataaaattct cttgctctgg atacgttaat 103740
atgaccactg ggttggtatt cctcccgtgg cttcaaagca aaggtaatca tcatcgcacc 103800
cggatcatcg gggttttaa tcgcattgcc tccgtagtgg aagggtatgt aagagctgca 103860
gaactttgat ggaaatttat cgataagatt gataccatga gcagttacgg aaatgttttt 103920
aataataggt aatgtgatcg gatacgtaac ggggctaata tcagatatag atgaacatgc 103980
gtctggaaga gctgtatctc tatcctgaaa gcttatctct gcgtggtgag tgggctgcat 104040
aatggcgtta acaacatgtc cgaacttgtg ccaatctcgg tgttgatgag gattttgatc 104100
ggagatgttc caggtaggtt ttaatcctat aaacatatat tcaatgggcc atttaagagc 104160
agacattagt ttttcatcgt ggtggttatt gttggtgtgg gtcacctgcg ttttatggac 104220
acgtatcagc gaaaagcgaa cgcgttttac aaaaaggttg tgtatttcag ggttacaaa 104280 caggttattg atgtaaagtt cattattcgt gagcgagatt tcattaatga ctcctgggat 104340
aaaccatggt ttaaagcgta tattgcgtct actggggcgt ccagctataa aacgtgactg 104400
gcgtacaaaa agtccaggaa attcattcac caaatccttt tgcgatgcaa gctttatggt 104460
gataaagcgc tcgccgaagg gaatggatac tgagggaata gcaaggttca cgttctcatt 104520
aaaccaaaag cgcaacttaa tccagagcgc aagaggggc tgatagtatt taggggtttg 104580
aggtccatta cagctgtaat gaacattacg tcttatgtcc agatacgttg cgtccgtgat 104640
aggagtaata tcttgtttac ctgctgtttg gatattgtga gagttctcgg gaaaatgctg 104700
tgaaagaaat ttcgggttgg tatggctaca cgttcgctgc gtatcatttt catcggtaag 104760
aataggtttg ctttggtgcg gcttgtgcaa atcatgaatg ttgcatagga gagggccact 104820
ggttccctcc accgatacct cctggccaac caagtgctta tatccagtca ttttatcccc 104880
tgggatgcaa aatttgcgca caagcgttgt gacatccgaa ctatattcgt ctagggaatt 104940
tccatttaca tcgaatctta cgttttcata aagtcgttct ccggggtatt cgcagtagta 105000
aaccaagttt cggtacgcat tctttgtgcc gggtacaatg ggtcttccaa aaggatctac 105060
aagcgtgtaa acggcgccct ctaagggtgt ttggttgtcc cagtcatatc cgttgcgagg 105120
aaacgtttga agctgcccat gggcccccat ctgggacgtg ccctgaatcg gagcatcctg 105180
ccaggatgaa tgacatgcac ccaatatatg atggcccacc atatcatgga aaaagtctcc 105240
gtactgggga ataccaaagg taagcttgtt tcccaaggtg ggggtacccg tatgcgggcg 105300
tactttattg tattcaaacc ctactggaac ataaggctta aaatgcgcat taaaatgcac 105360
caaatgtgtt tcttcgattt gactcaaagt gggttcggga tcgggtttcc cataactttt 105420
gttcacattt ttaatgttag agatcctgct attcagcaag tcttgggcca atataatctt 105480
gtcggccttc ccatcgttag caataagaca aaaagctcct cctgatgcca tatataatgt 105540
tataaaaata atttattgtt tttattaaat atggcggttt atgcgaagga tcttgataat 105600
aacaaagagt taaaccaaaa attaattaac gatcagctta aaattattga cacgctcttg 105660
ctggcagaaa aaaaaaactt tttggtgtat gaactacctg ccccttttga cttttcctcc 105720 ggcgacccctt tggccagtca gcgcgacata tactatgcca tcataaaaag cctcgaggag 105780
cgcgggttta ctgtcaaaat atgtatgaaa ggggatcgtg ccctcctttt catcacctgg 105840
aaaaaaatac aatccattga gataaacaaa aaagaagaat atctgcgcat gcacttcata 105900

-continued caagacgaag agaaagcatt ttattgtaaa tttttagagt ctagatgagc ttttacgcaa 105960
tgttgtacag tgttgtatat atgtcttgta agcatttgtt gtagagtaat aagtaaaaga 106020
taaataaaaa tgactattaa aataaagccc aaaccattaa aaatattttt atctgttaga 106080
tttaatttaa taaatggctc atggaatgtg tggtgcgccg ctgcatgagg tgtggccgca 106140
tgggatgtgg tcgcataaga tgtagctaca tgggatgtgg catttgcttg catgtaagga 106200
tcatgatgtg ttgggtcttc atcccagcaa taatcgccat ctttatctag ctgaattgta 106260
taccccatta tatatcactt attatttttt tttaatgttt catgaatttc attataggcg 106320
gtgaaagggt cctcaggccc cttctgtaaa agattataga gatcttcgga cgctttatgt 106380
ttcgtgcgaa ttaaggcggg atataacaaa agagagggcc ccagttccaa acaaatttta 106440
cttagcgggc tcatattttg caccaagttt cccactactt gcgatgtttc ataacgcatt 106500
ttaaagagct ttatcataaa agtgttatgc aggccggtgt agtctggcct atagttaagg 106560
aaggggattt ctctggtacc gtcaaacacg atctcaagtc ctctagcaag cccgatcaaa 106620
atttcttcag caatggatga gtatctaatt cctacattac gaagcgtaag catttctata 106680
acatcatcta tttcctgcat agaggaatct attgtaggaa ttttaatatc atctgtgctg 106740
atttgttcat tcccaagata ggtaagcagc atattaattt tttctagctt tactagctta 106800
gtcttacgct cataatcatg atcttttta taaaaagagt tgggatcacc gttggaccgt 106860
agatgattaa taaggcggtc tacttgcttt gtactaggtt taatactttt ttcactatac 106920
tcgctttcag catagtggtt tttacgatct cttttagaaa tagctgtttt ttgagatgcc 106980
tcagactctg catatttttt tctatgcgta gaaagagaat aaccgcggtc attacgtgaa 107040
ctactgttgc atgcaaggcc tcggcgcgtc ttaccgctgc gcacactgcc attgcgtata 107100
ctgccatcgc gcacactgcc gctgcgtata ctgccattgc gtatactgcc gctgcgtatg 107160
ctgccgctgc gtatgctgcc gctacataca ctatcactac atatgctgtc agtacatacg 107220
ctatcgcggc gtatgccgcc gtgtacctta tcgccgcccc tacccgaggg ttttttagat 107280
ataatactgt gtggggagtc aagcgaaaat tcagggtcat taaagttaat gcccaatgac 107340
tttgccaatc cattaagctc ttcatcaaaa tgatcggtag gaaaactttg ttgcttgccc 107400
atgacctgtt tttcaagttc ctccaaattg gcttgctcat ttatatggag attattcata 107460
agcgtcgtaa ttccagcaag atttgctcct tctaaaaatg tggtgtcctc catcggatat 107520
actatactat ttaaaagctt ttaaataaaa atgtgtttgg aagaaatgct ctcttcaagc 107580
gtgtgtagct cagatataaa tgcctcctca gaaagctttc caccatactc ctttctcatc 107640
gtataggagg gcgccggttt aatgtaggaa atccactggg aggtaaaaaa ccggtacaac 107700
atatttagca gctcgcgggc ctcccacctt ttgggctccg tatagtgcac atcaacataa 107760
gaggcggcgc atgaaaagct gcaaaagttg ccgagaacgc ccatctcaat ctctcctcgc 107820
tcattttcac gcatataggt gggcacgaat tttgggacag tcttgaaata gagatgacat 107880
gtccagcatt taaagctaga atgggtaacc catttggaaa cagtggtgaa tacggagggt 107940
agcttttttt cgacctcggc ttcatcgtca ttcgtattta acgtatcggt ggcagttttt 108000
ttggattgca agcattcttc aatggtaatc ccggataagt ataaaatatt aggacaatta 108060
gtttccataa ttttgatagt tatttttata caacatggat ttaattaaag ataaatggag 108120
gacgaaacgg aactgtgttt tcggtcaaac aaggtgacga ggcttgaaat gtttgtctgc 108180
acatacgggg gaaaaattac cagccttgca tgttcgcata tggagttaat taaaatgttg 108240

-continued caaattgctg agccggtgaa ggcattgaac tgcaactttg gccaccagtg cctaccgggc 108300
tacgaatctt taataaagac tccgaaaaaa actaaaaaca tgttgcgccg tccgcgcaaa 108360
acagaaggcg atgggacttg cttcaatagt gccattgaag cctccatttt gtttaaggac 108420
aagatgtata aattaaaatg ttttcctagt accggggaaa ttcaggtccc gggcgtcatt 108480
tttccggatt ttgaagacgg aaaaaacatt atacagcagt gggtagactt cttgcaacat 108540
caacccattg aaaaaaaaat ccagattatt gaatttaaaa cgattatgat taattttaag 108600
tttcaaataa acccagtgtc tccccgcgtc atcattcatt taaaaaaatt tgcagctttg 108660
ttggaacaca tccctactcc atatcccata cgtgaaataa agcctccatt agaagactca 108720
aaagtatccg caaaatttat ggtcagtccg ggaaaaaaag tacgcattaa tgtttttctt 108780
aaaggtaaga taaatatttt aggctgcaac acaaaggaat ccgcggagac catttatacg 108840
tttttgaaag atcttatcag cgtacattgg caagaaattt tgtgcgtgtt accggtaccc 108900
gattaaagaa tgttttcatt aataaggtaa tcgactatgc taaaaagaat aacaagaaaa 108960
ataccttgaa gaactatacc aaagtaggta ggtttctgc atgtcacggc atggttaaaa 109020
ttgctaataa tgtagtccac aaaagcattg ctcaatacga ctaaaaatag taaaaaaagg 109080
ataagtgctc tttttatatc catatacttt aaaacttatt ttttacacta ataatttcct 109140
gcggccgcaa tataaactgt aggtcatcta taacgcccag acctgttaaa agtagagtac 109200
tatgttttaa gggatttaaa atatccgccg caagaatgtg aatataattt tcaaagtggt 109260
ttacaggaat gcgtaagcgt tttttttgc actgcggttg gtttagggtc gaatactggc 109320
aggaggtata tatattaata agaccgcggt cgatggtttc aatatcttca tagaattcaa 109380
tgcgcggcgt caaaagtttt ttaagatgtt gacataactc atcatacgtg taggactgga 109440
ggggggaaag aagggtgtag tcaaagttaa aaatgttttt ttgaagaacc tttaaagcat 109500
gttccgcgtc cgtggtttcc aaaatatgtt ttatggtatg aatgtcattt aaatctacaa 109560
agtctgacag ctttgtgtag aactcggtga cggaggttat tttctggaaa tcggtttttt 109620
gaaaaagatt ttcaatgtgt ttgcgggttg agttgctttg cagtccatac aagacatcaa 109680
aaaattcaat cagcaaaaac ttatacaaat ggttaatata aaaagctttg ttggccttat 109740
tctgctgagg atatggttcc tctaggggat atagaatggc ttggtctata tccctaggat 109800
caatagtcaa tgttgcgatg ggaagctttt ccagcgtagc gggaagagtt tgggttggag 109860
cgtagtaaaa gtatagcccg gtttttccct ctgaaagaaa gcccacaaat tcttttttta 109920
tattttgcag caccgctgag ggtacgattt cgtactgttt atactgtttg ttgaaaaggg 109980
taataaattt ccaggtttct tcaaagcttg caatctgggt gggccgcaga tcaaagtcga 110040
tgggaatgtc gtcatgaatg taggatgata gtcttatagg aaaataaata gggcgatcgg 110100
tgtctgaatc gataagtaaa gcataacaaa agttatgcct gttgataagt tttttaccaa 110160
ccgtgtagcc gggaatgttt ttcacgtcat ggatatccca ccagttatcc ttgcacataa 110220
actcgctcat agactggatg acctccatca cagggtcatc ttcggtaaaa atatactggg 110280
cctcactgtt tttcagaaat ctttttttgct gggtgatggc cattgggtag atcccttcgt 110340
ccgtgtcaaa gataatggct atcttcttcg atgggctaag aattttttgt attgtgctgg 110400
gggacacctc aaacccgatg tcgccctgtt tatctttaaa aaagacacag tgaaggtcgt 110460
agcatatggc aacaaggtcc agaaagatgt cctgccatgt ggtgtcccat tgaagcagtt 110520 ggttttttttg ttcaacaaag gtttgtaaga taaggtttgc cagctccgcg ccgctggaaa 110580
acatgttgcc ggccccattc cccaaaatat agtactgcgg tgtgttggcc gcctttgcaa 110640
tttcaatggc aagggccttg ggggcaagat ccaaaattcg agcaagggaa taaaaaagcc 110700
cggcattgct aattccaagc atggtttgct ccacccccac aatgcaaaaa atgtcgggct 110760
cttttatcgt atttaaaaac agttcatctg ctatctggtg gggtagaaag gcaatccggt 110820
tcaccggtat tttttttcca taggacaagg tatgacgcga tgtttgtgta ttaagatcct 110880
ccaggtcttg ttctacaaac gtgtgcttgg tgaggcaggt attgttaata tagaaccgct 110940
ttgtgcccag cagggccttc gtcttttggc agcacggcag acagtaattt agggggtggc 111000
ggccttctag taggcttaga tgagggtagt caggatgcgg gcagctatag taggcaggta 111060
ccccctccgt gaaattccaa tactttacta gctccttgcg cttggctggc ggcatggact 111120
tcacctcggc ctctgagtaa atgacgggtg gccgtgggtg ctggcatagg acggagtaaa 111180
ccgttgcctg cgtgtcgtac ttgcgcaggt catacaggtc ggggtcctgt tcttgaagcg 111240
cacgtagctg agaggctccc tttccttgtt gtttatcgtg cagttgagag agtttattaa 111300
ccaaaatttt gtcaggcccg gtgatcaagt tatctaaaaa cacaaatagg taaacccaaa 111360
gatagttaaa ctcttcctgg gtaatgttaa acatttctat tttgatatct gtaaccctat 111420
ggtagatgcg aatgttgcgg ccgccgtaga ttgtttccca ccgggccgca acatttgtgt 111480
caaagaggta cgcatacgtg ttttggagca acgcaacatt gatgtccatt ttgcgccccg 111540
gaccggagga aataatgatc atccgttcga tttcgtgggg atcatacgaa taaatcccct 111600
ttttaaataa aaaattgtag accccggttt gctggaggcc ccgcacggaa ataatccctg 111660
cttgctcgta ttcccgccaa cgacttttga gctcggtaaa tcccttgcta gaaagcgtat 111720
agggccaaaa ggtggacacc gacatggagc tgatagaaat ttggatgtcc tcgttggagg 111780
gaaggggcag actccctcca cgaggaaacg cggcaggccc catatcatta attgtatgaa 111840
taataggatt tatgaaatta tttagggtgg acaccacgga gttaaagtcg tggcgctcgt 111900
tttctgacca attgctttcg ataaagtagt gcccattatt ttgtatggta agaataaagg 111960 ccttttttatt gataaagcgt attaaaataa tagtgggtac acggaatgtt ttattgctga 112020
atttttcagg ctccgtggaa gttatgtggt gtttggaaac cacggtggga cctgttttac 112080
tataaaagaa caccaccagc tgaggaatat cgggagtagc tggaaatagg tcgaaaacat 112140
tgcgcacatt aatttgaata tttacgaggg gtgaaatttt aatcattgcc gaggtgacgg 112200
ccaacgtgcc gcgtgttagt ctattcccct cgtacttggc aatgacttgt tgtgctctgg 112260
catacgtaaa gtttattagt ttttgctcta ggagaagcct ctttttaaga ctggtcaagg 112320
atggagaaag agcaggatac tgtttttcca tttgtaaggg agattgtacc aatagtttaa 112380
aggcatcggg ggaaagaaga ggccaatact tcataataag gccgtaatag agtaagtcaa 112440
attggtaatt atcctctatg gcaatggaga tttggcgccg catgggggcc actagcgtgt 112500
tgaggtctgc tacaaagatg tgatgaatgt tttttatgag ctggaagctg tcgagcgctt 112560
ccacatagag ctcatctttt tgactttcca tagatgcgtc gatgttcacc ccacccacct 112620
gttgaaactc ctttttgtag tcgcgaatgt ctaacgccac cccgctaccg cttaacaata 112680
ggcgatacgt tacctgaagc gcattgtttt gaaaaaagaa aatgtgttgt ctataagggg 112740
ggatccctgt ggcaacgtaa atttttctc gaatgtcttt aaaagtgtct tcagggaaaa 112800
tactatactc gctatacatc gtctcaattt ctggcatcat cacgtttgtc tcctcgccac 112860
gatcctccac aaaaagtttt tcaaactcat ctaaatcatc gctatctcca cccaccacgt 112920
attgggaaag ctttttctcc caatcctcgc cgtaaaaatt ttgtaaaatt tctttgtcct 112980 tagggggttcg ctgcaggtct ttgcggcagg cctgtaacac gtttgcagga acggatccca 113040
aaaaaataaa cgtcttcgtg tactcatttt ccacaggatt ataaagagta actcgtagag 113100
gatttgttaa aaagtcattt tggaaatcca ttatacccgg tatagaaaat aaaatttaaa 113160
ataaaaacgg atgatatcta tcatggaccg ttctgagatt gttgcacggg agaacccggt 113220
gattacccaa cgagttacaa atctcctaca aaccaatgct cctctactat tcatgcccat 113280
tgatatccat gaagtacgat atggagccta cacacttttc atgtatggtt ccctcgaaaa 113340
cggttacaaa gcagaagtaa ggattgaaaa catcccagtt ttctttgacg tacagattga 113400
gttcaatgat acaaaccagc tttttttaaa gtcgctactg acggctgaaa atattgtgta 113460
tgaacggctg gagacgctca cccagcgtcc tgtaatgggg taccgcgaga aggaaaaaga 113520
gtttgcacca tacattcgaa tattttttaa aagcctgtat gagcgacgaa aagccattac 113580
ttacttaaat aatatgggct acaacacggc cgcggacgac acaacctgtt attaccgaat 113640
ggtttcccga gaattaaaac tacctcttac aagttggata cagcttcagc actattccta 113700
cgagcctcgc ggcttggtac acaggttttc cgtaaccccc gaggatcttg tttcctatca 113760
gaatgatggc cccacagacc acagcatcgt tatggcctac gatatagaga cctatagccc 113820
tgttaaggga accgttccgg acccaaatca ggcaaacgac gtggtgttca tgatatgcat 113880
gcgcattttt tggattcact ccacagagcc tctagcgagc acgtgcatca ccatggcacc 113940
ctgcaaaaag tcctcagagt ggaccaccat tctatgctcc tctgaaaaaa atttgttgtt 114000
aagctttgct gaacagttta gccgctgggc tcctgatata tgcacagggt tcaatgattc 114060
tcggtacgac tggcccttta tcgttgaaaa atctatgcag cacggtattc tagaagaaat 114120
ctttaacaaa atgagccttt tctggcacca aaagctggat accattctaa aatgctatta 114180
cgtaaaggaa aagagagtca aaatctcggc cgaaaaatcg atcatttcct cctttttgca 114240
taccccctgga tgcctaccca ttgatgtccg caacatgtgt atgcagcttt accctaaagc 114300
cgaaaaaaca agcttgaaag cgtttttaga aaattgtggg ttagattcga aggtagacct 114360
gccgtaccat ctcatgtgga agtattatga aacacgagac agcgaaaaaa tagccgacgt 114420
ggcctattac tgcattatag atgcccagcg ctgtcaggac cttctggtgc gccacaatgt 114480
tatccccgat cgcagagagg taggaattct gtcatacacc tcgctgtatg actgtatcta 114540
ctacgcggga ggacacaagg tatgcaatat gctcattgcc tatgccatcc atgatgaata 114600
cggccgtatt gcttgcagta ccattgcccg aggtaagcgg gaacacggaa aatatcccgg 114660
cgcctttgtg atagaccccg ttaaagggct tgaacaggat aaacccacca caggtctcga 114720
ctttgcgtcg ctgtacccct cactcatcat ggcctacaac ttttcgccag aaaaatttgt 114780
agcctctcgg gatgaggcaa atagcctcat ggccaagggt gaatctcttc actacgtctc 114840
ctttcacttt aacaatcgtc tcgtggaagg atggtttgtg cggcataata acgttcctga 114900
taaaatggga ttgtacccaa aagtactcat cgatctactt aacaaacgga ccgcccttaa 114960
acaagagctt aaaaaactag gtgagaaaaa agaatgtatc catgaatccc atcctgggtt 115020
taaggaacta cagtttcgcc atgccatggt agacgcgaag caaaaggcgt tgaaaatttt 115080
catgaacacg ttttacggcg aggcaggtaa caatttgtcg cccttctttc tgcttcctct 115140
agccggagga gtcaccagtt cgggtcaata taatcttaaa cttgtctata actttgttat 115200
caataaaggt tacggcatca agtacggtga caccgactca ttatacatta catgcccaga 115260
tagtctttat acagaggtaa cagacgcata tttaaacagc caaaaaacga taaaacatta 115320
tgagcaactc tgccacgaaa aagtgcttct gtctatgaaa gccatgtcta cactatgcgc 115380

-continued cgaggtgaat gaatacctgc gacaagataa tggcaccagt tacctacgta tggcctacga 115440
ggaagtactc tttcctgtgt gctttacagg caagaaaaag tattatggta ttgctcatgt 115500
aaacacaccc aattttaata caaaagaatt attcatccgc ggaatagata tcattaagca 115560
gggtcaaaca aaactcacca aaacgatagg aacgcgaatt atggaagaat ccatgaaact 115620
acgccgccct gaggaccatc gcccccctct tattgaaatc gttaaaacgg ttttgaagga 115680
tgctgtggtt aacatgaagc agtggaattt tgaagacttc atccaaacag atgcgtggag 115740
accggacaaa gacaacaaag cagtccaaat ctttatgtct cgcatgcacg ctcggcgtga 115800
gcaactaaaa aaacacggcg ctgcagcatc gcaatttgct gagcccgagc cgggagaacg 115860
cttctcctac gttatcgtgg aaaaacaggt acagtttgat atccagggcc accgcacaga 115920
ttcctccaga aagggggaca agatggaata cgtctctgaa gcaaaggcta aaaatcttcc 115980
tattgatata ttgttttata tcaacaacta tgttctaggc ttgtgcgcga gattcattaa 116040
tgaaaatgaa gaatttcaac cccctgacaa cgtcagcaat aaggatgaat acgctcagcg 116100
ccgagctaaa tcctacctac aaaaattcgt gcaatccatt caccctaaag acaagtctgt 116160
cattaagcaa ggcaatgttc atcgacagtg ctacaaatac attcaccaag aaattaaaaa 116220
aaaaataggc atctttgccg acctttataa ggaatttttt aacaacacca caaaccccat 116280
cgaaagcttt attcaaagca ctcagtttat gatacaatac tttgatggag aacaaaaagt 116340
aaaccattct atgaaaaaaa tggttgaaca gcatgctacg gctagtaatc gagctggtaa 116400
gcccgctggt aatccagccg gcaatgcgct gatgcgggct atatttacgc agctgattac 116460
ggaagaaaaa aaaattgtac aagccttata caataagggg gatgcaatac acgatcttct 116520
cacctatatc attaacaata taaattacaa aattgccacg tttcagacga aacagatgtt 116580
gacgttcgag ttttccagta ctcatgtaga actgctatta aagctgaata aaacgtggct 116640
tattttggct ggaattcatg tggcaaaaaa acatctgcaa gctttttttgg attcatataa 116700 caatgaatcg ccgtctagaa cattcattca gcaggctata gaggaagaat gtggcagtat 116760
taaaccatct tgctacgact ttatttccta atacttctta agaaactctt taaacaagga 116820
cttcgcatgg tcaaaggttc taaacccatg gcccttatga ttcgccaaaa aagcggtttc 116880
atcaagattt tctaaccctt tcacggatga agaaataagg tgttcggcct cgtttgccca 116940
ttttctatga tttttttca cctcgggttc tagatctgtt ttctccatat actcattgtg 117000
gtcatatttt tttttgggag gaggcgtggg tggaggaatg ggtggaggaa gtacacccga 117060
ctttcccgct tcaaccgttt tataaaaaaa tagaagcata atacaaagaa taaggactat 117120
cgcaaatatg ataaccagtg tcccagtcga gggcattttg ttatataagt aacgtttttt 117180 ttattttta taattcgaat gaagaaccat gttgaatagt cttctactca aagacatttt 117240
gttatacggt aaatgagaat ttataaaatc cgaatatcac tatcatactg tttatctgag 117300
aaggtctcac tgggtcctgt gatggagaac ccatactctg taatgctggg gtttataatg 117360
tggtcaggac tgacaagcac atttctgaac tgcgagagtt ctaggtttag acgcagtcgt 117420
aatagtcgct gtatatttgt aataaatatt agattgcgta tgaggcgagt gtcaaagcga 117480
tcctttccaa tttgtactaa ggtgggcttt tgtattccaa ctcccacttg tttaacgatg 117540
gaccagggtc cttcttcccg attttgttcc gtgatatagg tcagcacact attttctgta 117600
tatgaggtat gatgtcgcat attaatacct ggtgccattc caactggcgg ttgtgcaatt 117660
cgggctgtac cgggacccaa ccatcgtgga gttttataaa catatcgttc tagcgtattt 117720

-continued aaaaattcct taaggttatt tacgagtagc atgaagggtg ctattaaaac aggtggatgg 117780
tttataacca ttgtcataaa ccattgcatt gcttcaatat cattttgtaa tgcttgacgg 117840
ggaggcgggg caggtaatcc acgtatgttg aataaagcgg ttaattgtgc accggctgtt 117900
tggggcgtaa tattttgtat taaatttatc atcgaattgg cttgcccggc atttcctata 117960
agatcgatta aattggttat ttgacctcga tattgttgta cccagttttg aatggcagcg 118020
atgatctcag ggttggattt gttttgaatt tcaggtgttt gtattagatt attcacttct 118080
cttcgtgtat cttcaagctg agtcctaaat gcatttaact cgcctataat ttggtttcta 118140
tcaataacat ttcttaaacc tcgaactgtt tcagccaatc gtatagtacg cacaatttca 118200
tgtaaggcct ggtttatgta tattgacatg ggatggcccc accgctcacg tccacgttga 118260
atacctgcgg ccaaactagg acctgcctcg tcataatcaa attgtgtagg ataaaggctt 118320
ccaaatagca ctttattgaa aatttggtca gaaagaaatt tagggcggcc catatttagc 118380
gcgttgtccc ctctaaagat gcgtgacatg tatccggcgt tgcctttgga tagtaactca 118440
ttcccatatt gagtaataga gaccgagaca taggggttta taagaagttt tagcataaat 118500
tctcgagtat ttatgggggg acgattcgga atgtttaata cctctgcaac atctggttga 118560
ggagccgtgg tgtccagaga tcgtactttt tcagccgaaa tgccgtacat aagacaagca 118620
atttcttcaa aactatagtc atagttgtaa atattggcaa gtggtataga tcgcatcagc 118680
gcatttacat tgataggtat aatattcata tcaaacaagt taaatatgcg ctcgcgctct 118740
ctattagagc caagagtgcg tgtttgacct ttcggcgaca ctattttgtg aatatgattg 118800
atttgctcct cttggtaaga gctttccacg aaggaaatta cgtcttgcaa tgttttacga 118860
agcgaataca ctgcattcat ccctattccc gctgttataa tgggtttatc gtctctgttc 118920
tcgctaataa gattaactcc accaaaagta ttttcattgt acatcatcac tgttttaaaa 118980
ctacggatat ttatgataaa tcggagagcc tgaatggcgt gggtataaaa gtgttcaaat 119040
cgcgtgggag taatttgttc gcgagcaact accgtttcat tatagttttt catgataagc 119100
tgtactccgg gcatatctga gagctgtacc ggatcatttc ccagtaattt tcttgtgccg 119160
tatagtagtt taaactcggg ggagccgctt tcaaggttcg ggtaaagaag aggatcatat 119220
acctcattat tttctattct taggtcatgt aaataataga gcgaaagtga aaatggcata 119280
agaggctcct tattgtaccg ggacatatag ttttgaatga agtgttcttc tgtttcaaga 119340
tagatgggat gatcggtaag ctcgtgcagg acctccatgg cagaatctgc cagagtgtga 119400
gagcctctaa tgatcccgtc gatcactgcg accagtcgct ttcgcacaac atcgctcgta 119460
ttattttgtg cgtctcctag gggcataagc gtaacattgg gacgaaatac gccgccaatt 119520
ccccgcaggg ccgcctgacc gacggatagt cctgtcgcag gaacattgtt attattataa 119580
taaataacgg aatcattatt ggctcccaag agtgccgtca gattagggcg agctagttgg 119640
acatttgtgt attgtataaa ttgttttaga agctctccct ggctaataag aatattaaac 119700
attttgttaa atagtggaag attggctcta taattttctt taaggtaaat gggaatttct 119760
gttaaagtag aaataagatg ctgactcagg ccctggcgat tggtatcctt aataagccgc 119820
tgaagtataa gtcccaaaga cagaagaagc accgactgct ctgtggggtc gcctctatga 119880
ccaaagacgt tgttattgcg tgctaagtca gggtgagcat atcccatctc catcactgct 119940
tggctaaagt tcccattagc gaatgcatta ataagattta gatatatttt tccgctggga 120000
gcatcataaa atcgggtaat atatgaagct atgagctggt taaacaccat catcatacta 120060
cgattatttt gaataccata gtctgatccg tataggcgat aacgtcgaag gttgtttgcg 120120

-continued gcatcattga cattggcata ggttctgagc gctatgttgt cccagtagct aagagtattt 120180
tcctcctggg cgttgttggt acgaataaga ttggagagtc taaagtctcc tagtgccacc 120240
tgctctacac gaagtccaga gttattctcc aaagcatcgt aaaatacgag tctactgaat 120300
actcttccgt attgttcaaa gcgttcagag gattggggat tgttatttat ttgaatatta 120360
gccgcgtccc ttctttgcgc cccacctcga agttgcagta cattataagg ctttgtaagc 120420
aaggtgtagg ttttattaat gatttggtta accccctcca ggcccaattc accgccagga 120480
agcggccttc ctccggcatc ggtaggtggt ttaataagtt tgtcaattaa atgttcttcc 120540
aaccagtaaa atgagccagg attagatcta ttttcatagt attgaataat gtttttatca 120600
atatgcgggc gtagaagatc aagaaaatac ttcgtgtcgg ccatcaaaga atcaattaag 120660
gaaataagac ctgtaaaatc taaatgcact tgagcggtgc tggtttcagg gaagcgaact 120720
tgaaccattt tgttaaaact ggaggtcatt tcgaagatat tggtcaacag gagctgcatg 120780
attcgctgat tatctactaa ataccttgcg gccaactctt gctccggacg aactcctcca 120840
ccagcaggaa tacccacata tggtacaatc caagcaaaaa gagtttctgt ggttaaattt 120900
cggtcttggg ctgctgcagc cgcttcggta gtgggatcag ggtacaccat agaaagccgc 120960
atattgattt ctttaatgac taatcctgga tttctaatct cagagatggc cccgtgtttt 121020
cttccgagcc agtcaataag attggcgcgg ttcacgttgg cagcttgtgt ctctcgtaac 121080
cattcgataa tgctttttg aatcgtatct aggtctaaac ctttaatgtt attacgaaag 121140
ttattaagaa gtacgtaaat agcactcaat aagttaagac ctgtaataac ggtttcatga 121200
aacagaaata ttttgttaac atctgtatct gccagtgact cagagccttg aataagtttt 121260
gaaacgattt gaattttatc ggtatgctcc tttttgagtt cattgatagc ctggcgaatg 121320
agttcttggt aggaaatttt gcccaattct tgttgcagac tgggatcttc aaacatctca 121380
ctaagctgtt tcctaaattt ttgtaccaaa tcccactggg agttgggctg cagcattcct 121440
gtttggacat ccacagagtc tatattgtat agtgccgggc gccacttggg ggtaggctgg 121500
gttgaaggac taataaacct atcggaggga agtaattgtg aggattgtgt atagccatcc 121560
tcatcaggaa gaatggagta gttggtttga ttcatcattc caaaatcatt catagttcgc 121620
gcttcctgaa caatgcgttg aaatttttcc cattcggtgc gtgtaatgac accgaatctg 121680
cggtttattt catttacaaa atggataagc gctttttgg ttgcttcttg ttcaccatac 121740
tctaagttaa agtgttggta aatgacgttt atttctttga taagctgacg aatttcggtt 121800
tctgagtagt caccaatgtt aataagctca ataggacgca taaagataat gcgaataagt 121860
cctgagaaga ttccttccag ctcaggaagc atcgagatct gtacattttc atctctaaag 121920
gaaaacaact tttgataaaa ttcggcgagg cggggaaggc ggaagtaaag ctctgctgcc 121980
tcgggaatta cctcgggctc tagctcatcg gcacccccca atatcatacg cgtgggtata 122040
agtttgtaca cgggctcagg ccgttcaaac atgtcgtaaa tccctaatac aataaaaatc 122100
ttggcggcca tacttttcag catgaaggtg aagaagacgt cctcggtttc ccagcgggtt 122160
gatagggcgt cgttaactct cacagtagag aggtagaccc gctgagccgc ttcctcggca 122220
gtctgtgcaa gcgccatcct ttgtcctcca atttctgatt gatttagatt tttaagtccc 122280
acggaaagcg cagaatgttg aagatattca agcaaggttt tatagatttg caggggcgac 122340
atgggcacca tttgccgcag ctcctctccc ccaagcatgt ccccaatccg ggcaaaggca 122400
ttgatgatat ttttaagcgc ctgaaagtta gaaagagagc gcccgataag gtcgcgaatg 122460
tttttagcct ggcttgctct gacgggacgg agggtaccaa cgcttcggcc ttgttggatt 122520
tcagccgcaa ctttttcgta gtagtggccc gcaggagcat tatccgtaaa gacgttggag 122580
tcgttgcctg tggaggtggg aaaactttca aagacttgtg caagcgtgtc ccctgttgtc 122640
tcggtgaacc atcgtcctat aatgcgcacg ccatccagca tctgttggac tgtttgaata 122700
gaatctatgt tgtttacaaa cgttttggta atgtttttaa gataaagatc tagcccttcc 122760
agagctcgat agaatcggcg ttttacatca tactccagct cgatggcgct tacggttgcc 122820
ttccagtcta cttcctgggc acctccagga tttgggccca cgtgtcctct ggcaagatct 122880
acagccggag aattaatgcg cgcatttttt tccgtatcca actgcatgag gcgtcccgca 122940
atagcatctc cgagaatagt ggcatagttt tcctcgtagg attgaaactc ctgtttgtta 123000
tgcgttaaat tggagtaaat ctgggccaca taatagtaat acataaaggt gttaattgcc 123060
tggttgaggt caacctgcga tcgcgcggcc ttgctgagcc caagctcttc aactgttagg 123120
gcagcaccgc ctacccttgt acactcgcag tcctcctcgc ctccatactt tttttgcaca 123180
atatcggtat aaaaatcaat aatctgtagc aagcgagagc aggagtcata aagattttta 123240
aaattagggt cggttttaga tatctcctcc aaaacatttt taacaagcgt aagctgtgtt 123300
aagaaggttt cgcgttcttc tcgtgcggcc gcattggtgt aaaagccgat aagacttaga 123360
tcaagtgcga tggtgcccat atcattaatg cgcgaaagag catctcgaag cctcgttatg 123420
ttcggcgtca aggcaatttc tttaacaagt ttgatgccta ttttttttcac atttccaaa 123480 aagtcgttat aggcttgtgt gcttttattc aaaaattcca tgaggatgtg ctttctatcc 123540
agtctttgcg cttcaatcct cctatctagt ggcgttttct cctcatcgcc cccctttttg 123600
gcacaactgt tctcaaggat tttgtggcgt tcattaaagg tctgtcgcaa caggttcacg 123660
gctttttcaa actcagcaat gttttctgcg gagacaagac cactaaacct tttgaggtca 123720
agctccttgt caaactccgc ccagtttttg ctttgaaggt actgttcaac cttgagtcct 123780
actttctgga gagccttatt aattttattc gcaacagacg cagcaatacc tagattacaa 123840
agtgtgtacg aaagtacttt tccaaaattt ttggttccca agacactatt tgtatcattt 123900
aaaagtttaa taatatccac ctcatccgtc tgcagtttat caagttcctt ttgggtggga 123960
gttaaaatat tgtcaataaa attcgttaaa atgttgattt gcaggttttg ttcatttaaa 124020
agtcgacgat atactgcttc aatcatggtg actgcattaa tgacttcctc attgggggct 124080
gctttggtta cctccgtcac catgcgctcg tgaagttgct taatggcgtc gtttaacagc 124140
ttgatatttt caagtgtatt ttctatactg ccgtgtacat caagatactc tgcgcgcagt 124200
ccatgagtta gggagttaat gtacagaact atttgtcgac atatactggc ggccccttcg 124260
gtggtatcta taagcttatc ctgacctaaa tcaataaatt cctggttaat ggcgtctgca 124320
atcattttac agacggtctc ctgtttttcc gcatttttta caaaggtgga accggctcga 124380
ggatcgggca gttgtttttt gatatcttta agaatatctt cgatgggctg ctttgtgtct 124440
actttgaacc ctattttggc aatcgccctg ataattcctt ctataatccg cagctttgct 124500
ttactcgata cggagtctat gtgataatct ttaatgtgtt gtacaggatt tttgtccccc 124560
ccgccattaa aatatcctcc ccctgaaaaa ggacgagttt gtctttgtat atgatcctgt 124620
aacttcgcat atatatttgc ttctgatgaa ggcagtggtc tactagaggt tgaagatcca 124680
cggttaccca ttataataaa aaaaataaag atttaaaact acaaatattt tgctgtttat 124740
aaacccaatc atataagact aactaaaaca ttaaatgtag gtgagataaa agcttatttt 124800
ttttaaaagt ttaataacca tgagtcttac cacctctttt tcttcttcct ttagaggggt 124860
tccataaatg gtttgaataa aattatgtgc tctaataacc ttgttaaaat caggtgcctt 124920
tccatattgt tcaatatgtt gcacagtctt ttgtgcaagc atatacagct tggagtcttt 124980
aggtacctcc gatgagggct cttgctcaaa caacgtttca aaggaggatg tgcattcatt 125040
ggtttcatta tcattttttt catgaatgtt ctccgaagat gctgaggatt ccgtctcctc 125100
ttcaaacagc acatgcagaa tcatattcca ttcttcttga gcctgatgtt cagtataccc 125160
ttgccctgca tatatacgag cagatttcac aatatcatac ttaacagtac taagcaatgt 125220
ttttatagcg gtcgtaacaa ttctaccgct attgataatc tcaacagaaa accaattata 125280
caggctaccc gcatgaaaca caacttgtga agatgatctt aaatccgttt tgaagatgac 125340
ctccattttc atggatatat ttaaaataaa atccattcaa ttttaaaatt ataaaataat 125400
aagaagatgc cctctaatat gaaacagttt tgcaagattt ctgtatggct acagcagcac 125460
gatccagatt tattagaaat tatcaacaac ttatgtatgc ttggcaattt atccgcggca 125520
aagtacaaac acggagttac cttcatttac cccaaacagg caaagatccg cgatgaaata 125580
aaaaaacatg cctactccaa tgacccttca caagccataa agaccttaga atcactcatc 125640
cttccatttt acattcccac tccagcggag ttcaccgggg aaatcggctc ctacaccgga 125700
gtgaaattag aggttgaaaa aacggaggcg aataaagtta ttttaaaaaa tggagaagcg 125760
gtcctagtac cggcggccga ttttaagccc tttcctgatc gccgactagc ggtctggatc 125820
atggagtcag gctctatgcc cctggagggt ccccccctata agcggaaaaa ggagggtggg 125880
gggaatgacc cgccggttcc taagcatatc tcgccgtata ctccgcgcac gcgtattgcc 125940
attgaggtgg aaaaggcctt tgatgactgt atgcgtcaaa actggtgtag tgtcaataat 126000
ccctatcttg ccaagtcggt ctccttgctg tctttcttgt cgctcaacca tcccaccgag 126060
tttattaagg tactgccgct tatagacttt gaccccttgg tgacctttta tctacttctt 126120
gagccctata aaacgcatgg ggatgacttt ttaattccgg aaaccatttt attcggccct 126180
accggatgga atggtacaga tctgtatcaa agtgccatgc tggagtttaa aaagtttttt 126240
acccagatta ctcgccaaac ctttatggac atagccgatt cggctactaa ggaggtagat 126300
gttcccatat gttactcgga tcccgaaacc gtacattcct atgccaatca cgtgcgtact 126360
gaaattttgc atcacaatgc cgtcaataag gttacaacac ctaacctcgt cgtgcaggcc 126420
tataatgagc tcgagcaaac caataccata cgacattacg gccctatttt cccggaaagt 126480
accatcaacg cactgcgttt ttggaaaaag ctgtggcagg atgaacagcg atttgttatc 126540
cacggcctgc accgcacgtt gatggatcaa cccacctatg aaacctctga gtttgcagag 126600
atcgttagaa atttacggtt ttcgcgtccc ggcaataact atataaacga gcttaatatt 126660
acaagtcccg ctatgtacgg cgacaagcat accaccggag atattgcgcc caatgataga 126720
tttgccatgt tggtggcctt tatcaacagt actgactttt tatacaccgc gattcccgag 126780
gaaaaggtag gggggaatga aacccaaacc agtagcctta cagacctagt tccaacacgg 126840
ctacactctt ttttaaatca taatctaagc aaacttaaaa tcttaaaccg cgcgcagcaa 126900
acggttagaa atattctttc aaatgattgt cttaatcaac tgaaacatta tgttaaacac 126960
acgggaaaaa atgaaatact aaagttactt caagaataag tatgttgata cctgtggtgt 127020
gttttacctg tgggtttcct attggaacct acgcggcaat ttttgacaag gctcgtaccg 127080
agtatattaa aaccaaaatg ggcggaacat tgccgcaaaa tatcccatta gatgcttctc 127140
tccagattga gttaaaagac ctcattacag ctctgggaat cccaatgcgg gtgtgttgtc 127200
gcactcattt aattactacg ttggattatc gtaaatatta ttaatatcta aaattgaaaa 127260
aatattttta atgttactag taaaaatgac tacacacatc tttcacgcag atgatctcct 127320
acaagcattg caacaagcaa aagcagaaaa aaatttttca tctgtatttt ctttagattg 127380
ggataaatta cgcacagcga agcgtaatac aacggttaaa tatgttacgg tcaatgtcat 127440
agtaaaaggc aaaaaagctc cgctaatgtt taactttcaa aatgaaaaac atgtaggaac 127500
cattcctccc agtaccgatg aagaggttat acggatgaat gctgaaaatc caaagttttt 127560
ggtgaaaaaa cgtgacaggg atccctgttt gcagttcaac aaatacaaaa tctcgccgcc 127620
attggaagat gatggtctca ctgttaaaaa gaatgagcag ggtgaagaaa tataccccgg 127680
cgacgaagaa aaatctaagt tgtttcaaat tattgaactg ttagaagaag cctttgaaga 127740
cgctgtgcaa aaaggtcctg aagccatgaa aacgaaacat gttataaaat taattcaaag 127800
aaaaatttct aatagcgcgg ttaaaaacgc agacaaacct ttgccgaatc ctatcgcacg 127860
cattcgtatt aaaatcaatc ccgctacaag tatactaaca ccaatattgc ttgataaaaa 127920
taagcccatt actttacaga atggtaaaac aagctttgaa gagttaaaag atgaagacgg 127980
cgttaaggcc aatccggata atattcataa gcttatagaa tcgcattcta tacatgatgg 128040
catcattaat gctagatcta tttgcatcag caatatgggc atttcatttc cgctttgctt 128100
ggaaatggga gttgtaaaag tttttgaaaa aaataatggg attgatgtga actccattta 128160
tggctcagac gatatttcaa ctcttgttaa tcagattgct attgcttaaa caatttgctc 128220
aaaacaagct tataaacgtt tcttaggtat gcgatacgta aatcctaatt ctttaataag 128280
ttctttttca gtagtgattt ttagaggtac taaagtttga tttttaaata atccatactg 128340
atttagctta taattctttt tttttaacgc agctcgaatt cttattaaat aagaaacggg 128400
acccgtaaaa tgaagtactg cgtatggctt ttcctcggct aaggccgtaa aaagatcaag 128460
ttgatatgtg ttttttttcc attcaataaa aagtacacac tttcgttctc cgcagacttt 128520
tacagaaaaa gaaagatcct ttatgcgaat gttgggcagg acgtgtttta aaagtttttt 128580
ttctggaaca ataataagaa gatccacgtc attaagcatt ttctcttcgc gtcttaagct 128640
accaacagca acgatgtttt ttgataaaat ttttataagt tgtccattat attcaaacgc 128700
aagtcgggag cgtaagtcat ttacaatttt ttttccttga ataagcgtta acattttata 128760
tttaatatta aaatcttttc attttatata ttatatacgc aaaatggcac ttgatggttc 128820
aagtggtgga ggctctaatg tagaaacatt acttatagta gcaatcattg tggttattat 128880
ggcaatcatg ctttactatt tttggtggat gccccgccag caaaaaaaat gtagcaaggc 128940
tgaagaatgc acatgtaata acggaagctg ttccctaaaa acaagttaaa acatgcaatt 129000
atatgcatgc atataaacgc atgcatataa acgcatacat ataaaatgcg taaatactat 129060
ataaaaaact ataacatatc aatcaaggaa tcaacacttt tataattttc cgtaatatat 129120
ttttcatcca taatgatgtc agagtacatg gtccctatgc gaggaacaga gcccataagg 129180
gtaggcgcgg caataccgta aatgggattc acggcggagt caaccgcagc atctgtcaag 129240
acctggactg gagacgacaa ggccattcgc aacaacacgt tggaaggctc tcttgcatta 129300
agccctgcct tttctagaga ggtaacctgt cccgttcttg tcatgagatc tgcgtacatg 129360
agtaaatgac gatggttggg acccttgtcc cccataaccg ttctaatttc actaataatt 129420
ttttgccgtg ccgcttctat gccgtaaagc tccatggtgt ctcctataga ggacgatacg 129480
atggtgtatg ggtcgatgtt atcatcaagc attgcgccaa aaatattagt cccgtttgtt 129540
ttgatggcgt agatattgtc tagtcttacc agtttcccct gggcatccac acggtggcgc 129600
ataagcttaa caacattcgc atttttgatg cctggtattc ctctaatcgt gctatttaat 129660
agtttatcca ccacatttac ggcaattttt tcatccgtag ccattcgggt attggtactg 129720
cgtctaaagg cgctttcccg taggtatatg cgaataatga tgggaatccc tgaggccgtg 129780
ttttccacag aatgcatgat gtaggtgttg gggtgtttag ctcttagact attaataata 129840
ctttctagac taatgctttt taatatcatg gttgttttgt ttaattccaa gcggatacac 129900
cagtttgcaa tatcctctgg gggctgtagt agaggatggt tttccagaaa atccgtcatc 129960
cattccacat cacttgcaaa atcggggtac atcacatttt tttttgtgct tgaatacgtt 130020
tcgtacaata ggtgccactg caatatcaac cgttcgaacg ttataagctc tatgctgtta 130080
gcaatttctt gcgcatatgt tttatttgtt tccacttccg ggttctttag acgtaaaagc 130140
atttcagagg attgttcagc ctctacgggc ttcgcgctaa agatctcctg gggccgcaca 130200
attcccgact tgttggttcc cccggccacg gaccggtggt gggagtccag catatattgt 130260
gtcaagggct ctgatacgga ctgcgccgcc aggattccca ctgcctcacc gtagttaata 130320
agactttgag tatattgtag ccttatgagg tccaggatgg cactcatctg ctcgcaggta 130380
atgtttaatg ttttaacggt tgccagttcg atgcgaataa gcatgcgcat cagagaggca 130440
gcccgtttaa gataaacggg tatgggcgtt tgtagtcgtt cctgaatgtt gttaataaac 130500
acgtatggaa gatttttgca aaacgttttg accatcgcgt atttttgtag aatacttttt 130560
tcgtcgaagg gaagcacgcc actggtggag ctcagtagaa tgttttttac gatgctggcc 130620
acgtttaccg gcacctgtct aacatctgta agcagctgac tgaaattaaa attttcgacg 130680
tttaggaaga tctgtcgata tttatctcta tccttttaa ggcgtgaaaa ttcttcttca 130740
aacaagggcg attgtatccc ggtgtacttg aatttgtctt caagttcctg gtccgacagc 130800
atgatggttt caaaccgtac ggtttcaagc tggcgcgcat caaggccgtc ctctccgtac 130860
aactgctgca caagacgcgt atcgatggaa acccgtcggt aataatccac aatacaggat 130920
tgaaggccaa agatggcttt acggttggca tagcctgtgg atgatgtcga taatgctttg 130980
ttgatcaagt cgaatcttcc attcatttcc ccaaagataa attcagggga ggtaaggccc 131040
gcaatatagc tgttgcagat gaacccgtag gcctgcgcct ccagggcaaa cctggggtag 131100
tacaccaggg tcctaccgaa ggaaaactgg ggttgaatgc gttgtgtatt aatttcaatt 131160
tggccgatgc ccgccatgat gtgaatcata ttggggtttg agcccttggc gccagtggcc 131220
accatctgaa aaagcccatt ggtttccgga ttaatggaat tcataatcgg ctttaaaatt 131280
ctatcgggaa atttaagcgc attcagctgc aatttttcgt agaagtcatg cgttgtcagg 131340
cctataggcg gcatgatgtc tccatgaagc agccggttgt ttatttcctc cgactcaagc 131400
agcagttcat tgataatttc ttggacctcc tgatgtgcct ccggggttag gagcatgtcg 131460
gccgtggaca ctgtgaatcc ggcgttgcgc acgtagttta gggcgagctg ctgggtcgca 131520
aatatcattt tcaaggcctg ctgcggccca tacctacgcg aaataaggtg atagattcca 131580
ccggaggaac ccgctccgac ggcctttttg tcaaggacgc cttcaatgag ttcgccgttg 131640
cgtatttgtg tagagatgtc ctgcttgtta taatgcatgt agggtgcata cacttctgag 131700
taccatgtgg gggctcgttg ataattgatg ggggtctgcc tcagtagcat agatacaacc 131760
gatttgccat ccagcaggtc agttggggag tagttggcaa aacaaggtgg gtcggtttgg 131820
gttgtttgaa acaaccccat ggcgtgcagc ttgttcatca catttttccc catgggggtg 131880
ttcgtgcgtg taagcaaaaa gcttcccacc gtggagtcct gcacctgccc attaacggga 131940

-continued cccgagctct ttgtggaaat gaaccagttt cgcacagaac aaagtagttc ggcctcaacg 132000
cggctcatga cgctccaggg aacccagaga ttcatctgat ccccgtcaaa gtccgcatta 132060
taccaggcac atgcgctgac attcatttga aacgtagaaa tttttgggtt ttcaagaacg 132120
acaatccggt gaacccctat gctgcttcgt tcgagagaag gctggcgatt aaaaaacgcg 132180
acgtcgccag tgacgacgtc acggtaaagg atgtctccta cctccagcct aaagtcttgt 132240
ttgagaccct caatgtcgtg aacggattgt gttatttgct tatacactct tgaacaacca 132300
gggtactggc gctttccatt taaaaaatag ggcattaatc tattaatatt ataatgttgc 132360
actgtttccg caacttgcag cgttcgtgca aaggaaatgg gatagccaac ctcgtccagg 132420
tgaaggtctg agttcccgca gatggtggac cggctgatcg accatacctg gctgcccagt 132480
agggatttac gaattcttcc ctccttgcga ggaagtcttc gcatgatgga gggagcaggg 132540
cgtgccccca tgacgatccc acgctttccc gtgcctccct gggttgcggt ggtggaaacg 132600
gaatccaaca aaaagttata gtaaagttgc tgtatggttt gcaaattgcg gtcaatattt 132660
aaaggtattt tttggccgcg cacgatttgt aggtccttcg ggatcagcag attctttcga 132720
accagatact gaatcacgtt gttaatgtcg tgaaagcttt gggggcctga cccgattccc 132780
aatctgatgc caggtcgtat gctgatgggg gggatctgaa tggccttaag cacaagtttt 132840
tcgggatggg agtttttact tcgccccagt tttacaacgg tgtcgtaggt tacgcgcgaa 132900
aaaatctctc tgatgatctg cgggtacagt ttgtcaatct tgccctgctg atccgcccaa 132960
aaggtaaaat aatcttccga gtccttaaca attttggggt gtactgcctt acagacgtag 133020
cactgctttc cttcggtttg gcttgaagcc gcttcaataa gacgcttagg cctaataagg 133080
tgctcgtacc tctttaggtc aacgatggga gccccgcagt tgagacatat aacccttaac 133140
catcgtcgta tttcggcgat gaagagcggc tgaagcaccg gagcatgcat ctgcagtatc 133200
ccagggtgtc ccatacattg cttgcgctgg tgtgagcaag tgatgcattt ataatggtga 133260
tcggtggttc ccattcgcgc atcatagata ccccccttcgg cgggaagggt gccctcaaat 133320
aaattagaaa tggtaacctc cataacgcct tgcctcttat gatcattgtc accggcaata 133380
ttgaactgaa cggcggctat ttcggcatat ccagcctcca tatttttgct aaatacataa 133440
taaaacttca aatgttaaaa aaaataacat cggttggcat attttttttgt taaaaccaag 133500 tgttaaatga tttctaaaac atttatcggt tcacgaaaac ctaccgcacg ggcctgaaga 133560
ggaatgccag ttttgggggga aagctcggca tattccacgg taagctcttt tccataaaga 133620
tgttttttaa ataaggcggg cgtgagtttt tgaaaaagag cataacgatc cgcgtacgtc 133680
aaatgcttag gagtgactac aaaccgcttt ttgtttggca attcgcaaac ccataaaatg 133740
gcgcctaagt cctttccctt ttttccctga gtatagtcca ctaaaataaa ttcagcgtct 133800
agcagcggtt tcagcttggc aagatgcgct gagtggtagt tgttgtatcc cggctcatag 133860
ggcccattgg cattgcgtac gatggctccc tcgtagccct ccttaataaa ctgcgcctta 133920
agcctaaggg cctcatccac attcttcacg ctaaaatttt caacttggtg gataaaggta 133980
agatcttcct tctgtttaaa aatatttgtt aatagctgtt gtctcttgtt ggaaggcatt 134040
tgaagctgat cactccaaaa acagtcaaac acgtaaaagt gcagctcgga ggaatctgtc 134100
ttcgcattcg cctgccccgc gatccattgc agaggtttgc ggtgtaaata aagctcacca 134160
tccaaatata ctctcacgtc tataaataaa taaagctgtt tgagctcttt tttaatattg 134220
tcaagaccta aaaattcctt tttcgtgcgc gaatacaaga gaatgctacc atcgccctgc 134280
tggcaggcca cagctcgaac gccattacgc ttgcgctgca cgatgggatc tgtttcttct 134340
tcaaaaaatg tcttaggaat tatattaaaa tattttacca gcataggggg gataattcct 134400
ctatttgtgt gggctccccg cttttgtctg gcatggcgat tatatttact aagggcgtcc 134460
ttgaatgcct gatggactac cgttgtggca ttttttttac ccaagttttt tccctcggta 134520
acacgtgtca tttttgatat ccgcaccgcc ccttcttcca caaaaaattt tgtgaaaatt 134580
tcagcaacgg cgtcttttac atctgtggaa aacatctcat ctgtgatggg aatgatcgtg 134640
ttgtgctgca ccacttgcac acaaataatc catgaggcct tttttccgct tttcgtttca 134700
gactcaatcg gaggaaaaca aaaaatgttg tttgaatatt gcccaggaaa ttgatttagc 134760
atggttttaa caataaaata agcctatcaa ttttttttata atttgaatag ttattccaaa 134820
ttcaatatgg cttctttaga taatttagtg gcacgatatc agaggtgctt taatgaccag 134880
tctcttaaaa atagtactat tgaacttgaa atacgttttc aacagataaa ttttttatta 134940
ttcaaaaccg tatatgaggc acttgtggca caagagatcc ctagcaccat ctcccacagc 135000
atccgctgca tcaaaaaagt tcaccatgaa aaccactgcc gggaaaaaat tttgccgtcg 135060
gaaaatcttt acttcaaaaa acagcctctc atgtttttta agttttcaga gcctgcatct 135120
ctgggctgta aggtctcgct ggccatcgag cagcccattc gtaaatttat cttggactcc 135180
tccattctcg ttcggctcaa aaatcgtacg acctttcggg tatctgaact ttggaaaata 135240
gagcttacca ttgtaaagca gctgatggga agcgaggtct ctgcaaaact tgccgctttc 135300
aaaacgcttc tgtttgacac cccagagcaa caaacgacaa aaaatatgat gacgttaata 135360
aacccagatg acgaatatct ttacgaaata gaaatagagt atacaggaaa gcccgaatcc 135420
ctaacggcgg cagatgttat aaaaattaaa aacacggtgt tgacacttat ttctccaaac 135480
catttaatgc taacagccta ccaccaggcc attgaattca ttgcctccca tatactgtcc 135540
tcagaaatcc ttcttgctcg tattaagagc gggaagtggg ggcttaaacg cctcctcccc 135600
caggtgaaat ccatgaccaa agcggattac atgaaatttt atccgcccgt tggctactat 135660
gtaacggaca aagcagatgg aattagaggc atcgccgtca ttcaggacac gcaaatttat 135720
gtggttgcag accagttata cagcctaggt accaccggca ttgaacccct taaaccaacc 135780
attttggacg gtgaatttat gcctgaaaaa aaagaatttt atgggtttga cgtcatcatg 135840
tatgagggca atctattgac gcaacagggg tttgaaacaa gaattgagtc tttaagcaag 135900
ggcattaaag tcttacaagc gtttaacata aaagcagaaa tgaagccctt tatttcgcta 135960
acaagtgcag atcccaacgt gctcctcaaa aactttgaaa gcatttttaa gaaaaaaact 136020
cgcccatatt ctattgatgg catcatttta gtagaacctg gcaattctta tctaaataca 136080
aacaccttta agtggaagcc cacctgggat aacacattag actttttggt gcgaaaatgt 136140
ccggagagtt taaacgtacc agagtacgcg cccaaaaaag ggttttccct gcatctacta 136200
tttgtaggca tctccggaga gctttttaaa aaattagcgc taaattggtg tccaggatat 136260
acgaaactat tccccgttac acagcgcaac caaaactact ttccagtaca gttccagcca 136320
tcggattttc cattggcatt tctttattac cacccagata cctcgtcatt ttctaatata 136380
gatggaaagg tccttgaaat gcgttgtctt aagagagaaa tcaatcacgt cagctgggaa 136440
attgtaaaaa tccgggagga taggcagcag gatcttaaaa ccggcgggta ttttggcaat 136500
gatttcaaaa cagccgaact cacatggctt aactatatgg atccctttttc ctttgaggag 136560 ctggcaaagg gcccttctgg aatgtacttc gccggtgcca aaaccggcat ataccgcgct 136620
caaacagcac ttatttcctt tattaaacaa gaaatcatcc aaaaaataag tcaccaatcc 136680

-continued tgggttatcg atcttggaat aggaaaaggg caggacctag gacgttacct ggacgcaggg 136740
ataaggcatc ttgttgggat cgataaggat caaaccgcgc ttgcggagct tgtttatcga 136800
aaattttcgc atgctacgac ccgacagcac aagcacgcta ccaacattta cgtgttgcat 136860
caagacctcg cagagcctgc gaaagaaatc agcgaaaagg tacaccaaat ttacgggttt 136920
cccaaggagg gagcttcttc cattgttagc aacctgttta ttcactatct tatgaaaaac 136980
acgcagcagg tggaaaacct ggccgttctg tgccataagc ttcttcagcc ggggggaatg 137040
gtgtggttta ccaccatgtt gggagaacag gtcttagaat tacttcatga aaatagaata 137100
gagctcaatg aagtatggga ggctcgtgaa aacgaagtgg tcaaatttgc tattaaacgt 137160
ctctttaaag aggatatatt acaggaaact gggcaagaaa ttggagtcct gttacccttc 137220
agcaatggcg acttctacaa tgaatatctt gtgaacacag cgtttttaat taaaatattt 137280
aaacatcacg gcttttccct agttcaaaag cagtccttta aggactggat tccagaattt 137340
caaaacttta gtaaaagttt gtataaaatt cttacagaag ccgataaaac ttggacaagc 137400
ctttttgggt ttatttgtct gcgcaaaaat taaatatttt ttcataagaa gtactaccca 137460
ggttttaaag aaatagctaa aaatatcata tggatactgc catgcagctt aaaacgtcta 137520
ttggtttaat tacatgtcgt atgaacaccc aaaataacca aatagaaact attctggttc 137580
aaaaacgtta cagccttgct ttttcagaat ttattcattg tcattactct ataaatgcta 137640
atcaaggtca tctgattaaa atgtttaata acatgacaat taatgaacga ctgcttgtca 137700
aaacactgga ttttgaccgc atgtggtatc atatttggat tgaaactcca gtctacgaac 137760
tataccacaa aaaataccaa aaatttagga aaaattggct tctcccggat aatgggaaaa 137820
agcttatttc attaatcaac caagcaaagg gctcaggaac acttctatgg gaaatcccta 137880
agggtaagcc gaaggaagac gagtcggacc ttacctgtgc catacgggag tttgaagaag 137940
aaaccgggat tacccgcgaa tattaccaga ttctcccaga gtttaaaaaa tctatgtcat 138000
actttgacgg taaaacagaa tataagcata tctacttcct tgcaatgtta tgtaagtcgt 138060
tggaggaacc caatatgaat ctttctttac aatacgaaaa ccgaattgcc gaaatttcta 138120
aaatttcttg gcaaaatatg gaggctgtac gttttattag caaacgccag tcattaaacc 138180
tggagcctat catcgggcct gcatttaatt ttattaaaaa ctatttacga tacaagcact 138240
aggatgccgc attaaaatgc cacataaggt aatacactag gaatgtcgca cacgcacaag 138300
aatacaacgt cgccggagat ttattatcta gtacacgttt tatgtatgta caatccgcct 138360
tcatttaata tattgagcgg atgtactatg tatttatttt aacaaaaaac attatttttt 138420
ttaatcttca tcatctgttt ttataaactc agtaatatca aaagtagctt gtggggtttc 138480
agagggttca ccttggttat cctccgtgag gataacatgt tcttcaggtt cgtcgtcact 138540
ggagaaccca tcatttaatt cctcttcact caacatctgt aaaaaatctt ccaagctttc 138600
gctatcgtta aaatcctcat catccataag aataatggta ccttcctcat cgtttcctcc 138660
ttgtttcgtg tctaaatagg cctgcatggc atttgcaaaa gtatcaaaat aggctgagtc 138720
agattgctgt tccaaaatat ggccttgcgt attaaatgtg gttgcatcgt tgttaaatgc 138780
ttgcaaatac agtaagggat ttatatccat tattattaag caaaaaaaat ttaaattatt 138840
tttcgaccga tgttaggtaa aattaaacaa ttgctatagg tgttaagcaa tgtttattga 138900
ttttaagtac tcaacaacca tgatgtaaat actatacagc acttttggat ttttaatcaa 138960
atccagatta atactaactt cttttgtgat acagttcgta ataatagtat cctgctcatc 139020
gttttgtaag atttctttta atatattttt ttttaccggg atactaagca attgattatt 139080

-continued ttcttttaaa aactcctttt gatattcaat cgtcttattc attgaatatt tgtatataac 139140
tataattaca aatgttcaat gaattgttat tcatgtcggg agatggctat ttaaaaatca 139200
tgtcctattt ttctttgctc aataagcatc caaatatttt catggcgttt tattaattgt 139260
tcattattga acgtatcaca aagatcattt ataaattgca gatagtttat tatttctttc 139320
aagagagtaa caaacattac ttcagcagaa catataatag gtaattcagt ggcgttaaaa 139380
gaattttgat cttgttgata cgccaatggc gaggacttaa ggagatttgg gggtcttgcc 139440
caaaacccta ggctgctgtt cttgtttttt agggcgtcat aaagaaatga aagcacattg 139500
caaggcttaa gccgcgacat ctccttcccc ttgggccctt tccatatttt tagatctaag 139560
atctcatccg agcttataga gtaggtatag taaagttttt caaaaaagca tatctgcttg 139620
aagtcttttt tagaacgact ttcaagaagc atttctataa tgttaacaag ttttgttagg 139680
tttaaggcct gttcctgtgt aagctcctct tgcacgtgat agactgaaaa agtgtgctta 139740
ggaatgaaaa tactccccgt ggcactggcc tgttgtctgc caggtatata gtacacgctg 139800
ctgttagcaa gctgtaccgg cacaatttgc cccacttctg caacattatt ttgcgattcg 139860
gacgagggta tgacaatagt tacgggttca gtcaataggc tttcgccgag aataatatta 139920
ctgtcatttt taataatttt aacggccgct attaaatcaa aggcatttaa gtaagaaaca 139980
acagcagaaa atcttacatg catatatcct cttccgctat tattcgtacg cataataaaa 140040
caaggggagc gttgtataac gccagtaata ttaagaataa aactgttttt gaaacactta 140100
cccacataaa tgttttcaag ctccttcaaa agatgagcct ccacatttgt acaaaaattg 140160
gtaggatcat caatattcaa cgttgtctca aaaatttttt ggtcgatcat atctataata 140220
tattctgtct atttcaattt aaataatata cgaataaata acgagattat tttattaaat 140280
aagcaatggt gtatacactt tgtatttact ttgagatata ctttgtgtat cacaacgtgc 140340
cctaagatgt gtgcacaagt gacggcattt tgtcgttaaa aaggtaaaac cagcggattc 140400
catcctgcat tccatttggt tgattacgag cctccatttc tttttgcaaa aggttattgc 140460
gaatgagtaa gcagagcttg atggcactaa tctttgtaag gtttaaactt atgcccaatt 140520
ggtcagcaat tttttgttgc tcctcccgtc cgcgtgtttc gcatacggct ccccggttta 140580
gcatgcgaat atcagtaatc tcattctttt ttaaaacctg gataggtggg cggattttaa 140640
atttaagggc ctttcccttg ctttccatat agcctatgac gatgtcgttt tcttttcgtt 140700
taacattaat attaagcata taaagcggaa tttcatgcca ggttttatct tctcgcgagg 140760
taataagtcg cacggagtcc tccgtggcat agcccactag agtgttgtca tccccaggca 140820
cgtggcttat aattttaaaa atgtccggaa atggctgaat atcttttttt gaaaaagcga 140880
tgaaaaactt tttataaacc tcgacaaggg cccccatacc tgcaagatta tctataataa 140940
gtgcttctag catcgtatag tgaaatgaag cggggtagtg gatgagtacc tgctccattg 141000
gctcatcctg aaaatccttc tgaaactttt catacaatac ttgaaagggt tctttggtct 141060
gcgagtgttc gaggtatttg gtaatacgga tgctgtgcat cgcgggaggc tgaaaatccc 141120
gaatatatgt ttcaatatct aataccggtt cctttttatg gttaagcacc gcagcgacgt 141180
acaaatgctc aggctttgcc ggcacatgca taatggtgca aagacgattc tgtatccata 141240
attccttgca ctggtttttt gagtagcata gagaaatgag cgccagcgcg aagttgtcct 141300
ctgagaagag tttattatcg atggtaattc cctgtatgag cttgggagtg gaaacagcct 141360
tccatagctc ggagtacgtc cacacggggc gtgccataaa caaagatata ataatattag 141420

-continued

```
aaattgtttt tacctcttgc tccccgtatc cataggcctc aaaggtattg aggacggtgg 141480
ctccgacgtt tgccggcgtg atggatggac taaggggcag actttccaac ataggcttat 141540
caatcttaat ctggttggtg aacccatcaa tggcgtgctt tcgcagcgcc ttatccccct 141600
cctgtattaa aatgtattct tttaattttt gtgcgtactt agcgagctct ggccctccat 141660
cgggtgttgt cgatacgtac aaataaattg tcacgttgcg ctcactgggg gggagctcca 141720
tgtgtgaatt ttttcgcacc accctcccaa atacctgaat aagccgggga atatcaaggg 141780
gcaatgacat aatcatctcg taccgcacgg cctgaaagtt caaaccctcc acaatcacct 141840
tggacccgat gagaatacgc agctggtggc cttccaggtt ggacgaggcg ttaaaaagag 141900
ccaggcttcg ttcgcgtaca gcgggctcta tttcgctgtg cagaatggtg aaccgtactg 141960
gaataaactg atggtcgcta tgtgtgtgct catcgcgaat cgcggcgcag atggagcagc 142020
gggtcgttcc cacaggggac gaaacttcat ttaaaatgcc attactttgt aaaatttctt 142080
gcaagataag aacccccgac atgcggaccc gattgtggta aattaaaatt ttcccccggc 142140
cttgccgaat aatggaaaga atgtctttca tcatttgagt gtattttccg ctataaaagg 142200
ccaatcccga gatgtgcgtt ggtggctgca gcgacaaaaa gctgccactc acattaaagg 142260
gggctctacg cgaaggctca ataatctgta ccccgttttc cagaagccag tctgtgcttg 142320
ccatagaaag ggcggtgggg gtttccgtcg agttaaacag gccgtaagcc ttgggttccg 142380
tttgttttga aaattttggg ttgggaaaca ccatgtcata aatgctgtac gcattactcg 142440
agattttagg gtcagggccc agctgtttaa gcgtttcaag ctgatactca gacatggggc 142500
attcgatgaa atgtaagtac ggcaatgttt cgtctttata ggacaacatc tttccggcaa 142560
atattctttc ggggtaaaaa ttggtgttgg tatccaacaa aaaagatacc cttccggtgc 142620
tcagtctttc cacaagagct agggcgtcct ttttccattt aacggaatgc ccactgctgt 142680
caaacagttg ctggcgctgg aggggctggc cgttgggcag ctcatgccgc ggaaccaaaa 142740
ggtttaacag gtcgacgtat tccatgacac tcccggttac gggcgttgcc gacatgaaga 142800
cggccctggg ggcctggtga ggtggaaagg catccaggac atactgtaaa gcgatgccat 142860
aattatttcg ttcctggata ttgtacacgt tgtgtatttc atccgcaatg agcagtcctc 142920
ccctaagttg ctccatgatt ttttgattca cccggatgag gccgtttgtc tcggcctcgc 142980
taattttttg cacgaactga gatatatcgt tctcattcaa tgtatcttct gcttcgtcag 143040
aacgatgaaa cagagaaagc acatcaaagt ttttctcttc acccttactc gtaatattga 143100
aaagcttgga tgcaaattcc ttatagccgt aaaactgaaa aaagcctccg cggtttctat 143160
cggttaaacg gcgctttaac gtactaacga acccatttag atgccgtgat tcgaccgacg 143220
tggtgctgcc agactgcttt gcaatgtgaa gaagccggtg tagctcagcg acctccttgt 143280
aagaaacaaa tcccagctca ggacgtctta gcatttctgt ttgaatgatg gcgcgtgtaa 143340
agcctaccac aaaaatccag ggcgcatttt caataaaatt catgtagtgg ttcataaatt 143400
gacgcgcgat ggcaatcgcg gcaatgcttt ttcccgtccc ggtctgccag tttaataaaa 143460
gacgcgagta gggcgtgttg ggattttgaa agttttggac gaaaagctgg gcattatgca 143520
attggagacc cttgatggaa ggaaagggcg acgcgtaggg gtcacacgga aaaaacgctc 143580
gcccccccctt ctcgcagcca ggcccaccga tctggacaaa atgagcccgc agatcacgaa 143640
tgagctcttt ttggtcgaca ggaggggaaa tcaacgattt aaactccttt cttcgcgcca 143700
actgctgcaa aaagtctgcg gcatccaatt cgggatacgc catattatca taaaaaaata 143760
aacctttttta tgaaaacttt tatgtgattc tgtattgcaa ttgtttttta tgaatactgt 143820
```

aaataagcgt atcaacttgt ttttctaacg aagaggcgtt attctttttt tctggatata 143880
aaataataat aagtataata attaagacta aacagcaggc aatcactatc aaactcatat 143940
tatacttact tttttataaa aagtattata tcttatgaat gcgcaagttc agctaattgt 144000
tcgtcgcttg gaatgtggga ctgcagggag gtggagtttt tcctttttct aaagaatacc 144060
gggaaatggt ggtgaggctc aggttgttgt acatagtagc taggaggagg tttaggtatg 144120
ctcgacttgc agtcaatagt ccggttatag taaacgatgg caacgatgat aagaataata 144180
atgagcaaaa tcaaaatgcc caggagaatc gcagttgttc cgggatattt ggcgattgta 144240
tgggctaaaa ggccttgggt gctttgttta attccctcgc gggttgacag gttatgagaa 144300
agcagtggag acgtttcagt gtccatttat tacaattgaa cagttatatt aatctcaaat 144360
aaaatataac acaaaattaa ttatggccat gcaaaagtta tttacgtata tttacgagtt 144420
tattgaatat cgtaagatgg tgctgttgga agaaaaggta ccatatgata agtttgttca 144480
aatggtactt aatacaggat tttttcgtat taacgcggag acgctgaatc acggaatcgt 144540
atccgtgttt atctttggag caaatggcaa gtacgttcac cacggaggcg acatgagaac 144600
gcttttaacg aatacgctta atgaaaaaaa acattatgaa gaattaattt taatcgttga 144660
taagcccgtt ttaagcaaaa aaaatatttt agatataatc gtcgagcagc gcgctgcaaa 144720
tcccacgatt gtaataaaca tatatcccta ccacctgttc tgcattaaca ttcccaaggt 144780
gagtgccatt cctaaacata aactaattac tcaggaggag gcgcaggagt ttttaggtcg 144840
cgaatatctg caaccgcagg acctcatgca aattagcgcg tcagaccccc cggtggtctg 144900
gctgggagga agaccgggag actttgtgca aattgagcgg ccctcagaga cagctatgca 144960
cgctgttgtt atccgcttta tcaccaagtc caaaatttga gtcccgtgtt taaagatgac 145020
agacagctaa gtaagcatat ctgtaaaatt gtcgatgtcc tctgtggata gagcgctttc 145080
ctctgagcag caaatttttt catacatctc catgggggat ggcgaggctt taatagtatg 145140
taggtcacgt aagaactgtt gtatgatggg atatttgtct tttaaaaact ggggatgttt 145200
cataactgga attatttgaa agataaagac cttccatcca aagtagccaa ccacatttgg 145260
catttcggga cacgcggttt cataaggcat agaatagtga atagtgtact gatctttttg 145320
atacagcgtt tcaagtagtt ggcgaaatgt ttccgcgtcg agcgtgccaa aatcttgagg 145380
agcctcggtg tgctcctgtg tagagcagat cgtgatgatt ccccaggcaa gcgggagcat 145440
ggactctgga gggtggatat ccgtattggt ctcattattc gatcccagct gatgaatgcc 145500
gcacacgcga aacatggcct cgacgtagat gcccatagag ataggcggcg aaagggcaag 145560
accggattgt atttgcggca tatagtagga gggcaccgag tttttttattt ttcggttgaa 145620 tggggacttt atttctacca gcacggggat gcgtttcgtg gcctcatagc gtacgttgtt 145680
aaaaattgtt ttgatttccc aggactgttg agtgtatccc agcgttaggt gacaaaaccc 145740
atcggggcta ttactatgtc cggggtatcc caaataggtc ccatcaatat gaatattgtc 145800
acctatgacg gtggtttggc agaacaactc aagcagatct ttactaacac gctcaaaaag 145860
ggttccccag ctacaagcag cgcggttcaa attcttctta aaaagatttg ctttttccgc 145920
caaggttata taatagcttt tgtaagggtt taaacctaaa acgctggcaa ggtcagagcc 145980
acccacctga gtgcgacgaa tagcatgcca ggcatcggag cgctgctgag gagagtcttt 146040
aaacaggcgt acaaaggttt ccattatact tgttttaaca ggaattcaat ataaaaagtc 146100
aacacagttt gcaatttttc caatctcaag atatagccat acattttttt ttccaattgg 146160
cgaatatgtt taagctcatg tgtttcaata ttagcatccg gaaatttaaa tgcataaaga 146220
tgttcaaagg cctgatttat acacgtatca aaggatctgt ggtatgttat tagcttcagc 146280
atgtgtgcca gatcttcaag atggtctaaa tttatacggt tttccacgtg gtggatcatg 146340
tctgccacat cttgagcccc catccagggg atcacaaggt actccccctt aaagatgatt 146400
cgtcgttttt ttaaaaaatc atgaaaacgt tttaaagctt caagaaaggg gcagttgggc 146460
tttgacccca aaatgctgac gacgatatcc tcgggcatga tgtattcgca gtgaggatag 146520
tagtttacgg actctaattc agcggcccgc cgttttattt cgtatcttgc ccagttattc 146580
agagagtact ccacgcctcc gaccacaaca gacatcctat ctattaaaaa ataacaataa 146640
aaaccttatg aaatctatgt atagtggccg ctaaaatgtc tatattagaa aaaattacgt 146700
caagtccctc tgaatgcgca gagcatctta caaacaaaga tagctgttta agtaaaaaaa 146760
tacaaaaaga gctcacctct tttttggaaa aaaaagagac actcggttgc gattcggagt 146820
cctgcgtaat tacccacccc gccgtgaagg cctatgcgca acaaaaggga ctggacctct 146880
ccaaagaact ggagactcgg tttaaagcgc caggacccag aaacaacacg ggtcttctta 146940
caaacttcaa tattgatgaa acgctgcaga ggtgggccat aaaatacacc aagtttttca 147000
actgtccttt ttccatgatg gactttgaga gggtccatta taaatttaat caagtggata 147060
tggtaaaggt atataaggga gaagagctac aatatgtaga aggcaaagtg gtcaagcgtc 147120
cttgtaacac cttcggatgc gttttaaaca cggacttttc aacgggcact ggaaaacact 147180
gggtagccat ctttgtggat atgcggggcg actgctggag catcgaatat tttaattcga 147240
cgggaaattc tcctccaggt cccgttattc gttggatgga acgggtcaaa cagcagctat 147300
taaaaataca ccacaccgtg aaaacgcttg cagttaccaa cattcgtcac caacggtcgc 147360
agaccgagtg cggcccctac agcctgtttt acatcagggc acgcctcgac aacgtgtcat 147420
acgcccattt tatatccgct aggattaccg acgaagacat gtataagttt agaacccatc 147480
tgtttcgcat cgcataaact aataaagttt gaattcttta taggaataaa aatggaagcg 147540
tttgaaatca gcgatttcaa agagcatgcg aagaaaaaaa gcatgtgggc tggcgccctc 147600
aacaaagtca ctatttcggg tcttatgggg gtctttaccg aagatgagga ccttatggcg 147660
ttacccattc acagagacca ctgccccgct ttgttaaaaa tttttgacga gatcatcgta 147720
aatgccacgg atcatgaaag agcttgccat aacaaaacaa aaaaggtaac ttacattaaa 147780
atttcgtttg ataaaggtgt gttttcttgc gaaaacgatg gcccgggaat ccccattgca 147840
aagcatgagc aagccagtct tatcgccaag cgcgatgtgt atgttcccga ggtggcttca 147900
tgtcactttt tagccggaac gaacatcaat aaggccaagg actgtatcaa ggggggaacc 147960
aacggcgtcg ggctgaagct cgccatggtg cattcgcagt gggccattct taccaccgcc 148020
gacggcgcgc aaaagtatgt tcaacatatc aaccaacgcc tagatatcat tgagcctcct 148080
accattacac cctccaggga aatgtttaca cgtatcgagc tcatgcccgt ataccaggaa 148140
ctagggtacg cggagcctct gtctgaaaca gagcaggcgg atctttccgc ctggatttac 148200
cttcgcgcct gccaatgcgc ggcctacgtg ggaaaaggca ccaccattta ttacaatgat 148260
aagccttgcc gcacgggctc tgtgatggcg ctagccaaaa tgtacaccct gttgagcgcg 148320
cctaatagca cgatacatac ggcgaccatt aaggccgacg caaagcccta tagcctgcac 148380
cccctgcagg ttgcggcggt cgtgtccccc aagtttaaaa aatttgaaca cgtgtccgtt 148440
atcaacgggg taaattgcgt aaaaggagaa catgtcacct ttttgaaaaa gactattaat 148500
gaaatggtcg ttaaaaaatt tcaacaaacg attaaagata aaaaccgcaa aacaacatta 148560
cgagacagct gttcaaacat ctttatcgtt atagtgggtt ccattccagg aatagaatgg 148620
accggccagc ggaaggatga acttagcatc gcggaaaatg tttttaaaac gcattactcc 148680
attccttcta gtttttaac aagtatgaca aagtctatcg tggatattct tctgcaatcc 148740
atttctaaaa aagataacca taaacaggtc gacgtagaca aatatacgcg tgcccgcaat 148800
gcgggaggaa aaagggcgca ggactgcatg ctactcgcgg cggaagggga tagcgcactt 148860
tccctgctgc gcacgggact aaccctggga aagtccaacc caagcgggcc ctcctttgac 148920
ttctgcggca tgatctccct gggaggagtc atcatgaatg cctgcaaaaa ggtgacaaac 148980
attacaacgg actctggaga aaccattatg gtgcgcaacg aacagcttac caataataaa 149040
gtgttgcagg gaatcgtgca ggtattgggt ctagacttca actgccatta caaaacacag 149100
gaagagcgag caaagctgag atacggctgc attgttgcgt gcgttgatca agatctggat 149160
gggtgtggaa aaatccttgg actgctgctg gcctactttc acctgttttg gcctcagctt 149220
attatccatg gtttcgtaaa acgactgctt accccgctga tacgtgtgta tgaaaagggt 149280
aagaccatgc ccgtggaatt ttactatgaa caagagtttg atgcctgggc aaaaaagcag 149340
accagcttag ccaaccatac cgtaaaatat tacaagggat tggcggcgca tgacacccat 149400
gaagtaaaaa gcatgttcaa acattttgac aacatggtgt acacgtttac cctggatgac 149460
tcagcaaagg agttgtttca tatttatttt ggcggggagt cggagttgcg aaaaagagag 149520
ctttgcaccg gcgtggtgcc gctcaccgaa acccagacgc agtccattca tagtgtccga 149580
cgaattcctt gcagcctgca tctgcaagta gataccaagg cttacaagct ggatgccatc 149640
gagcggcaga ttcccaactt cttagacggg atgacgcggg cgcggcgcaa aattttagcc 149700 ggggggggtga aatgcttcgc ctccaacaac cgtgaacgaa aggtttttca gttcgggggc 149760
tacgttgcag atcacatgtt ttatcaccat ggcgacatgt cgttaaacac aagtattata 149820
aaagccgccc agtattaccc aggctcctcc cacctctatc cggtattcat aggcatagga 149880
agttttggct ccaggcacct gggaggaaag gatgcaggat ccccaagata catcagtgtg 149940
cagcttgcgt ctgaatttat taaaacaatg ttccccgcgg aggactcatg gcttctcccc 150000
tacgtctttg aggacggcca gcgggcggaa ccagagtact acgtgcctgt gttgccgctt 150060
gctattatgg agtacggcgc caacccatcg gagggctgga agtacaccac ttgggcccgg 150120
caactggaag acattttggc cttggtgagg gcctacgtcg acaaagacaa cccaaaacac 150180
gagctactgc actatgcaat aaaacataag attactatac tcccgctgcg gccctccaat 150240
tacaatttca agggccattt gaagcggttt ggccaatact actacagcta cggcacgtac 150300
gtcatctcag agcagcgaaa tataattact attacggagc ttcctctgcg tgttcctacg 150360
gttgcataca tcgaaagtat aaaaaaatcg agtaaccgca tgacatttat tgaagaaatc 150420
atcgactaca gtagttcaga aactattgaa attctggtga aattaaagcc aaatagtctt 150480
aaccgtatcg tggaagaatt taaggagact gaagagcaag attccataga aaattttctg 150540
cgcctgcgca attgtttaca ttcacatcta aactttgtaa aacctaaagg tggcattatc 150600
gagtttaaca cgtattatga aattttgtat gcgtggctac cttacaggcg tgagctttac 150660
caaaagcgtc ttatgcgtga gcacgcggtg cttaagctgc gcattatcat ggaaactgct 150720
attgtacgct acatcaatga gtctgcagag ctaaatcttt cccattatga ggatgaaaag 150780
gaggcaagcc gcattctaag cgagcatgga tttccccgc tgaaccacac gctgatcatt 150840
tcccctgagt ttgcctctat agaggaactc aatcaaaaag cactgcaggg ctgttatacc 150900

-continued tatatactat ctttgcaggc tcgagaattg cttatcgcag ccaaaactcg tcgggtggaa 150960
aaaataaaaa aaatgcaagc tcgtcttgat aaggttgagc agcttttgca agagtctccc 151020
tttcccggcg ccagcgtatg gctggaggaa attgatgcgg tggaaaaggc tattataaaa 151080
ggaagaaata ctcagtggaa atttcattaa acgctaccgg ttttatgatg tccaataggt 151140
gttaagcaat cagttcatca acattttttt caagaatttg aaaagtttgg ataatgttct 151200
gaatactttt ttctaaaaga gttatcaaat cttcttgtga ggccttatga ataattgtta 151260
ataccatttc ttgcttatgg ggaacacact gataccccac aaagctaata tcaggaatca 151320
tttcataaat atatgttttt agcagatttc cgatggtatg ggtttcatct tttatcgtga 151380
taatggcctt tgtttttttcc tcatccatgg aaaacagcac aagttccggc tgcggctctt 151440
caaagttttc ataaattttt tgaatgcttt ggattcggcc aataatgatc cggcaggcgt 151500
tttttaaata cgtgcgaacg gcctggttga tatgtggcag cggcaccgct ggaaagcaaa 151560
gccccaggcg gtggtgacgc gggtctgagg tcatagagct ttgcttgtaa ccgctaagcg 151620
ccatatattc ttttttatcc gttgggtact gttcaatgtc aaggtgggaa aaatgtgttt 151680
taacggcaag attaaaggcg gcatgctttc gtcctatgcc ctttttaata tagatatcct 151740
ctataatcaa cgattttccg ggttgtagga agccaatctc aaaggtagga ttaaaaatcg 151800
ggtatttaag cttagggcct gccacctgga tgagatcgcg gctatagatg gttttaacct 151860
cacagctatt gtttaaactc cgcagagcaa ataccagtgt ctcgttttc gcataaatcg 151920 gaatgaaatt aatgcggttt ctaataaatt gttccgtcat aaacaggtcc gtggaatcct 151980
cgatcttata cccaccgggc ttaatatcta gcatataatt gggaatttca tcttgcaaga 152040
cccgcgacag gccgtggacc gcggctctgc taatgccctt aaagtccata acaacattga 152100
ccgggacgag gggcaactgc tcctcgagct gaaatagttt tttggccgca tttttaataa 152160
agaggttgga aaagtctatc aaaaaacggtt tgatttccac gttttggaaa attttttcca 152220
tttgtattat aaatatatct atatatattc aaattatggt agtttatgac ttgctcgttt 152280
ctttaagtaa ggaatccata gatgtgctac ggtttgtaga ggcaaacctt gcggcgttta 152340
accagcagta tatttttttc aatatccaaa gaaaaaactc gatcacgaca ccccttctca 152400
ttacgccgca gcaggaaaaa atttcgcaaa ttgttgagtt tttaatggat gaatataata 152460
agaacaatag aaggccctcc gggccgccgc gtgagcagcc catgcaccca ttattgccgt 152520
atcaacaatc ctcggacgaa cagcccatga tgccgtatca acagcccccg gggaatgatg 152580
atcagccata tgagcaaata taccataaaa aacacgcgtc gcagcaagta aatactgaac 152640
tgaacgatta ttatcaacat attcttgcat taggcgatga agacaaaggt atggacagca 152700
tgttaaaact tccagaaaag gcaaaaaggg atagcgatga tgaggacgac atgttttcta 152760
taaaaaacta acgacgtaac aattaaacaa aaataaaaat cattataaaa tgaatcttga 152820
atacgtccaa gttgttcaaa aatttaatca agtactccta gaacttacca aaaaagtatg 152880
taccgttgtg ggcgggagca aacccaccta ttggtatcac cacattagaa gggtttgctc 152940
agaatgtcca tccatgccga tgagtatgat aggtccgtat ctgaatgtct ataaagccca 153000
aattctaaca agggacaaga attttttttat gaatttcgat cccgcgcata atgagtacac 153060
ctttatcatt caaaaactaa aagaagcagc ccgaaatatg ccggaagacg aattagaaca 153120
gtactgggta aaacttttat ttttacttaa aagctacata aaatgtaagc cctttattaa 153180
ttaaagaatt gatgcataac taataaatgg ccggtcgtgt taaaataaaa cagaaagagc 153240
tcatagactc tactgtaaaa aacaaaaatg tgatgaatct gttccatgaa attataggct 153300
caaaaggcaa tattaatttt agcgttgtct ggcccaagtt taaaaaaatc aaacagagcg 153360
tttatgacta catttccact ctttctgtgc tggaaaaagc aaacgttatg caaaactttg 153420
aagctgataa gaaactgttg gaactttttg tacaaaagct gtgggctgcc tatgaaggct 153480
atttcaaata tcccgagatt gaaaaatatg aggtggaagg ccaggtaaat ttcaatctcg 153540
tacctcagtg cgtcctcgaa aagtttagcc agttgtatag gataagaatc aattcagagc 153600
ttgtcacact catcctaaac agctgtgcct ttatgagtaa atataacgat tatattctca 153660
aaaaagatcc ctacatacta accataaccc ccggcctatg cttttccccc attcccaact 153720
tcgaggacct aaattttaaa catctttaca acagtgataa aaattctcag catgacaaag 153780
agtttatcat gtttatatta tataagcttt atacggctgc cctaggagtg tacaatgcca 153840
tctcgattcc agacatcgac gtagaagacc ttgaaaatat catcctatcc tcggtgagcc 153900
agattaaaaa acaaattccg cgctgcaaag acgccttcaa caaaattgaa tcttcggtac 153960
acctgttgcg caaaaaattt aacacatatt acagtgacta tgtgggctca ggctacaacc 154020
caaccatcat tatggaacag tacattaaag acatatcaca ggattccaag aacatatcac 154080
cacgcatttc ctaccagttt agaaccatca tcaagtatta ccgcgacatg attgccacca 154140
ggcatcaaac gatggacccc caggtattaa acctcgtaaa gcacgtcgaa aagaaattag 154200
atatgcttga tagagaaaaa aattagtata tatagttatg gtgaatcttt ttcctgtttt 154260
taccttaatt gtgattatta caattttaat tacgactcga gaactatcca ccacgatgct 154320
tattgtttct cttgtaacag attatattat tattaataca cagtatacgg aacagcagca 154380
tgaaaacaat acatttttca tgccgcaaaa aaattctttt aacgaatctt ataataaaga 154440
caaaaaatct aatatacata ttccctacca gtggctggcg cctgaactga aggaagctga 154500
gagcaagtac tggtggggca attatgatcc tcatagcgag cccgttctcg ctggcgcatc 154560
ttgaatatct tcatacgtgg cacgtcacca tcaaaaacat tgcccaacag cacgggcttg 154620
atataaaggt ggccattgtg gtctcaacat cgcatttaaa taattttttg ccaatttccg 154680
gggcgcttaa catcgaatgt ataaccttcc ccagttgcgg catcaaggag atagacctcc 154740
tatgggcgcg cattaaacta tttcaacatt actgcgccat cggtgcccgt cttttatggc 154800
tggtaagtgc tgacatcagg ccccctgttt cagcgtggcc agccatcgcc gacagtctaa 154860
aaaagggagc agatgcggtc gttattccct accccctcccg atggaacaat cttataccta 154920
ccgtcatcaa agaaatagtt gtccaccaaa aaaaatgcct tgtggcggtg gatgcacgcc 154980
accttgatac agatacccag attgtagggg ccgggatggg ctgcatcgtc ctaaccctaa 155040
aggcccttat ggtgcgccta agtattggca aacagcccgt taagatactg tggcccgacc 155100
ttcacggcac tgccgagggc attcctctgg agggggtgga ggttggctgg tttttaaacg 155160
cttatgcgca taaattaaat atacgctgcc taggggctga tcatattgcg cagcacttaa 155220
cttaattctt tatttaaaaa gtccacgcat ccagtggcgg cctacattaa gggcctacgc 155280
acataaatat acactggcta gaagtacgcc ttcatttaaa ccattgaatt atttatataa 155340
tggctgcaaa cattattgca acaagagccg tgccaaagat ggccagcaaa aaagagcatc 155400
aatactgtct gctagactcc caggaaaagc gtcatgggca ttatcccttt tcatttgaat 155460
taaagcctta tgggcaaaca ggcgcaaata tcataggagt acagggctca cttacccatg 155520
ttatcaaaat gacagtattt ccatttatga ttccttttcc tttacaaaaa actcatatag 155580
atgattttat tggtggacgc atttatttat tttttaagga actggacatg caagcagttt 155640

-continued ctgatgtaaa tggaatgcaa taccacttcg agttcaaggt tgttcctgta agccccaacc 155700
aagtagagct tcttcctgtg aataataaat ataaatttac atatgctata ccggtagtgc 155760
aataccttac cccaatcttt tatgatcttt cgggaccgct agatttccca ttagatactc 155820
tttcggtcca tgtggatatc ctctccaatc atatacagct tcctatccaa aaccataacc 155880
taacaacggg tgatcgtgtt tttatttctg gatataaaca cctgcaaacg attgaattat 155940
gtaaaaataa caagattttt atcaaaaata taccgccgct ttcatccgaa aaaataaaac 156000
tatatatact aaaaaatcga atcagaattc cgctatactt taaatcttta aaaacgtcta 156060
agtaataaca tttttatagt ctactcctag ttccgaaata ggctgaattt cttttttaag 156120
tcctttaaac caaggatgtg atacaagact cttaaaggaa agccgcttat tttcattaat 156180
tgttaaacat tccgtgataa actgttttcc cgtctctgaa atgttctcgg gaatataatt 156240
ttcccgtttc aggatatcat ttaaataaaa attttctgca cgaaatctaa aaagattaac 156300
cgcgaccata cctatcgtcc acacggttaa aggaagctgg tagtaataac cataataata 156360
aaattctgga cacacgtatt cccatgttcc aaacatatta tattggggac gggtttcgtc 156420
taatctaaca gcgcttccaa agtcaatgac cttaatgatc ttttgattta tgtctataat 156480
aaggttctca tccttaatat ccccatggat aaagcccttc tcataaatgt tttgtataat 156540
aagaataagc tggaatatta tttttttggc ttcggtttcc tcaagttttt taaagtaatg 156600
ataatgaagt agatcaacac tatttggaat atattctatg attagtatat gatacatagc 156660
attttcggta tattcgataa gcttaataac accgggagta tcttgcaggg ctttcaacac 156720
gatgacttca tttcctggaa tttctttttt agaaacgtac ttaaatataa tgggttgccc 156780
tacttgatga cccaaaaaga cgttatttct gccaccctca aacatgggtc tcgtcgcaat 156840
gaaatacatg tgctgcgttg tggagatcct ttccaccttt gctgtaggat aaaacgcata 156900
ttgtgcctgg ggattttta acatttttt aagctgttgt tccggcctgg acatgtttta 156960
ttagctttat atataaaggg ttagaaggtt taatttcaat atatgcctta atgatgggat 157020
tatattcgta aaaggtatag cctaatccta cgtctttgtt tttttggtaa aaaaactgtt 157080
tgccctcgta ggatatgcta taggctttta cttcggcttt tacaagcggt tggcagggat 157140
tgggcaaacg taaatcgcgt tcaaagtttt catgaaaaag caaagcattt gtgggctgac 157200
acatcagaca gccgctttcg ccattgaagg cacattcaat ggccgccctt tttagtaaat 157260
cgcggaaagc agaattaaga tggctctttt caagcccccct ttcgtgaaaa cgctcatcaa 157320 tcgtttttg ttcctgactg ccttcgggaa tactataaaa cattttttga ttagccaccg 157380
cgatgtacaa aaaaggctgt acggttttct cctcgggcgg tagcgcatcg tggctaccaa 157440
tgcgtataat gcgcgccttc acttgatcct ctcgggcctt atcccagtac ggctctagga 157500
tatgaacctg ccgcccgtat ttgagatcca atccctcagc tcctgtttta gagacgagta 157560
aaattttaat aacctctccg tgtatattca gcggcgaatt ccaaagctgc tggatcatgt 157620
cgcgctcttt agataaaatt ttccctgtaa taagcgtaaa tcgtgttatt ttggaggaca 157680
ggactaacgt atgggtcggc ccatcttccg caaagttttt caccataaga tctttcccat 157740
ccttatgaag gaggatggtg ttgtgccctt cttccaatac ttttaggggc tgaaggcact 157800
ggtagccctc tatttctaaa aagcgggcca cgacgtgaag gcccaattcc acaaactgtg 157860
agtaaatgag cacagggccc ggagacgttt taatattttt tagcatgcgt actattttgg 157920
gactagaatt ttctgtgaag gcctctttgg gcagctgctg aacagcctct gataattttt 157980
catcctcctt tactgttagc atttcggacg cgaagatgct gatcatacgg gaacgcacat 158040
agtaggagga gcctgactct tgctccgatc ctggcaggca gagggcggcg gcatttattt 158100
tttcatacat tcctgagctg gcgtgctttt ccgcgttttc aacgtctcgg gccagcagat 158160
attgcctata ctgctcgggt gacatttcaa ccttttctat aataagagga agctctgtgg 158220
ggaatagctt gttgagctca ttctggtttc cagcgtagct tatcataccc actaggcggt 158280
ttagtagttt gtccgcgttt aaagggctat tcgttgtttt attgacataa gcggtgtaga 158340
atctttcata gtgaagaggt aataagattc gcccgcttag catattaaaa cagggcacca 158400
tttcaaaggg gtccttcgaa cacggggtgc ctgttaaaaa cagaatacga atatttttag 158460
cttgcataat attattgtac agctggcggg catttgtttt atcattggcg ctattgataa 158520
ttcctctaaa gaggttgtgt gcctcgtcaa cgatgagcag gcatccattt agggaccctc 158580
ccgcctttat gatctgctgc cccatgttgt aagcgtctag ggacacaaac ctgaagcgcc 158640
gcgagatttt ttgtagctct ttggagtgat ccgtcgtttc cggatataaa agtttaataa 158700
gctttaacaa agactgttgg aagtttgagt gcaacgactt gggtgcgatc agaatcgggt 158760
tgtaaatatg tgaaagtgag atggcaagcg acaggctcaa aatggttttc cccatgccca 158820
tctggtgata gatgaggagg ccccgtgtgt tttccccctg gcctatccca aatttaggat 158880
ccgaaaaggc ggtgtaaatt aaaaactggt agtatttcag ggctcgtgca aagcgggcag 158940
tgagtgaggt gtctttgctt tcctgaagct ctttatattt ttcatatacc tcttttaggt 159000
atgcttctat ttggacgggg aaggaggtgt tgttgtgcac gcaagacatg actcgttata 159060
aggatcccat attaaaactt cattagaaga atagggctgc tgatagctag cgctgcactt 159120
aaaaatgggg tagccctttt tcttgtaaat ccggtgcctg tcgtagacct ggctagaaag 159180
cgggcttagt gtatctttaa tgtccacaac gatgcgtacc tttttttcat ccgatccctg 159240
ccgggtaata cgtcccaaga tttgctccat gttgtttctg cggggcgttg ccatgatgat 159300
cgatgtcata tgcttgaagg aaatgcctct acgcccgtag ccataggtca gcaagataat 159360
ggaagcgctg tgtgcctgag aaagagcggt atttgaaacc ccgccgcata ggagcgccac 159420
ctccggaacg ataatttgaa catctttgaa ttctttggaa agcgcctgat aaaaaatttc 159480
taaaagtttg cgaaattcca cgaaaatgat gatgccatac ggctcatcgg tcccccattt 159540
gtgaggctca gcggtatgca gggagtaaag ccgctttgcc tcatttacga caagttgtat 159600
acgcgaagga tcttgaagta gtttatcaat ggtggcaatg gccgatacct tttcattaat 159660
atacacaggg ctaacgaagt caggatgtcc ctgatattcg atttccctca cgtacccgga 159720
aaaggttgtg gtgggactta cagtcctctg gggctgtcct agatggtgaa taataatctt 159780
gtccatacca tcgggccggt ccaggggtgt agcggacagt cctaatatcc gactaagttg 159840
tattttccaa aaaatttttgt aattctccgg cgagtgtaat tcatgtgcct catctaacac 159900
gactagacca aagggctcaa agaactgctc aggcttcttg cgcagggtat taatgattcc 159960
cacgatgacg tcgtactctt tgctcgtcat gtccttttttc ttgcacgctg cattattgta 160020
agcagctaca cgtaggtggg gcaggagcaa tgttagctcg tcgatccact gtatttgaat 160080
cgccttggtg ggcacgatga ccagggtagg gtacaaaagt ttttgaataa tgctgatcgc 160140
aatacgcgtt ttccccaaac cggtatttag atgtaggtaa aagcgcccat agggggacag 160200
gagcttttta tgaatcttat cgaccatttc ttgctggtag ttaaatagtg gaaattctgt 160260
ttcaacgcat gggagggccc gcagcgacac ggggcgcgtc gtgtaaacca tgttaaacat 160320
ttcaaactgc ttttgcagca atatgggaaa ataaatgtat tccccctgca gcgtgaaggc 160380

-continued agtttcctgt cttatggcta tgtgctttgg ctgcccgggt aatgcccgcg ccgtaacggt 160440
gagcgcctta agaacgcgcc cgaaatcatg ttgtaattta ctttgtagct tcttataatt 160500
tattcctatt ccagcaaagg atataatggc ctccattctc acgctggacg ggttatatgc 160560
agaggttcca aaattcttac cagaggcgtt acgagagggc tgtgctggca agaatcctct 160620
aagcttttat attcaacaaa ttttaaattt aatgggatgt gacggtaacg agtaccatgt 160680
tctttttacc agcagctccg aggaagcaaa tactcatatg atcatggccg ccgtgcgtcg 160740
ccatttgctg cggacgcagc aaaggcctca tgtcattatc ggagcagccg agccccctag 160800
cgtcaccgaa tgtgtgaagg cattggcgca ggaaaaacgc tgcgtataca ccatcatccc 160860
cctaaaaaat tttgaaatag atcctgttgc ggtatacgat gccatacaaa gcaatacctg 160920
cttagcgtgc atttcaggca ctaatgctgt tgtcaaaacg ttcaacaaac tccaggacat 160980
cagcaacgtg ttaaaaggta ttcccctgca ctcagaagtg agtgatcttg tttatcaagg 161040
atgtattcaa caaaatccgc ccgctgatag tttttcaata aatagtctct acggcttcct 161100
gggagtcggt gttttgggaa tgaagaaaaa ggtcatgcaa ggattggggc cgctcatttt 161160
tggaggaggg ctgagaggcg gaagccctaa tatacccgga attcatgcca tgtataaaac 161220
gctaacccag caaaggcctt ctatgaaaaa aaataaatac aatacatacg ctgttcatga 161280
aaactttaaa aaacatcagc atgtatatct acccataggg ggcgtgtctg cagaggacac 161340
gtctgcagaa aacatatcta caaaagacat gcctgttgaa ggcccgaagg gactcccggg 161400
ctatatttta tttagcgttg gccgtcgcgc cgaggagcta caaaaaaaaa ttttcactaa 161460
atttaatata aaggttggcc gtgttgttga cttacaagag atactgtttc gtatcaaaat 161520
accccaaaaa tactgggaga cattattgtt catccaatta agagataatt tgaccaaaga 161580
ggacataaaa agagttatgg ttgttttgat gcatttagat accatcactc ctcgtggctc 161640
tcttcctcct ccgagccact cttcttcttt ttcttaatcg tttttgtttg ttctataata 161700
agggaaaaga actccgtggg atcttgttcc ccgtacaggt tatctgcgac cataaggatg 161760
cttagaatgg taaacaggtg agaatacata agggtttgcg ttttaagaaa accctgacgt 161820
tgaatcataa ttgaaaacac cttgcaaagc cgactcatca gttgttctgt aatggcgtta 161880
agcattttct ggaattttc ttggttttcg ggtgtgattt tatattcatg tagaaagtgt 161940
ttcacacctg aggagaagaa tctttcctcc ttcgagagcc catctttgat gatgggaagt 162000
tccttgatca gggcaaacca ttcctcctct tgggcttgcg gattctgaag atactgatgg 162060
cagatatggt ttagaatggt gcacacgtag ctaataagct ctgagctgat tctttggttg 162120
gttttcaaat gttggcgaaa gtagtttttc accgaagtgc atgtaataaa cgtcttcatt 162180
ttcttataat atacaacagt atgttgagtc tttaatttaa aattacaagg agttttctag 162240
gtctttatgc gtataggtgt ttctttgtcg taaattttca atagccgaca ttgtttgtga 162300
agcagtgttc tgagtagtga ctgtcgtgta aggctcagcc ggatgagcag gagcactcgc 162360
ggccgcaggt gcggccgccg gcccgccagt tgccatgact agtctgtccg taactgggtt 162420
gtccgtaact ggtttgtttg ttgctggtct gtttgttgcc ggtctgcccg tgactggctt 162480
gcctacactt gctgtagtcg ctccagctgg tttagaggta cctggttgtg gagtgacttc 162540
tacccactgc tgatcttgat aaggatttat aaactgtata tcttcctcct caatagcagc 162600
agcttttttc tttcttgaag agaatagata gattagaacg atgataatga tgactaagac 162660
cacgatagca atgagaatag tatacatatg tgtggagaag aagcttggtg tagtgactgg 162720
tgacaaacac tcaccataat gccgcggata aaccggttga aaaaattcag aatccattta 162780
agatactatt ataaataata tataaaaatg ttgtggcgca atgaaattac agaatttatg 162840
gaccaacttt ccaagtattc tcaagaaatc ttaaaaacgt ttaagcaatt gcgtcctagt 162900
gaatataaac aatacaatga atttttaaca caagttacac cgttgctgca aaaaacccct 162960
gaaaaaattc cagagttggt tgaccatata ttcaattacc tagacaacgt tgaaaaaatt 163020
tgtgagctcc tcgtgaatgc tagctcaatt attattagtt caaaaatacg agaacaagta 163080
aaacacggaa tgagcttcag ctataaagcc gacctcgact ccttggcgga cattctctct 163140
caaaaacagt acgtgcttat gcatctttca aaaaatattg cggccgagta ttttaatacg 163200
tgtttaaacc aagggaaatc caagttagat ctcaaagctg cctctgtatt tttatagtagt 163260 cgttcccgaa cggcaagctc agcagaactc tatagaaaaa tgctatacgc ctatggttca 163320
ccgcaggaaa ttaattatta tactgaaaaa gcccgaaata agacgttgga tgtggaggag 163380
agcgacagca tggccatcat cgaacgaacg gcccgacaca acctttccct tatgcacccg 163440
ctagaagcca tggggcttac ctttggggca accaacacgg acgccgaccc ggaggatctg 163500
aaggacaaaa cggtgataaa tttaacgctc ccgcaggcaa cagaaagcat cacctaccat 163560
cttaaatccc taatgcagct aaaaaaagta agtacggctt caggactaaa tacaaacatt 163620
ttgaaagcat ttgataatat tatttccacc cctgtgaaaa aaaataaaat ggcctccaag 163680
ttggcgcccg ggatggatgt cgtgttcact agcgataacg gaaaaacatt ttttactaaa 163740
aacattttaa gcaaaaacat gctagcgggg cccaaagagc gggtgtttgc atataataat 163800
ctcattagta atttaaataa ctcctgtttc atacaaaatc acaacgattt tttaagacag 163860
caggactctt ggcccttcta tgacgcgcac aattttacca acaagttttt aatgcagcct 163920 atttttttcgg ggcagacccg tcctcggctt cagggagcca tggaggcggc gcatgtggaa 163980
acgcatctca cggcattttt acaaagtatt cagccctcta ggccacaaga tccctctgtt 164040
ttggcttccc ccaagttatc tgctctaatc ttgaactaaa aacagccttt cttggactta 164100
aatgatggtc taccagtttt tgaaataact tagagaacta tgaagatttt catgaaattt 164160
aaattagaga tttgcaaagg ttacttgcgg tcattttctg ttgaattaaa taattattcg 164220
aatagtataa tgtctgaaga tattcgtcgt ggtcctggca gaccgccaaa gaaaagggtt 164280
gttcccaact ttgagcgcaa gggcattctg gaaaaaccag ttcggccaca aagccgtctc 164340
gagttttcct atgataaccc gctgatattt aaaaatcttt ttatttactt taaaaacctt 164400
aaaagtaaaa atattttggt gcgatgtacc cccaccgaga ttaccttttt ttcacgtgac 164460
cagtcgcagg caagctttgt tattgccacc atcgacggaa aaaacgtgaa ccattattac 164520
gccagtgatg tcttttggct aggcatcaac agagagctcg ttgaaaaaat gtttaacagc 164580
attgatcgct ctttttttaaa aattaccatc gttcaccgct atgacaagcc tgaaaccctg 164640
ttttttatct ttacggattt tgacattgac aaggagtgca cgtatcagat tacggtctcg 164700
gagcccgagc tcgatatgga ccttatcgaa atggaaaaaa gcatcagtga agaaagactc 164760
aagaactatc ctctgcgctg ggagtttacc tccaagcagc tcaagaaaac atttagcgac 164820
ttatcaaact acaccgagct cgtgaccatt gaaaaactcg gcggcgatac gccgctgcac 164880
ctgtatttcc aaaagtttaa ctccatctca taccacgaga tgtataaatc ttccaacaag 164940
atcaacctga cctcgaccat tcctaagtcg caggtgttcc agataaatgt taaaattgct 165000
cacatcaagt cgctggcctc ggctatggtc accgacaaga tccgcattct gtgcgaagaa 165060
aatgggaacc taatctttca atcggaaatg gatgccctta tgttaaatac gattaccttg 165120

-continued aacaccacga tatagttcgg taacattaga tgttctaata tttagcatct aaataatacg 165180
ctgtagtccg gtcagggttg cgtcacagtt ttcccatttt tttgcctcgt cggcggtggc 165240
caccgttgcc ctatcattta cgcccggtaa gacaaagcta aaggcgttca gcggggcttg 165300
gcaatgcccg cccagcgtga aggagctcgg aggattttgc gcatcccgaa atcccttagc 165360
catgttgttt aacacttcgg ttacgtcaat cgagtgaagg gatcccttgg gatccgtgaa 165420
tgtaaagacg cagtttctaa agcgcatgta tgcgatggac gattcatcgg gggttttgaa 165480
ggtaacagtg ttccccttgc tgtacttaaa gggggaccat ccggtaaaat tataccaaat 165540
gaaagcaata ataattaaaa taaccaacac aatagttata gacaacacaa agtctgtagt 165600
gccgcccatt attaaataaa aatattttag accgccggct taaaatttac ttattgctca 165660
tagcttaagt ctattttatt catagcttaa gtttattgct catggcttaa gtctattgct 165720
tatagcttaa gtctatttta ttcatagctt aagtctattg ttcatggctt aagtttgttg 165780
ctcatagctt aactccatta ctgatagctt actgatcatg acttaaataa aaatattttg 165840
cccgcttaaa aattgtttag gtttgaaaaa ataagagatg gagggggcaa cttatcgtca 165900
ttgtgtttac ccccactgga agacatcaaa cggtaaataa ttataagaat caaaatgatt 165960
aatataaggg ttaaaaaagg atgattcatc acattaatta aaaacgtatt tataacgctg 166020
ttgcagttga aattttggta taggtcggaa atattgcccg agcctccgta ttctgcaatg 166080
ttctgacata tggtgagtcc ggaggggcac tgcttgttgg tcaaaatatt tctttgctcc 166140
gttgttttat aggcattttt atttccatta cacggagcaa acgcacattc aggccatagg 166200
gtgccggagt tcacacaggc acaatactgg ctatacgcat actcatcctt tgagcacaat 166260
ccctgtttat cgcatatgct cccaataata ttgtcatcct ccgccgtttg ttgatttgta 166320
tgcgagcgta aaatagcggc ccaggccttg ggctcctttt tttgcagctc ggaaatcgaa 166380
gggcctgtac agctaaagtc gacccaaata tcattgcatt tcgtggaaac tggcatgcaa 166440
gacataattg aaataattaa taagtatata tcatggcaac aaattttttt attcaaccta 166500
tcaccgaaga agctgaagca tactacccac cttccgtgat aacgaataaa cggaaggacc 166560
tgggggtaga cgtatactgt tgctccgacc tagtgcttca acctggacta aatattgttc 166620
gcctgcatat taaagtagca tgcgaacaca tgggcaaaaa atgcggtttt aaaatcatgg 166680
cgagaagcag tatgtgcacc catgaacggc tgctcatcct tgcaaacgga attggtttaa 166740
tagacccggg ttatgtgggc gagctcatgc tcaagatcat taatcttggc gacaccccgg 166800
tccaaatatg ggccaaagaa tgtttggtgc agttggtggc ccaaggtgac catgtgcctg 166860
accatatcaa catcctaaaa agaaaccaaa tatttccgct gtttgcgcct accccaagag 166920
gcgagggtag atttgggagc acgggcgagg ccgggattat gagaacttaa ttttattttt 166980
tttcttaaca taatgggagg ctctacaagc aaaaattcct ttaaaaatac gaccaacatt 167040
atcagcaatt ccattttcaa tcagatgcaa agttgtattt ccatgttgga tggcaaaaat 167100
tacataggcg tattcggtga tggaaatatt ttaaaccacg ttttccagga tttaaactta 167160
tcattaaaca caagttgcgt gcaaaagcac gtaaacgagg aaaatttcat tacaaatctt 167220
tcgaaccaaa ttactcaaaa tttaaaagac caagaagttg cgttaaccca atggatggac 167280
gcaggaactc acgatcagaa aacggatata gaagaaaata taaaggtaaa cttaacaacc 167340
acacttattc aaaactgcgt ttcatccctg tcgggtatga acgtgctggt ggtgaagggg 167400
aatggcaaca ttgttgaaaa cgcaactcag aagcagtcgc agcaaatcat ctctaactgc 167460
ttgcagggga gcaagcaggc catagacacc acaaccggca tcactaacac ggtaaatcag 167520
tactcacact acacctcaaa aaactttttt gacttcattg cagacgcaat ttcggctgtt 167580
tttaaaaaca tcatggtcgc ggctgtagtt atcgttctaa tcatcgtagg gtttatagcc 167640
gtcttttact ttttgcattc acggcaccgc catgaggagg aagaagaagc tgaaccactc 167700
ataagcaaca aggtattaaa aaatgctgcc gtttcgtaat aatttaatta aaagtaaaaa 167760
aaaaggtatt gttatagtga tggcagattt taattctcca atccagtatt tgaaagaaga 167820
ttcgagggac cggacctcta taggttctct agaatacgat gaaaatgccg acacgatgat 167880
accgagcttc gcagcaggct tggaagagtt tgaacccatt cccgactatg accctaccac 167940
atcaacttcc ctgtattcac aattgaccca caacatggaa aaaatcgcag aggaagagga 168000
tagtaatttt ctacacgata ctagggagtt tacttcactg gtccccgatg aggcagacaa 168060
taaaccggaa gatgacgaag aaagcggtgc aaaacctaaa aagaaaaaac atttgtttcc 168120
aaaattaagc tcgcataaat cgaagtaaaa attgaagcga aaaaaagtag aaaaaaaatg 168180
tttggagctt ttgtaagcca ccgtttgtgg tcagatagtg gttgtacgac cacctgcatc 168240
acaaacagca ttgctaatta tgtagccttc ggcgaacaaa ttggatttcc ctttaaatca 168300
gctcaggtat ttattgccgg ccctagaaag gctgtgataa atattcagga agatgataaa 168360
gttgagcttt taaagatgat tgttaagcac aatctttggg ttgttgctca tggaacctac 168420
ttagatgtgc cctggtcccg taagagtgcg tttgttacac attttataca acaagaacta 168480
cttatatgca aggaagtcgg tattaaaggg ttagttttac acctaggcgc tgtggagcct 168540
gaacttatta tggaaggact aaaaaaaatt aagccggttg agggggttgt catttacctg 168600
gaaaccccgc ataacaaaca tcatacatat aaatacagta caattgagca gatcaaagaa 168660
ttgtttttac ggatacgaaa taccaggttg aaacagattg gtttatgcat tgatacggct 168720
cacatctggt cttccggtgt caacatctcc agctataatg acgcggggca atggctgcgc 168780
tcgctggaaa acattcattc cgtgatccca ccaagccaca ttatgttcca cctaaatgat 168840
gccgccacag aatgcggaag cggtatagac cgacatgcaa gtctttttga aggaatgatt 168900
tggaaatcat atagccataa aataaagcaa agcggtttat attgttttgt tgaatacgtt 168960
acgcgacacc agtgtccggc tatattggag agaaacctcg ggtcttccat gcaattacaa 169020
accgctttaa ccgcagaatt tactacatta aaatcgttat taaaataagg atgagtttta 169080
gcgaatgtcc cttagttatt agtgcatgca aaaaatttct acaaaagcgt attacaatag 169140
agaatgaagc acttataaat gccttaataa ccgctttagc gcagaccagc acgttgaatg 169200
atctttgttt attacctatt caaacctatt tgcttagtta taaaaatgct tttgagtgga 169260
tacacttcgt atgtattgca atcaccacta ttttggataa taagtataac tggaaggact 169320
gtacggtaga tattaattat atttttctcc atgtaaccta tatttacaat attaaaacca 169380
aggaatacct agactactgt tcttaaactt tatttttttct atatttacgc caaagagaat 169440
atttaaagtt tttttgaaaa aaataatata tgtagataaa attcagttac atgatatatg 169500
tgtaaacatg tgtggtaaac aacatatggt tatgctttat aagataaatg cgcataaatat 169560 atgtaaacaa aatatggtta tgtgttaaat gcatataaat gtattttaac gtatatcttg 169620
tgataatgga tatatgcatt tattaaaaga ggctgtattt attataaatc ttgctaagga 169680
tgccattgtc aacatatatc ccatgttgga caaattgcgt tgcgatccag ttcttttttt 169740
ttgattttgt ttaatgctat cctttttgaa gggatggttg tccaccatat ttattcgatg 169800
ttcaatgaat aggtctgctt tttcgtaagg cagtgaaggt cgttccaaga ctccttgaac 169860
gatggacgtg ttttcttgga tccacttaaa aagcacgtgg cattcaaaaa caggacagtg 169920
attggatcct tggatatgct ttggacagcc aatgcttgaa gagatgtagt cccttttctt 169980
taggacaagc ttctccacgc tggggcaaca gagatcgttc aagttctgga cggtcgcatt 170040
tggaatgttg aaacttcgta tccattcacc ctcgggtcct cccttatgaa gaaggagtat 170100
ttgctcatgg tccttagtaa tcttaaccaa atgttggaag atcatttttt tacctgcttt 170160
aaaggcctga agggtgtcag ttggcaaagc tattgaattc gggagtgggc tttcatcaag 170220
cgtgaaatgg tgaatgtgac gcgactggaa agaaaacgac cgttgattta tttttttcaaa 170280 gattgggtcg attccgccat gaaagaacag ctgcaagatt ttagaaggcg tatttttttc 170340
ccaataaaaa atgaccactt ctcgtgggat taaaatcgtc tgtgtcccat tttcattata 170400
taattggccc ataaagccat caacgtcaat caacaccaaa agcatggtat agagagcttt 170460
tagaaccgga gttcgttaaa aaaatacaaa gttcgtttaa aacgtgtaat gttactaaaa 170520
aaatgtaatg tttaaatgat aatgatacca catgcattaa tgaaaaaaac ttttaaattt 170580
ttgttttaat atttgcatga aaatggaaac atttttagtc tgtttatttc acaatgcaga 170640
tggtttacat caacagattc aggaaatttt gtatttattg cggatgcata tttacgaaac 170700
aaatctttac ttaaagcagg aactatcacg gcttatatat ccaaataggc aactttcttt 170760
tgtgttactt atgccccttt cccttctaag aaactgggat gacattgaat atttaacgga 170820
cgttgtagat gataagcaga ctctacatta cgcggcaaat ttgctgacaa actacgttct 170880
acatctatcc atgtttcaaa agctgacaaa accatacttc cttttagcgg tcaagcgggt 170940
cagcgaaaaa ctcaacaaaa agcagcgaca ttcattttac gaggtattgg taacctccga 171000
aaccttgaat aattatgaaa acctatctaa aaacatttta aatacgttga tgtttgccgt 171060
gcgctacgta tttaaaccta cgccgaacta ttcagaaatt ctcgcagagt tggaaaaaaa 171120
aaataaaatt caccatatta tttttaatat ggtaattacg gattttgcgc aaatccgtga 171180
acaacaaatg gataaacatc tgtgtgaaac aaataatgag cttcgtcagg aatgtaaaga 171240
aactattttt gatttaaagg tggtaggaaa tgtttagcca ataaactcat gcccgcattt 171300
tttacaggta caaaatatcg tggatggctc atcgagggcg cgtgtttgta cttctctgta 171360
ggtacacata cgctgcttgc agttgggaca cttataaagt tgtgacgtct tttcggcgac 171420
cttttgctgc gaacgtagag taatttctgt cttctccttt aaggcggcag aggggcaaag 171480
ctcggcgaac gtcatgctac caattgcctc cggttttagc tcgccagaaa ttagcttatt 171540
aagggcatcg ttatcctgtt gttggtgact tttttttcg cagttaataa tatgattgat 171600
cgtcccacaa cgggttgaat attcttctaa aaaggttttt tcttgttgct ggtacgtata 171660
atgataacac gaggcctcga ttttttgcgc gtattcggtg cataaatcag tatgttcctt 171720
aaaaaacata tgtttttgaa gcgttctaaa aaacatcatt tggatgatat cacgcatttc 171780
caaaataata tagggttcta gtcttttgga atctttcata actagatcgg tggtaatatt 171840
cttagtcata caatttatta aaaatggttt aatatattgt aaatattttt taggcgtgtc 171900
agcctgtaaa aaacattctt gttcaatctt atttgtaagg atagtatttt gcaaatactt 171960
atttagcaaa aatacgatag aatcgcgggc tatatgcatt ttcatataat ttttttttaa 172020
aatttaatac aaaaaaaaga agtatagact cttcttctag tccggttagt tcgttggttg 172080
cctcaacatg gagactcaga agttgatttc catggttaag gaagccttag aaaaatatca 172140
ataccctctt actgctaaaa atattaaagt agtgatacaa aaagagcaca atgtcgtctt 172200
acctacagga tctataaata gcatactgta cagtaactca gaacttttttg agaagattga 172260 taagacaaat accatttatc ccccgctttg gatacggaaa aactaattgt aaccagtagt 172320
acatttaagg atagtttaag cagtaaatgt agaataacac agttaagcaa taaataacaa 172380
gtatatagga atatatagga atatatagaa atatatagaa atagctaagc ttaatactaa 172440
ttcagctttt tttttaacta aaacctgaat agatgcgaag tagcggacat atacatacta 172500
aaataagcca tacatttact ttcttcttga acatgaaacc ttttttttctt ctgttgttgg 172560 tatataaaca ataggactgt ttgctgaggt tgtatgatct tctacaactg ctgtctcagg 172620
atgacgatgt ttttttaaac taaaagtgta ggatggaatg agtggaatat agttatggct 172680
cgacttatcc tgtttcgtac aggaatattt tttacaaata gaacgcaaca agcatatgaa 172740
taaaaacaga aatgatatac aggagcataa aatagatatg aacactaagg ggtagcagct 172800
tttataacgt tccgtatttt tcttagctat caattgattt accgtaatat ttatctcggg 172860
aaactttgtt ctacaatatt ttgtttggta ttccagaaac tcatgtcctg gcttattccc 172920
gcagcttaaa aaatgataca aaaatgtgtt attgttacta aaattaattc ttcttaagaa 172980
aaactgcgga agacgcttta ggtacgtctg ttcctgtttt agtaggaagt agtataaggg 173040
acaatttctt tttccacaca ttagattatt gtaatatagg taggttgggg tgttggagcg 173100
aataagtttt ctgagtatgt tataatctat gacttgtaaa tcgttatacc ttaggtccaa 173160
aaacttgagt tctttaccaa agccacctgc aatttcagaa atatttttca tcccgcagcg 173220
gataatacgg atgtcctgaa acgtctttaa aatacttgta ttgtagtgaa tacttatgtt 173280
atttttttgt aaataatcta tgtcatgaca agtgcatgaa atgccagcag cattgcttgg 173340
tatagtatta tatgcaggaa gaactatact actattgaga atagtcacat tgtacttata 173400
ccatgtatta ttttctgata taaagtattt gcaggtgacc tgtggtttaa tcctacctgt 173460
taagccactt cctaaaaaaa caaaaaaatat gaaaaccctt agcatcctgt atatactatt 173520
aaaaatttat aaaattttct gtttaaattt catttagaca aaaaaataat atatatacat 173580
cagcaagaaa ttatatacag attatataat tttctgattt ttttttgcca caataagcat 173640
cattatatgc attaaaatct caatactaaa cactaaaatc taaattctaa gcattaaatt 173700
ctaagcatta aattctatgc actaaactgt aagcactaaa atctaagtaa ctaaaatcaa 173760
cactaaatgt atgcaaccta aaatgtaaag cattactcat catcctcctc ttcttcatcc 173820
tcatcatcat aggttaagat atatgtgtca tcctccattt cttcacattc atcttcataa 173880
gcatcactgg gtattggtgg aacattggat gcagcatttt taaaatattc tatgtcttct 173940
ggtgaacact catctaatga ttttttgaca gtccttttaa cttccatggg atatgattcc 174000
aaatcctctt tatataagag tttacggtag cttttagctg catccacatt tgctggagaa 174060
tctggatttg gctcattgag cagtgaaatt acactaagaa gaatggtatc aatcttttga 174120
gccggagacc aagtcattcc ctgttcttca gcattgtctc cgtgtaagat agagatacat 174180
agttttccat cagagtaaat attaggatgc cacatttcag aggtgaatgt taatctgggt 174240
ggtgcatatg ggtattctgg aggaaaggcg atttttgcct tgaataagcc tccctcataa 174300
aaagtgtcag gtgggcccct taagatcaca tcccattcag tcatatcctt ctcattcacc 174360
gaaattttga aattctcaga gggattctct atcaggtgtc tgtactctgc tattaaaaac 174420
ctggaaacca tggttattta atattaatta aattccctgg tttattcctc cttaaaagta 174480
gatgaacctc ttttgttttt tattgggttc atttttacta aatttatgaa ctggaaaaaa 174540
ctttaacggc ataattatca aatgcgaagg gggatccgta taaaatccta gcttgccggt 174600

-continued aatggctatt aagttaaatt tggtaccagt aacactaata tttaaaaagc cctgatcatt 174660
aactttccac attaaaagat tattatattc gaatgtttgt ccaatatgga caactttgtc 174720
accagatgtt acatttgatt tggttgttag tggctgaagc ttggcacaat caaaaataag 174780
cccattaaca ctaagatata gaggagtggg ttgatctatt ttctcatagt ttaatattcc 174840
atctttccac gtaatagctt gataattatc cgcagcaatg agttgaaatt ttataaatag 174900
tacaggggtt ttagttgtcg ttatacattt aaagggtgtt tttataaaaat aaaaataata 174960
attgttaaaa gtatgataat aatcgccaaa ataatttcat acattttta taagaattat 175020
acatagtatg gtatttaaaa tattagctaa atttaaaaaa acttcatgat ttttaaaaca 175080
gggaaaaagg ggattaggtt gaataaaaaa ggtaagcact tgtctatata ttttttttac 175140
aatgttgcct tgagtcgcat ttttaactgg ctggggagta tcagagtgga atatcactgt 175200
agtaggtcta taaggtcttg ttaaaatatg atcggtcatt gttttcgtac tagtgtcatt 175260
tagggtcgac ctgatagctc gatataaagt tataggggat aacctatcaa atacagtctt 175320
atctgtgctg aaatgtatat cgtcttcttt atcactaata atattaggaa tggctgtcat 175380
taaataatta ctacttgttg ttgtgggtga aatagttgta ctggtattat tggaaatggc 175440
tgtcattaaa taattactac ttgttgttgt gggtgaaata gttgtactag tattattaga 175500
aatggctgtc gttaaataat tactacctat tacaagtaaa ctaatgctaa ctacattttt 175560
aacctcaata aacctaaaaa gccatactaa atacctaaac aacatcctgt tataatatga 175620
gcagaaaaaa aaataagtat aattagggaa ttattcttat tcgcttacta ttaagaataa 175680
ttcagaatct tatttagtta gaaactatca taaagtgaat aggactcatc gtcggatgaa 175740
gattccgttt cagagatagt ttctttttct tcctcagaat aatctgttcc tacaatagaa 175800
tcggtgtcat cctcagaaag agaagtattt aaatatggac tatctatagc aatatcctct 175860
tctatctcgc aatcctcctc ctccatttcc atagtgtgta ggagaatatt tttatcatca 175920
tgctcacttc tttttttgtt gaaagatgaa ccgtcctcaa tacggttcat gttaagttcc 175980
ttcatcttat gtataatttc cgtaatccgt gatgtttttg acatgtaaga tggttttaag 176040
gttatatcca caataacagg agaatctcta tcattttcat ttgataaact ttgatctttg 176100
atttcttcgt ctaaaattct tgtctttttt tgggtactag atgaaataga ggaattcata 176160
ttctgaaacg atatatcaag gggagctgga cgctttttc caattaaacc gtttttcgag 176220
atactatgat tagatgaatg atctttagcc aagctgtcct tggatatact atagttagat 176280
attttacctt taaataatat tcttctatac aagttattct taggtaaaga attagtatgg 176340
attcctatat ttttatctga aggagtgtcc atatcggaga acgtcctctt acgaatattt 176400
tgaccacgag ccatttcatc cactataggc agtattttgg ctggctatgg ttctttgttg 176460
tgacaattct atgagatttg attgcaaatc aatttttagt tttaaatata ttggtaccta 176520
ggacaaagaa agtatatata gccaataatt attccactaa attgatttcc agactgatgg 176580
gtatggagcc atgttgtctc tgcagacgat cgcaaaaatg gccgtagcaa caaacaccta 176640
ctccaagtat cactatccaa tactgaaggt ctttgggctg tggtggaaaa acaatacgct 176700
aaatggccct attaaaatat gtaaccattg caacaacata atggtaggag aatatcctat 176760
gtgttacaat catggaatga gtctggatat agctttgatt cgggcagtaa aggagcgtaa 176820
tatatcctta gtccagcttt tcaccgaatg ggggggaaat attgactatg gggcactttg 176880
tgctaacact ccatctatgc aaagattatg taaaagtttg ggagccaaac caccaaaggg 176940
ccgaatgtat atggatgctc ttatacatct ttcagatacc ttgaatgata atgatctgat 177000
tagggggtat gagattttg atgataatag cgtgttggat tgtgtcaatc tcatacgact 177060
caaaataatg cttaccttga aggcccgtat acctctcatg gaacaactag accaaattgc 177120
cttaaaacaa cttctgcagc gatactggta tgccatggct gtacaacaca acttaacaat 177180
cgctatccac tattttgata atcatattcc taatataaag ccatttagtc tgcgctgtgc 177240
tttgtatttt aatgatccct ttaaaatcca tgatgcttgc agaactgtaa atatggatcc 177300
taatgagatg atgaacattg cttgtcaaca ggatttaaac tttcaaagca tttactattg 177360
ttatctttta ggggctgata ttaatcaggc tatgctaatg tctttaaagt atggtcatct 177420
ttctaatatg tggttttgca tagatttggg ggcggatgcc tttaaagagg caggggcgct 177480
tgctgagaaa aaaataaaag agtgttacaa cacatattag gtcttaatat ctttaagcga 177540
gagttgattc ccccctgtaa agatcctgat ccttatcaaa tccaaattct gttaaaaaac 177600
tacattctaa aaaatgtctc aactgttttt acatattatt gccagtagcc attgtttata 177660
tcagaaaata acccatttgt ttatcttttt ttgtggggca accattaaga cccgacgcaa 177720
aaaaagatta atcttttatc agatacctaa aacgttctat aagggagtct atgagatgga 177780
tcatattttg atggtcatag taagaagcaa gctttttggc gaaaacaacg gagttaaaga 177840
atttaacccg ctcatgtttg gataggactt ttaacagcga gccaaaacag tatttaaaaa 177900
tttggcaata gttttttgg gatgcaataa acaaacactt gatcagtgcc cgcttcactt 177960
tctgatcaga catgtttgcc gcataacagg cctttttaaa cttagtaata taattatgtt 178020
ccgcaagcac cattaacaag ggaacgatgg gaagctgctt ttcttggtga aatttacgta 178080
aatattcgat ggccaccgct tggacgactg tgtaatttac taagttagaa atgatagctt 178140
tcatggttgt aaaaatatac ataggatttt ctttttctgt atacagtttg aaaagcttat 178200
gattacgtga aatgatggcc atttttaata caagatggta tagtgtatct ttaggtaaaa 178260
atgccttgca agccgcgatg atgtcgatgt tgtctccatg aacagcgata gaaactaatg 178320
tttccaatct aaatgttttt atctgcatta atagaagaat gcagtcaatg ttattatact 178380
taataatact gtaatacacc gaatcaatga ccgtcatctg agaatcaagc tgacttatta 178440
gtaaatttaa cgtttttttg gaggcatgac ctttgatcgc ggcactaagt gcacacagta 178500
tagcaaaatt gttaaataca ttttgattta ggagaaggag taatattttc cttcggttat 178560
agtacgcagc atctgtgatg attattggcc gataaatgtt aaaatgtgtt aacagctttt 178620
taaaaaaacg gaagtaattt ttttggatcg ctgtttgcat catcgaaata atgagataat 178680
cagggtatat aatgggtagg tcacatgcta cctctaacaa agaatagtcg cccaatctaa 178740
aggctgtgtt gaaaagcgta ctatcatcat acgtatcgag tacccctgct gttacaaacc 178800
aagcgataag atgaatgtgc cgttccttgc aagctatcgc aaatagggag tttcctatgg 178860
aatgtcgaat aatgtactcc ctattttttt ccaaaatgtt tggaaaattg tatagcgttg 178920
cggcatacag tagacactcc attctggcgt tataattttt acttttacat atgaataggt 178980
ggaagaactc gaataattct tgagaacttg ttaaatgcat aatatggtga tattttggtg 179040
tcgttaaatg gtatgagaaa atgcattcta atacatcttt tcggttatgc tttagcgcct 179100
gagctaaggc atattcaggc tcgacccata ggactagtgt ttctataatt gagatattcg 179160
cctgctttgc cagggcatac tttaagacgc tccggttaga aaaaatgttg ttatgaagat 179220
ggataaccgt atccattttt acgatgggac cattccagta tagtcctaaa tgctgtagca 179280
gatcttttgt tagttgtgaa gcgttctcgg gtgtcatata aatatgttgc agggcttttt 179340

-continued tctgtaagga gaacatttcg tcgtaatcgt acaaaaaaaa ttaaaatttg ggcatggatg 179400
attcaaacat aacaaaatca agattttata acagtttgca ttaacctata catatatgca 179460
agtaaatgag atattatcta tcataacgaa tcaagggata tttgtatata tcaggagttt 179520
ctgaaataaa gatatgaaga ttatcatagt agtatccatc aatcacaatg caacttcctt 179580
taaggcataa tttagtaaac tcagcactcc catcttctgg atgctttaca actaacatta 179640
aaaactcctc agtcatatta tctgtaataa aataagatcc tcctggagcc atttgtagca 179700
tgtctcttat tcctacaaaa tctttttgg gatggtaaaa actcagcagt ttcaaactct 179760
tttttagttt tttttcctgg tatttaagcc atttgttata aaacagtttt cttatgaaaa 179820
tgcatttgaa aatattggga atgtttaacc atgcttcttc cgagcacatc tccagatact 179880
tactttcttt gtttcccatg tctaatttat tgctcactaa gttagtaatg aatctatttt 179940
aataatctac tttactaatc tatcttaata acctatctta taatctatct taataaccta 180000
attataacct atttataatt ggctaatgct gccggcattt catgcctatc taaacaactc 180060
ctactaagca atctactatt acatatatag attcactttt tatatttgta aatcatgaga 180120
attataaaat cattactcat ttttattgta aattagtggg tatttgtaaa aatcttcaaa 180180
cgttttaaga tagttttcta gagagaagta atctttgcca tcaatatata atgcttttcc 180240
tttaaactcc agttttgcta tgtttagtga gccgtttcta gatcttttg ggcaataaat 180300
agattttcat tggttgcatc gtccgtaagc agaaaggtac cactaggcac gttaaaaaac 180360
atacgttcta tttcatggtc ggatttttga gaatagaaaa aatctaattt tttaatccgc 180420
gttaactctt ttttatcaat ctttccagac tgttttatat atactttatt gcaaatctta 180480
caatcctcta tggcttcatt atacttattt tgcttatcct ctattgacat gtccgtattt 180540
gataggtaac ttccgttaag gcggttcccc atggttttag atagattttt aattcagttg 180600
tatactttta ttatgaggct aaaatataga agtttgatcc taaaaaaata aaaagatttt 180660
gtacatttat ttatggttta tagcggtata gaggccgata aaaggtatcc gggtagtctc 180720
ctatgatatc gtcaattttg gtataataac agttgttatg gtagtattgt ccaaaccgag 180780
tatgtatgcg ccggtgaagc gtccgcccgc taatggtaca gttccaggtt aagacaatca 180840
tatcacaccc aaaaagagag gaaacagcat aggtgcccaa aggttcatta tataacatac 180900
gccgcatata ttttagtttt ttttctccat ggtaataatc acaggttttc atgtcctgct 180960
taataggatg attccccatg tatgataata tataataaat ttagttttta gctttttcaa 181020
aaaattgggc gctcgaaact aaattttcct tatcacagcg tttggagaaa gcgtatttaa 181080
agatatatct tcttctaaca agactgcaaa aaaaatctta cccccttattt ttataatgtt 181140
catcatagcg tttgaagata tcagaaggtg ccaggtttta taaaaatatc ctttaggatt 181200
tataacgata caagggtcta taaaatatat gcgggtataa tcttataaaa tcatcgattt 181260
tttcataata ttctccgttt atacaataaa gatcataaca gatattgatg cgtagatgca 181320
ttattcgcgt gttcgttggg cagctaaagg atatcacaac gtagtttttt ttaagaaaag 181380
acgaaactac ataagtccct aagggttcat tgaatagtaa acgccatatt tgttttaaat 181440
tttgttgttc accatagtag tattcgcact ttttcaagtc ttttttaata agcctattcc 181500
ccatgtatgc ttataaataa aaatttagaa atgtgctata ttatttgttg atgaatcatg 181560
aacacgtctt atatgttgat atgttacttt aaaaacattt gtattttcaa cagacgcgtt 181620
ctattcttat taagaatgat gccgtcttta ttttaaacct tggtttaaaa tttaaagaag 181680
tatttataaa ctataatcat gggaactttt tcagtaactg cctctgcaaa aagtgacgat 181740

-continued gctgtttgta agtatttaga agaaccaata gatgaaaatt acagaaacat attaagaaat 181800
gagcatgtta aaaaaaattt aaatgaggct ctgaatcgac atattactac ctataatcca 181860
gtagttgatt ggtgtaataa ctattcaaca ttttcatctc aggatttcga tgaatataaa 181920
atttatatac atagcgatct tatggatgga cgacctcgtc caaaaaaaac atggtgtgtc 181980
atcatgtaat gtttgttagt tttatataaa cgcaaaaata ttcttctagg agatgttgat 182040
atactaccta ttgaattcaa tatattaaag tacatttctg gctattccca ttacggtatt 182100
attattacta tttttaagag ctagatgtgg atttaagtaa taataacatt ctcccgttcc 182160
tcctagagac acctcatcaa attcccatcc tatgcaacct ttatgttgta aacataatga 182220
ttgacagcat tcatcttctt ttgaccaagt cgtccaaatc ctaccaagat ctatacgtgt 182280
ttttccaaat ggagattgaa gatcagcagt agtggcatta aacctataaa aaccaggtgc 182340
ataatcacat gaacggatcg taggatctaa tttaatatct tttatatctt gttttactgc 182400
ttctagacaa cttttatcag tacatgttcc acgtacacag tggtgtcctt tatccttaca 182460
atccgtatct gtcttacatt ttttttcgg cggtttatgt ttcagatggt aaaaacccag 182520
tattaaaata atcacaagaa taattcctat aagtacttga acaacaggat aaaacatttt 182580
aatattaaat atatttttta attaaatgaa tagatttaat ccaagtagta ttaaaatttt 182640
ttagaaatag tgttctacaa ataatgaaat gaatggtcca aaaaaaataa ggtgtacaat 182700
aatgtaatat attgttaggc taagtaaatt taatatttta aagtatttgg aaaaatattt 182760
tttaacatat gatgtctagg aatatttttt agacatttaa aaccatatag ttactttatt 182820
tattacactg aacttgaaaa gacttattac ctaaaatatt aatagatgaa gtaatattgt 182880
gtaattgagt ccataacatg ggtgggaaac aaaaatctcg taatatgaaa aataaacatc 182940
ctaaaaagag tgcaattgtt ataagtttat gtaactttat tttaaagtaa gaatataaaa 183000
atatgagtac aagaggaata ggggccatta ctaacattgg ctccaacatc ctgttgtcta 183060
caaaaaaaaa tatttttttt agcaaaaaaa aatccatgga aggatattaa tacacataat 183120
tatttgacat cacattagtg tacttaccaa atagtaatat acaaccatcc taatattcac 183180
ctttatgaaa tgatcccaac ctatacggta aaatagtata ggttttaata aagaaaaaag 183240
atattctgtg gtttttattt ttgtatagtg tgtgaataca aaataaaatc ccaaatttta 183300
accttttctt ttttttctat acaggatgtt agaaatagta ttggcaacgc tgctaggcga 183360
cctgcagcgg ctccgggttc ttacccctca gcagcgggca gttgccttct ttcgagccaa 183420
tactaaggag ctagaggact tcttatgctc agatgggcag tctgaggagg tactgtctgg 183480
ccccttctt aaccgtctac tagaaccctc aggccctctt gatattttaa ccggatatca 183540
cctatttcgt cagaatccca aggcaggtca gttgcgcggc cttgaggtca agatgcttga 183600
acggttatac gatgctaata tttacaatat actgtctcgg ctgcggcctg aaaaagttcg 183660
caacaaggct attgagctat actgggtttt ccgagctatc catatttgtc atgctccttt 183720
agttttagat attgtacgat atgaggaacc ggactttgct gaactggcct ttatttgtgc 183780
tgcttacttt ggtgaacctc aggtaatgta tttgctctac aaatatatgc ctctgacccg 183840
cgcagttctt acggatgcca tccggataag tcttgagagc aacaaccagg tagggatttg 183900
ctatgcttac ttgatgggag gcagcctcaa gggactagtc tccgccccac tgcgtaaacg 183960
tctgcgcgcc aaactacgct cgcagcgcaa aaagaaggac gttctttcac cccacgactt 184020
cttactgctg ctccagtagc tttttttgcc gcaggagcac cgcggatagg agctcctcca 184080

-continued cgctcgcgat ccggcgctgg aagcggaacc gatcgaccgc cacctgctcc cagggaccct 184140
tgcgctcgat gtcgtcggct tcccacacct cgacggctgt ggcaaaatgg acatgcttcg 184200
cgtcgttcgt ccgtttttg cgccgcctcc ccattattct tcctgtaaga ttagtgttta 184260
atacctataa taacataatt ttaagattta atataccaaa acttaaacta tttttgtata 184320
gtaactatta gcatgtctac acatgattgt tctctaaaag agaaaccggt tgatatgaac 184380
gatatatctg agaaatcagt tgtcgtggat aatgcacccg agaaaccagc tggagcgaat 184440
catatacctg agaagtcggc ccgcgaaatg acatcatcag aatggattgc tgaatattgg 184500
aaaggtataa aacgtggaaa tgacgtgcca tgttgttgtc caagaaaaat gaccagtgca 184560
gacaaaaagt tttcagtatt tggtaaggga tccctaatgc gctccatcca gaagaataat 184620
taaaaaaaat atttttttta gcaagttttt aaactattta aataaatgtg gtaaaaaaat 184680
tcacataata attaaagtga acgtgttaga attaatattt ttttataatc ggatataata 184740
tccattaaat caataaatga tagtgttgct accacactaa acaataacaa acagaaacgc 184800
acgatacctt tcctcatgat ttataatagc gtgttatcta aagatttttt tgaaaaaaat 184860
attaaatttt agttgattat ttttttcagt tacaacattg ctttagaaaa aatacctaat 184920
tactacatag caaataaagc gagcgcattg ttacaaacaa catttttttt gcgcctggat 184980
actcctatat atgagaacta taatacggta tattaatcct attaccaaca ttgtcaataa 185040
tagtatgtag gcaatgacat actttaaata ccaaatatcc atggttattt ctaaaaatct 185100
tgaaaaaacg ttaaatttta gatcggtcac ctacgacagt aatactaatt ttaataattg 185160
atgactgaaa tcataatata atgccgtgcg aaaaataatt atttttcggt taaagatacc 185220
attacataaa aaatatgcca tctactctac aagtgcttgc taaaaaggta ttggccttag 185280
gggagcataa agaaaatgaa catatatcta gagaatatta ttatcatata ttaaagtgtt 185340
gcggtttatg gtggcatgaa gctccgatta tactttgtta tgatgggagt gagcaaatga 185400
tgataaagac tccaatcttt gaagaaggca tattacttaa tactgcatta atgaaagctg 185460
tacaggagaa taattatgaa ttaataaagt tgtttactga atggggagca aacatcaatt 185520
atggattaat ttccattaat accgagcatg cccgggatct atgtcgaaaa ttaggagcta 185580
aagaaatgct tgaaggaaat gaatttatac aaattatatt caaaacatta gatgatacca 185640
ccagtagtaa tataatttta tgtcatgaat tattcaccaa caatcctctt ttagagaatg 185700
taaatatggg ggaaatgagg atgataattt attggaggat gaaaaattta acgaacctat 185760
tattaaataa tgactctatt agtgaaatat taactaaatt ctggtatggt atagcagtaa 185820
aatataatct taaggatgcg atccaatatt tttaccagag attcatggac ttcaacgagt 185880
ggcgagtaac atgtgctctt tcttttaata atgtgaatga tcttcataag atgtatataa 185940
cagagaaggt tcatatgaat aatgacgaaa tgatgaatct agcctgcagc attcaagaca 186000
gaaatttatc aaccatttac tattgttttc tattgggggg ctaacatcaa tcaagcaatg 186060
ttaacctcag tattaaatta taatattttt aacttattct tttgtataga cttaggggct 186120
gatgcctttg aagagggtaa gaccctggcg aaacaaaagg ggtataatga aatagtggaa 186180
atcttatcat tagatatcat ttatagtcca aatactgact tctcatcaaa aatagaacct 186240
gaacatatta gttctttgtt aaaaaacttt tatccaaaaa atctgttcgc ttttgatcgt 186300
tgcaaccccg gtttatatta ttcttagagg accgctacaa aaattatttt ttttcttgat 186360
caaagctcca aaataattat tagattaaag tcgcctatag cagcagccca ctccaaaaaa 186420
agtattttat agtacaaaaa acacgaaaaa tagtttgcgg ccggcggcaa actatttgtt 186480
gttgtctaaa acttaatgtt tttttaatat ttttaaatgc aaccatggat tgttggacta 186540
tcagggagaa gaactatagc tacatcatat tgtcaatact ggtaatacta ttaatatggt 186600
atcttatact taactattgt cgatcgaaaa aaaatgcagt tacaaacaac atgccgccac 186660
catacacggt gtcaagtagc tgttctcaat aatagggttg attgacgctc ttcgtaataa 186720
tatgttgatt gacgcatcat aaaatgctgt ggttgattaa tatgttgatt gtcgcctact 186780
ttattatata agtaatgatt tttgtataaa atacgggttt gtgagggctt tattttttct 186840
tattagaaca aagcatgcaa tttaaggcct acagcaagag taatttaaca cctacaacag 186900
taattttaag gtcagtaata atgtttaatt aaggcctgac cactaaaact taaacgattt 186960
tgtaaaaaaa aatgtctact ccactttctc tacagactct tgttaaaaaa gtgctggcca 187020
cacagcacat atctaaagaa cactacttta ttttgaaata ttgtggttta tggtggcatg 187080
aagcgccgat tacgatttgc attgatgagg atagccaaat attgataaaa tcggcaagct 187140
tcaaagaagg cttatcttta gatatcgcat taatgaaagt cgtgcaagaa aataaccatg 187200
atttaataga gttgtttacc aagtggggtg cagatatcaa ctctagctta gttactgtta 187260
atacggagta tacccggaac ctttgtcaga aattaggcgc aaaggaagct ttgaatgaaa 187320
gggatatttt acaaatattt tataaaacac gtcatcttaa aactagcagt aatattattt 187380
tatataatga attgttttct aataatctcc ttttccaaaa tatagagaga ttgagtttaa 187440
tagtttatag gggcttgaaa aacttatcaa tcaactttat attggatgat atttcattta 187500
gcgaaatgtt aactagatac tggtatagta tggcgatatt atataacctt actgaagcca 187560
tccaatattt ttatcaacga tataggcatt ttaaagattg gcggcttata tgtgggcttt 187620
cttttaacaa tttgtctgac cttcatgaag tatataactt agagaagacg gatatagaca 187680
ttgatgaaat gatgaagttg acctgtagta cgtatgatgg taattattcg actatttatt 187740
attgttttat gttgggggct gacatcaatc gggcaatgtt aacctcggta ataaactttc 187800
atattggtaa cttgttcctt tgtatagatt taggagctga tgctttcgaa gacagcatgg 187860
aactagcaaa acaaaagaat aataatatat tagtagaaat attatcattt aaaaattatt 187920
atagttcaaa tacctctctt ttatcaataa aaacgacaga tccggaaaaa attaatgcct 187980
tattagatga agaaaagtat gagtcaaaaa atatgttaat gtatgaagaa ttatctcatt 188040
gatacaaaat tattttttat aacagaactc tctgatggtg acaaatctcc gataggaata 188100
tatgacgtaa cataattatt tttttcgccc agaaaaaaat tataaatgtt attattgcca 188160
gcacttttat caactatacg tacaaaaagg tgttgaccaa aaaaataatt ttttttcttg 188220
atcaaagtat gtaaacgccc gcttacagca aggatcttaa gtgagagcca ttaaatttta 188280
ttgatagctg cttgccacca gtagaatacg gccaaaccac ctaacaggaa atacaaggcg 188340
gcccttcggc caataaggtg gataaaaatc acgcataaga cggttgtaac atagcacttt 188400
agtgcgaata tcaggaatgc caatagcatg tagataaggc accaaacatc gcagctatac 188460
atggctaaag atcaaccaga aaaggtttaa attttaacgc cggcccaaaa cttaaacttt 188520
ttttgatatt tttaagtgca gccatggatt ggtccggcca taggatgacc tatgcctacg 188580
tggcattctc attgatggca atagcaataa tatggtatat tctacttatc tattgccgat 188640
cgaaaaaaaa tgttgttaca agcggtaata cgctcgcttt agcgccaata tcgcatatgt 188700
gaaaaatgtt cgccgaaaaa aacattaaaa tttagaaccg ccgcggcatc tcaggggcgg 188760
caacattttt ttttatatgg atattgtcac acaccacctc atctatgacg caatatatta 188820

-continued ctgctaatat caggttcccc aatagtatgt agagaaacca cacaagatag atattcatgg 188880
cgatttttga cgaaaaaaca ttaagtttta gcttctttga cgcctgtgta ctaataatgt 188940
ttaacgcctg tagtataata attgatacct acagcagtaa ttgataccta cggcgataat 189000
gtctctctgg ccgccccaaa aaaaagtatt tacggtaggg tttattaccg gcggcgtaac 189060
accagttatg gtcaattttg tctggcccgc cgcccagccg caaaaaaaaa tcaattacaa 189120
ccgcaaaaaa aaatatttcc ggccgcggcg tttcaaaaaa taatctttgc gaaataattc 189180
cgcatcttgt gaaatgaacg cctacagtaa taattttaat ctttgacacc tacagcagta 189240
gtaataattt taatctttaa cgcctgcagc agtactaata ttttaatctt taacgcctac 189300
agcagtagta ataattttaa tgtttaacgc ctacagcagt agtaat 189346

<210> SEQ ID NO 2
<211> LENGTH: 119
<212> TYPE: PRT
<213> ORGANISM: African swine fever virus

<400> SEQUENCE: 2

Met Leu His Trp Gly Pro Lys Tyr Trp Arg Ser Leu His Leu Tyr Ala
1 5 10 15

Ile Phe Phe Ser Asp Ala Pro Ser Trp Lys Glu Lys Tyr Glu Ala Ile
20 25 30

Gln Trp Ile Leu Asn Phe Ile Glu Ser Leu Pro Cys Thr Arg Cys Gln
35 40 45

His His Ala Phe Ser Tyr Leu Thr Lys Asn Pro Leu Thr Leu Asn Asn
50 55 60

Ser Glu Asp Phe Gln Tyr Trp Thr Phe Ala Phe His Asn Asn Val Asn
65 70 75 80

Asn Arg Leu Asn Lys Lys Ile Ile Ser Trp Ser Glu Tyr Lys Asn Ile
85 90 95

Tyr Glu Gln Ser Ile Leu Lys Thr Ile Glu Tyr Gly Lys Thr Asp Phe
100 105 110

Ile Gly Ala Trp Ser Ser Leu
115

<210> SEQ ID NO 3
<211> LENGTH: 191496
<212> TYPE: DNA
<213> ORGANISM: African swine fever virus

<400> SEQUENCE: 3
gaatatacca tattattgct attgccatca atgagaatgc cacgtaggca taggtcatcc 60
tatggccgga ccaatccatg gctgcactta aaaatatcaa aaaagtttaa gttttgggcc 120
ggcgttaaaa tttaaacctt ttctggttga tctttagcca tgtatagctg cgatgtttgg 180
tgccttatct acatgctatt ggcattcctg atattcgcac taaagtgcta tgttacaacc 240
gtcttatgcg tgatttttat ccaccttatt ggccgaaggg ccgccttgta tttcctgtta 300
ggtggtttgg ccgtattcta ctggtggcaa gcagctatca ataaaattta atggctctca 360
cttaagatcc ttgctgtaag cgggcgttta catactttga tcaagaaaaa aattattttt 420
ggaccccccc ccatgtttta tacaaaaatc atataataaa gtggcgacaa tcaacatatt 480
aatcaaccac agcattttat gatgtgttaa tcaacatata ccatattaat caaccacagc 540
attttatgat gcgtcaatca acatattatt acggagagcg tcaatcaata taatattgag 600
aacagcgact tgataccgtg tatggtggtg gcggcggcat gttgtttgta acagcatttt 660

-continued

```
tcatcattcg aagcttacaa aagatatgta taagatagca tattaatgtt attaacagta    720
atatcaataa ggcgtagcta tagatcttca ctttggtaga ccaataatcc atggttgcgc    780
ttaaaaatac caaaaaaaac attaagtttt ggagggtaag attggttttt caccattggt    840
aaagattatt attctaaatg tttaccccat agatgtgaaa caatgattct tcatatatta    900
acatattttt tgacttatac ttttcttcat ctagtaaggc gttaattttt tccggatctg    960
tcgtttttat tgataaaaga gaagagtctg gactgtaatt tttaaataat aagatattta   1020
ttaatatcca attattcgtt tggctcgcta tttccatgct ctcttcgaaa gcatcagctc   1080
ctaaatctat acaaaggaat aagttacctt cacaaaaatt cattaccgag gtaatcattg   1140
cccgattaat gtcagccccc aacataaaac aataatatat agttgtataa ttacaatcat   1200
acatacaggc caactgcatc atttcatcaa tgtctatatt tgtcttctct ttgttataaa   1260
tttcatgaag gtcaaagacg ttgttataag caaccccaca tattaaccgc caatctttaa   1320
aatgactata tcgttgataa aaatattgga tggcttcagt aagcttatat agtatcgcca   1380
tactatacca atacctagtt agcatttcgt tgaatgaaat attatccaat gtaaagttaa   1440
ttgataatgt atctagttca ccaaaaattc ttaatttcag ttgagcatta tttaggaaaa   1500
ggggattatc agataataat tcatggcata gaataatatt actgctagtt ttaacatact   1560
gtacattata aaatatttct aaaattttat tttcactcaa agctttcctc gcacctaact   1620
tttggcatag gtcctggtgc actccatatt gacagtaacc aacccaaagc tgatgtctgc   1680
accccattcg gtaaacagct ctattaaacc atgattgttt tcctgtacag ccttcattaa   1740
tgcaacattt aatgttaaac catgtttaaa acttgctgtt tttattaata tttgttcatc   1800
tatacaagta tgataaatcg taattggggc ttcatgccac cacaaaccac aacgctctaa   1860
aatacaataa tcatctttta acacaggctg tgtagctagt actttttag taagtgcttg   1920
taaagtagat ggcatcttct atctgcaaaa taattatttc cgaaaaaaaa atcaaattaa   1980
aatactaaat tctatttttt tttttaataa agcctgtaaa ttatataata aatctcgccc   2040
accgtattat ttccggacac aactttttat acctcattat atttttagat ctatagtttt   2100
ttaacaaggc attaattttt tctggatctg tcgtttttaa agataaaaga gagacgtttg   2160
aactataata atctttaaat gataatattt ctactaatat atcatgattc ttttgttttg   2220
ctaattctaa gctctcttcg aaagcattag ctcctaaatc tatacaaaag aacaagttat   2280
tcatataaaa gtttttacc gaggtaacca ttgcccgatt gatgtcagcc cccaatacaa   2340
aacaatagta aatggttaaa aaattgctat ctctcataca ggccagatat atcatttcat   2400
caatattcat atcaaccttt tttatatgat acatttcatg aagatcagac acgttattaa   2460
aagaaagccc acatattagc cgccaatctt taaaatgact atatcgttga taaaaatatt   2520
ggatggcttc agtaagctta catagtatcg ctatactata ccaatatcta gttagcattt   2580
cgttgaatgt tatttcattc aatataaagt tgatcgatat cttctctaga aaacaacaaa   2640
ttattacttt taattcctct atattctgga aaaggggatt attagataac aatttatggc   2700
ataaaataat attactacta gttttaatac gatgtatttt ataaaatatt tgtacaatat   2760
ccatttcatt caaaattttt gcgcctaact cccggcagaa attccaagta tgctccgtat   2820
tgacagtgac taagctagag ttgatgtctg caccccattc agtaaacaac tctattagat   2880
catagttgtt ttcctgcaca gttttcatta atgcgagatt taactctaaa ccatctttaa   2940
aaattgctga ttttatcatc aattgattat cctcattagt agaaagcata attggagctc   3000
```

-continued

```
catgccacca caaaccacaa tatttcaaaa taaagtagtg ttctttagat atgtgctgtg   3060
tggccagtat ttttttagca agagcctgca gagaaattgg agtagacata ttttttttttg   3120
caaaatggtt taagtttttc aagaatacag attggataaa ttaggttgtt gacttagtta   3180
caggaggtat taaatattat gtagacataa aaatgagatc ctccaaaaaa ataaacaaca   3240
aaaaaaatat gtttaatatt aaaatgacaa tttctacatt gcttattgct cttattatac   3300
tacttattat tattttagta gtgtttttat actataagaa acaacaacca ccgaaaaagg   3360
tctgtaaagt agataaagat tgtggtagtg gagagcattg tgttcgtgga tcatgtagct   3420
cattgagctg cttagatgcc gtaaaaatgg acaaacgaaa tattaagata gattctaaga   3480
tttcctcatg cgaattcact cccaattttt accgttttac ggatactgct gctgatgagc   3540
agcaagaatt tggaaaaaca cggcatccta taaaaataac tccatctcca agtgaatccc   3600
atagcccccca agaggtgtgt gaaaaatatt gttcatgggg aaccgatgac tgtacaggtt   3660
gggaatatgt tggtgatgaa aaggagggaa catgttatgt atataataat ccacatcacc   3720
cggttcttaa atatggtaag gatcacatca tagccttacc tagaaatcat aaacatgcat   3780
aaataaatac attaggctca tcgtatcttt ttaaaatcca taaatattcg tttgatatat   3840
gctgaaattt ttataaaaaa aataactatt tcctataaat catctagaaa tagtcctcgt   3900
tttgatcggt ttatatctta taatattgtg catcgatgca caactgcttt ttttggtcct   3960
tctggaacat cattatattt tctttcatta atataccatt cagatgtaaa cgttgaataa   4020
tttttatggc aacaatctac cattgaatta tatttagtaa catctaatac atcgtttgtt   4080
ttatcaggct cagctctata atcttgataa tttttgttat cagcttctaa agctccatca   4140
ttatttttca aagaagtatc cataattatg tttggtaaaa atactttaag ttttaatgtg   4200
atatttaaaa tggttgttat ataaatttac cgcttacagg taatctttat tcagtgtcat   4260
aaactatact tttgatgatt cagtattttg tgaatcagta catttattat cattaatatt   4320
tttaggctgt ttttccaatg ttttattgtt gcaatgagcc tgctcctcct ttgacgagga   4380
agtgtctgtt ggagtcatct gtttaggaag agtatcatcc atatctatta tgaagaaaat   4440
atataaatat tgatatacaa tcaaaaatat ttttgatcac gtctttgtta tctatcgata   4500
ttgttgataa cgtcttgaat aacctacatc atttttttac ataaaaaaat agatataatt   4560
tttattatat ctcaattatt ttaaagataa ttatcaatac agcaaatatc ataagctaac   4620
atatttttcg aataatagtt ttttagtaaa gtattaatct tttcaggatt ggtttctttt   4680
gataataaga taggattcgc tttataaatt ttttaaagata atatattcac aatgatagaa   4740
taaccgtata tatctgctaa tgtcttactg tgttcaataa cattagcccc taaatccata   4800
caaaagaaca tattttcaat acaaaagttt tttaccgaga ttaacattgc tcgattagcg   4860
ttggctccca atgcaaaaca gtagtaaatg gtcaaaaaat tattatcgcg catacaggcc   4920
agctccatca ttttattaat actcatatga attttcgttg tgttacatat ttcatgaagg   4980
tcaaacacat tgttgaaaga aagtgcacaa attaatcgcc attcatcaaa atgcctgtat   5040
tcttgacaaa aatattgaat agcttcttta agattatatt ttaccgctat gccataccaa   5100
tatttggtta gcatctcact aaatgagatc tcatttaaca tagaatttgt tgttaaatcc   5160
ttcaactccc aataaatgat catccttaaa tccaccatgt ttacattttg taaaaaaggg   5220
ttattagaaa ataattcatg acacaaaatg acattactac ttgttatttt acactttgtt   5280
tcaaagaaaa atcgtaaaat ttcacttgtc tcaagctctt ctttagctcc caattttcgg   5340
cataggtttc gagtatgctc gttattaata aaaagtaacc cataattaat atttgcaccc   5400
```

```
cattcagtaa acaacatgat tagatcatca ttgttttcct taactgccaa taccaatgca   5460
gtattaagcc ttataccctc tttaaagcat aatgtcctta tcattatttg attatcatca   5520
tctatataca ttgagatagg agcttcatgc caccataaac cataacgctc taaaatataa   5580
taatcatctt tagatacgtg ttgcgtggcc aatgcccttt tagcaagtgc ttgtaaagtc   5640
gatggctgca tgtttattct gttaaaaaaa atcaaattat cgggtaaaca taaggatcaa   5700
cccgtagtta atatttgcag tagtattttt taacaatgaa ttataataaa aaaataattc   5760
attactatct attataaaac ccatctttaa ctttaaagaa gaactagatc atcttttttt   5820
tgttgtgtca gaacttcttc aatttattac ccacatttta tctaaaaaaa taaaaactac   5880
atcatatctt gtttcttcat caaattatca taccatttat agggtgtagg ttgggaacat   5940
tccatcatgt ggtaatcagg gtatttatat attttttgat agtaacatct atttggcaga   6000
tgtattgtcc aacaatcatg tctaataaaa tcattttcac ctatgggggga atcatcttaa   6060
aaaccttatt cctacagatt ccattttgac agtcccagca aaagtcacaa tattttccat   6120
gagtacacca atgttcaagc tctctttcgg gaggaatgct gccaatttta tgttttttag   6180
cttctaactc tctgtacaac atcagttggg aaagcagaaa gaagattacc aggagaacca   6240
ttaaatatat aatagtctgc aaactacgtt tgcgaatgta atttgcaact aaaacacaac   6300
ccacaaggta aaatccataa gttaataact tttgccattt tcgtatgaca gcctcgtgcc   6360
attcatggtt gtgttgtggg cattctgttc ggtaaacttc atgaggcttt atagaagtta   6420
catagtaggt acagaattca ttgtgacgaa aaacactgca gttagctatg tagtcatttt   6480
caagaatggg agaatggttt tcaaagacct tattcttaca gatgccatct tgacagtccc   6540
aacagaacct acaatgattt gcataggtgc accagtattc aagctccttt tcaggagggg   6600
ttcttgttag atccaggagc tctagctcat atgtataaag aagagttgga atggatagta   6660
aagtaaatat ttgcagacca agcatggcta cttgtgaaca agtggctgct cgtcaacaaa   6720
tagctgttta tcagcaaata gctgtttatc agcaacaact aattatcagc aaatgctgct   6780
tgtgggtaag ccaataaata ggccataccc ttgaaaggag aattcagttt gataaaaaaa   6840
ataacgagtt ttctaataac ccggtcaagc atttaataaa tgaatagcat cacacgtctg   6900
catcgtgcat tctgcctgga aaatgggccc atctctaata tatttacact gacggtgaat   6960
catacagtgt tccatgggat agctatgctc ctgtacagga ggcatatctt ttagaacttt   7020
attcttacaa agaccatctt gacaagccca gcaaaaccga caatttttca catattgaca   7080
ccagtatcta agctcctctt ccaggggatt gtcggtcgaa aacccctgta gactagctag   7140
gccagctagc agcaagccga ggtaactaaa gaacctcatt gtagtgttat attacgaaaa   7200
aacatgttaa aatttggaaa aaaaagccct ttttatagat ctggaaaaaa attttcacaa   7260
atctaattaa aagccttaca gatcatcctt ttcataaatt ttcattaaca attggtgggg   7320
gcggttgtga ggtactggat cagaacaatc cataacatgg taatgtccat ttccttcacc   7380
atatgtacac tggttatacc agcgagaaac ctcacaagat gtcaaataac tgttctcaac   7440
aatcaatggc atgctcttat tcaccttgtt cttgcaaatt ccatgtgcac attcccagca   7500
aaacttgcag ttttccatgt aagtacacca gtatccaagt tcttcttgtg gaggattatc   7560
cgttgaacga agatgccctc ctgcctgagt aggtagtcct aagacctgat tggccagcag   7620
gccaagaatt tccaagaaga tcaccaacat tgctacggct ggctgaacag ctggcagata   7680
gctagctaat tagcaaacca agtgactcgc cctctctact cttaatatga gaatttaaga   7740
```

-continued

```
ttcggtccgg ctttttttccc atgttttaca gggaaaaggt atttttagcc tatgaatgta   7800
catggttccg cacattaaaa aaaataaaag aaattattta atattggctg ttattttctt   7860
tcaactagca acaagccagg taactaaaga acttcattgt agttttatat tacggaaaag   7920
gttaaatttt ggacaaaaaa atcatatcta attaaaaatc ctcacagatc tttcttttca   7980
taaattttca ttaacaattg gtaggggcgg ttgtgaggta ctggatcaga acaatccata   8040
acatggtaat gcccatttcc ttcaccatat gtacactggt tataccagcg agaaacctca   8100
catgttgtca agtagctgtt ttcaataatc aatggcatgc tattattcac cttgttcttg   8160
caaattccat gtgcacattc ccagcaaaac ttgcaccttt ccatgtaagt gcaccagtat   8220
ccaagttctt cttgtggagg attatccgtt gaacgaagat gccctcctgc ctgagtaggt   8280
agtcctacga cctgattggc cagcaggcca agaattccca agaagactac caacattgct   8340
acggctggct gaacagctgg cagatagcta gctaattagc aaaccaagtg actcaccctc   8400
tctactctta atatgagaat ttaagatccg gtccgacatt tttccgatat tttacaagaa   8460
aaagatattt ttagctacaa atacacttca tatatcccta aaaaaacaaa aatttattta   8520
attttaacta ttattttctt tccactctct ctttaagatt ttgtaaggat tccagggctt   8580
tggttcagaa caggccatta catggtgaat cccctgtcct agatcataca tacatttatt   8640
tagccagcgg gaaactatac atgattgcac atactcattt tcaagaattg ttgtattctc   8700
caatttgccc tcacaaaggc cattttgaca attccagcaa aacttgcagt tttctgtata   8760
agtgcaccag tattcaagtt cttcttgtgg aggattatcc gttggatgaa gttgtccagc   8820
tggttgatta ggtagcccta agacctggtt gcaattcatg gtatggtaga tacccttatc   8880
taaatcatac atacatttat ccagccaacg ggaaaccaga catgatttca catactcatt   8940
cttgtaaatt actgacccat ctattttgtt tatacaagtg ccgtcttggc agtcccagca   9000
aaattggcaa ctttccatgt aggcacacca gtattcgagt tcttcctctg gaggctcctc   9060
tgttggacga agttgtccaa cgagctgact tgaaacctgg ctggccagaa ggccaagaat   9120
tcccaagaag atcaccaaca ttgctacggc tggctgaaca gctgactgaa tagctagcca   9180
attagcaatc cactgtactt ttcataagat catttaagat tcggtcggca tttttttcaat   9240
agtttgctag gaaaaaattt ttaattttat agattcacac tacttcattc tcatgcttag   9300
gaaaaaaaca aactaaatct tacaatgtat ctggatctaa tgagaagcta gaattcatct   9360
tttttcaaat cctttctggg atgttcattc tttttccact ccttccttgc aattttataa   9420
ggattccagg gctttgggtc agaacagttc atgctatggt aaatgtgctc ctccacatca   9480
tatctacata ggtcacccca gcgggaaacc tcacaatatt ttacatagtc attctcaata   9540
atacttgtgg agttgtttcc ccaaaccctg ctggtacaaa tcccatcttc acaatcccag   9600
cagaaccgac agctttccac ataagtgcac cagtatccaa gttcattctc tgggggttca   9660
aatgttagag gaagatgtcc acctacccga gtagaagtgg aggatgaaac caggttgcta   9720
ctggccagca ggccaataat tcccaggata atcaccagca ttgtgctcaa ccagcaacgg   9780
ctagcaacga ctagcaactg actagcaata gctagaaatg gctagcaatc agtagtagct   9840
aacgctctac tctttataag aaaatttaaa attcgatcag atttttttag aattgagaat   9900
gagtaaaacg cttatattct ttttctagct agaaaaaata agctagttta agataggatt   9960
tcccttacta acggtttaat ttttagcaaa ggtataggta aaatacactt gtacttagct  10020
gcaaaaaaat aagcttatgg cgtataagcc gccataagtt tatttaatta aaatgttaaa  10080
ctctgtgata agactggaat cttaggcagg tttgatgtgg agaacagcat gaaatacaag  10140
```

-continued

```
agtgcctgtt acacgaataa gttctctcaa accggggatg gtcatactca catctatgaa  10200
atcctggtct aggagattca tttgatgcat gatggccgca cccacactta tgagacactg  10260
aagaactaaa gggtttaatt ttgatctgaa tggtactata taggatgatg gcaatccata  10320
tcaagattag agcaatcaaa atcacctcct caagaagcat gatgtagcct taaatcttag  10380
actgctttaa accttaggcc ctcactatct ttaatgaagg agtttaaatt ttgatccctt  10440
tttcaagacc catttagaag aaaaaataaa gtttatatca atctaattca taagtcatct  10500
ctttcataaa tcttcatgta ttctctatgt ggataagtat gggatgttgg atttgcgcag  10560
tccatttgat gatctgtatg gtttttgggt ccttcataat aactacatat accattccag  10620
cgggaaaccg tgcaatttat aatccagtca ttttgatgaa taactggcca atctgtttga  10680
atcctgtttc ggcagatacc gtggacgcat tcccagcaaa agtcacattg gtttgcgtaa  10740
gtgcaccaat aaactagctc atgttcagga ggataacggg ttggtagtaa atcttctaat  10800
ttacgtatag gagcggcttg aaggacaacc acccccagta gtactagaat cagtaccttt  10860
atagtggcca ccctacacta gacctctaag ttgaagacaa agaactaaaa tttagagccg  10920
tttaattact actaataatt atattttta ttgtctacaa taggattcta ttaaaaaata  10980
atgattttta ccaagaaata tttttataaa aaattaatat attttgtaat aaactttatt  11040
tccaatgact gttaaaataa ggaaactatc cttagttagt cgaggaagat ggttaggtta  11100
tttcgcaatc cgataaaatg tttattttat cgtaggtctc gtaaaatcca ggaaaaaaaa  11160
ttacggaaga gtttaaaaaa gctaaatttt taccaccctc cagaagattg ttgtcaaata  11220
tatcgtttgc tagaaaatgt tcctggagga acttacttta ttacagaaaa tatgacgaat  11280
gatttaatta tggtcgtaaa ggattcggtg gataaaaaaa ttaaaagcat taaattatat  11340
cttcatggaa gttatattaa gattcatcag cactattata ttaatattta tatgtatctt  11400
atgagatata cccaaattta taaatatccc ttaatttgtt ttaacaaata ttataacatc  11460
taagtaaata ttcttggaat ggattttctt atagaatggt tacaggatat gtcagcgaca  11520
ggcttaataa caaatttgtt aatatttttt tgttaaataa atgaacaggc caccatttaa  11580
tattacccgt tgcaaaataa gaaaaaaaaa caaacttata gttacaaatc atcttgatta  11640
atcacatgtc gttttaactc aatgaaccat tctaaatctt tgggttgtga acaattcatg  11700
ttatgttgat agtgtatcct aaagtgagct tcatacatac accggtcatg ccaccgggaa  11760
actgtacaat taacaatata atcattttgc gtaataatag ggtggtcact aaacacttta  11820
tttttacaca ttccatcttt acaggtccag cagaagtcac agtgttttgc ataggtgcac  11880
cagaacttga gatccctttc aggaggccta cgcatttgca tcggattatc tgtggaaaga  11940
ggtaggttca ttattatgtt cgtcatcaaa attcctaaaa gaacatagaa gccaagaaag  12000
ataagcagtc ttgtagcggc ttgcattcgc attcgtgagt attgtttgcg aacatagctt  12060
atgagagcaa tggtagctat catacaaaga caagtatgtt tgatattctc agtgtcaatg  12120
accctatcct cctttatttg cattaactca tcaaaccaat cataatatgt gggatttgta  12180
cagctcatga tgtgaaagcg gcgtatccta gagtctgtaa agtagctaca tctttcatta  12240
tagcgagaaa ccctacatat ttgtatgtaa tcattttttt tgatgagagg gtgtttttca  12300
aaaaccttat ttttacaaac cccgtgtcga caattccagc agaagtcaca cgattttgca  12360
taggtgcacc aatactcaag ctctctcttt ggaggtctcc gggtcattgg taactctcct  12420
gttcctggaa aagattggct ttgaatgacc ggctgcatga ccgccagtac caaaaggaac  12480
```

-continued

```
acaatcacct tcatggctgc aacttataag ttgcaactta tgggttgcaa tactgcaacg  12540
tataggttgc accttataga tcgcgactca aaaggtatga aaaccttacc ctcaatacag  12600
aatttaagtt ttaatcctga taatgtatct gtttatgaaa aaaaattttt tttactcatg  12660
tatgaattct tatacgaatc ataatatgta ggctgagaat aataattcat atacggtgtt  12720
gcgggctcaa taaaaatttt gttaccacaa aaaataaatg ctggattttt aagatatata  12780
tctattaatg actaaaccct ttatacgctg taggctgaaa acaatccata taatgaatat  12840
acggtgattt gggtttaata aaatacatac aacggtcaaa atagcgggca atactacatt  12900
gactaatata atcattttgt ttaataagag gcatatcatc ccacacttta tttttacaaa  12960
taccgttcct acattcccag cagaaatcac agtgttttcc atacgtgcac cagtattcaa  13020
gctctcttat aggaggcgta taagtccttg gtaaattttg tttcatataa aagatggaaa  13080
ggggtcgatt taaacccggc tgagatagcc aaatcaaaat acataaaaga gcaagtagtt  13140
tcatagtggt atttagatgt aaatttttat agtatgcaaa tacaatgtaa cctacaaata  13200
caatactaaa tacaaggtaa aaacaacaat gtcttataat gattggccaa taatcacccc  13260
cccccccccc atttttccat gaatatttca tttcctgtat agggtctagg atgtgaacac  13320
tccatgttat gatgattagg cattttaact gatatttcat aaaaacaccc ccaggaattg  13380
cgattaacta tacagtttac aatcgaattc atcgaattag actcatttgt tatcttattt  13440
ttacaaatgc cattttgaca atcccagcag aagtcacaat tctttacata cgtacaccaa  13500
tatggaagct cctccttagg aggatgctgg gttcttggta attctggtaa ttcatgtgca  13560
agaatgagga ctgagtagcc caacaaaagt cctagaacct tcatgttgtg tccaaatggc  13620
acctgtcatt ttaaaaaaga tttaaatttt gctaccgcaa aaaaaatcca gtatgtattt  13680
ttttaataca tataattatt gaagtcttat aagataaagc cgagaacact atattttgta  13740
tagatgatgt atccggtatt caaactctct tataagtaca tgtaggaaat ggtcaattat  13800
tcaagattgg ctgagataac aacaaaacca aaatactcaa aagcataagt aatttcatgg  13860
ttgtactcag tcgtagattt ttgcagatcg caaatgcaac gcaaccagca aatacaaagc  13920
taaatacaag gtaaaaacaa taatacctta taatgattgg ccaattctta tccctccatt  13980
tttccatgaa catttcatgt tcataaagtc taggatacga acaacatttc atgctatgat  14040
gattaggtat tttaagtgat atttcataaa aacaccacgg ggttgttggt gattgatagg  14100
taagaataag gatggttgaa taacctagta aaagtcctag aaaaaccttc atattgcgtt  14160
cataccacag atgttattta aaaaaaatat aaattttaca gtatgtgata tacacatacc  14220
acaaaaatgt tcttatatta actaaaatat gtgggcagag agcaattcat ataatgaata  14280
tatggtattt taggctcaat aaagtacata caacgatcaa taaaacgggt aatactacat  14340
ttactgatgt aatcattttg aacaataaga ggcatatcat ccaaaacctt atttttacaa  14400
ataccattct tacaatccca gcagaaatca cagtgttttc catacgtaca ccaatattca  14460
agttctctca taggaggcgt ataggtcctt ggtaaaattt gtttcgtata aaagatggaa  14520
aggggtcgat ttaaaactgg ctgtgctaac caaaccaaaa tactcaaaag aacgaaaagt  14580
ttcatggttg tactcagacg cagattctta caaagcgcac atacaaagca gcctgtatat  14640
gcaataccaa tgatgaaata gagacagtat tgctttatag ataattgttg atggtcaccc  14700
cccccccccc cccatgtttg catgaatatt tcatttcctg tatagggtct aggatgtaaa  14760
cattccatgc taaagtgatt aggcatttta gatgaaattt catataaaca ggattgagtc  14820
ttggaatcac ggaaaactct acagtttaca atagaatgat tggagtcaat gaaacgagat  14880
```

```
tccgttatct tatttttgca aatgccatct tgacagtccc aacagaaatc gcattgtggt  14940
acatacgtac accaatatga aagctcactc ttgggaggat gctgggttct tggtaagtct  15000
ggtaattcat gtgcgagaat gaggactgag tagcccaaca aaagtcccag aagaaccttc  15060
atgttgcgtc taaatgacac ctgcacttac aaaaaaaaat ttaaattttg aatataacac  15120
aaaaaaacca ccttaaaatt tcttatatta tttcttggat ctgccccgac gtcatacaat  15180
gtattaaaat tatagaccaa tcatcttttt gtatataggc taatcatctt tatatataga  15240
ttttagatgt ttgcttgttg tatcaactta actgctagcg aagaaaatgg ataaaaactt  15300
tctgtatttt tataggttga aatcatttta tgcacatcgc taggatctaa tattttattt  15360
tgaagaaccg aatgtgggct taaaattttt ttcttagaaa aaagtagaat cataatattg  15420
ctatgttttt gtttaatgat ttcttgtatc ttttttgtat acgggttggc acccaaacct  15480
atacaaaaat atacattact caaataacta ccttctatac ataatctttt ttccccacgt  15540
attttcctat ttatttccct atttatggaa ttaaaggata tcaatctctc taaggcacgg  15600
tcaaggtctg cgcctaaggc aaaacaataa tatataccta atttattccc agggcgtgca  15660
caggcaagaa acatcatgac gtttagccct aaacgtatat tttcctgaaa atacgcatga  15720
tgaacttcat caatattacc taagtatatg gccgtttgta aacgccaaag atctaaatga  15780
ggaaattttt tactaagata atgaataggt tttgtgagat taaaatctat ggcgaactta  15840
taccaaaatt ttaatacaag tgtatttctc gtcatttctt cttcttttc atctaaatat  15900
aagataaaac gattgtaaac aaagtctatc aataggtgaa aatcattgct attaaagctg  15960
tcgagaatca aaatattgtc ataataaatt tcgatcgcca gtaaaacctt ttttcgtttg  16020
acgagataaa caaacatatt atacaaccct acatctaaaa attctggatt ggctcctagt  16080
tggatacaca ggtctttagt ctgcttcgtt ttggcacaca tgatgccaaa attaatatca  16140
gcaccccata aaacaaataa cttgattaga tcagtctggt tttccttcac agcttttact  16200
aaggctctgt caagctcata gctgtcgaca tcagagcatg acatagagcc accggttacc  16260
attttacatt gcttacaaaa acctatgggt ccgttttccc accatagtcc aagctgttgt  16320
agaataaaaa tatcatcctc atgataattt gaaaaagcct tggtttctat caagactttt  16380
tttgtaagaa cctgtaaaga gttcatcgta ttattatgaa taacaggagt aaacgtaatc  16440
aattataaaa gtgatttttt cgaaaaaaac tttagatggt tgaaaatgat aatgtacatg  16500
ttcatacaaa aaatagatgc agtgatgtct aaaatcaaaa tttaattttc tatgtaaaaa  16560
gtacagactt acttatttgg gttaaattgt ttattttaaa ctttaattaa ccgtttgagt  16620
tagcgatgtt tgatttatct tccatactca tccggggggg gggggtcctt atagctctga  16680
cattattgtg gattattgaa tataatgaat acttcataga tgctaaacat tttaatagta  16740
gttctgaggc ttaattgtac tctataaatt tataaaaact ttttgatcaa aatttaattt  16800
cttataaaaa gagtacagac gtcgcttgtt taagcttcat catgtttcat tcattacttt  16860
ctacaattac gggggggggg agtcccctca tagctttagt attgctatgg tttactaatt  16920
attatgtaga atttatagaa gcatatgtac ctgaaagtat acctactcta taaaattaaa  16980
taatttcagt atattttttt tatgaataga acggaaatga tataaaaata atttaatatt  17040
gcaaaaaaaa ttcataatgt tggtatgtat tataaacata atagcatgtg taatttataa  17100
actgactcct ctatataatt attagatgag gtaccaacct acttatgata tgccgatgat  17160
agatattgta tactataaaa caaaattatt ttaaatgtat tcatggatac attataacat  17220
```

-continued

```
ttttaccgca aattgtctct cagcgaagaa aatgaatgaa acgtttctgt atattcatag  17280
gttgaaatta ttttacgcac ttcactaggt tctaatattt tcttatgaag tattgaatgg  17340
gggcttaaaa gtcctttctt aaaaagaagt ttcatcataa cattcttttc ttgtctaaga  17400
agagtttctt gtattttttt tgtataagga ttggcaccca aacttataca aaaatgtaca  17460
ttactccaaa taccataatt tgaaaagaaa gttatttccc tatttacttc atgattaatg  17520
aaacctatca acgtctctaa ggccgtattg atatttgcgc ctaaggcaaa acaatagtat  17580
atacccaatt tattttgagg gtacatacaa gcaagcgaca tcatgtcatt tggatctaaa  17640
cgtatatttt cctgaaaata tgcatgatgg atttcatcaa cattacctaa gtatacagcc  17700
gtttttaaac gccaataatc taggtgagga aatttcttac taagaaaacg aataggtttt  17760
ataagattaa actctatggc gatcttaaac caaaatttta atacatatgt attttttatc  17820
atttttttctt tttcatctaa atttaagata aaacgattgt aaataaagtc tatcaacacg  17880
taaaaatcat ggctatcaaa actgtcgaga atcgaaatat tgtcataata aatatctata  17940
gctaataaga ccttttgttg tttaattaga tcaacaaaca tattatacaa ccctacatct  18000
aaaaattttg gatcagctcc tagttgaata cacagaactt tcgtcctttc cgtcttggca  18060
catatgatgc cataattaat gttggcaccc cataaaacaa ataacttgat tagatcagtc  18120
tggtttttct tcacagccct caccaaggct ctgtcaagct catagctgtc aacatcagaa  18180
catgacatag agccactggt taccatttta cattgtttac aaaaacctat gggtccgttt  18240
tcccaccata atccaagctg ctgtaaaata aaaatatcat cctcatgata atttgaaaaa  18300
gccttgtttt ctatcaagac ttttttgta agaacctgta aagaattcat cgtattatca  18360
tgaatgaaag cagtaaatgt aatcaattat aaaattgact tattgaagag aaatgttaaa  18420
tgagtgaaat cggtgtttat gatgatgtac atgatcatac gaagaaacac gttcactggt  18480
gtccatgatc aaaatttaat gttttacgta aaaagtacag atgttaactg tttagtttaa  18540
acataaattt aacctttagt ttaaacccta gttaatgatg tttaatattt cttctatact  18600
cattcaggga agtgtaatga ttctaatact gttgttatgg attattaatg aaaactttac  18660
agatgctgga gggaataatt ttaatcatac tgttttaatg tagctatata agctttcatc  18720
aaaatttaat ttttttata aaaatacacg aattaaacta aagtctaaac tttagtttga  18780
ctatttgagt taatgatgct taacttatct tccatgctta tcaagggggg gtcctaatag  18840
ttttgatact attgttgtgg attgttgaat ataataaata ctttatagat gctgaaatgt  18900
ttgaaaataa tagtacatca atgttgtaag tttgatcaaa atttaatttc tcataaaaaa  18960
ggtacacatc aacattgctc atttaagttt catgatgttt gattcattac ttcctacaat  19020
tactgggggg gggggggggt ctttaatagc tttagcattg ttatggtttg ctgactatta  19080
tgtagaattc atagaagcac gtttagatag taatatcact gcagtgtaga ttatgaaata  19140
catactaaac taatttcagt atattttttt tgttcatata agttaaggta caaaaatgat  19200
taaacattgc aaaaaaagaa aatcacaatg ctattataca tagtgatcat agtggcttgt  19260
atcatttcta aactagttcc aaatgaatat tgggcaatac atctattttt tatcattatg  19320
atttttatgg tatatatgta tgaaaagtta gatatacatc aaaaatctca gttctggaat  19380
tataccatgt caggcttatc tggacataac gtacaggtaa catgtaagtg ttactaaata  19440
ctatgaagta tctatttttt ttgttgtaaa aaaaagaact tgatagtatt ttttaaaaaa  19500
taaaataatt aattgtacgt caacttcctt attttattct ttaaaaataa ctcgtaagta  19560
ttatttatct attttttgaa aaaatagatg taatcggttt catcatttag gtgtgtattt  19620
```

-continued

```
cttttttagca tctatcaaga attcattgtt tagtgatatg aaaacaatga atgatcatta  19680
tcttctattt aacaaccacc taaataaatg aacgtctttt tcatcttaac tgattaccaa  19740
aagttatttt gcgaaaaggc atacatatga tcaatatcag acctacaatg aatatttcca  19800
taatatccct ttattgtaat aattctattt ttgcattccg atatctcatc atctgtgcta  19860
ttatatgttt ccataactgt ttcatcatca aacataaatc ctgttaaata ggcaaaagac  19920
tttaatcccg gatagatttt taccattttc ctgagagccg tgtatagctt gtaataaatg  19980
gccaaaaata tgcaataaag cgtagaaaga gagtaatttt tggcataaaa gattttgaag  20040
gtttgatgaa tggctaaatc gcatataata taagatacga ttttaaagcg cacctgttca  20100
cgcagatttg ttgaaaaatt cgtggaaaga tttaacaaat aaaaggttat taatagttgc  20160
tcatcattcc ccttatacga catcgtcaga cgctctaata ttttactact aggcacatct  20220
gccacatgtt gaacatttaa agcctgttct tcttctgtgt tacggcaaaa gagccgtgcg  20280
tattcaggtg aagctcccca ggataacaac gtccttgcta cggctaaatt tttttgacg  20340
atgactttta tcagaaataa gtctttattt ttgcattgat cactatgcga atttgtatag  20400
ttgacgccgt tgcattgagt acattgatat aatgttttac aattccagcg tagccctaaa  20460
tggtataaaa gaactgtatt ttcgacataa gcatgctgat taacgatgtt tttgagacaa  20520
cacgtcgtta aggacaccat attgtctcca atttgttaga taaaagtctt tactaaaaaa  20580
atagattttt agttttaaca atcgagattt tattatttgg atgcatcatc aaaaagattt  20640
ataagtataa gaggttgtat aagaaaaaaa tgatgttata ctatttatgt taaaatttaa  20700
tttatcatat aaaaagtaca gatttaatca gttggttaaa ctatttagtt aattaaacta  20760
aatagtttaa ccatttagtc agactacttg gttagcaatg tttgagcttt cttccattct  20820
tatccggggg ggggggtcct aatcgttcta atactattgt ggatagttga atataatgaa  20880
gactttatag atgctataat gatgaattct agtatgcctg tataaaataa ttaacctttt  20940
tgatcaaaat ttaatttttt tataaaaagc tacagagtag tgttttatta aacgtggctt  21000
atttaaaagt tacacaatgt taaaatctct acttacttta attctttgtg gggttttatt  21060
aactttatcc atattatggc ttactactta ccatgtagaa cttatagagg caatagatga  21120
tttctacgac tgaaatatag aatagtccat tttctatttg taaaataatg atttatattc  21180
tttcctaaaa atgatacttt atatggtttg aaaacaaata ttaacaactt gatttttttt  21240
tctataaata aactataaat gaaaatagta aaactcatag agtcttataa gtgaacatct  21300
tcataatgtt actcaaacgt tggactatta aaaaatattc cgtgtgcatt attgctttta  21360
atcagtatga ttactttata cgaagccgct attaaaacgc ttatcacaca ccgaaaacaa  21420
attttaaaac accccgatag ccgtgaaatt ttactagctt tggggttgta ctgggataaa  21480
actcatattc ttgttaaatg tcgtgaatgt gggaatatga gtcttaccgg aaaacacagt  21540
acaaaatgta ttaacattaa ttgtctactt attcttgcca taaaaaaaag aataagcgta  21600
ttgttgatac cttgatagga atgggcgcgg atgtaacata tatacatctt ttaaagaata  21660
agataaaact gtcatacaac cagctgtcta tgcttaaaag caactcgcag atttcattga  21720
aggagcttca tgctatatgc tatcttttat atggtcggct tcccaaaaaa attaaacaag  21780
ggatgcgact gtgtaaaaca atggcgggac tatgtggtga acttttatgt gcatttttag  21840
ctccgtaaat gataatatgt atttaaaaca aacagatatt accaaaatat attctatgta  21900
cataatatct gggaaattat ttttttttct catacctta aatataaaaa tattgggttt  21960
```

```
cttcactaaa ctttagaggt aaaaattttt ctttgttttg caccatcatg tatgggttta  22020
ggctgtccca gggattgttt atttgaatat ttcctaaata ggaacacaac gccatgatca  22080
tatatctttc attctggtaa gctttttgat acatcttcaa agatgccgta cctccgagtg  22140
tgtaacagca aacaaacgtc cgtacttttc catgggtcgc agcccattcc attccgtagc  22200
tcagcatctt ttgctgtatt tttttattcg ctttataaaa aaagtttttc atccattcca  22260
cgttctcata aaaacaggca cttaaaaaga gcactagggg tagtgtagtc ttattataga  22320
atgtaggaat gtatgtttta gttatttttt tcaacgcgtg ttccatacta tgttttaccg  22380
ccataaaaat acaaaaccaa taccaacttt ttctataaaa ggttttgctg tacacatata  22440
aacgagcaaa atatatttca aactctatat tctttttata aaaaaactcg agacagtcgt  22500
ttatgttacg actttttcta aatacctcaa aaacagtaat taattcactg tcgctgtgga  22560
aatgttcgta agctaactgt ttaatgtctt taggggtcaa ttcttttttt gggagcagtg  22620
gtttgagatt cggcaaaggt cgtctaaagt agtgagcgaa cttttcattc gctccccaac  22680
acaaaagccg ataagccagc atgtagttat cacgttttac cgcgtaaata agcaaatagt  22740
ttatattgat acatgtacca tgttgctgcc cgtttggaca tatgttgccg cattctgaac  22800
acttatgaat gagatcatag ttcttacaac ataaccccaa acgggttagt acttctttgt  22860
cacgttttaa aaactcgaca tgattcttta atgttaatgc tttgagcgca atgttaaata  22920
aactctgcat tttattaaaa tgaggttagt atcatgtttt agtataaaat ttagcggctg  22980
tttacataat gctaaataaa cttaacgttc ctactaaacc aaaaaaaatc aaattgacta  23040
agtcatagag aatttgacga tgttggtagg taattttta acatggtata tatttttta  23100
gggtcggtta tattaggtaa taaaagagga cgtgccgtta aagtattttg cttaagatcc  23160
tttagatcct tacaaaaata tagattgttc gtctgatgat gccactgtgt tgcagtgatg  23220
gcttgatcaa tatcacctcc caagacaaaa cagtagtata tcgttaaaaa gttgtaatct  23280
ttcatacaag ccaactgcat cattttatcg atgtccatat gaacgatctt ttgctcgtat  23340
atttcatgaa ggtcaaatac attgttgaag taaatggcgc acatgagtcg ccacatacta  23400
aggtgcccat atgtttgata gaaaaaggag atagctcttt taagcttata ttttactgct  23460
atggcatagc agtatttaac gaatacgttc atgggtacat tatctaagat ataaaatatg  23520
aaaaacttta actctcgatg aatctcttcc cccatttcct gtacatttag agcttccaac  23580
ataggatttt tatcaaatat ttcatgacat aaaataatgt tattgctcgt tttatgacgc  23640
attaaaccgg tgaaaatttc cttattattt aaactatctt tagctcctaa ctttcgacac  23700
agctcctgag tttgttccgt cctagcacag gtcagcccat aataaatgtt tgctccccac  23760
tcggtgaaca gccttattac gtcatagtta ttttctttta tggccatgat taatgccaca  23820
tcaagatgaa gaagttcccc cttaaagggg gttgagctta aaataacgta attacagtag  23880
tgacataagc taatgggctt gttttgccac cataagccac aatattttaa aatataatga  23940
tactcctcag gcacgctctg tttggccaca gcctttttgg ccagggtttg caaggagagc  24000
atgataactt cttgaaaaaa aaactcaaat taagttccta ctttttttaaa atattagtat  24060
ggacagatct accatcatat gaaggaattc tttcatcgtt aaacactgaa gagataatac  24120
tttcatcgta tagagaatat catgtcaatc catatattga atgttatata tcattaaacc  24180
catcattaat atagtgttta tgtgctatgg acaggttttt tgaatgataa tcttttaaca  24240
tacgttttat aacttcggga tcagtttctt ttaaagataa agaatcattc atgttataac  24300
aatttaatga taacatgctg gcaatgaacg agttgtcttt ttgatgcgct agagtctttc  24360
```

```
cctcctcaaa ggcattggcg cctaagtcta tacaaaagaa tatgtttccg atattataga  24420
actgaataga atgaaacatg gcctgattga tatcagcccc taagacgacg caacagtaat  24480
aaatcgttaa atagttatag ttcttgcgac aggcccactt tagcatttca ttcatgtcta  24540
tgcgaatcct ctccttttcg tacacttcgt gaagttcaaa cacattattg taaaaaaggg  24600
cgcacataag ccgccaccga tgtagatgag catatctctg ataaaaatag caaatcgcct  24660
ccttaaggtt acattctatt gccatcgcgt accaatattt agtaaacatc tcgcttaata  24720
tatcggtttc taccattaat ccctccagtt gttcataaat cattcccttt acttcaaaac  24780
gatttatggt atctaaaatg ggattattag aaaatacctc atggcagaaa atgatgttac  24840
tgctagttag atcacgtttc aatgtgtaaa aaaatcgtaa aatttcctgg tcatttaact  24900
gttctttggc acctagctgc ctgcacaggt ctcgggtgtg ctccgtgttg acagaaagca  24960
aaccgtagtt gatgtttgca ccccactcgg tgaacaattc tattagatcg tgattgtttt  25020
cctccacagc tttcaccaag gccgcgttaa gatttgtgcc gttcttaaaa tacggcgtcc  25080
atattttctt ttgatgatac atgatagggc cattatgcca ccatagaccg cagcacttca  25140
aaaaatgagg atggcatttg gccggatact ggctggccag caccttttg gtgagagtct  25200
gcagagagag gaccatattt cttttttttg aaaaaatcaa attaaaaaaa tcatgcttgt  25260
ttagcataca tgtaatattg ttataattac gttataatta cgttataatt acgttataac  25320
tatattataa caatggtata acaatggtat aacaatgtta taacaatgtt ataacgatgt  25380
atcattgatg tcatcattca actaggccaa catacttttt aatttatagt tttttaatag  25440
atgatatatt ttgttaggat ctgcttcttt taacgttaat agcgaggagt ctgcactata  25500
aatgtctaat gataaatgat gagatatcaa atagtaattc cgttgctctg ctagggcctt  25560
tgcctcttca aaggcgtcgg ctcccagatc tatacaaaag aacaagttat ccatattata  25620
aaatcgtacg caggcaagca tagctgaatt aatattagct cctaagagaa aacaataata  25680
tatggttaaa aaattgttat cttttgtgca ggccatccgc atcatttcat ccacgtccat  25740
gcggatcttt tccttttcat acaaattatg taggtcaaac agcttattaa aacaaagagc  25800
acagattaac caccacgtat ttagatactt aaaatgttgg taaacataag aaatggcctc  25860
cctaagatta tcctgcaatg ccactataaa acagtatatc gttaacatat caccatccga  25920
catattactt aatatgtcgg tgtcttctac taacctttc aacttccaat atatggatga  25980
ccttatttcc cttataatga cataggctgg aaagggatta tcattaaaaa gtttaagaca  26040
taagataata ttactgctag tagtgccagg gtgtattaat ttaaagaaca tgtgcataat  26100
cttcttttta tccacgcggt acttggctcc taattcccag caaaattctc gaacaggcgg  26160
cgtattggcg caaattaacc catagttgat gtctgcgccc cattctgtaa acagttttat  26220
taactgatag ttgttttcct ttgtagccaa cattagtgcc gtattaaggt ccaagccgtc  26280
tgcaaagctt ggcagcttta tcagcatatg tttgcaatca agggaaattg gggccttata  26340
ccaccatagt ccgcagcgtt ctaagataac atggtactca atagatactt gctgtctggc  26400
tagtaccttt ttggcgaagg attgtaagga aggaaacatc ctgtttcttt ttttttaaaa  26460
atcaattatc tttgttcata atcaagaaaa atccccatat ttattgagtg ataatttttt  26520
aacatgcaat ttattttttc agggtccgta acgatcgaca acagagaaat aaccggattg  26580
taatgcttta atgataaggc atgggctatc agataatttt ccttttgttc tgccaaagct  26640
ttgccctcct caaaggcatc ggcacccagg tctatacaaa agaacaggtt tccaagatta  26700
```

-continued

```
tagttttgta tggaaacaag catggcttga ttgatgttgg ctcccatgat aaaacagtag  26760
taaatggccg aatagctata atcttggatg caggctatgt gcatcatttc atcaatatcc  26820
atgcggaccc tttctatttc gtacagctcg tgaaggtcga acacgttgtt gtaaaaaagg  26880
gcgcacatga gccgccacct atgtagacgc gggtatttct ggtaaaagta gcggatagca  26940
tctttgaggt catagtccac cgctatcgcg taccagtatt tggttaaaac agtgctaaag  27000
ctatcatcat ggtccagcat gaaggttatc tccatgagcc ctcttaactc ccacatgatt  27060
tcccccctca gatccagatt atctataatc cttaaattgg ggttattgga aaacacctcg  27120
tggcaaaaga taatattgct actggtttta tcgcgcgttg tatcaaagaa aatttttaaa  27180
atatactctc tttctaaata ttctttggct cccagctctt tgcacagatc acgggtattt  27240
tccgtgagag cacaaatcat tccatagtta atatctgcac cccattcagt aaacagcttt  27300
atcaagtcat gattattctc cttcacggct ttcatcagtc ctatgtttaa ctcgatacct  27360
tgactaaaac aggttgacct tataaataat ttattgcgtc gaatatgaag cataatgggg  27420
ccattatgcc accacaggcc acaacacttc aggacatgat attgatctac cggtatacac  27480
tgcccggcca gtactttctt cgtgagggat tgcagggaag gcaacatgcc tttccatcct  27540
ttgacggaaa tcaaattatc tactaataac tatcagtgtt tatattaagt atttagatat  27600
tatcccgggc tggatacgta gtatcgctat tcacatgtac ttccaactct agccggagcc  27660
tgcagggtca tttattttta atattgattc ttttttgtat ttaatcattt agagaaggtc  27720
atcataggag ccagatgttc tctctccaga acttatgtcg aaaaacatta cctaaccgta  27780
aacttcctga attttttgac gaatatatat tacaactgct gggattatac tgggaaaacc  27840
atggaactat tcaacgagca ggaaacaact gtgtgcttat acagcaacat accctcattc  27900
ccgtaaatga agccctgaga acagcagcat ctgaagaaaa ttatgagatc gtgagccttt  27960
tattagcgtg ggaggggaac ctttactatg ctattatagg ggctctagag ggcaaccgcc  28020
acgacttaat tcgtaaatat gatgaccaaa tcaaggacca tcatgaaatt ctgccattca  28080
ttgacgatcc agtcatattt cacaaatgcc atatcatgcg gcaatgcttt tttgattgta  28140
ttttatatca agctgtaaaa tatagtaagt ttcgcgttct tctttacttt aaacatagat  28200
tagaggatga tttgcccttc actcatttac ttattgaaaa ggcatgtaaa gatcataatt  28260
atgaagttat taaatggata tatgaaaacc tacatatcta caatatgata gatacctttg  28320
aatgtgctat tgcccataag gatctacatc tatattgttt ggggtataga tttatatata  28380
acagaatcgt acccgataag tatcatcatt tagatattcg catgctttca agcctacaac  28440
tcctacataa ggtggcagcc aaaggatact tagattttat cctagaaacc ttaaagtatg  28500
atcataataa agataatata aatattattc taacacaagc tgcaacctat aaccatagaa  28560
aaattttaat ctatttcatt cctcaatcaa cccacgcaca gatagaacaa tgtttactag  28620
tggcgataaa agcaaaatct tccaggaaaa ccttgaactt actactgtct cacctaaacc  28680
tttccatcaa cctcatcaaa aaaataagcc attatgttgc cacttacaat tcaacaaata  28740
taataggcat tctgagtatg cggcggaaaa agaagatata tttagatatc atattgacaa  28800
aatttgtaaa aaaagctatt tttaataagt ttgtcgttcg atgtatggat acattttcta  28860
taaacccgga aagaatcctt aaaatagccg cgcgaataaa taggatgatg ttagtgaaaa  28920
aaatatctga acatgtttgg aaaaatcatg cggttagact taaataccttaaacatgcgg  28980
tacacacgat gaagcataaa gatgggaaaa atagactcat gaactttatc tatgatcgct  29040
gttattacca tatgcaaggg gaagaaatct ttagcctcgc aagattttat gcaatccatc  29100
```

atgcaccaaa gttgtttgac gtttttatg attgttgtat cctagatacg atacgattca 29160
aaagccttct tttagattgt tcacatatca taggtaaaaa cgctcatgat gctaccaata 29220
tcaacatcgt gaacaagtat atcggcaacc tgtttgttat gggagttctt agcaaaaaag 29280
aaatcttaca ggactatcca tccatttatt ctaaacaata catgccttag tttatttttt 29340
ttgcggccga aacattattc ttaccctaga aaacgcttat agtcatctta aatcataggt 29400
aaggaagatc atcatatttt ttgaaacgta attttttaac gcatgatcta tgatttcagg 29460
gtccgtgctt ttaggcaacg gggtggtggc cggactataa atctttaggg ataaaatgtt 29520
ctttataagc tcataccctt cccctaaagc tgtagtaccc tcttcgaaaa catcagcccc 29580
cagatctata caaaagaaca tgttttctat attatagtac tgtattgagc taagcatggc 29640
ttgattgatg ttggcgccca ggacatagca gtagtacatg gttgaaaggt tgtggtcttt 29700
gatgcaggcg atccgcatca tctcttctat gtccatatgg atcttgtcct tttcatacgc 29760
ctcatgaagg tcaaacacat tattaaaaca aagagcacat gttaaccgcc acgtattcag 29820
gtgtgtatat ttttggtaaa aatactgtat ggcctctttc aggttatagc gtatggctat 29880
agcgtaccag tatttgagta gtaatgtact gagcgaaaac tcattattta gcagatcggt 29940
ttttactatt aactccctta actcccagaa aatttctatc ctcattttta tattatttac 30000
tttttgtaat atcggattgt tggaaaacac ctcatggcat aaaataatgt tactactagt 30060
tttatgaaac tttagatcta taaaaatttg taaaatttct tcttcattca aggtttcctt 30120
ggcacctagc tctcgacaga ggtcccaggt gtgctccgtg ttgacagata ccagcccgta 30180
gttgatgtcc gccccccact ctgcaaacag ttttataagg ttgtagttgt tttcccttac 30240
agccttcact aacgccgtat ttaggtttaa gccctcttta atacctgctg attttatgag 30300
ccttaggtta tgatcaaacg tgatcggagc atcatgccac cataggtcat aacactttaa 30360
aagataatgt tggttcgtgg gcacgcattg tccagccaac acctttttgg tcagagattg 30420
cagggaaggc aacatgtctc ttcatctttt aaaaaaaaat caaattaatt agccgaataa 30480
atttttcttt cgagggcttt ttaaaagagc tctttaagag ctctttaaga gctttttaag 30540
agattaaaaa attattcttg ctggcattct gccaagtatg cggcattcct atcatctata 30600
gtatattatg agaatattcc caaatgatgg ataagttttt tgatttataa tcttttaata 30660
aactgcttat ttcttcgggg tcctttaagt ttagtggcaa ggaagcatct gagctgtaaa 30720
tatccaaagc caaactatgg ctcagaaaat tataaccttt ttgttccgct atggcacgac 30780
cctcttcaaa ggcattacca cccaaatcta tacagaaaaa tatattaccg atgttataat 30840
attgtactga agtaagcata gcttggttga tgttgccccc cagcgcgtaa cagtaatata 30900
ttgttaatgg attgttatcc ttggtagaag ccagacatat catgtcatgg acgtctattt 30960
ggatgttttc cttgtggtac atctcatgaa gctcatatat tttgttataa tacaggagac 31020
attttaatcg ccattcatta agatccgtat atttctcatc tagaaaacaa atggcgtcct 31080
tacaatcgta ttgtactgct ttggcgtacc aatacttcac tagtaaacca tttaactcgt 31140
ccgtttcttt tatttctatg agccccata gtcttttata aattaagccc cttaattgta 31200
taacaaattt gttttctaaa ataggattat tcataaaaat ttcatggcac aaaataatac 31260
tgccgctggt tttattgtgc attatcctgg taaaaatacg gaaaatatcg ttgtcctcta 31320
gagtttcttt ggcgcctagc tgtctacaca actctcggat gtgcttcgta ttgatagaaa 31380
gcaaaccata gttgatattt gcgccccact ctgtaaagag ctttatcaga ctatagttgt 31440

-continued

```
tttccttaac agctattatt aatgccacac gaaggtctat atcttctcct aaaaatcctg  31500
attttatttg tattcggcca cgatccatac aaagcttgag aggagcatca tgccaccata  31560
ggccacaata tttcaaaatg cagtgttcat ctattgacaa acactggctg gctatcgtct  31620
ttttgacgag ggtctgcaga gagagcggca acgacatgtt tctttttcac caaaaaaaat  31680
caaatgttct cgtctttaaa ggttaattca tgttcttaaa atgttcattt catgatagtg  31740
attaataata tggtttaata acgctagaag gcttgtttat aagacagtca taagcagtct  31800
ataagacagt ctataagcag tctataagac agtctatgac ttagtctata actataattt  31860
ctggatgggc tgtaagatac tcttcggctc gtttcagatt ttttgaagta tatgtcttta  31920
gcatatcata tatttcctgg ggttcggtta catctaatac caaggtcaca tcacggctga  31980
aaagctgctt tactaagaaa atgttgctca agttatacat ataagctttg tgcgcaatga  32040
gttgtgccct atcaaaatcg gcagccccca aatcaataca gaaaaacatg tttaaagtat  32100
tattgttata gatagaaaga ttcatgccat aatcgagact agcccccaac ctatgacagt  32160
aataaatggc cgcgtaattt ttttcccgca agcaagcaaa tttcatcatc agattagggc  32220
tgatgcaaat ctctttttca cgacacaact cgtgtatgtc aaaaatgtta ttaaaataaa  32280
ggctacaagc tacccgccaa tagaggtgat ttttatgcct tttatagaaa tagtgaatag  32340
cctttgtaaa attatgtcgt aatgccaggg caaaccaaaa ctttgttaat aggtggtgcg  32400
ccgtatcccc cgtcaacgga atgtttgaac aggtgtacgt aactgtgtct aaagtggttc  32460
tagttacggt ttccaagagt ggattatgac aaaacatgtc ataacccagc agaactcctg  32520
cacaggattt tagcctggcc acttctttta aaatttccag aagacggggt tcggatacag  32580
gcgttaagcc tcccagttcc gcacacagcc gctttagata cacggcagga acacgtataa  32640
gcccatattc aggatttgcg ccccaatcca caaataaacg tataagttca agattatcgc  32700
tcttcacggc ctttactagc gccgcttcga gacaaagatc atcctcagaa aaacactgta  32760
aatgtttata cgaaaaaact tgcttacaat tgttacatag gtgaatagga cctaaatccc  32820
accacaaacc aaaacgctgc aacgtataat catagtcact tgaaagataa ttgcatgcca  32880
caactttttt ggccaacgtt tgtaaagaca acatactaag tttaaaacat cttaaatcta  32940
agctagctaa ctttcaagaa aaccctctat ccctaagaat atatcttata actagactta  33000
tagcagtaaa aatcaacttt ggttattctt tttaatataa aacgtctaat tacttgcaaa  33060
ggactataaa gcccattttc ctcagctaga atttttattt tttaatgaag tagggggata  33120
tgttttccct tcaagacctt tgccgaaagc atctttttat tcttcccgat gtttttggcg  33180
agcatgtact acaacgatta ggactgtatt ggagatgtca cggctccctt caacgcatag  33240
gagacgacca catactcata cgacgggatc tcatcctttc caccaacgag gccttaagaa  33300
tggcgggaga ggaaggaaac aatgaagtag taaagctctt gttactgtgg aagggaaatc  33360
ttcattacgc cgtcatagga gccttgcagg gtgatcaata tgacctgatc cataagtatg  33420
aaaaccaaat cggcgacttt cattttatct taccattgat tcaagacgcg aatacgtttg  33480
aaaaatgcca cgctttagaa cgtttttgtg gtgtttcatg tctgctaaaa catgctacaa  33540
aatacaacat gctccctatt ctccaaaaat accaagaaga gctgtctatg agagcgtatc  33600
ttcacgaaac cctatttgaa ctagcatgcc tatggcagag gtatgatgtc cttaaatgga  33660
tagagcaaac catacatgtt tacgacctaa agattatgtt taatattgcc atctccaaga  33720
gggatctgac tatgtactcc ttaggatata ttttcctttt tgatagaggg aacaccgaag  33780
ctacgttgct aacgcaacat ctcaagaaga cagcggccaa agggctcctc cactttgtgc  33840
```

-continued

```
tagaaacgtt aaaatacggc ggcaacatag ataccgtcct gacccaagcc gtaaagtaca  33900
atcatagaaa acttttagat tattttctgc gtcaactacc tcgtaaacat attgaaaaac  33960
ttttgttgct ggccgtgcag gaaaaggctt ctaaaaaaac attgaactta ctgttgtcac  34020
atttaaacta ctccgtgaaa cgcatcaaaa aactaccgcg ctatgtgata gagtacgagt  34080
ccaccttggt gataaagatt ttattaaaaa aaagagtgaa cctgatagat gccatgttgg  34140
aaaagatggt aagatatttt tctgcgacga aagtgaggac gatcatggat gagctttcga  34200
ttagtccgga aagagtcatt aagatggcta tacagaaaat gagaacggat atcgtaatcc  34260
atacttctta tgtttgggag gatgatctag aacgtcttac tcgtcttaaa aatatggtat  34320
acaccataaa gtacgaacat gggaaaaaaa tgttaattaa agtcatgcac ggcatataca  34380
aaaacttatt atacggcgaa agggaaaaag tcatgtttta tttagccaag ctctatgttg  34440
ctcaaaacgc ggccacccaa ttcagagaca tttgtaagga ctgttacaaa ctggatgtgg  34500
cacggtttaa accgcggttt aagcaactaa tattagactg tttagaaatt attactaaaa  34560
aatcttgcta tagtatcctg gaaatcttag aaaaacatat tatttccctg tttactatga  34620
aagttatgac tgaagaagaa aaaaacctat gtttagaaat attatataaa gtaattcatt  34680
ataaaacaat acaatgttaa aattcaatag atatccatca ttaatattga ttatattttc  34740
gaatattatc ttctatggtg caagataatc atctagcgcg tgaaacatgt cctcttctct  34800
tcaggaactt tgtcgaaaaa agctgcctga ctgcatactt ccagagtttt ttgacgacta  34860
tgtattgcaa ctgttaggac tgcactggca agatcatggt tcccttcagc gtatcgagaa  34920
gaaccagata cttgttcaac aggaacccat ccatatcaat gaagcactca aagtagcagc  34980
atcggaaggg aactatgaaa tcgtagagct gttgttgtca tgggaggcag atccccgcta  35040
cgccgtcgta ggagccctag aaagcaaata ctatgacctg gtttacaaat actatgacca  35100
agttaaagac tgccatgata tcttgccgct gattcaaaat ccggaaacat tcgaaagatg  35160
tcatgagtta aacagcacct gttcactgaa atgcttattc aagcatgctg tgataaatga  35220
catgctgccg attcttcaaa aatatacaga ctatctggat aggtgggagt attgcagcca  35280
gatgctgttc gaactggcat gtagtaaaaa aaaatatgag atggttgtgt ggatagaggg  35340
agttctaggc gtcggcaaag ttacatctct tttcaccatt gcgattagca acagagacct  35400
acagctgtat tctctgggct actcaattat ccttgagaat ttgtactcct gtggacagga  35460
ccccaagttt ttactaaatc atttcctgcg agacgtttca ataaaagggc ttctaccctt  35520
tgtaatcaaa accatagaat atggtggaag caaggagata gccataactc tggctaaaaa  35580
atatcagcat aaacatattt tgaaatactt cgaaacctgg gaaagctagg ttcagtatgg  35640
tgtactcact attgtagtga atcgtatcct gtaaattttg taaaaaagct taaacttttg  35700
accacatcat attgttttag aaatctcaaa ccagtgaaca acagtcttat catacattaa  35760
aattccagta aaatttatat tttttttggt aaacaaatgt tttctcttca agacatctgt  35820
cggaaacatc tttttcaact tcctgacgct tttgatgaat atatattaca agcgctagga  35880
ctatactggg aaaaacacgg atctcttcaa cgaataagaa aggacgctgt gtttgtacag  35940
cgaaacatcg tcctttctac caatgaggcc ctgagaatcg cagcctcaga gggaaacgaa  36000
agggtaataa aacttctgtt atcatgggag ggaaattttc attatgtgat cataggagct  36060
ctagagggtg accaatatga cctaattcat aagtatgata gtcaaattaa agactaccac  36120
atgattttat cattgatcca aaatgcaaat acctttgaaa agtgtcatca gttatccaat  36180
```

-continued

```
agtaatatgt ggtgtcttat acagaatgct ataaaatata atatgctccc tattctccaa  36240
aaacacagaa atattctgac acatgaggga gagaatcagg aattgtttga gatggcatgt  36300
gaggaacaga aatatgacat agttttatgg ataggacaaa ccctaatgtt aaatgagccg  36360
gagtttattt ttgatatcgc cttcgaacgg atagattttt ctttattaac aatgggttat  36420
agccttcttt ttgataacaa gatgagtagt atagacattc atgatcaaga agatcttact  36480
tcattaccaa cagaacacct cgaaaaagca gccactaagg gatgtttctt ctttatgcta  36540
gaaactttaa aacatggtgg aaatgtaaat atggcagtct tatctaaagc tgttgagtat  36600
aatcatagaa aaattttaga ccattttatt cggcggcaaa aatgtttatc acgtgaagag  36660
attgaaaacc tattattaac cgccataacc aattgtgcat ccataaaaac gttaaactta  36720
ctcttgtctt acctaaacta ttccgtaaaa aatatcattg gaaaaatagt acaacatgtc  36780
ataaaagatg gtgattatac catcatatta cttttaaaaa aaaagaaaat aaacctagtg  36840
gaacctgttt taacaggttt tatagattat tactatagct attgttttat aaaacatttt  36900
atccaagagt ttgctattcg tccggaaaaa ctgattaaaa tggccgcgcg aaaaggtaaa  36960
ctaaatatga ttatcgaatt ccttaacgaa aaatatgttc ataaagatga tcttggaact  37020
atatttaaat atctcaaaac cctagtatgt accatgaaac ataaaaaagg aaaagagaca  37080
ttaattgttc ttattcataa aatatatcaa gatattcatc tggagactaa agaaaaattt  37140
aaattattaa gattttatgt catgcatgat gcaactatcc aatttctatc tatgtgcaaa  37200
gactgtttta atttagccgg ttttaaacca tttgttttag aatgtttgga tattgctatt  37260
aaaaaaaatt accctgatat gatacaatat atagaaattc tatcgaaatc tgagtaaaat  37320
ttattttttt gatcagagta agaaaatgtt ctccctccag gagatctgtc gaaagaacat  37380
ctactttcta cctgactggc tcggtgagca tgtgattcag cgactaggtc tgtactggga  37440
aaaacatggt tctcttcagc gaatcggaga caactatgta cttatacaac aggacctcat  37500
catccccatc aatgaagccc taagaatggc aggggaggag gggaatgatg aggtggtaca  37560
actcctatta ctatgggagg gaaacattca ttatgccatc ataggagctt tggagagtga  37620
ccattatagc ctaatacgta agctctatga ccaaatcgaa gactgtcacg acatccttcc  37680
cttgattcaa gacccaaaac tctttgaaaa atgccatgaa ttagataaat cttgtaacat  37740
tttatgtctc gtattacacg ccgtaaaaaa cgatatgctt tgcattcttc aagagtataa  37800
aatgcatcta agtggagagg atattcaagt ggtgtttgaa acagcatgcc gttcacaaaa  37860
aaacgatatt gtgtcatgga tgggacaaaa tattgcaata tacaaccccg aagttatttt  37920
tgatattgcc tttgataaga tgaatgtgtc cttattatct atagggtata cgcttctttt  37980
caatcatcat ataaataata cgaacgaaaa tattaattct ttattgacac aacatcttga  38040
atgggctgcc ggcatgggcc ttcttcattt tatgctggaa actttaaagt atggcgggga  38100
tgtaacgata atagtcttgt ctgaggccgt aaaatatgac cacagaaaga ttttagatta  38160
ttttctccgt cgaaaaaact tgtaccaaga agatcttgaa gaactattat tgttggcgat  38220
acgtgcagat tgttctaaaa agaccttaaa cttgttatta tcttacttaa actattccat  38280
aaacaatatc cgtaaaaaaa tattacaatg tgtaaaagaa tatgaaacga ccgttattat  38340
aaaaatttta cggaaaagaa agataaatct gatagagccc attttggcag actttatagg  38400
atatcatagc tatacctata tggtagattt tatgcgtgag ttttccatcc atccggaaaa  38460
aatgatcaaa atggctgcac gagaatcgag ggaggacttg atcataaaat tttccaaaaa  38520
agtttgcaaa gagcctaaag atagacttca ctatctcaaa agcttagtgt atactatgcg  38580
```

acataaagaa ggcaaacaac tgttaattta tacaatccat aacttataca aagcttgtca 38640
tctagagagt aaagaaatgt ttaatttggc acgattttat gcacggcata atgcagtgat 38700
ccagttcaaa tcgatttgcc acgatctctc caagctcaat attaatatca aaaacttgtt 38760
gttagaatgt ttaggtattg ctattaaaaa aaattacttt caacttatca aaacaataga 38820
aacggatatg cgttatgagt aacattttta gatgagggaa gattctacca aactaactaa 38880
gacctttcgc tagaatgtat cttattgtta atatagatga gatatgtcat tgtgaaaaaa 38940
tagattaggt aggttgtgaa aaacagatta aacttaaaat tatgtgtatt atgtaaaatt 39000
ttagaaataa aaatttattt tttttattga gggtacggaa aatgttctcc ctacaggacc 39060
tctgtcggaa gaacattttc ttccttccaa atgattttag caagcatacc ctacaatggc 39120
tgggattata ttggaaagag catggatccg tccatcgagc agaaaaagac agcataatga 39180
tacagaatga attggttctt tctatcaatg atgctttaca gcttgcagga gaggaggggg 39240
acacagatgt agtacagctc ttgttattat gggagggaaa tctgcattat gccatcatag 39300
gagccttgaa gactgaaaaa tataacctaa tatgtgagta tcatagccaa attcaggact 39360
ggcatattct cctacccatg attcaagatc cagaaacatt cgaaaaatgt catgatttaa 39420
gccttggatg tgactttatt tgccttctcc aacatgctgt aaaatacaac atgctttcta 39480
ttcttgtcaa atataaggag gatctactaa atgcaaggat taggcatcgt atccaatccc 39540
tgtttgtttt ggcatgcgaa aatcggagaa ttgaaattat tgattggata ggccaaaatc 39600
tgccaattcc tgaacctgat gccattttta gcattgctgt tgctacaaga gatttagaac 39660
tgttttcctt agggtacaag attatttttg attacatgca aagacaggga atcattcaat 39720
taaccaatgg agttcgcatg gttgtgctaa atcgtcacat tagcatggca atagataatg 39780
gtcttttacc ttttgttctg gaaactttaa aacatggtgg gaatatacat agagccttat 39840
cttatgcagt aacacacaat agaagaaaaa ttctggatta tcttattcgc cagaaaaata 39900
tagcccctaa tacaattgaa agacttttat atctggccgt gaaaaatcaa tcttccagga 39960
aaactttgaa cttgttgcta tcttacataa attacaaggt gaaaaatgtt aaaaagctgg 40020
tagagcatgt agtaaatgag aaatccactc ttgtgttaaa aattttatta gaaaaaaagg 40080
aaaatctagt ggatgctgtt ttaacaagac ttgtaaaaca ttctacatat ttccaggtga 40140
gagaatttat ccaggagttt tccatcagcc cagaaaaatt cattaaaata gctgtgcggg 40200
aaaagaaaaa tgtgttaatc gaggctattt ctgaagatat ttgggaaaat cccacagaaa 40260
gaattactta tctcaaacag atagtgcaca ccataaaata tgaaagtgga aggcgatttt 40320
tggtagacat cattcacagc atttaccaaa gttactcact aaaacacgaa gatattctta 40380
aactggcaac attttatgtc aaacacaatg caatcaccca ttttaaagac ctctgcaaat 40440
atctttggct gaacagagga acagaaagta agaaactgtt tttagagtgt ttagaaattg 40500
ctgatgagaa ggagtttcct gatattaaaa gtattgtgag tgaatatatt aactacttgt 40560
ttactgcagg agctattacc aaggaagaaa tcatgcaagc ctatgatgct ttagagtagc 40620
catgtattaa cattctgaaa gtagaataaa atatactata tactaaaaac caaattagcc 40680
atttttaact atcttcttct taaaaactct ggataaaaat ttattttttt taatttgggt 40740
agggaaaatg ttctcccttc aggacctctg tcggaagaac accttcttcc ttccaagtga 40800
ttttagcaag cataccctgc atttgctggg gttatactgg aaggggcatg gatctatcca 40860
aaggataaag aatgatggtg tgcttataga gcatgatctt actctttcca tcaatgaagc 40920

-continued cttaattctt gcaggagaag agggaaacaa tgaagtagta aagctcttgt tactatggga 40980
aggaaatctt cattatgcca tcataggagc tttgaggact gagaactata acctagtatg 41040
tgagtaccat agtcaaattc aggactggca tgttctcctc cctttgattc aagatccaga 41100
aacattcgaa aaatgtcatg atttaagcct tgaatgtgat ctttcatgcc ttctccaaca 41160
tgctgtaaaa tataacatgc tttcgattct tgttaaatat aaagaggatc tactaaatgt 41220
actatttagg caacaaattc aaggactatt tattttagca tgtgaaaatc ggaagcttga 41280
gattcttacg tggatgggtc aaaatctgcc aattcctgat cctgagccta tttttagcat 41340
tgctgttgtc acaaaagatt tagaaatgtt ttccttaggg tacaagattg tttttgaata 41400
catggaaaac caaggacttc atttaaccca ggtagttcgt atggttatgc taaatcatca 41460
ctttggcatg gtaataaata aaggactttt accctttgtg ctggaaattt taaattatgg 41520
tgggaatgta aatagagcct tatcttatgc tgtcacacaa aataaaagaa agattttaga 41580
ccatgttgtt cgccaaaaga atatacccca taaaaccatt gaaagaatgt tgcatctggc 41640
tgtaaaaaag catgctccca ggaaaactct gaacttgtta ctatcttaca taaattacaa 41700
ggtgaaaaat gttaaaaagt tgttagaaca tgtagtgaaa tacaactcta ctcttgtgat 41760
aagactcttg ttagaaaaaa agaaaaacct gctggatgct actttgacaa gatatgtcaa 41820
agattctaca tactttcagg tgaaagaatt tatgcaagac ttctccatca gcccagaaaa 41880
attcattaaa atagctgtgc gggaaaagag aaatgtgttg atcaagggta tttctgaaga 41940
tatttgggaa aatcccgcgg aaagaatcag gaatcttaag cagatagtgt gtaccataaa 42000
atatgaaagt ggaagacaat tcctgataaa tatcattcac accatttacc agagttattc 42060
tttgaaacct gaagaaattc ttaaattggc aacattttat gtcaaacaca atgcaaccac 42120
ccattttaaa gatctctgca aatatctttg gctgaacaga agaacagaaa gtaagaaact 42180
gtttttagag tgcttggaaa ttgctgataa gaaggagttt cctgatatta aaagtattgt 42240
gagtgaatac attaactatt tgtttactgc aggagctatt accaaggaag aaatcatgca 42300
agcctatgct ttggagtatg ccatgtatta aatttctgaa tcagtaagca atagatagat 42360
tttagaatat gctgtattaa gttagtttct gaataagtaa ttaatagata gattttagtt 42420
tatgtaaaaa tgttaacatt tgttcataag ttttagatac cattttagag ttactttttt 42480
agatattact attttagcca ttattatctt aaataatcac tattttagat aggtccccgt 42540
attaaaaacc aaattaacca ttatctatgt ttttaataat actttttaaa aaccctccat 42600
aaaaatttat tttttttcat aaaagtagag aaaatgttct ccctacagga tctctgtcgg 42660
aagaaccttt ttcttccact tgagccctta ggcaagcatg tggttcaacg gctgggatta 42720
tactgggaag gccatggttc agttaaacga gtgggtgatt gctttatatg tgtagaccag 42780
atttggatgc tatcaatcca taaggctata caaattgcag cctcggaagg aaatgagaac 42840
attgtcaagc ttttcttact atggaagggg agtctacaat atgccatcat aggagcctta 42900
gagggcaggc aatatgatct gattcaaaaa tattacaacc aaattgggga ctgccatcag 42960
attctaccac tgattcaaga tccagaaatt tacgaaagat gtcatgaatt aaatgttaca 43020
tgtacctttc aatgcttatt tcaacatgct ataagagata acatgctgcc cattttccaa 43080
aaatatggag aagatctgaa tggaaacagg agaatggttc aacttctgta tgagatggca 43140
tgccgattac aaaattatga tatcatcaaa tggataggat ctaacctgca tgtttataac 43200
ttggaagcca tttttagcat tgcttttgtt agaaaggatt taactttgta ttctttaggc 43260
tacatgcttc ttctgggtag aatgagtact gaagatagaa actttatctc aatcataaca 43320
cgccatcttg aatacgcatc aaaaaaggga ctttttgact ttgtactaga atctttgaaa 43380
tatggaggtc aagtggatac agtgttgttt caggctgtaa aatacaacca taggaaaatt 43440
ttggcccatt ttattcatga aattccccgt gaaacggttg aaaagctgat actccatgct 43500
gtggagtcac gggcctccag aaaaacattc aacctgcttt tatcttccat aaactactgt 43560
gtgaaccctt ttgtcaaaaa actactgcac gctgtggtga aacacaagta catgcttatc 43620
ataaagcttt tgctcgagcg gcccaaaaag aagataaacc tggtagatgc tgctctattc 43680
aaacttgtaa aatactctac ttatacagaa atagtaaaat acatgggtga gttttctgtg 43740
gacccaaaaa gggtggtcaa aatggcagca cgactcatga gagtggacct gattaaaaag 43800
atttctaatg atgcatggga agataaacta gagagaatca agcaccttaa acagatggta 43860
aataccatga accacagaaa tggaaaaaat ctattgatgt acaatattca caatattact 43920
ggatatacct atctgaacac caaagaagca tttaacttaa caagatttta tgctgtccac 43980
aatgcaacat gtttgtttaa agaaatgtgt aaaagctgtt ttgtacatga taaaatacag 44040
ctcagagaat tgcttgaaga ttgtttacat attgctaata ggcatgatta tatccagatt 44100
gcagaaaccg cagatgaatg tatcaaatat atagatctta ttacatttaa gtaaaccatg 44160
tatatatcaa gtaaatccag attaaatcag gctaattgta aatagttgta gataccatat 44220
aatgaatgtt ttattaggat agtagttcag ttaagatagt agtttagtta agatagtagt 44280
ttagttaaga tagtagttat gttaagatag tagttctgtt aagataatag tttagttaaa 44340
actagttcat gttaagttaa tagttttgtt aagacaatag ttcatttaag tcaatagttc 44400
agttaagtca atagttttgt taagtcaata gtttagttaa gtcaatagtt tagttaagtc 44460
aatagtttag ttaagtcaat agttatatta agacattagt tctgctaata cattagtttt 44520
gttaagataa taaaaattta tttttttca tcagggtaga gaaaatgttc tccctacagg 44580
agctctgccg gaagaacatt tacattcttc cttacccctt ggctaagcat gtacttcaac 44640
aactagggct gtactggaag ggacatggat ctcttcaacg aatcggagat gaccatgtac 44700
tcttacagca ggacctgatc ttttccatca acgaggcctt aagaatggca ggagaggaag 44760
gaaacaatga agtagtaaag ctcttgttac tatgggaggg aaaccttcat tatgccatca 44820
taggagcttt agagggcgac cgatatgacc ttatccataa atattatgat caaattgggg 44880
actgccacaa gattcttcct ttaatccaag acccgcaaat ctttgaaaaa tgccatgaat 44940
tgagtaactc ctgtaatatt cgatgccttt tagaacatgc agtaaaacac gacatgcttt 45000
ctattcttca aaaacacaag gagcaaataa gattacacat ggcattaacc caaatactat 45060
ttgaattggc gtgtcatgaa cgtaaaaatg acatcattag atggatcggt tattccctgc 45120
acatacacca tctagagact atttttgatg ttgcattcgc ccataaaaat ttatccttat 45180
acgttttagg gtatgaactt ctcatgcaca aagtaaatac agaggctgca tatatagaat 45240
tacccaattt gctatcatat caccttcgaa ctgcggcggc aggaggtctt cttaacttta 45300
tgttagaaac aataaagcat ggtggatatc tggataaaac ggttttatcc gcggctatca 45360
ggtacaagca taggaaaatt gtggctcatt ttattcatca ggttccccgt aaaaccgtta 45420
aaaaactgtt actctatgct gtgcaggctc gggcccccaa aaaaacactg aacctacttt 45480
tatcttcctt aaactactcc gtgcacacca tcaccaaaca actcgtacac aatgtcgtca 45540
tctacagttc cacgcttatc gtaaagcttt tactcatgcg gcgaaaaaac aagttaaacc 45600
tagtagatgc cgttttagcc agacttgtaa aatattccac ctatacagac attgtacaat 45660

-continued

```
tcatgggtga gttttctgtg agcccagaaa gggtgatcaa aatggctgca cgggaatcca  45720
ggacctttct gattgaaatg atctccaaag ctgcttgggg aaatcaccca cagacgttga  45780
ttcatcatct caaacaacta accaatacca tgaagcctca atctggaaaa gaccacatca  45840
tatataccat ccactatatt tatctaaact ctaatatgct ggtagcggag gaggaaaaaa  45900
atatttttaa attagcaaaa ttttatgcga atcataatgc ggtaaacagg tttaaacaaa  45960
tttgtgaaga ctattatata ttagatgcac gatttaaaac acttatttta gaatgttttg  46020
aaattgccgt ccagaaaaac tatcctagaa ttgcaaatat tgtggatgac tatattcgat  46080
tcctttttta caggggaaat ataaccgagg aagaaattcg tgaagcctat tctttaaaag  46140
atgctgaggt ttatgtagat ttaaaatggt tacaacaagg agaaatggtt taaaccaaat  46200
ccggtttaaa ctaaatccaa tttaaactac atttggttta tcattagtca ttgaaaccat  46260
cgaaaaaaaa gctatttgtt tatccccata aactcatctt ttttttgtct caaagtttga  46320
cactaaaatt cagtgtttta tagtgtttat aattaagtgt tttgcatgca ttgcagaaat  46380
tttcatcttt tttaattggt tcaataccac atgtcataca atatgttgtt tgattatcaa  46440
gattaacttt atgaaaggaa agtaagtgag ccgcaaattt aaaagtaaaa tatctttcat  46500
ttaaaatgat cttatgaatg tattttcgat aaggaggaat gaaagcattt gccaaaataa  46560
atcgcataaa aggcttggaa aaacccatat cttctaatct tttgtgggta taaaccctat  46620
tttggtgttt tacaaaaact tcattgttat aatagtcgtt atagctatca atcatttttt  46680
taagtcctat aatgcccaag gttgcacgca taaagccaca gtttctgctc caaaaagcat  46740
gcacctgtaa agggtgcttt tcatataacc aattacaaaa tttcattccg caacagtagc  46800
atgttatttc agtgggggat gtatagaata atccggcatt cgaaaatttt tcataatttt  46860
ttatgtcatg gattgcgaag ctttgatttc gtgcatctat ggagctatag cctacatatt  46920
taggttttac ttcaaataat cgcaaagaga tgtatggatc tatcgtattt attttaggaa  46980
acatttcata attttaaatt cttatatata atataaaaaa aattacaaac atttgtaatg  47040
atcatcctca attgaaggct gagttgtagg ctttattttt ctaattatac gaagaaggta  47100
ggttctcata aagccttcaa gatgactatt gatgtttcca atacattttc tcaatgagtt  47160
cataaaccca gacattttgc taatggcttg gcaaagtgcc aacaagttgt ccacaaagta  47220
ctggtagatt gccactagct atagctagct atagtgagcc aacctctctg tatgtatttt  47280
atatatttca ttttttaata gatttaatat ttttataaaa aatatttagt tttttataca  47340
agaatgtcga caaaaaaaaa gcccacaatt accaagcaag agctttactc cttagtagcg  47400
gcagataccc agttaaataa agcattgatt gaaagaatct ttacaagtca gcaaaaaata  47460
atacaaaatg ctttaaagca caatcaagaa gttattatac cacccggaat caagttcacc  47520
gtcgttacgg tgaaagctaa acctgctcgc cagggccata atcccgccac aggagagcct  47580
attcaaatta aagctaaacc tgaacataaa gccgtaaaga tacgagcatt gaaacctgtc  47640
catgatatgt taaactaaac tataaagtca tattcttctt tatcgttatt atcttcaata  47700
tatttttgcc aatcgaaatc gaataaattc agatcctgga catttaaata cttatcatcg  47760
tacattttaa tataatttaa acatgagttg ttgtcaaaaa cttttagcgt ttttgttaaa  47820
attatcatat gaataatttc cttattaaga gttgccggaa taatacaaaa cctattttta  47880
ggtacatcat ccatgataat agtaaaatta gtaaaaattg tttcttgttt ttcttttgtt  47940
tcaaataaac gttgtaaggt taaaggtttc tcgttcaatg gtttctttga agataaaaag  48000
aatgtataat ctggtttaaa ggtattttg gtttcaatcg tgattccatc tgcttgagca  48060
```

```
tatactaaac cagaccaaat ataacggtcc actattacaa tataatttag cttaagtagc  48120
actgcaattt ctgcgataaa ttcactacga tgttttgtaa ataatttatg taattgttcc  48180
gatgacattt ctatggtttt atttaacacc tgcaatataa gatcaccggt ggtcgtgtct  48240
ggattaggaa aatgtataca tatagcatta taatccatgc attccaatgt ttcttttaat  48300
ttcattgcct gtgtgctttt tcccacacca ttgattccct cgatggcaat gagtattcca  48360
cgcatgatta ataaaaggaa aaaaagaatt cagtttttaa catttcttac aaatcttttt  48420
ttatacaaca ttgtacaaca ctgcattagc ggtatatgat gttatagctt cattaaatat  48480
ttgcttttat ataatcttta ccaacctata tttggtagat cactgcagat ggtcataaat  48540
aggccataac taagataaaa attatttcag acgctactac ggtagtatta ttaaaatcat  48600
gtgtggcaat gtatgacgtc ttaatagata aaacatttaa ggaaaacaaa tttgaataaa  48660
aaaataattg ttatgatggc gttgttacac aaagaaaagc ttatagagtg catctatcat  48720
gagctagaaa atggcgggac aatattgctt ctaacaaaaa atattgttgt gtcagaaatt  48780
tcatacattg gcaatactta taaatatttt acctttaatg acaatcatga tctgataagc  48840
aaagaagatc ttaaaggagc aacatccaaa aacattgcta aaatgattta taattggatt  48900
ataaaaaatc ctcaaaataa taagatttgg agtggtgagc cgcgtactca aatttatttt  48960
gaaaatgatt tatatcatac aaattacaat cataaatgta taaaagattt ttggaatgtt  49020
tcaacttcag tcggtcctca tatctttaat gatcgtagca tttggtgtac taaatgcaca  49080
tccttttacc catttaccaa cattatgtcg cccaatatat tccaataaat tagatatctt  49140
tgctattaaa atagttaaaa accttatagg ataattaggt actttattac gataaattat  49200
gatattttat aattagttac tttattataa ttaatctctt tattaatgaa ttatcataag  49260
ataactaatt atttttttcc atatatcaga taataaatct gatatgggct aaaagtatgt  49320
ttcaaactat ttacaataga atttctgtta agaaaacata cataatttga ataaaatttt  49380
tttaaatatc accgaaacaa tcaacatggt gttaatagag tttttaacag gtttcttcta  49440
tttatatgga aagagactgt tttccattag taaagtcatg gacatgatat gtctagacta  49500
ttataccatt attcctgctc ctctggcgat gatgttagcg gcaagactaa aaaactatga  49560
cctcatgaaa cgactgcacg aatgggaaat ctctattgac tacgctctac ttgtagtaga  49620
tgatgtgccg tctattgact attgcttaag tcttggcgct agatccccga ctagagcaca  49680
aaaaagagaa ctgctgaggg acaacacgtt taatcccgtg tataagtatc ttatgaactg  49740
ttccggcttc ccaacaaaga gagaaaaaaa cattccttgt gatgttcaat gcgaaagact  49800
gcaaaaaaac attataaaag aactggtatt taactgctct gtactgcttg aaatggtact  49860
gcacacagaa agagaatatg catacgccct acactgtgct gcaaaacata accaattgcc  49920
catcctcatg tattgttggc aacaatccac agacgcggaa tctattttgt tgaaaacctg  49980
ctgttctgat aagaacatca attgttttaa ctattgtatt ctatatggcg gcgcccaaaa  50040
tttggatgct gcaatggtgg aagcggcaaa gcacgatgcc cggatgctga taaactactg  50100
tgtcatgctt ggtggaagat ccttaaacga agcaaaagaa acggctgcca tgtttggaca  50160
cattgaatgc gcacaacact gttttaaact gcagtcttac gtcgtggaca catcgaatac  50220
agacgacact gattaaagcg acaatcttac gtcatgaacg actgtctttt gagtatctat  50280
acttacatta tattttttta tgaaaaaaat ataaaggttg tatacaaacc tttgtataca  50340
agaaatttgg atcattaaac aataattaat ttggacacag gaaacgatct agatcgatca  50400
```

```
aaaagctatt ttttttgcac acagaacatt tagataattg agagattact ttccatactt  50460
gttaagcttt tttacacaca ggaactttgg attctgttca ggaagttttt catagacatt  50520
atgtttacag ccagtaataa taattttggg ctttttctta aaccaccggt ggaaaacatc  50580
cagcttgtaa agagggaaat gcatgtagag aggttttggt agtcatggtt aagagatttg  50640
actaactcca tgtttcctgt aaagactgcc cagtcccaag cagtaaaacc tctatgatag  50700
tctttttgag tcggatctgc tccaaatttt atgagagaaa gcatatttaa agaacggccc  50760
cgtattgcgg ccttcatcac aggagtcatc ccattaaaat tcggtaaaca aattctggtc  50820
ccattttttc cgaaatagcc caacacccct tccaggatta aatgattttt tttctcagct  50880
aaataatgta aagcagagtt tccatcttta tccctcctat gagggttaat tatttctcca  50940
ggataagatt cttgttcaaa aagaaatttt aaaaagtcta tacgtccgta gatgcatatc  51000
cacatgaata ccgaggatcc atttttatcg catctattga caatccacgg atctgtttta  51060
aaaaattcct caaatagtgt aagattccca tttctaatat gtttttttaat ccatttaaca  51120
aacaagtttt ctatctccct ttctggaaac atgtgttcca ttttgaatgt cgcccctact  51180
ccactatatg attttactcc tttaattttt aatgtccttt tttttcggac ttctttggat  51240
aagctgttta ttaccatctt taaatgcctt atagcgggga ggagccaggc cctttttccca  51300
tatgtgcggt aattcttggt gtttatgctt gcctttggca taaccaggcc agtatttttc  51360
gatatattca gggtttgttt ttacgtattc tttaaaggtc cgataggctt cttgaataca  51420
ggtaggctca ccggtataat ttccatgttc atcttccttt aaaaagccat taaccctgtc  51480
ctttctccac ttaagattgt gctttccaaa aatgcgatca agatcttgcg cctgctgggg  51540
tggaatcata aatccctttt taggtcgaag ctttttattt tttccatagc ttcggccatc  51600
gcgttgcgaa acagtggtta ggacgcctga tagtctttcc atgggcgtcg catctaatcc  51660
tatccatcca ccctgatgaa tatcaatggc aacaagctct cctttatttt gggcaagcca  51720
agtttccaag aatgccatgc tttcttccca gggataaggc ccgccaacac cacgggttgt  51780
ccaatcttgc aaggactcca ggtccgacac ctggtaaggc tctaaagaag acggttcctt  51840
gtttttgtac tgcaaataag atttaatgac ccatttatac catgtgtcga accgcagcgt  51900
ggcgcctcca aagtgaaagc cgtcgttgat tttaggatat ctgcaacata tttcaaccgt  51960
acgtttgagt tctgcaaaag cggccttcca aggaagtctt tcgctgcggg taagacggtc  52020
tattttgccc tgcgtgccat agcgtatggc atgtcgtgcc aattgcaaca attctgacac  52080
cgatccgtgg gccccgatcc agtttatcgg ataggcaacc tccgaagggt ttaaaagatg  52140
ctcgtaaaag cgtggatctt cagatgccaa ggcgtctgca aaggggataa tgctagaaaa  52200
cctgtctaga catacgtttt ctgtgtttac ttctaaaggt agaaaaatgg ttgcgtgagg  52260
cttttgaacc tgcttgttca gcggtctgca tatgctttga ataatgtctc taggactatg  52320
tcgcggcgct gcaaaaaata ccgcgtttag ttctggaacc tctacgccct cttgaaagag  52380
tcgacagttt aataaaataa cgggttcctt tgaggaacaa aattctgtaa atgttttgag  52440
gataacctgt cgcggcaggg ttgagtgagc tatcagggca tagacccctt ggtctaccaa  52500
cgccgcgtat agctccttgg cctgtttaat atcacgggta aataccagca ttttaggagc  52560
cggtatattg gtttttaaat aggctaaggc cattataatt tgctttacta tgatctgttt  52620
cgtggtctcc tctttggtac tcggttggtg ggccaattta ggcgcggcta ccatctgcaa  52680
ttcaaaatca tttacatagc cggcctctat gccttctcgc agatagtagc gaaaggcaac  52740
gccgccaaaa agttcacgat ttttcatgga aagcggggtg tcgtacctgg gcgttgccgt  52800
```

taaaaaaagt cggtgccctt ttttaaagtt gagcaacacg tgggtaaagg gccgtgtctc 52860
ccattcgccg caaatccggt gacattcatc gctaataata agatcgaaat catccaccag 52920
tagcgtggag gattggtagg tggcaatcac aagaagagaa ggggcctccc gtatccgttt 52980
tgcaataaag acaggattgg tggtcatttc tatattgtcg tgatttagca caatgcgggt 53040
ctggtcagac cccacaagca aaacgttctt caaagaaatt ccatactgat agagtttttc 53100
cagagtctgc cgtagtaggg acaggcccgg caccaggtac aaaacttttc cttgaagata 53160
attggagagg ataagatagg cgacgcgagt tttgccgcat cggcaggcca tctgcagaat 53220
ggccctccca cttcgccgca gctcctgata gcccatattg gccgcctcct tctgataaag 53280
tcgatcctcg attgcagtcc gtgtctcatc tgtagaaaaa aataatacgt catctgcgaa 53340
atgttcatct tccacaggag ttatcaccag gtgtctcagt ttctccttgc ttatcagcgg 53400
atcagagggc aaagatggct caaccactat cgtggaatca ttcatctcat aggcgggaga 53460
atcacacaaa gtatagctta tgtccagaca gtttgcaaca tcctcagcca attgttttat 53520
tttttcgggt aaaagacata cgagttcttt gtttttgacg cgaaaaaact gtgcacaata 53580
taacacccct gcttcaattt tttgcgcatc cttctttgta gatgtttcca atgtgaaaca 53640
atacttccat tcatccgtaa aacaggttgt ataagatcca tcatgaagcc tagcggccaa 53700
gtttcctgtg tgcccaactt tatgtaagga ttgggcctcc agccagggat gaaccgccac 53760
gtaaaatcct gcgcacatgc tatatcaaat tgcagtttct taataactgt acacaggatc 53820
tgaaaaacat gtgattacaa aatttagata agaaatattt aatattaaaa atcacagaat 53880
acatgtcact gtgtagagag aaagccaaaa actcctcttg accgccgtgg gaaatcatcc 53940
agggtagtag gttgtgtttc ataaagttgt atgccgtagt gatcaccgtg gactccagat 54000
ggttattggc atctttgcaa tactttgcca tcttggcaga aaagacgata aatccacaaa 54060
ttctacccca gttgataaga tccttaaaca gctcagtcac aaccccagta aactgggttt 54120
taatttcttg aacactcgta agagaaaagg taattgtaac ctgtttgttc aaacactcat 54180
cataataggt taaaattttt tttatttgtt gttgatatgg gctaagctca tgctctgaaa 54240
tatcattaat gtaatattta atatatccca ctagtatttc attaatgata ttatgatata 54300
ttaactcttc tccctccata gcggcaccct atattttttt atttaggttt caatgttatc 54360
acaattgcga tacaattgtg atacaattgt gacacaactg tgttgtatac aacaaatgtt 54420
aggccacgta tagcaaccta tatgttaaga aatattttta tcccaacatt agttggaaac 54480
gagcagccgc aaagaagtca tttaaaataa gccatttaaa gatttagaat ttatatgtat 54540
acaactgtac aatggaagca gttcttacca aactcgacca ggaggaaaaa aaggctctcc 54600
aaaattttca tcgttgtgct tgggaagaaa ctaaaaatat tataaacgat tttcttgaaa 54660
tccctgagga acgatgcacc tataaattca actcatacac aaaaaaaatg gagcttttat 54720
ttacccctga attccacacc gcctggcatg aagttcctga gtgcagagag ttcatattaa 54780
actttttgag actcatttcg ggacatcgag tggtattaaa aggccctaca tttgttttta 54840
caaaagagat caagaatctg ggcattccta gtaccatcaa tgttgacttt caggccaaca 54900
ttgaaaatat ggatgatcta cagaagggaa atctcatcgg caagatgaat atcaaagaag 54960
gctaaataaa acaactaaca tcaaaaaaca ttaaaggcta tgttgtggac gatgcctttg 55020
tctcaatagt ttcgaggtca tccaataact catgtaacgt aaaaaagttg gtccattttt 55080
ttgaaaacat taaaagacgt tcgtcttcat aaataaaaaa gtcattcgaa ggaaaaatga 55140

-continued

```
tatactcaat accatagtct tgtaatattt tttttaggtc tctcagggtc cagggattta  55200
ccaggcttct acgcgaagtg agcatcataa aaatatctaa tattttttgc gccataagcc  55260
agcgcggatt ctcattggcc cacaaatcaa caataattct cttatcaacc gtgagcattc  55320
ctacttgatt cgaagaaatg attagatgcc cagcagtcca ccccatgagt agataacgca  55380
gcgttgtaga aatgtcacat atggaaggca ttcctccaca acatgaaccc aaattaggat  55440
gcgtgtgaaa cacaaacata gcaggcttgt tggccaccct gctataaata tcagcaggca  55500
tcatagcctc gctgccaaaa taaatgttct ctcctgccct ataggggctt ggaatgattt  55560
ccactatctc gggtacaccg tttatcatat taatgcggcc gcaccattca cggtcatcgt  55620
ccaaaaattt tttgatggca ccccgaacat tgtcccagtt aagcaacaga gtattcacaa  55680
tctcattacg ctccgcccag tattccttaa aacttctttt agacttgctg agctgttccc  55740
aggattcgaa ctcagtccaa tgtttttttt cttttgggga agacttccct tttgaaacat  55800
tttttgcggc tccaccatct acactatgat tttccaaaat aatctccttc atcgtttgag  55860
ttatatgggc attgctaagc accttagtgg taacctgttt acctatgtga tttagcagaa  55920
aaccaagttt gtccatttgt gtctcaacca tttattctta acaaaacaaa aaaaattaaa  55980
aatcatcgtc gtttaaaaag agtttgaagg caaacgcatc atccttaaca cagttctgat  56040
actgcgtagg tcttaactcg aaaaagttgg tttttctac ttcattaaga aagaatttag  56100
tcatctgagg aaaagggttt cccaccttat aaatgctttt gcactgcatc atgaagcaca  56160
aattatctgt aaagtagcgt atatattgaa atagcatttc ttttgaaaaa ccgggaactc  56220
ttcctcttgc cttgtcaaag gcatagttaa taaactcatc caccaactcc acagcctcct  56280
tcaaaatttt gtgaatgatc ttttcctcgg gaatgttata cacgtaattt gagataagaa  56340
aacacgcaaa actacagtgc atcccttcat cacgtgagat aaactcatta tagcttacaa  56400
gccccggcat aatattctgt tccttaagaa actggatcgc cacaaagtgg ttttgaaata  56460
aaatgccttc tacggcggcg aagcccacca gccgctcacc tagagtgttc ctgtcggggt  56520
ccatccactg ccgcacccac tgcgccattt tttttatgat agggtgtttt tcaatgccgc  56580
taaagatgcg ctgttgttcc ttctcatccg ggatcagcgt ttttacctgt attgagtagg  56640
cttcgctatg aacgcactct tgggcagcct gcattgtata aaagtataac acttccttta  56700
ctttaatttc gcgcataaaa ttggttaaaa ggttttcgat aacaatttcg tcggcaacaa  56760
caaagaaggc taaaatttgt ttataaaatt cgcgctgtgg ctttggcatg gcttcccaat  56820
catcaatgtc cttacacatg tccacctcct gcgccgtcca cgtcaaactt tctaattttt  56880
tataccagtt ccaacattcg ggtgctgaa taggaaaaat agtgaaacgt tgggaatttt  56940
caattagtaa ttcctccata tttgaaataa atattaacat cttcaaattt attggctgcc  57000
atggagacgt tttttattga gacgttggca tctgatgtgt atggaaaggc gttaaatgtt  57060
gatttagata gactatcgca ggcgcaggtt aaatataccc ttcaagagct tatttcctac  57120
tgcagcgctc taaccatttt acattatgac tattcaaccc ttgcggcgcg tctttcggtg  57180
taccagctgc accagtcaac ggcctcctcc ttctcaaagg cggtgaggct gcaggccgca  57240
caatcctgct cacgcctgtc cccccagttt gtggacgtcg tttacaagta caaagccatt  57300
tttgacagct acattgacta tagcagagat tacaagctgt ccctcctggg gatagaaacc  57360
atgaaaaatt cttatttgtt aaaaaataaa gatggggtca tcatggaacg cccgcaggat  57420
gcttatatgc gggttgccat catgatctat gggatgggaa gagtggtcaa tatgaaaatg  57480
attctgctaa cctatgacct gctttcccag cacgtcatca cacacgcgtc gcccaccatg  57540
```

ttcaatgcag gcaccaaaaa gccacaactc tccagctgtt tcctgctaaa tgtaaatgat 57600
aatttagaaa atttatatga tatggtcaaa acggccggca tcatttcagg cggcggcggt 57660
ggaatagggc tgtgcttgtc aggaatacgg gcaaagaata gttttatttc tggtagtggt 57720
cttaaaagta acggcataca gaattatatt gtgctgcaaa atgcttcaca atgctacgcg 57780
aaccagggag gcctacgtcc cggagcctac gccgtctact tagagctgtg gcaccaagac 57840
atctttacat ttttacaaat gcctcgccta aaaggacaaa tggctgaaca acggcttaat 57900
gcccctaatc tcaagtacgg cctatgggtc cccgacctat tcatggaaat acttgaagac 57960
caaatacaca acagaggcga cggcaaatgg tacctctttt cgccggatca ggcccccaat 58020
ctacataagg tctttgattt ggaacggtcg cagcacgaaa acgcacaccg cgaatttaaa 58080
aagctttact atcagtatgt tgctgaaaaa aggtacaccg gcgtcacaac ggccaaagag 58140
attatcaaag agtggttcaa aacagttgtt caagtaggga atccctatat cgggtttaaa 58200
gatgccataa atcgtaaaag taatctttca catgtaggca ctatcacgaa ctccaatctt 58260
tgtattgaag tcacaatccc ctgctgggag ggtgataagg ctgaacaagg tgtttgtaat 58320
ctggccgcag taaatctagc cgcctttata cgtgaaaatg gctacgacta ccgtgggctc 58380
atagaagcat caggcaatgt cacagaaaat ttagataata ttatagataa tggctactac 58440
cccacagaag ccacgcggag aagcaatatg cgtcaccgac ctattggcat cggggtcttt 58500
ggcctagccg acgtgtttgc gtctttaaaa atgaaatttg gttcacccga ggccattgcc 58560
atggatgagg ccatccatgc ggccctatac tacggggcca tgcgacgatc catagaactt 58620
gcaaaagaaa aaggaagtca tcccagcttt ccggggtctg cggcctcaaa gggtctactg 58680
cagcccgacc tatgggttcg ctgtggtgat ttagtttcct cctgggaaga acgcgtggca 58740
cagacgacgc agggtgtgtt gacgccgaaa aggtggtcgc agctacgcct ggcggctatg 58800
cagggacttc gaaatggata tgtcacagct cttatgccca ccgcaacctc ctcaaattct 58860
acaggaaaaa acgaatgttt tgagcccttt acatccaatc tatatacacg tagaacgtta 58920
agcggggagt ttattgtttt aaataagtat ttaatagacg atttaaaaga aattaatctt 58980
tggacagaag ccattcaaca gcagctacta aatgcgggag gtagcattca gcacattttg 59040
gatataccgg ccgagatccg cgatcggtat aaaacctcca gggaaatgaa tcaaaaaatt 59100
ttaacaaaac acgcggccgc acgaaacccc tttgtatccc aaagtatgtc cttgaactat 59160
tacttttatg aacctgaact aagccaggta cttacagtgc tcgtcctagg ctggaaaaaa 59220
ggtttaacta ccggttccta ttactgtcat tttagccctg gagcgggtac ccaaaaaaag 59280
attataagaa actctgagaa agcgtgtaat gcggactgcg aggcgtgtct tctgtaggtg 59340
tctcgcggta aaagagcagc ggggaccata tggtaaaccc caacaagagg ataatgaata 59400
aaaaaagtaa acaggcatcc attagttcca tattaaattt ttttttcttc tatataatgg 59460
aatattttgt tgcggtagac aatgaaacct ccttgggggt ttttacttct atagagcaat 59520
gtgaagaaac gatgaaacaa taccccggcc tccattatgt cgtttttaag tatatgtgtc 59580
cggcggatgc agaaaataca gatgttgtat atttaatacc ctcgttaacc ttgcataccc 59640
ccatgtttgt agaccactgt ccaaatcgta ccaaacaagc acgacacgta ttgaaaaaaa 59700
taaacttagt gttcgaggaa gagtctattg aaaattggaa ggtttcagta aatactgtgt 59760
tcccccatgt tcacaacaga ttatctgcgc cgaaactttc catcgacgag gctaatgaag 59820
ccgtagaaaa gtttttgata caagcaggac gactcatgtc tctgtaaatg tctcttcctt 59880
tatgggtgac gtctcttcct ttgccgagga agtctctgtt atgggcaaga ggtttgaaac 59940
aacgcaagga ctctgcttaa tctgctgtct cacaaaggga atcaaactac ctgctttcgt 60000
atttttaatg tagtaattac ccttgttgtg atgaatttta agaccatagc gtagtcccag 60060
tactttatta atgaatttta aaattgtttg agggtccgtt ttattgggct ttttaagctt 60120
aaactcaaag ctgatcgcgc ttaaatcata ctgaacaaat tcatcaacga gtttcgtcat 60180
taattgttca ttggtcaata tattagggtc ctgaacgcat ttaaagccgc acttagttaa 60240
tagcataata gcgtacatat gagattgaaa actataatta aattgtagat catgatgctc 60300
tgcgtgttgc atggcccatt gatgaaagtt taattcctga gtttgtaaca tagtgagcga 60360
ctcgtatact gtctttccgc ggcttatttg gacacggcca gtatagttct gttttgtcat 60420
aaaactattg tattgttcaa caaatttggg agtaatttta tgaccgtgcc atgcataaaa 60480
ttcgagtagt ttatactttt catacgcaaa taggtcttgc tggtctactg tgatgccttc 60540
ctttaagttt tgtttaattt gtaaagcttt attggcatca atggtttcag ccgaggcaat 60600
gtttacatag tcctggtgtt taatttccat tttaatgctt gtatattgtt tgactgtctc 60660
cagcttttca cccgtcagta taaacacctt agcgccggtg tcggcgatct ggttaataaa 60720
tcgggttata aagtgatttt ttgatagatg ttgtatccgc attgtttcga gccatagatg 60780
gtagtatgga gttttataat atatcggcct acctgtttcc ttactatacg tgaaggaaag 60840
ctggtgattg cttatggtct gaaaaagggt gtcacgtttt tgtaacgtaa acatttcaat 60900
gtcttcgatg gtttctggat agtaattttg tttcccctgt aagcagattt tataacactt 60960
actttttaat tcacgcacgc ggcccaacat ttggcaacat gtttctacgt cacacgacat 61020
attgttaaaa aagccgtata aaacatcaaa tctcttatct tcgtatgaaa cacccgctga 61080
aatcgtgggc gtatagataa ggatatcaac gagcccccaa taatacgata cattattaaa 61140
atgggattcc cgttcatgag cagtgctttt agaactataa aacccaattt tttttccgg 61200 aaactttttt tggataaatg attgcaacag ccgggcctcc attaatgaat ttgtagggat 61260
aacaattttt ttgtcttcta gcaaatcctt taaaaggtta tttaaccaag tttctcgtga 61320
agaggtaaaa taatacgtgt catgctgggc ccttttatat tgattccagt gaaagaagat 61380
agggacatcc ccgcgaaaac gctgtagaat attatacgtt cgatttccta ggtttgcgtc 61440
caagcatata acataatttg ccgtttcgag catccacatg aaaatggcaa aagagggagc 61500
aaagtatttg tgcaggccgc tattgaattg attaaaaatc gattctacct catccaaaat 61560
aagtaggtct acaggctcgg ctgtggaggt tagccggaaa agtgattcta cctgaatgat 61620
gactctttcg tagctgtcca aatctccagt tacttcgctg tacaatgtga aattcggtag 61680
ccgggattgt atattttttg agaagatctg tcgaaacgtc acaaaccgta tggtttgttg 61740
ttttgaaata gaattattgc cgtagtattt ttgcaaatag ttgcgcagtt ggacggtttt 61800
acctattttc atttgagcct ttacaacaag cgtagggact cgttcatatt ctcgcatact 61860
actttcatca tagatgtgtt tttgagtatc aggcagttct tcaaagagaa tggactcatg 61920
aacctctatg ctctttgtca tcacttggtc cacatatgtt tccacaaaat tatttgtgcc 61980
ggaaaggctg cccatgagaa ggctatgttt attgtcatgg cgacagtgtt gatacacttt 62040
gtttcccgtg actcttaaaa ttagggtatt gtccttatca tgcatacgct tacatatttc 62100
gcagtaactt ggacttgtac gtttaaacaa tactaaattt ttatgaacac ggaggaagca 62160
atgattttta catagtgttc ctgcaaattt taatacctct tcaagttcac tttgttggat 62220
agtatcgcag gaactcggtg ttgtttcttt tacatttgtg aagatacaag gtaaacacgt 62280
cgtttcaaag ggggttgcta taagggtatc actctttttc gtggttgtac tggtctcaaa 62340
cacctctgca agctcctcat taaacatttt aacacgcatg ctaccttttt tatgagaccc 62400
tatgatgcga aaattttgaa tacttttgtt gacctggggg tcaacaaaag gataaacgtg 62460
tttgggaaga ttttctaaca ctttggatgt aaagactttg gcctcattat tgtttaatac 62520
tgagtatgta taaagtatga tatgaaagga gtatttaagt tctcgctttt tatttaatcc 62580
gatagaatct gttagcaaaa tttgttcacg cgttagattg atgttataag gtaaagaata 62640
tgtctcgtaa aatacatcca tgatgacgtt aattatcatg tcaaggatgt catagacatt 62700
gtcttcgaca ttatcattgt catcaacatt gtcatcagag tatgacttat ttaccggaaa 62760
gtcgatgtca aattttaagc gctgaggcaa aaacccaaat accacttcgt ggaaacactt 62820
ctgctcaaag ggctgagccg cctcccactc ccaaaagtca tcacgacttg aaaaaactct 62880
aaaaagatta ttatattcat ctcgcaccac gaagtgattc tttaaggttt cgagagaata 62940
tttatcctct acggcttctc cttgggagtt acagcgaaga aacttgaatg tttcttgcat 63000
tttgatattt aaaattaaat caattatgat gcggccgcta atgcggcggt tgacgcggcc 63060
gcgccgctga cgcagccatc atacataaag cggcatggcc gttttataac gactagtcgg 63120
ccgttatatg acgaactata taaaaatgaa ttcttttaat tagagttaag tattgttgat 63180
tgtataatcc atcatggttg agccacgcga acagtttttt caagatctgc tttcagcagt 63240
ggatcaacaa atggacactg taaaaaatga cataaaagac attatgaaag aaaaaacgtc 63300
ttttatggta tcattcgaaa actttataga acgttacgat accatggaaa aaaatattca 63360
agaccttcag aataagtacg aagaaatggc ggccaacctt atgaccgtca tgacggatac 63420
aaaaattcag cttggagcca ttatcgccca acttgagatt ctaatgataa atggcactcc 63480
acttccggca aaaaagacaa caattaagga ggctatgccc ttaccttcat caaacacgaa 63540
taatgaacaa acgagtcctc ccgcctcagg caaaacaagt gaaacaccta aaaaaaatcc 63600
cacgaatgcg atgttcttca cgcgtagcga atgggcatcc tcgaatactt ttcgagaaaa 63660
gtttttaaca ccagaaattc aagccatatt ggatgagcag tttgcaaaca agaccgggat 63720
cgaaagattg catgccgagg gtctttacat gtggagaacc caattctctg acgaacagaa 63780
gaaaatggtc aaagagatga tgaagaagta atatttttgg taaaaatatt tttatcaaaa 63840 tttttttacca aataataaaa atatttttac tttttttctt cataatatac atagaatgcc 63900
tacaaaagct ggcacaaaaa gtaccgcaaa taaaaaaaca acgaagggct cctccaaatc 63960
tggttcttcc agaggccaca ccggcaaaac ccatgcttct tcgtccatgc attccgggat 64020
gctctataaa gatatggtaa atattgctag atctagaggc attccgattt accagaatgg 64080
atcgcgtctt actaaaagtg aattggagaa aaaaattaaa cggtcaaaat gaatataatc 64140
aggaaactta agcctggaac aattagcctt gtgctgggac ccatgtttgc cggcaaaact 64200
acgtttctta ttcattgcat ttacatgctc gaacgtttgg aaaaaaaagt agtcttcata 64260
aaatctacca aaaacacccg agacaaaact attaaaacac actccggtat acagctacga 64320
cccaaacaat gtaaaatcat agaaagcaca cagttatctg acgtgggttc tctcaccgat 64380
atccatgcag ttgtcgtaga tgaagcgcat ttttttgacg atttaatcac atgccgcact 64440
tgggcagagg aagaaaaaat tattattctt gcgggactca atgcttcctt cgagcagaaa 64500
atgtttccgc ccatcgttcg tatttttcct tactgcagct gggttaagta tattggccgc 64560
acctgtatga aatgtaacca acataatgca tgctttaatg tgcgtaagaa cgcagacaag 64620
acgcttatcc ttgcgggagg aagtgaactg tacgtaacat gttgtaacaa ctgtctaaaa 64680
aatacattta ttaagcagtt gcaacctatt aaatattaaa aatcttatac aataatggat 64740
cattatctta aaaaattaca agatatttat acgaagctcg agggtcatcc ctttcttttt 64800
agcccgtcga aaaccaatga aaaagagttt attactctgc taaaccaggc cttggcctca 64860
acgcagcttt accgcagcat acaacagctg tttttaacga tgtataagct agatcccatt 64920
gggtttatta actatattaa aacgagtaaa caagagtatt tatgcctgtt aattaatcct 64980
aaactcgtta ctaagttttt aaaaataacg agctttaaaa tttacattaa tttcaggctg 65040
aaaacttttt atataagtcc taataagtat aataattttt acaccgctcc ctctgaagaa 65100
aagactaacc atcttctaaa agaagaaaaa acttgggcaa agattgttga agaaggagga 65160
gaagaatcct aagtcgctta catttttttt tgctattttt atagaatgta cacgcatgtt 65220
gatgttgtcg gaatagctga agcctcagcg gccctctacg tgcaaaaaga tagggatcgc 65280
tacttagacg tgctaacaac cattgaaaac tttatttacc aacacaaatg catcataaca 65340
ggggaaagcg cccacctact ctttttaaaa aaaaatattt atctttacga attttactcc 65400
aacaatgtgg cggagcacag caaggctttg gcgaccctgc tttataaact tgatccggaa 65460
tacctcactc gttacacagt actcattacc aaaattccca accattggta tgtgattaac 65520
gtagatcagc gagaatttgt gcgcctatat gccatcccgg cagttaaaca acacttaccg 65580
attcccattt tacccttcta ttgcaccagc gcactcaccc agcaagaatt gttttgttta 65640
ggacctgaac tgcagttaat acaaatatat tccaagctct gtaaccccaa ctttgtcgag 65700
gaatggccta cgttgctcga ctacgaaaaa agcatgcgga tgttattttt agaacagttt 65760
ccgcaaagat tggaaatgac gggcgggaag aaggaggaga aggaaaagca tgaaagtatc 65820
attaaaaaaa taatactaga aatggtctct acccgtcagc gaatcgttgt tgggggttac 65880
atacaaaaaa acctgtacaa ccatgtactc aagaatagaa atcgtttaca gcttattacg 65940
agcttaaata tttatgaaga aaaagatatc atccagcaat tttgtgattc aaatggactg 66000
aagatcaaaa tacgtatcaa caatccgctc ttgcctacaa atccggaatt acggcgtttg 66060
actatttatt ttaatcataa taatgatgat gatcagtcat atctaatagt agatatgtac 66120
aacacgggaa gctatgagct agtgcctaca aatcagataa acacgcttga tggcagcttt 66180
ttaataggaa cacccttcgt gcaagcgcga tttttgttgg tagagatctg ggtgcttatg 66240
cttattgcgc agcaaactaa aaaggacacc aaaaaaataa tacaattttt tataaatcaa 66300
tatgaaatgc ttatgaatag tccttggccc agtatggagg ccctttttcc ctcaagcagt 66360
aaaagatatt taggcaacta tgtagaccct aacgcgctca taaagtgggc acaactcaaa 66420
ttaaaaagaa taccgccttt ttatcctgga aagccggatg aagaatcatg ttaagccgat 66480
taaaaaatca tgttaagctg gttgaaaaat catgttaagc tggttgaaaa actcttggtg 66540
aaagcacgga tgtaatatta acattggccg ctcgcatttc gtgttgaaat acgatggaag 66600
agcgacggct atctaccatg ccgatatcgg cctggacatc acagttcatg cacttgtaga 66660
tgggatgact cgcgttatag atggcaggct cgccacagtt tctacagatg taggagatgc 66720
agccatccga gtcgtcgtgc gatttttcta tgatggtttg catggcgccc tgcgccgtaa 66780
gcacccaatg ctccatttct cccagacgaa gacctccgtg cgatcgtttg ccgtccaacg 66840
gctggcctgt gagggcatcc gtgggcccat agcttgcaac ggcgtatcgg tcatccagca 66900
caaatttttg caggcgctgg tgataggtcg gtcctatgaa gatggccgca tcaaagtact 66960
cgccggtctg gccgttgaac attttttggc atccattgaa gcgtagacct tcttgcgcca 67020
gtctttctga aagaagctgc acattaatag gcaggaatgc ggtgccgtct gttaccaccc 67080
cctgtagggc atttgctaga ccaaccgtgg tttctatcat ttgaccgttg gtcattcggg 67140
agggatgtga gtgggggttt acaatgaggt cgggctgcaa tccgtcctct gtgaagggca 67200
tgtctgaagt gggcagggcc agcgccgcaa tgcccttgtt cccgctgcga gaactcattt 67260
tgtcgcctat attgagattt ctttcatagc gcaggcgcat gaggccaaag atctcgtcat 67320
taggcccatg gggacgcatc acagcatcca cgacggccgg ctcatcgaag ccgtacatga 67380
cagaccggtc gatgtatttg ttgagttcgt ctttttcgcc ccgtattttg gccacttttc 67440
ctataatgat gtcgcccttt ttgaccaccg ttcctacggg cacgaatcca tctacaagct 67500
tttcgtaatt agcaccaggc ttaagatttt tggtgattaa agggtcgggc ttcccaaacg 67560
actctatatc gctttctaat tctacttttt cttctcggta gaaggtgccg gcaaagccgc 67620
ccctgtcaat aaaggactgc gacacgatca cagagtcctc ctgattgtag ccgccgtaga 67680
tcatataagc cacaatggta ttaagcccgt tgggtatgac atagttatgt gctatggtct 67740
ttacaagcgg catttcattg taaaactgga agaagcggtt catgtcgaca cgatatggcc 67800
agctaaagca ataccagccc cccgtttgcc ggccttggtt tgtttcatag gtaacacgcg 67860
caggttgggt acagtttgcg tagggggaca ctagggcggc aaggcccaaa atagcttggg 67920
gcacgtccac gtgtgtgaaa cgacgcgtta catcatgttt atgtttgcgt agctcgatga 67980
tggagaaggc aacaagacag ttttccgcct cctcgggggt aatgaactca cagatgccct 68040
gtgctacgag atcttcaagt gtaagcgttc cggctaaaat gtcttttgcc atttgaggcg 68100
taaatcgcgt attttgaatg aaagggattt tatgtttttc ccagtcttta tcgccttttt 68160
ttctggcctc tgcggccttg tagcaggctt gattgtattt ttcaatatta ttatctacaa 68220
tgagtagggg gcgggtcagc ctaccgacgt ccaaccaaaa ttctacttcg tctaccatgc 68280
tatcccagta gatggtggta tggggatgca caaccttgcc ctcacggcga agcattctat 68340
accgctgagc aagctcaaag gcattggtgc agcagccgat ccattctccg ttgataaata 68400
cgcgcgctag gccctttcgt acaatgtcct tgttggaaac atcggctaac tgttgaatgg 68460
ccggatctga tagaaggcgt tgttttaacg aaagtacttc tccggcggtg cagacattgg 68520
cagtgatggc taactgttta gacatgccta ctttttcacc agtatcggct gactgggcta 68580
cgcagatgta tccaggatag gatgcgtgca cgcgacgcat catgtcagcc ctttctgttt 68640
gtttggatgc gttggtggtg ttatgagtat ttaccgtacg caatgctgaa atggtattta 68700
ataaattttt tctttccaaa ctttgagtag atactctgtt tacaatgggg cgctgtcgca 68760
ccatgatggt tttatttcct gaaatgatag actgttccat actgcgatta agatcggagg 68820
cggtattttt tgataaagcg gcagaaaatg cctcgataat gtttcgctga gtaagctcct 68880
caaaggctgt ttgtttaaga agttctttga acccattgat gatgggtgct atcacggaag 68940
tattaaaaat agccttaaag gccttggcga gtgagacccc tgagccgtgc acccgcttgg 69000
tgcggtagct atcacggtcc gtgggtggaa acacattcat aatgacaaga agtattttat 69060
gaataagcag gcctaaaaag cgcagctttc gtacacgtgt atctgcggtt tggcccatgt 69120
gtggcagcaa tattttgtct aaaatagtaa gttgtctttc atttaagtat tgtaccgcat 69180
tttcatcgct tttgtaagca gatgggtttg agacaaattt ggaaaccttc tcggataaaa 69240
actggataat tttttctcgg ttcagctcgt gttggaccgg ttgaaatatg gggtctaaaa 69300
catgaatgga tttttccaga atttctatca tgaaggtatt cacaagggag ttggattcta 69360

-continued

```
gatcaaatac cacttgctca atgatgctgt catcgcctgt cattccaaac atgcgaaaga  69420
tgagatacca aggtatgcga agttttgaga acttggtgct attgatttca atggtaatgg  69480
cgccggtggt catgtagcgt ataataattt gagagctatt ttcgaaggca cctcccggtt  69540
gggagataaa ctcgccgcga atgatttcat tattcccttg ttgcatggta tggtaatgga  69600
tgtgaagcgt gttaaagcgg atgttttcta agaggtctac gacccattcc ccgcctcggg  69660
ctataaagta gccgccgggt tcattagggt cttctcctat ttcttttttt gcggtttttg  69720
ataggtgatg agtgtggcag cggttgctgc cccgcatgat gggaaatgta gatacctgaa  69780
aaggaggaat acttgctcgt tttacctcct gccgaccatt gctgtagtgc gccgttaaaa  69840
taacctcggc ggctagatta accgggcccg aataggaaag gccacacagg cgtgccttat  69900
tgggtagtaa atttatcttg tttccctgtg aatagtttcg atgttgcggg cgttcaatgt  69960
tcacatctgt aaagttaaat tggatctgaa ctgattcccg aagcttatct atttcagtat  70020
ggtcgcgttg gtctttataa gtaatatcca cgttaaacat ttgttttaca atttgcggaa  70080
ttccattgtc cataagatcg tcgaagcttt tgatgttata ccctatcaat cctgtagagt  70140
ttactgcagc ggagataaag ctcagcatat cagcctctgt aagctcctca ttatccacgg  70200
tttcaatggg gccgtaggtt atttgcggcc gcaagggttc catgattatg aagtactaca  70260
ttaatattca gttattcttt aaaataaatc tttatttata aatcttattt ataatataag  70320
aatgccttat gcaagagaca tcacaaagtt tattacggca acggaaccag aggtgggtct  70380
tcccctgttg gcgctgcagc gctccaaatc catcataggg gttattcttc ttgtaataag  70440
tttgttattt attttcattg gcattattat attatcagtg agtagtggtc ataccacagc  70500
agcctctata tttatcgtat tgagtcttat cctaggtggc ggtggttttt ttcttattta  70560
taaagataat tcttaaccca cataaaattt gaaaaaatat agagtaagaa aatgtccaat  70620
tactattatt actatggcgg ggggagatat gattggttaa aaacagtaga acccactaat  70680
tttttaaaaa tcgggttgcc ttaccaggca cacccattac atcttcaaca tcaggcaact  70740
actcccccat ctatcttaga aaaatttaaa cgagcagaca ttcttcttaa tgaggtgaag  70800
gccgaaatgg acccactcat gttacaacca gaaaccgaaa aaaaactatt ccagatattg  70860
agtagtattg atatgttcaa aggtctgcga aaaaaagtag aattcacgta caatgctcaa  70920
attgttacga atgcttggct taaaatgtat gagctgctaa ataccatgaa ttttaataat  70980
acatctcagg cattttgcaa ttgtgagctt ccaggagggt ttataagtgc aattaaccat  71040
tttaattata caatgatgca ttaccctact tttaactggg tagcttcctc cctttacccc  71100
agttcggaaa cagatgccct ggaagatcac tatggtcttt atcagtgcaa tccggataac  71160
tggttgatgc aatctccttt actgaaaaaa aatatagatt ataataacgg ggacgtaacc  71220
atcgctagca atgtaaaaaa cctagcgctt agagccacac aaaggctgac gcccatccat  71280
ctatatacgg ctgatggggg tattaatgta ggacatgact acaataaaca ggaagaatta  71340
aatcttaagc ttcactttgg tcaagccctt acgggtttgt tgagtcttag caaaggcgga  71400
aacatgatac tcaaacacta taccttaaat catgcattta ctctttcttt aatatgtgta  71460
ttttctcact tttttgagga actatacatt accaaaccta cctcctctcg gcccacaaac  71520
tctgaaacct atattgtggg taaaaacaga ttacgcttat ttaccccccaa ggaagaacaa  71580
gtccttctaa aacggctaga attttttaat gatacgcccc tcgtagacct aagtctttac  71640
caaaatttac ttgaaagcgt ttactttgcc gtagaaacaa tacatctaaa acaacaaata  71700
gaatttctaa acttcggaat gaaatgttat cgacattttt ataacaagat taaactactt  71760
```

aacgattatt tagctccgaa aaaaaagatt tttcaggata ggtggcgtgt gcttaataag 71820
ctttatgttc ttgaaaaaaa gcataaactt aagctttgtg cctcctaggg atctgttgct 71880
taatttaaca gatgcaatct taacagatgt aaactaaaaa gtgtgttcat acaaggattg 71940
tatttatgaa tatttattaa catataaggt tgtgatgtaa cactgtataa cctatataac 72000
tacactatga agcacggcgt ataataattt atattgaaca cgatgttgac tcatttattt 72060
gcaaacaaat atttgtttgc aagacgtttg catgcattta ctaatatgtt gttgactagt 72120
ttatttgcaa actagatgtt tgattgcaaa ctagatgttt gcacgtattt atttgaacta 72180
atatacactc cttgttttat ttgttatata cacagcatac ataagtgtat attgtttaca 72240
cttatgttta taactcgacg taataacatt ttacacgctt ttttttgca aatcttaata 72300
atattgtatg ataaatcaaa caatgtctta tatatgtggt ttattatttt aggcgccgca 72360
agatgtactc cattctcatt gcatgcttgg tgttattact ctgtctagtt atatatgtcg 72420
gtcatcgtgc cgatcatgca cgaaaatatt tagaaggaat gtggcatgga gatccggttt 72480
ttctaaaaca gtcggggcta caatcctttt atctctacat acaacctgac catacatgtt 72540
tttttagcat tgtgaataaa aatggtgaaa agctgatgga aaccaaaata ccttgtacga 72600
taacaaataa aatatatatg ttttttaaac ctatttttga atttcatgtt gtgatggaag 72660
acatacatag ctacttccct aagcagttta actttctgtt agatagtaca gaaggtaaac 72720
ttattttaga aaacaatcac gttatttatg ctgtattgta taaggataat ttcgccaccg 72780
cactaggaaa aacggttgaa aaatatataa cacaaaatta atcatgtttt ctaacaaaaa 72840
gtacatcggt cttatcaata agaaggaggg tttgaaaaaa aaaatagatg attatagtat 72900
attaataatt ggaatattaa ttggaactaa catcttaagc cttattataa atataatagg 72960
agagattaat aaaccaatat gttaccaaaa tgatgataag atattttatt gccctaaaga 73020
ttgggttgga tataataatg tttgttatta ttttggcaat gaagaaaaaa attataataa 73080
tgcaagtaat tattgtaagc aattaaatag tacgcttact aataataata ctattttagt 73140
aaatcttact aaaacattaa atcttactaa aacatataat cacgaatcta attattgggt 73200
taattattct ttaattaaaa atgagtcagt actattacgt gatagtggat attacaaaaa 73260
acaaaaacat gtaagtttat tatatatttg tagtaaataa tatttttaat tacttaaaat 73320
ttttatatat aagtttttga tactatatta taaaacatat gttcataaaa tgataatact 73380
tattttttta atattttcta acatagtttt aagtattgat tattgggtta gttttaataa 73440
aacaataatt ttagatagta atattactaa tgataataat gatataaatg gagtatcatg 73500
gaattttttt aataattctt ttaatacact agctacatgt ggaaaagcag gtaacttttg 73560
tgaatgttct aattatagta catcaatata taatataaca aataattgta gcttaactat 73620
ttttcctcat aatgatgtat ttgatacaac atatcaagta gtatggaatc aaataattaa 73680
ttatacaata aaattattaa cacctgctac tcccccaaat atcacatata attgtactaa 73740
ttttttaata acatgtaaaa aaaataatgg aacaaacact aatatatatt taaatataaa 73800
tgatactttt gttaaatata ctaatgaaag tatacttgaa tataactgga ataatagtaa 73860
cattaacaat tttacagcta catgtataat taataataca attagtacat ctaatgaaac 73920
aacacttata aattgtactt atttaacatt gtcatctaac tatttttata ctttttttaa 73980
attatattat attccattaa gcatcataat tgggataaca ataagtattc ttcttatatc 74040
catcataact tttttatctt tacgaaaaag aaaaaaacat gttgaagaaa tagaaagtcc 74100

-continued

```
accacctgaa tctaatgaag aagaacaatg tcagcatgat gacaccactt ccatacatga  74160
accatctccc agagaaccat tacttcctaa gccttacagt cgttatcagt ataatacacc  74220
tatttactac atgcgtccct caacacaacc actcaaccca tttcccttac ctaaaccgtg  74280
tcctccaccc aaaccatgtc cgccacccaa accatgtcct ccacctaaac catgtccttc  74340
agctgaatcc tattctccac ccaaaccact acctagtatc ccgctactac ccaatatccc  74400
gccattatct acccaaaata tttcgcttat tcacgtagat agaattattt aatatgtact  74460
atatattaat tatttaacct ttcaagctgg tcttcattta aatttaaaat ccactaataa  74520
aatgtatttt ctagtagcag atcatcgaga acatcatgtg attccttttc ttaaaaccga  74580
tttccatcac atgcatcaaa atcctataca aaaaaatcaa gctctcctag aaatcaaaca  74640
gctttttact ggagattatc tcatctgcaa aagcccttct accattctgg cctgtattga  74700
acgaaaaacc tacaaagact ttgcggcttc tttgaaagat ggacgttata aaaatcgcca  74760
aaaaatgctg tcgctgcgag aacaaaccaa ctgtcaactt tatttttttg tagaaggccc  74820
ggcatttcct aaccctcaaa aaaaaattaa tcacgttgcc tatgcaagca ttattactgc  74880
tatgacgcat cttatggtta gagatcatat ttttgtcatt caaacgaaaa atgaggccca  74940
cagttcccaa aagcttgtgc agcttttttta tgccttttct aaggaaatgg tgtgcgtcgt  75000
tcccacctcc ctcaccccca cggatgaaga gctatgcatc aagctatggt cttctctttc  75060
tggtatttca ggcgtgatag gtaaaatctt ggcaaacact tgttccgtag ctcatttggt  75120
tcatggaaag ctttcatcgc agaatattga tcagttaaaa actccctcca accgaccatt  75180
ccccaaaaaa gtaaaacgta tgcttataag cattagcaaa ggaaataagg agttagaaat  75240
aaaattgctc tcgggggttc ccaatatcgg gaaaaaatta gctgccgaaa ttttaaaaga  75300
tcatgcgctt cttttttttc taaatcagcc cgtagaatgc ttggcaaata tacaaatcgt  75360
tcaaaaaacc cgtacgatta agttgggaat gaagcgagcc gaagcgattc attatttttt  75420
aaactggtgt ggctctgccc atgtaaccga tgatagccaa aatatcacag aggcgtcgcg  75480
gtccacaatg caggtcgcga cgcagtccgc cgcaatacag cccgctgcaa cgcagccatt  75540
gcacgaagta tcagatgatg catcatcaga tgcttcatca cccgtagggt atcaaacatt  75600
atctaaagaa atgttattga acacagcctg atgttaataa ttcactacat ctaaagaaat  75660
gttaacctcg atactaaaaa gtcattgaac acaactactg gggcgctaag ttgtccaaca  75720
catctaaaga aatgtcaaca tcctcgatgc taaaagggtc atcgagccgg tcaataatgt  75780
cttccccaaa aagtccggga gaactgtagg ccgagatgtc gtccatggag ctatcttccc  75840
cagagcacac aaagtcctct ccaaaaatca taaagttaaa tgcaccgggc ttacttaaca  75900
gcttttcgct ttgaataata gtgttgagtt ctgtcagcgc aaactctctc acaatattca  75960
caacccagga gggctcttta atttcataca gcgttaagaa acttatacat aaaaattcta  76020
tagagtaaag caaggcgctg gcaggatctg ttacccgtag gtgtttaaat gtagtgtgat  76080
attcattcac aacgttaggc agcacctttt ccaaatcctc cttttcctcg tacgacaggt  76140
gctttacaag cctttcaaca tgtataggag gcttgttaaa tgtactaacg tgccgcaaac  76200
agttataatt atataagaaa atacgtacgg cagagtcgac cgccatgagc cttggatcat  76260
ccattgaggt aggtggtggc ggggcaccct ggccttccct gatgtctgcg taggagcgcc  76320
cctccatggc ccctatggcc tctatcacag caggactgat atccaaaatc ttggccgtct  76380
tgattatttt tccgtaatcg aaagtccatg gctcctgtgg aggcttgggt tgtgtttcgg  76440
tggagggcgt ggtcatatct ttctttattt gaatagaacg gatcgacatc ttttccttat  76500
```

```
cgtactggtc tttataatta ttataatagt catgaactaa ttcgggttga gaaagatgat  76560
cgtatataat ataggtaaaa agtccgcact tgacacattt tttatcctgg aagtcgtgta  76620
atcctccctt ggggcagcgt gactcgtaga aggcataaaa ggtgttaaat tctaagctcg  76680
cctttagggc tgtttggacc ttttttatgt ttaattgccc cacctcatgt tgtagcacgt  76740
ggcatacaga acagcgtaga tcggcaagtg cataatggtt gtcaattttt tttatgacgt  76800
ctttgcgtgt tacttcaatc tcggcgggtt tctgcgaact gtctacggcc ttgtaaacgt  76860
aaatggtcca cttatgagga agccccccttt catcgtatag ggttgaaatg ggaagccttt  76920
tatactcaaa cagccgagtc cgttggtcgg ctcttcctgt gttaggatca aatatgttat  76980
aaaatccttg ctgagcaagc agggcctttt gctcgccata agcattttcg tacgttttga  77040
attctgcaag ttcggagtta aaattaggtg cattttgtaa atacttaaga aataattcat  77100
aggctctaag gtaaatgaga gttgaggttt tttcctcatc ccgtcctccc caccacaccc  77160
gcaggctttc ttcttgaaaa tagatgtcat tcagacgcgt caactgcgta aaatcaggcc  77220
gatatttaga ggtataaatt ttatcataaa attctttttg cgataatagc tcggccgggg  77280
tacgtcctat cacggtttta aactcatatt cagcctcctt gggagtccgt ggtttgtgca  77340
tagggatgct gccgtcaata cgggccactg tggcagcata atcatacatg gggtccagca  77400
gaatctctgt caaaagtacc ttggtgtcgt cctgcacgct aagcccttgt agcccatttt  77460
ggtggataat tttttgaaa gcctcccgaa aattattagc aatccactga tccgtaatct  77520
cagatagctg atttattata ccgctatatt gctgcatcat tttctccaaa agaaaggtca  77580
cgtatgcatt caaagagcta tccgccttca ttccatgaat ggtaatcgta agaaattctt  77640
tattttttg cgagctataa atgagattca aaatataggc atagatgtag atcacagcat  77700
acagctgcgt taaaggatcg taatcctctt cctttttaat attttcgatg ctatacacga  77760
gcggcaggca gacatttacg gctatattgg caaactgttt cacgtctaca agctttccaa  77820
agtggataaa cgtgcaggcc ttcatggttt cctgccaaat aaaaacacgg agcttactat  77880
taagatcgcc gatgatgccc acatctgccg tacgatcctc ttgaataaaa tgggccagct  77940
cttcgccaca aattttgcaa aagtaggagt aaataagccc ctggttgttt tctttctcct  78000
tgtttattcc tgaaaatttc attagcttgg ttcgcatggt gtcgtaggac gcttctgccg  78060
cttgaagctg tataagcatg tccacatggg gacaaagcag cttaaacccg caggctttgc  78120
atagattcca attggtggta ttgtttttt ccttgtagag tacacgaata ctttctaata  78180
cttttaataa ctccgcgtat tgaagacccg aacgcaactg ttttaccagc ttgagatgag  78240
cacatgcatt tttttcttgg agttcccact gttttttaat gtttaggtat tctgttgtaa  78300
taagttctgc ctcctgtttc ccacaggctt taatgacttc ttgaaggatg ctgttagggt  78360
catccacttt accctccatt gtaagaattt cacgtatagc atccgactgc accctaccta  78420
ttttttcttc cataatttta aaatactgtc tcgcctgggt aatgacctct gtgagcttca  78480
tgtccacctg ctgcagaatc atttgctcct tttcacgctg ttcagcatgt tgtaaaaact  78540
tttgttctac agggttccaa agcacctcca aatagcctgc tctatatagg tcataaagca  78600
agggcatgta tcccgatgta aaaaccgggg acaccgagta catcgtagac aactctttta  78660
aaaaaaatat cacgcgctta atgttctcct ccggttcaat ctcctcggtt tcaacgatat  78720
tagatatatg actgccctga tcctcacggt ctagctttcg gtgtaccatc tcctctgcta  78780
gccgattaat gagccagcta tgcccgccgc tccgcaaaaa cttataaagt tcgatatact  78840
```

-continued

```
ggtgcgtaaa ctggatgatg ttttccttgg tggttacgac aacccccttct ccgttttttt  78900
tccaggtttc ttgatccacg catttcataa atactcgaat aaaattggtc aaattggctc  78960
ctgaggcgac gtagcccaag gtttcaggcg agaaggagcc tatctcagcc atacgcataa  79020
aacactgcgg ggaaaaagtt tttagccgca acttaagtcc atagatttca atgggggctt  79080
ctgcgggaac ggccaggtgc gtcccattaa ttaaaaaaat ttctttgcgt gtgctagggc  79140
gaacacgtaa ttcctttttt ttttcactca cgatggggac cacatcgggg tctaccagca  79200
gttgacgtat gtaggcctct atgggcatgg atagatcggg cagctttgac tgctcggcgc  79260
gaacatggtt cacaaaatct tttagagtga aaagaaagtc tattaaacgt atgtttttta  79320
tatcattaga ccctttaagg gtagagtaga tttcatccac tagtgcctcg atttcctcat  79380
tattgagcga taagatatct gtgccacggt ggactatttg cgcgatcgta attacttcct  79440
ccattagata gaaactgaat attatattta aaataaatac aaaatgtcaa atgaaagttt  79500
tcccgaaacg ttggaaaact tactttcaat gttacagacc aaacagcaaa acgcaattca  79560
gtcagaggtg attgaatggc tgcacagctt ttgtgaaacc tttcacttaa aaatacactg  79620
ccataaacag tttattccta gcggggaaaa aaaacgagct aaaataccccg ctcaagaaac  79680
acagggaaac acgcagccct cccaccatgt gtaccgggtt gttctctcca gagcacagcc  79740
agtcaaagca caggaatctc tgctaacaac catgtgcaac ggactggtgc tagatgcaaa  79800
cacatggaca tgcctagcca ttcctccgcc tgcgcccttt caacaggcga cccgccaggt  79860
ccaacacttt taccgtaaca atttctacga agtggttccc atccaggatg gcacccttct  79920
cacaatctac cactgggatg accctgaata tggcccctcc tggtgcctag caagtaccca  79980
cggatatgat gtgagtaact actgttggat aggcgacaaa accttcgccg agcttgtata  80040
cgaattgctg cagcagcact ctacctgcga cgtcaccctg gaaaaaaata aaacgcgggg  80100
aacgcgtctt ttctttgata acttaaatcc cgattactgc tatacgattg gaatccggca  80160
ccataattta cagccgctca tctatgaccc tcaaaatatt tgggcgattc aatctacaaa  80220
cctaaaaacg cttaaaacgg tatatccaga atactacggc tatataggca ttccaggaat  80280
tcagagtcaa gttcctgagc ttccccagta tgatttacct tatctaatac gatcttataa  80340
aactgctatg aatcaagcca aaaatgctat aaaaaatggc aaaaaagaca agggatactt  80400
taattatggc tatttactca tttcgcgagc gcctgccatt actaaaagta cttctaatgt  80460
tttgttaaaa tcgcctctgc tggtattttt acaaaaaagt gtgtaccaga aaaaacacaa  80520
tatctctaac agccagcgac tagaatttat tatactgcaa aactacttga tgcagcattt  80580
tcgagatcat ttcattgctc tatttccgca gtacatatcc tattatacga aataccaaaa  80640
catgttgaat atgattatcc atagtattgc aactaaagat aaagatcatc cctttgcagg  80700
agccgtggta aaaaaagtgt tggaagatat tgaaaacgcc gaaaacatta ttgatcatac  80760
aaccattcaa aactatgccc atcaaagcaa gtacgccatg ctttacttgt caattatttc  80820
ccatttttaa tctaatacgg ccaaagccgc gggtttttta ataaactaac atttaaaaaa  80880
actgttttat taaaaattat aatactttta ttatatatgg aacatccatc tacaaactat  80940
actcccgaac agcaacacga aaaattaaaa cattatgttt taatccctaa acacctttgg  81000
tcttatatta aatacggaac gcatgtccgg tactacacca cacaaaatgt tttccgagtc  81060
ggtggctttg tgcttcaaaa tccctacgaa gccgttataa aaaatgaggt aaaaacagca  81120
ataagactgc aaaatagttt taacacaaaa gcgaaagggc atgtaacgtg ggccgtccca  81180
tatgataata ttagcaagct atatgccaaa ccagatgcaa ttatgcttac catacaagaa  81240
```

aatgttgaaa aagctcttca tgctttaaac caaaacgtac tgacgctcgc atcaaaaata 81300
cgttaaatat aatttttgta gaggataaaa agctatttta gctaaaaaat aattcatata 81360
cgtttatgca gaggaagaac ggtggctttc aaattcagat tgcatccacg tagaccgtag 81420
cgtttttttt gcttctggtt tatatcgtaa accgtaataa acatcatcat ttgtatccgt 81480
tggatctttt tcccactccg gataaaaaat cggttttctt ttttttggtc gtttttttgca 81540
gtaagctgta aattaaggga atatagctta tcgaaaagtt gttcctgatc catataaata 81600
gcagcatata ttaaaaaaaa taaaaaaaga cgcttcaacg agtcagtacc actgcttgcc 81660
aacgatttac gttggttggt gcattatggt gatatagtaa tgagtgcctg cacaagtgct 81720
tgcacaagtg cctgcacaag tgcttgcaca agtgcttgca caagtgctta cacaagtgct 81780
tgcacaagtg cctgtacaca ttactgcatc gccaaagcac ctgcaatgcc tacttcctca 81840
acagagtacg ataactaaat gcttttaagc accgcttgcg tcgatgtgtc cttcggggca 81900
atcgggttca attggatcca atattattag tcataattac ctaatactta ttcaatttta 81960
tctttttttac cttgtaagat ttaaacagcg ttttagcttg tttaaagcaa cgtttaaaac 82020
aagctaaaat gctgtttaaa acaacgtttt aaacaagtta aaacaaataa gcttataaat 82080
ataccatgac aaaattagcc caatggatgt ttgagcagta tgtcaaagat ttaaacctaa 82140
aaaatcgagg gtccccctcg ttccgcaaat ggctcacatt gcaaccctca ctgctgcgct 82200
attcgggtgt gatgcgtgct aacgcctttg acatcctaaa atatggctat cctatgcagc 82260
agtcaggtta tacggttgct acgcttgaaa tccactttaa aaatattagg tcttcctttg 82320
ccaacattta ctggaaccgt gatagcgagg agcctgagta cgtctgctgt tgtgccacct 82380
atcaatcgca cgatggcgaa taccggtatc gatttgtttg gtaccaaccc ttcatagagg 82440
cttataatgc catagaggcg gccctggatc ccctggaaac cattatcctg aacctcattg 82500
cggcacgaga tctagacttc gttgttcaca tatttcctta taataagggc catgaagact 82560
atttggcctc cacgcaactt attctcaaaa tctttattgc gacgctttta atggacattt 82620
taagaattaa agacaacacg ttggacgttc acttaaattc cgactatatt attgtgatgg 82680
agcggctttg gcctcacata aaggatgcca tagaacactt ttttgaagcc cataaggact 82740
tactagggta cttaattgcc tttcgcaatg gggggaactt tgcaggaagt cttagaccct 82800
cctgtgggca aaagattgtt cccctaacga ttcgagaggt cctacaaatg aatgatatta 82860
atttagccgt atggcgggag gtgtttatta tgcaggaatg ttccgactta gtcatcaatg 82920
ggatagcgcc ctgtttcccc atttttaaca cgtggacgta tttgcaaggt attaaccaga 82980
tttttttttga aaacacgtct ttgcaggaga aatttaaaaa agattttatt gcccgagagc 83040
tttccaaaga aattatcaag ggccaaaaaa cgttgaatga caaggagttt aaaaagttaa 83100
gcctacatca aatccagtac atggaatcct ttctacttat gtcggatgtt gccattatga 83160
ttaccacaga gtatgttggc tataccttc aatccctgcc gggtattatt tcgcgatcca 83220
gctatttatc ccccatcgtg aaaaacattt tgatggacga agactctttt atgtccctac 83280
tatttgacct atgctatggc gcctacgtgt tgcataaaaa agaaaatgtg attcacgcgg 83340
atttgcacct gaataacatg acctactacc atttcaaccc aaccagtttt acagatcgca 83400
acaaaccagg aaaatacacc ttaaaggtca agaatcctgt gattgccttt ataaccgggc 83460
ccaaagtcga aaccgaaacg tacgtgttca agcacataga tgggttcggc tgcatcattg 83520
actttagcag agccattatg gggccaaacc atgcaatcaa gcttgagcgg cagtacggcc 83580
tcgcttttgt aaacaccttt taccgcaatc aaagtgagca tattttaaag gtattacggt 83640
actattttcc tgaaatgcta accaatcgcg aaaacgaaat acagggggtg attttatcaa 83700
actttaattt ctttttcaat agcattactg ccattgattt ttacgccatt gctagaaacc 83760
tacgtagtat gctttctttg gactatttac acacctctga ggtgaaacga aacgtagaaa 83820
tttcgcaaac atttttggat acatgtcaat ttttggagga aaaggccgtg gaatttttgt 83880
ttaaaaatct tcatactgtc ttatctggca agccggtcga aaaaacggcc ggggatgtgc 83940
ttttacccat cgtatttaaa aaatttttat acccaaatat tcctaaaaat atattacggt 84000
cttttaccgt aatagatgta tacaattata ataatataaa gcgttattct gggaaagcta 84060
tacaaacgtt tccaccctgg gctcaaacca aagaaatctt gacgcacgcc gagggtcgta 84120
catttgaaga tatttttcct agaggagaat tagtttttaa aaaggcttac gcagaaaaca 84180
accatttgga caaaatttta cagcgtattc gtgagcagct tgctaatgaa aatttgtaag 84240
gcttgcagtt cttgtatggt cagaacctat gtcgatggaa acattatttt tcgctgcagc 84300
tgcggcgaaa gcgttcaagg ggatagtcag aacttgctcg tctctagcaa ggtgtaccac 84360
accggggaaa tggaagataa gtacaagatt tttattaaaa atgcaccctt tgaccccacg 84420
aattgccaaa taaaaaagga ttgcccaaat tgtcatttag actatttgac acaaatctgt 84480
attggaagcc aaaaaatcat tatattggtg tgccgctgtg gctatatgag caacagagga 84540
taaaccatat catcccaccg aattatgaca ttcctttaaa accgtccgcc taaatagttt 84600
tcacaccttt ggtggcagac tattttataa aaagtaatgt tggttcatga agataaagtg 84660
tgccaaagaa acttttataa acaaatgatt aatgtaggtg ctagtcgtgt gtacttaaac 84720
agggtattct atagccaagt attttctata gccaagtatt ttctatagcc agtattagtc 84780
aagtatttag atgtcagggt atttttatag ccagtatttt tctatatgta caaactattc 84840
cagtaaacat atgtgtgttc tttattgagc agcatcatgg cattaacaag tttattaaac 84900
tgctctaatg ggcattaaat gacaactcgg tgcttagcaa aagtgcctat accttttaac 84960
aattagggcc gggaggcatt cccagctttt ttctataatc agccatacag taccccctgag 85020
cctcatacac gggaataagg tccttccatt ccttgttggg atcggcgggc cagctctcaa 85080
atgaggtgtg aatgtaaggg tcctgttctt tttccttaat gaagcgttta atctccattt 85140
gatgttgttt actttttttgt ttgcggcgga gcgtgttccg caccaatacg taaaaaatac 85200
caagaatcac acataaaaga attattaaaa aaaatatcat catcgcgggg tttaaaaaac 85260
gatcccatgc aacaggaatc gttcttaaaa ccttgtctgg cagggctgta aacatgaagt 85320
ctcctcctat aatcggggtg ggactgtagc ctaacagttc aaggtcctgt cgttctagat 85380
acttattggc gaactgccca ccctttgccc ccgttttttt attaatcaag cagcgctgca 85440
ttttccacca ttctaaatct tcaggagaaa gctcaatgcc atatatcaac tttaacgtta 85500
ttgcatcttt ttcaatatcc ttatcaattt ggctgagctt ttgagcttta agcgggtcta 85560
gtgtgtactt ccatttaaac ttagtgtcct gtagtttggc tacatgaaat acggaacatt 85620
tcggcggggc ctttgtgacg cccttacact gcggaagttt atcattagga caggcgcata 85680
gatgagactg cgccacagca tcgcgaacta catcgcagac ggagtacatt ttcctcctat 85740
gttaaacaat aaattttttt catagctgaa atttgtgggc ctatcttttc ccttgcccgg 85800
ataataatta taagggagtg ttgaaacatc tgggagagaa ttgcttaaaa aatgggtttt 85860
tgggaggggt aactgcgact gttgtacgtc gttggccagg gagattctat atgccgggct 85920
aaaggtgcaa cgttcctgtg aacaacttag tacgcgcgtt gttaatacaa atggactggt 85980
attagcaaac ctcgtaaact cttccggact tgtttgtttt tgtatgatgt ttagcaggga 86040
gtctgccttt tcgagaatcc aaagcgtcgc attgtagtaa aataaaaata gcgacttatc 86100
ggcaggcgtt gcaaaagcgc cgtatagaaa ataaagcagt aagtactggg gagacaccac 86160
aataaggtta tcttgaatga tagatatcgc tagctcttta aacatagtgc taaaaaaatg 86220
tatgtcgttc gtcttgaata tagggggact atagtccatg tagggctcac atatctcagt 86280
caggtgaagg cccatttctt ttatgacttc ttccgggttg tacgtcgcta acaccagcgc 86340
gggataggct ttgggcatat ccacggtaag tgttatgttt ttatcattct tatggtagga 86400
gtaagatggt tgtggaaatt ctgttttcca ctccgggact ttgcaggtaa ttctcagctc 86460
atttagagtc tggtacagga gggcgtatgc cgcaaagccg tgtatggcca cttgtttaaa 86520
gggaattgaa aacgttttac tttcgtatgt cgacttcaca ggaacaacgg gaatggggta 86580
atatttttct atgaggttat accgctgcaa atccttttta aacctgctaa aaacatcttc 86640
ccttggtggg ttatcaaaag gaaagcaaaa tgctaggtgt agcccggccc gctggtaatc 86700
ggggtgaatg attttaaggt ttttatacgt taatgtgggt atggtgttaa agatattggg 86760
gggcatatat gaaagatcag caacccacac aaagtccgtg cgcacccgca tggtctgcac 86820
atggatggcg cgcaccgtgc ccacctgctt gaagcccttt tcatacaaaa tgtcagcaag 86880
ttcgtaggcg tcctcaacgt ggttggggga aaacatatca aagtcgggtc tttctccctc 86940
gggataaatt gagctgcctt taagatgcag ggcataatca atggcaatcc ccccgtacaa 87000
aataagcttt ttctttatga taaattcgcg gaccacctcc aaagccgcct caatctccac 87060
ggcatttgcc tcacgttttt gagcaatgag ccggtactta gaaacattaa aatcagtctt 87120
tagtaaagac gtcataaata gtgtttaata tatattaaag gtttgaataa aatactaaat 87180
agtaaaaatg gatgccctat taaaggaaat agaaaagtta tcgcagccat ccttgcagaa 87240
agaaaacaat gatgtatgcg atctctgttt tatgcaaatg aaaaaaattt ctaactatca 87300
gcttttatgc gaagagtgcg gtcagctgaa ggactggttt gaacctgaat ataatgaaaa 87360
attcacggta tattctcgtc taaagatcgt gggtgccaat agttcctatc accagcgcga 87420
tttggacaag gccaactcaa gtgactatag ctccttgcaa tttcatcaca ttttagagga 87480
gctcaaatcc ctaaatgtta agtatatgga tgcggggcaa aagccctttc ctattcaggt 87540
gttaaaagaa actgctcaca gttataacca agtacaacaa catcgggtca tacgcagcat 87600
tacaaagctt cagatcttag ccagtattct acgtagcatt tgtttaaaat taaacattgc 87660
ttgtacggtg gcagacgccg cgaggtttac tcaacttaat accaaaggga tctcaagggg 87720
catggatctt ctgcgctccc tatttgtaga caataaaatt actttaaacg ttgatttaaa 87780
ccctatagac agctttatta atagtaccta cagtgcctta caaattaaac aaatccacca 87840
agaactgcag gaggaaaatg tttataattt aaaagaaatt gttaagagct ttatattata 87900
cgcggatgag aagaacatcg gcgtcgatct taacaggaga accgttgtga ttgctacgat 87960
gtataatgtt ttacgccgtg cctactaccc catagaaatt gatacggtgg tgtatcaatg 88020
taaaatacga aaaaatacaa ttacacgtgc tcttaaaatg tatgaggatt actactccca 88080
ctttaagtct ctttatgagc agtatcattt aaacgcggca aaaaaattaa tttaaactaa 88140
acgtttaaac taaatgttta aactaaacgt taaaactaaa catttcgact aaagtttaaa 88200
acctagtcta acagcgggat gcccatttcc ctggggttcc atatttcaac aattttttga 88260
ccttcgggtg ttaccttgat gcagcgcatg acgagcagtg gaattttcct attaaagagt 88320

-continued

```
tcttgcttag ctatatcaat aggactgcta tatttttttt taagcattgt agatccatta  88380
attgccaatt gttgcgctct aacggcgacc aaccttgtgg cctcaaaggt ggttaaaacg  88440
ttggaggtaa tgcgctcgtt atcgggtata atgaccaatg tttgcgacga ggcctgcaca  88500
aagccctcgc agatggacgg agactccacg atctcgtcct tgtcctcgga ctcctcctca  88560
ctgtcgacga ggttctcctc ttccgtttcc acatattcct ccacgaggtc atccatgata  88620
agatcctcgt tgtcattatc agccatatta cactgttatc aaatgtactg tttaatacgc  88680
aaatggattt actacgtttt aattgtatgt cttcatgtgc aggctctagt ggaaagtaat  88740
tttctcacaa tttttggcac cgttacactt gtgcccacaa aaacccgcga ttttttttatt  88800
ttatattact tttggaagta cgagtttaac cagtcgcttt caaaccttat gcgtctatct  88860
cgccaaaaaa cgctcacagc ggtgttggat attaccttta aaaaaataac attaattttt  88920
accacagagg gcgtattgcg tatggattct acgaataagc caggcgtgcc actcgatata  88980
gacccccagt tcattgacct tgatagtatt ttaatggaac tggatcatta ggacctctcc  89040
cgcccattta aatttttagt ttctacaata ataaaatgcg cgaggaatca tgggaagacc  89100
acgataccat tcagctcacc gctcagcgca aatacctcgc cgaggtgcaa gctctagaga  89160
cccttttgac tcgagagctt tcagtctttc tcacagagcc aggcagcaaa aaaacaaata  89220
ttattaatag aatcacagga aaaacctacg cacttcccag cacagagcta ctaagactct  89280
acgagcatct cgagcaatgt cgcaagcaag gcgccctcat gtattttttg gaaagacagg  89340
ggacctactc gggtctcatg ttggactatg accttaaact caatacaaat gctgttcccc  89400
cgctggaacc ccccgcgcta tcacggcttt gccatcgaat atttgtgcat ataaaaaaca  89460
gcagtgtgct gcctgagggc agccataaaa tccacttctt ttttacatta aaacctgaag  89520
tggttcaggg caaatatggg ttccatgtgc tcattcctgg tctcaagctg gcggcttcta  89580
ccaaaaaaag cattatagga tccctacagc acgatgccac cgtacaaaaa attctacacg  89640
agcagggcgt tacaaatcct gagtcctgtc tggaccccca ctccgcctcc gttccctcgc  89700
tcctctacgg ctcctccaaa ctaaaccaca agccctacca actgaaaacc ggctttgagt  89760
tagtctttga tagctctgat cccgactaca ttcccattca tcaaataaaa aatttagaat  89820
cttataattt agtttctgag ttgagcctta cgaatgaaca gggaagcctt gtaagacctg  89880
tctattgcgc ggcagacatt gccgctgaga aggaggaaga gatcccgacc gaggatcact  89940
cgctctccat attaatgcta catgatcccg aagcccggta tttacataaa attttaaatc  90000
tgcttcctcc ggagtattat gtagagtacc ccctatggag caacgtcgta ttcgctttgg  90060
ccaatacatc cgctaactat cggcccctcg ccgaatggtt ttcgcaaaaa tgccctgaaa  90120
aatggaatac gggaggaaaa gagaaactag aaaaactttg gaatgatgcc tcgcaccaca  90180
ctgaaaagaa aatcaccaag cggtccatta tgtactgggc ccacaaacat gccccccagc  90240
aatacaaaga aattgtagaa caaggctact tttccattct cgctgaatat gtgtatagct  90300
ataacggcat gcttgagcac tacatgatcg ccaaagtcat ctatgctatg atgggcaaca  90360
agtttgtagt ggacgtggat tcaaacggga agtacgtttg gttcgaattt gtgctaccgg  90420
gccagccaat gaatcaggga gaaatatgga agtggcgcaa ggaggtaaac ccggatgagc  90480
tgcacatcta tatttccgaa aacttttcaa gggtgatgga ccgaatcacg gagcacatca  90540
aataccacct cagtcaaccc catgaaagca atattttaaa ttattataaa aaactattaa  90600
aagcctttga acgctctaaa agtaaaatct ttaatgacag ctttaaaaag ggagttatca  90660
ggcaagctga gtttttattt cgccaaagaa gctttattca aactctggat accaatcccc  90720
```

-continued acctactggg ggttggcaac ggggttctct ccattgagac catcccggct aagctcatta 90780
atcattttca cgagcatccc attcatcagt acacacacat atgttatgtg ccctttaatc 90840
ccgaaaaccc ctggacaaaa ctattattga atgcactcca agacatcatc ccagaacttg 90900
atgctaggct gtggatcatg ttctacctaa gcacggccat atttcgcggc ctgaaggagg 90960
ctctgatgct tttgtggctt ggaggcggct gcaatggaaa aacttttcta atgcgacttg 91020
tggccatggt attgggcgat cactatgcct ccaagctcaa catcagcctt cttacaagct 91080
gcagagaaac cgcggaaaaa cccaacagtg cctttatgcg gcttaagggg cggggatatg 91140
ggtactttga ggaaaccaac aaaagcgagg ttctaaatac gtcgcggctg aaggaaatgg 91200
taaatccggg cgatgtcacc gctcgagagc ttaatcaaaa acaggaaagc tttcagatga 91260
cggccaccat ggtcgccgcg tccaactata acttcatcat tgacacgacg gaccacggca 91320
catggagaag actgcggcat tatcggtcaa aggtgaaatt ctgccataac cccgacccca 91380
gtaaccccta cgagaaaaag gaagatcctc gctttattca cgagtacatc atggatccag 91440
actgccaaaa cgcattcttc agcatactcg tctatttttg ggagaagcta cagaaggaat 91500
acaacgggca gattaaaaaa gtgttttgtc ccaccattga gagcgaaacg gaggcgtaca 91560
gaaagtcaca agatacgcta cataggttta tcacagaaag agtcgtggag tcgccctccg 91620
cagaaactgt gtacaaccta tccgaggtcg tgacggccta cgcggaatgg tacaacacca 91680
acattaacgt aaagcgccat attgccctcg agctatccca ggagttagaa aactctgtgc 91740
tagaaaaata ccttcagtgg tctcccaaca aaacgcgaat tctaaagggt tgccgtattt 91800
tgcataaatt tgaaacgctg cagcccggcg aatcctacat tggggtgtcc acggccggca 91860
cactcctaaa cacacccata tgcgagccaa aaaataaatg gtgggaatgg tcccctaatc 91920
cctctgcccc tcctgagaaa gaagcgtctg caccaactcc ttagggaata tccttagaag 91980
catgtctttc ggcagagcca ttaccggtag caaaaaagca acattgagta tattatatgc 92040
cttagcctgc tcataagcgt ccttttttt catggtattt tatgttttta aatattttta 92100
attatttttt aaatacgatg aacagttcgt gctccgaagg ctgtttacta aaaatcggtg 92160
tgaatccgca ttctttaaat atggtttccc attcggggat ggtatggaaa tccatgtctc 92220
tacgaatagt atggtgccca agtgcgtcct gcaggctgtg aagccagaag gcctcctgac 92280
cttgatgaag gtcgtacatg ataagaaaac catcaggttt caacagatgg taaagcttgt 92340
taaaatcgtt tatcgtaaga tgatgcgccg ccataggtaa ccctatgagc tccacagagt 92400
tttcatgctg gacatcgtcc atatcggtat aaaacgtttc acagtaaatg agacgcttaa 92460
acgagtatcg atgacaaaca tttatttcca agtaggtttg cactacgttt ttaggtatat 92520
cgggaatcat gttgattaag gttgtttcgg gaaacttaat catctgacta ggcttcattt 92580
tcaactcttt aaaggatttc ccggagaagt gaaaatgggt ctttacgtat ttatgtaaaa 92640
atacctgaat gggcagaggg ggctcctcct cttcgttctc gacgcctccc aaaatatttg 92700
gaatttcctg acgtggcaaa agaaagttta tgtccacgtt tacgaatcca tcgaggacgg 92760
acacaaagct tggctctaat ctccattcca tatactgttt agaaacggga gatagcataa 92820
tcctaggcgt cacaatgcac gaagggtttt taatcaccgc atcgtggtaa gaaaagtgta 92880
ttccatttct tccagtataa agaagcctat gttcgtcgta gcagaaacaa ttaaggcggt 92940
atgcctcata catacactgt ttcaaagtac aaacacgttt taaaaaggtt tctgcattgg 93000
cggaggccaa gcggttttgc cattggtgga aggggttcaa tcctacaatg gccagctcgt 93060

-continued

```
ttaaaatatc ttcgcggcgc gctaaaatct gcaccataga agaatacttt agcatttttt  93120
tttcgcacca ttcgcgaaga tgtttagcta cattattaac cttattattg ataaagtata  93180
cgatggcatg ttggaagcct tcaaaaataa agagcccctc caaaagatca tctgccaata  93240
gaagatggat gttggtgtaa gcattgtcaa tattttgtag aaacggcgga atgcctgcca  93300
aaaccgcttc agcaagcata gctccgttcc gttgtttact gtccaataga ttcgtaagtt  93360
ttttgtccgc aacagacacg acggctagga tggttgcaat gtcagaaatg gcggcttgcc  93420
agaaataacc cgaaaagcac atgcgcgctt cttctataga taaaaacgaa aagcgagagg  93480
caatgtctcc gagctgcgtg agttgaagac ctttttctcc tctggttaaa aggcctgcca  93540
caatggcccg ctcaatggct gatgccagcg catccgtggg gggaggatcc agcatatcaa  93600
tctcctctgc cttaaacacg ccttccttat ttttttaat cgtttctacg acaatgctaa  93660
gaaaaatggc cccagggcct tccgtaatga tttcaggata ctgctgcact ggtatttgct  93720
caaagacgtg ttttgtgtaa agcgggtaaa agtgcccagg aaatactctc cctacacgcc  93780
cctttctttg ctcgatacgg ctttgagccg cggggcgcgt aataagccct cccgcccatt  93840
cgggatagta ggtttcaatg cttctgttcc acccgggatc tatgacgtac ttcagcgttt  93900
caatggtaag gcccgtttcc gcaacaaccg tggaaacaat gacccttctt aaaggttttt  93960
ccactttagc ggttaaggga tttttcaccc acagattctt aatttccgct ttcaggccaa  94020
ggtaggcctc attttcctgc gcaatcgcct cactatcgat cggcaaaatc aacattaacg  94080
gcagcttttc tttggcaagg tccatatttg cattattcag caacatcgaa aggaagcgta  94140
tttcagccat accgggcatg aaaattaaaa tatctgcttc cgtgggacga tcatgaatgt  94200
tttctttatg aatagtgaga gccgtttcgc aggcggtctt aatgtagttg ttggtgttat  94260
acagcggcca gtgggtttcc acaccgtact gtcgtccttc caccaaaata atgttttctt  94320
ttccgatacc aaaataggtt gagtatttat gggtatcaat ggtggcggag gttaaaatta  94380
caaagggaat acgcagcgcc cctatgcttc ctctttgcaa catgcgctga agcatacttt  94440
taatatacat gagcataagg tcgatgccta gggctcgctc atgggcctca tctataatca  94500
taaaggcata gcgggaagct atctcatcat ccgtcattgt atgtagctgc gccaacagaa  94560
cccccgcggt tgcataaata aggccccgat tgggtttttc cgtcagaggc ttcgtttggt  94620
agcccactgt ttggcctaat atcatgtcgg ggtagtgggt tgaggcgccg atgtctttgg  94680
cgagggtcac cgcggttagg actcttggct gggtacaaat aaccgagcgt cccaagtatt  94740
tttggaaaga atgcgtgttt tcatttctca gaattctgaa cacgtgtacg ggtaaggccg  94800
tggattttcc ggaaccagtg cgtgacttta taatgagcac ccggtctgcg agggaggttg  94860
gaatggcccc tccaaactcc gggagacgtt gttttatcca agtgatgatg taatgaatag  94920
gaacatcatt cttgtgctca gcgggcacgt tatagagatg accaggctcc aataaagtcg  94980
gttttcccat attctattgt tttaaggatt gattgttcat aaatattttt atactctgac  95040
caagaaatta ttttttatt aagccggtta tttacgttgt tatggaacgc gaaggtccag  95100
tactgccgga gaaaagtcaa aaggggcagg caattcatac accaaaaagt ttttttttc  95160
tgctagcaag agcgtgtcaa taattttaag ctgatcgtta attaattttt ggtttaactc  95220
tttgttatta tcaagatcct tcgcataaac cgccatattt aataaaaaca ataaattatt  95280
tttataacat tatatgttac gtcctgtaga aaccccaacc cgtgaaatca aaaaactcga  95340
cggcctgtgg gcattcagtc tggatcgcga aaactgtgga attgatcagc gttggtggga  95400
aagcgcgtta caagaaagcc gggcaattgc tgtgccaggc agttttaacg atcagttcgc  95460
```

cgatgcagat attcgtaatt atgcgggcaa cgtctggtat cagcgcgaag tctttatacc 95520
gaaaggttgg gcaggccagc gtatcgtgct gcgtttcgat gcggtcactc attacggcaa 95580
agtgtgggtc aataatcagg aagtgatgga gcatcagggc ggctatacgc catttgaagc 95640
cgatgtcacg ccgtatgtta ttgccgggaa aagtgtacgt atcaccgttt gtgtgaacaa 95700
cgaactgaac tggcagacta tcccgccggg aatggtgatt accgacgaaa acggcaagaa 95760
aaagcagtct tacttccatg atttctttaa ctatgccgga atccatcgca gcgtaatgct 95820
ctacaccacg ccgaacacct gggtggacga tatcaccgtg gtgacgcatg tcgcgcaaga 95880
ctgtaaccac gcgtctgttg actggcaggt ggtggccaat ggtgatgtca gcgttgaact 95940
gcgtgatgcg gatcaacagg tggttgcaac tggacaaggc actagcggga ctttgcaagt 96000
ggtgaatccg cacctctggc aaccgggtga aggttatctc tatgaactgt gcgtcacagc 96060
caaaagccag acagagtgtg atatctaccc gcttcgcgtc ggcatccggt cagtggcagt 96120
gaagggcgaa cagttcctga ttaaccacaa accgttctac tttactggct ttggtcgtca 96180
tgaagatgcg gacttgcgtg gcaaaggatt cgataacgtg ctgatggtgc acgaccacgc 96240
attaatggac tggattgggg ccaactccta ccgtacctcg cattaccctt acgctgaaga 96300
gatgctcgac tgggcagatg aacatggcat cgtggtgatt gatgaaactg ctgctgtcgg 96360
ctttaacctc tctttaggca ttggtttcga agcgggcaac aagccgaaag aactgtacag 96420
cgaagaggca gtcaacgggg aaactcagca agcgcactta caggcgatta aagagctgat 96480
agcgcgtgac aaaaaccacc caagcgtggt gatgtggagt attgccaacg aaccggatac 96540
ccgtccgcaa ggtgcacggg aatatttcgc gccactggcg gaagcaacgc gtaaactcga 96600
cccgacgcgt ccgatcacct gcgtcaatgt aatgttctgc gacgctcaca ccgataccat 96660
cagcgatctc tttgatgtgc tgtgcctgaa ccgttattac ggatggtatg tccaaagcgg 96720
cgatttggaa acggcagaga aggtactgga aaaagaactt ctggcctggc aggagaaact 96780
gcatcagccg attatcatca ccgaatacgg cgtggatacg ttagccgggc tgcactcaat 96840
gtacaccgac atgtggagtg aagagtatca gtgtgcatgg ctggatatgt atcaccgcgt 96900
ctttgatcgc gtcagcgccg tcgtcggtga acaggtatgg aatttcgccg attttgcgac 96960
ctcgcaaggc atattgcgcg ttggcggtaa caagaaaggg atcttcactc gcgaccgcaa 97020
accgaagtcg gcggcttttc tgctgcaaaa acgctggact ggcatgaact tcggtgaaaa 97080
accgcagcag ggaggcaaac aatgaatcaa caactctcct ggcgcaccat cgtcggctac 97140
agcctcggga attgctaccg agctcgaatt tccccgatcg ttcaaacatt tggcaataaa 97200
gtttcttaag attgaatcct gttgccggtc ttgcgatgat tatcatataa tttctgttga 97260
attacgttaa gcatgtaata attaacatgt aatgcatgac gttatttatg agatgggttt 97320
ttatgattag agtcccgcaa ttatacattt aatacgcgat agaaaacaaa atatagcgcg 97380
caaactagga taaattatcg cgcgcggtgt catctatgtt actagatcat cgccagtatt 97440
taggtcccca atgcaacatt tataaccttt tgaaaaatct cattccatat agaggtaaat 97500
atttttttc catggagaat ttttttgcac tcttgaaggg attgcgccac atcgtcaaat 97560
gtttttgtt ttccatgtat tttggcgtaa ttccagccag tatctgtgtc atggtcctta 97620
atgtcatccg ctaactgaaa ggcatgtcca aaacaatggg cagccctttc aatcatccca 97680
atgtcttcaa cggatccagt tcctaaaacc cagcccataa taaacgcgat cttaaaaaag 97740
ggaatggttt tttctggagt gtctactaac tgaccggaac ccgcgctgtt tagagagtgg 97800

-continued

```
cttacaaagg tacacagcag cgctcccagt tggttgggat ccggaaacct tggacagtgt  97860
tccttaatcc agtcgatttg ccggcaaata ttttgaaatc cttgcatggt tagcgccaga  97920
gcgctcatct gcgccttggc tacgccaaag cgggcccaca ctgtatcttt atttcgccgc  97980
ttcacatcgt tgtcaaagga gggcatatca tcgataatca aagaagctac gtgaaagtac  98040
tccgctgcta gggcggcctc tgccggataa ataggcgccc caaaggaatg ttgcaactga  98100
caggcccgaa caatttccat caggataatg ggacggatat acttcccacc tcttagagcg  98160
taagagcaag gctctgttag ttgtccctta aagtccccat cttcaatagc attatttaag  98220
atggtctcaa actcttcact aaaggtttta taatttttag gattcagtgg atgtattcca  98280
tgaaaaagcg cgacactacg cggtgctgtg attctaaaat acttaggttt gcgcgtatag  98340
gatattaaaa taataataag aactacaatg atggagatat agatgagatg caacatgctg  98400
agttgtctcc ccgcagggaa tggtcctttt ccgcgcttgt taacggtacc gaggaggcgt  98460
tgaaatcttt aggaaaggtg ctgtctagtt tggaatctcc aattcctccc gtatatttag  98520
gtatataatt attgtgtcta gaaattgttt gctttgaggt atcaaaatat tcagcctgac  98580
cgctatttct tttagaataa ttcggtatag ggcttgagta gttggcaata ctcttaaacc  98640
ggggcaccaa ggtaacaata ttttccatat aatgggtttg atacgctttg tttaaaaatg  98700
ggcttaccgg ctttatgctt gttagttgtg cattgagtac cggtatgtct tctaggattt  98760
gtggctttat agaatgatta gcaaacacag aatgtagtat attagatact tgtagcatat  98820
gtctatttgc ggaaaattcc tggtattctc tgccgtgttg cgaatctttg ggcggaaggg  98880
gaccaagcat cggcacgtcc gtgtaggtac tggtggattt tatgagttcc tgctctatgt  98940
tcggtttgac atgtggattt cctaaaggaa tacctctacc tgcaatccct ttttctaccg  99000
acgcaggtag attgtgcgct aaacacaaaa tattgtacac gtctttgtgc ggaatatatc  99060
cgttatagtg ctggcccggc atctgatcgc caaggtgctg ctcatgctta atggtaccct  99120
ttgttctgag tttaggaaga tcctcgtacg aaaaaaattt tgtgtgctcg ctgaacctcg  99180
tagaaggaac cgaactattt tttgggtttt ttaaggaagg caatgaggaa ggctgggtca  99240
gacaattttt ctgtgtgccc tttaagctag ccacctgcgg aaatgttttt ttttccgtac  99300
gaacaacatt gcgcctaatt aggttttccg tatgggttga aaaagcagga cgatgatttt  99360
taaaatgatt aaaaagttta ttttttggaa tggagctgta cggctccaga tcttgcgcat  99420
cgccgtaacc aatgtttttg tgctgagggt tcagcataaa agaaaagtta cgtagatcac  99480
tgagttgcaa tccctttca gcctttcag gactattagt gtattcattg tatacaggcg  99540
cggctccatt tttgttgccg cagtaccggg aatttagtat attatcagaa taccggttat  99600
gacgcggcaa atcgctttcc caaagaggtg gatctgacct ataatcggct aacagctttg  99660
aagcataatc atgatacatt gtatataaaa gttaattatt atattgagaa ggcataatta  99720
cttcttgtag ggtacaaga ggctttgaat caggcaaact gacgggtttt gaatcggccg  99780
gctttggacc ggcaggtatc tttttaggtt gatcttcttc tagctcatta gacacggatg  99840
ggggagaaat aggaggaata atttcatctc cgcccttata tttgtcatgg atagaagaaa  99900
caattacatc catgtttgat ttattataaa tgtcgtttaa ctggtgattt aaaacataat  99960
aatgcaaaaa taatagggct acaatgcata tatatacgta aatagccgtc ttcgtttttc 100020
gttttttatc caccggcgga ttacaaattg caaaaaatac aactaatacc accgctgtaa 100080
tgattaaggc cacaatgaaa ggattttgaa aggatgtttt gaacggttcg cacgtataaa 100140
tttttctcc taaattattg atacccgcaa taaaatctac attcatttta tatatttata 100200
```

-continued aattatgaaa aatttagagt tacatctccg ccggaccaat cattgctaaa atttgaagat 100260
tcttcaaaaa ggcccgactg gttgaatgtc ttctgctcag gtttccaaaa attttccaag 100320
aatggatttt gaacaatagg ctcatcttga ttttcttctt caaggatatt ttctttgata 100380
tcaagaacag cttctttaaa ctcaggtgta tcttgattaa actcaggttt atcctgatca 100440
atcgcaaaaa tattatcttc ttcagatata tcctgtttaa tcgcaagaat agtttcttcc 100500
tcaggtttat cctgatcaat cgcaagaata ttttcttctt caggtttatc ctgaccaaac 100560
tcaacaatat ctttctcgct aaatccgttt ttagtgtgaa gctcttggtt ttgaagagaa 100620
ttatcaaaat ctattttagt tgttgtccta gaccgtggca cgggatagtt atctaatggt 100680
ttacttacta tagtcctcga atgtggcacg ggataattgt ttggtgactt gctggttagc 100740
tcttggcttg ttaatagttc ttgttttctc aataattcca tctctactac ttctttttga 100800
tccgctggtg tctcttttttg gtattcttca ttagaaaaat gttcagaggg taatgtttca 100860
ataaactttg tgagtggata gctgctcttt gatgtagaag agcgttgaat ttgctgataa 100920
aggagttgaa caagtcgccg gtattcactc tgtctttttt catatttttt acgtagcgtg 100980
gagagatctg ctaagagcga cttgttttca gatgttaatt cttcaatttg atgaagaagg 101040
ctgcgattgt atgaactaag tcttgcatac gtttcttcta attctgtctc cggctccaca 101100
taggcctgtt ttcgcagaaa tttattgtat agttccattc ttttttgag cagaaaggta 101160 agactataat cttgcatttc tttcgtaact ttatggtagt tttctttccg gtttttgata 101220
ataaagggca gcattttttc tgttgtgata aaggtgccca gattgctaat gtagtcgcac 101280
agtagcaatt ccaagataga ttctttcttt tcaaggctta tagattggct gtattcttta 101340
ggtatgaaag aatcaacaat cgttgttacg aagtttgaaa agtttaatgt tttgctgtta 101400
atttgggtaa tgttacaaaa atatttgtaa aaactatcta gcattttttc ataaagtttt 101460
ttattttgtt taacccctaa aatatagccc tttacttgat actgatattc cgtaacaatg 101520
gaatgttttt tgtatagtgc atttttgtat aaaaagttat aaaaaatgtt gataaaatac 101580
gcaccaaggg tttcaaaaat acttataacg tgggattctt cctgatccat tatatcatat 101640
gtaatattat tttaataaaa aattactgac gaataacatg caaaaaaaat atgtttaaac 101700
ttattttaag ctagcactta tttaaaagtg ttttaaacac gttttaaatt gtatgttaat 101760
acacttaaaa attaagccga aatttgctcc aataaggatt acttttatca atgaccacct 101820
ctttactata aacggcttta cataatttta ataatgcttt agagccaaag ctgaaggcag 101880
tgggaagcgg cactgtacta tggtaaaaat gttgccgatg ttcatcctcg cggatgtaca 101940
caagtttcct atatccttta aacacaatat ggctaatttc ttccacatac tccttatcct 102000
gtttggaata gcggttgctt tgacgggaaa aattcgacat acaaatagag gcatttgtaa 102060
aaatggaaac aaatgcgttt ttacgaagat tggcgggtaa atcggtatca tcttggcagc 102120
aaataatcat cgaaataaaa cagtgacgat tttggtaaaa aaacttttta aaaatttctt 102180
ttgtaaataa tgggtgcagt tcggccgcgc agtcgtctaa tattaaaagt aaacgaggat 102240
taagattgat atagtttaac gtaaactttt catcctctgt aaggcataag tttttataca 102300
tatgaatgtt ctgtataata attttttta aaagttgctg ataaagcgat gtaatctttt 102360
cttctttttt ttggtccgtt tgttcagcct ttaagcactc cacttttgca atattttgt 102420 tttcctttg ctgtatatcg atcggaagtt tatgatacaa tgtttttagc atatcgatgt 102480
tgtttactcg actgtagatg gaggacatca tagtttgccg ctgccagatg gcctccaaaa 102540

-continued

```
agcgttcagc gcccttgttg tcattttttt tttgcttatc ggcgagccac aagcggtagt 102600
gtattagagt tggatgtaca aaaccctcat atgaacgatt tgagggttcc gagggggcaa 102660
ccactaaaat ttgttcaata tggggttgca ggattttcat aatatgttta acgtacacgg 102720
ttttgcctgt ttttgagggg ccatatagca cagttgtttt atctataaaa tgatgtgctt 102780
tgaactgtag ttcaggaatt agcttccctg aatgggtcgt tagggccatc tctatattat 102840
tacaattctg cttttgtata taaaatttct ttttcgagtt tattattatt gttgacccac 102900
atatctaccc gtatcgtatc atcaggcaca ttgagcattt caagcgcatt atctaactgt 102960
ttttttgttt ttatcagctc gctttcttca tcgggggtta aattttcttt actaagcagt 103020
tgcttaattt tttcttcgca gtcgtctata aaatcatact ctcgagcttt tttgatattt 103080
ccagatgctt tttctaggtt ttttagctcc ttaaaggaaa gcagtccctt aatcccgcta 103140
tccgtgtgaa aggttgaatt atagatggag agccccggag catccgggcc agtttcttgt 103200
atatttttg ctttttgtg gtaaatagta tttcgtaaaa tctcttttcc tatctttagg 103260
tcttcctcat gacggtccaa aatccgtttt attatttcat tattttgatt aaaataattg 103320
tagcgctctc tgttggcctt aaagcttccc aggagtgtcc agttgcctaa ttgaatggat 103380
gaaacctctg agaaaatctg gtctttatat ttataataaa attcatcaac cttttgttgg 103440
ttgctgctat ccaccacatc ataaataatg aaggcaaact ctaggtcggg tttttctggg 103500
tagatgcttt ccgtagcggc ccgcaactct tcgtaattat cctcaatgta ataattccac 103560
ttataaaaag tatcctgagg tggaatatgc tgcgaaagat atctagtaat ttttgtgtta 103620
aagagaatgg gtttaaacgc cctcggattt tcaagcatat gtttaatgct ttggtgaagt 103680
tctatatttt gtaatatgtg ggctgctgcc ctatagccct gtggggtttg ggtgattgca 103740
tcaatatcgg cctgaagctc attaggcaca tttaatgttt tttgcatgat gtgtaaaggg 103800
atgcgctcag gatctgctaa atcggtgtat tctgtgcttg tacaagtgct tgcacaggta 103860
tctacattgg tatctgcaca catgcttgca caggtgtcta cattggtatc tgcacacatg 103920
cttgcacaag tgtctacatt ggtatctgca caagtatacg cactttgagc atgaagatta 103980
ggatcaaaca caaaatgttc tcgtaaaaag ctatcgatcg ttgttttagc ttccttgctt 104040
ttctgcgtct gggttttgca gctatctgct atagataaaa ttgtatttac taccgattca 104100
gagggaacat cattagtttc ctgtttcaaa gtatcaacta acgttattag ctcactgaga 104160
agagttttgg tcgtgtgggt aggttttgaa taggaaggca tccattcctg cagagctttg 104220
aagacatatc caataaagct agtcattata agacgtcgaa tatactgctc ccgcaaattt 104280
gtaaaagagc aaaaggccac cctgctatca tttttgaact gtttgtaagg gttcgtcctt 104340
tggtaaagct gtttaagcgt ttcttcggat atttcagtag agggatcctc caatacgttt 104400
ttgagaagct catcaatatt aaattctgcc atatcttaga gtttattata tacatattaa 104460
agctttaata taagggggt ataacaatgg acgaaatcat caataaatac caagctgttg 104520
aaaaactttt taaggaaatt cagcaaggat tggccgcgta tgatcaatac aagaccttaa 104580
ttagtgaaat gatgcactat aataatcata tcaagcagga gtattttaac tttttaatga 104640
ttatttcacc ttatcttatt agggcgcata gcggagaaac gctgcgaaac aaagtaaata 104700
atgaaattaa acgtcttatt ttggttgaaa atatcaatac caaaatatct aaaacgctgg 104760
taagtgttaa ttttttacta cagaaaaaac tttcaacgga cggggtgaaa acgaaaaaca 104820
tgtggtgcac caataatccc atgctgcagg taaaaacagc ccacaacctt tttaagcaac 104880
tatgcgacac acagtccaaa actcaatggg tacaaacttt aaaatataag gaatgcaagt 104940
```

attgtcatac cgacatggtg tttaacacca cgcagtttgg gctgcaatgt cctaactgcg 105000
gttgtattca agaattgatg ggaaccattt ttgatgaaac acatttttac aaccatgatg 105060
ggcagaaagc aaagtcaggt atctttaacc ctaaccgtca ctatcggttt tggatagaac 105120
atattcttgg tagaaatcca gaacaagagt tggggaccaa acaagatccc tgcggaacca 105180
aggtgttgca acaactaaaa aaaattatta agcgcgataa taaatgcatc gcgcttttga 105240
cggtcgaaaa tattcgaaaa atgttaaaag agataaaccg cacagactta aataattgtg 105300
tttctcttat attgcgtaaa cttaccggag tagggccgcc tcaaatatca gagtcgattt 105360
tactacgagg cgaatacata tttacagagg caattaagat acgggaaaaa gtgtgtaaaa 105420
aagggcgtat taataggaat tattatccgt attatatata taaaattttt gacgccattt 105480
tgcctccaaa tgataccacg aatcgacgca ttttacaata tattcatttg caaggaaatg 105540
atacgctagc taataatgat agtgagtggg aatctatctg tatggagctc cctgaaataa 105600
aatggaagcc cacagatcga acccattgtg ttcatttttt ttaaagatga agatttttta 105660
gatgattttt tttagttttt taaaagacga aaaaattttt taaaagatga atattcttaa 105720
accccgcaaa ttactttttt ttaggtactg taacgcagca cagctgaacc gttctgaaga 105780
agaagaaagt taatagcaga tgccgatacc acaagatcag ccgtagtgat agaccccacg 105840
taatccgtgt cccaactaat ataaaattct cttgctctgg atacgttaat atgaccactg 105900
ggttggtatt cctcccgtgg cttcaaagca aaggtaatca tcatcgcacc cggatcatcg 105960
ggggttttaa tcgcattgcc tccgtagtgg aagggtatgt aagagctgca gaactttgat 106020
ggaaatttat cgataagatt gataccatga gcagttacgg aaatgttttt aataataggt 106080
aatgtgatcg gatacgtaac ggggctaata tcagatatag atgaacatgc gtctggaaga 106140
gctgtatctc tatcctgaaa gcttatctct gcgtggtgag tgggctgcat aatggcgtta 106200
acaacatgtc cgaacttgtg ccaatctcgg tgttgatgag gattttgatc ggagatgttc 106260
caggtaggtt ttaatcctat aaacatatat tcaatgggcc atttaagagc agacattagt 106320
ttttcatcgt ggtggttatt gttggtgtgg gtcacctgcg ttttatggac acgtatcagc 106380
gaaaagcgaa cgcgttttac aaaaaggttg tgtatttcag gggttacaaa caggttattg 106440
atgtaaagtt cattattcgt gagcgagatt tcattaatga ctcctgggat aaaccatggt 106500
ttaaagcgta tattgcgtct actggggcgt ccagctataa aacgtgactg gcgtacaaaa 106560
agtccaggaa attcattcac caaatccttt tgcgatgcaa gctttatggt gataaagcgc 106620
tcgccgaagg gaatggatac tgagggaata gcaaggttca cgttctcatt aaaccaaaag 106680
cgcaacttaa tccagagcgc aagagggggc tgatagtatt taggggtttg aggtccatta 106740
cagctgtaat gaacattacg tcttatgtcc agatacgttg cgtccgtgat aggagtaata 106800
tcttgtttac ctgctgtttg gatattgtga gagttctcgg gaaaatgctg tgaaagaaat 106860
ttcgggttgg tatggctaca cgttcgctgc gtatcatttt catcggtaag aataggtttg 106920
ctttggtgcg gcttgtgcaa atcatgaatg ttgcatagga gagggccact ggttccctcc 106980
accgatacct cctggccaac caagtgctta tatccagtca ttttatcccc tgggatgcaa 107040
aatttgcgca caagcgttgt gacatccgaa ctatattcgt ctagggaatt tccatttaca 107100
tcgaatctta cgttttcata aagtcgttct ccggggtatt cgcagtagta aaccaagttt 107160
cggtacgcat tctttgtgcc gggtacaatg ggtcttccaa aaggatctac aagcgtgtaa 107220
acggcgccct ctaagggtgt ttggttgtcc cagtcatatc cgttgcgagg aaacgtttga 107280

-continued agctgcccat gggcccccat ctgggacgtg ccctgaatcg gagcatcctg ccaggatgaa 107340
tgacatgcac ccaatatatg atggcccacc atatcatgga aaaagtctcc gtactgggga 107400
ataccaaagg taagcttgtt tcccaaggtg ggggtacccg tatgcgggcg tactttattg 107460
tattcaaacc ctactggaac ataaggctta aaatgcgcat taaaatgcac caaatgtgtt 107520
tcttcgattt gactcaaagt gggttcggga tcgggtttcc cataactttt gttcacattt 107580
ttaatgttag agatcctgct attcagcaag tcttgggcca atataatctt gtcggccttc 107640
ccatcgttag caataagaca aaaagctcct cctgatgcca tatataatgt tataaaaata 107700
atttattgtt tttattaaat atggcggttt atgcgaagga tcttgataat aacaaagagt 107760
taaaccaaaa attaattaac gatcagctta aaattattga cacgctcttg ctggcagaaa 107820
aaaaaaactt tttggtgtat gaactacctg cccctttttga cttttcctcc ggcgaccctt 107880
tggccagtca gcgcgacata tactatgcca tcataaaaag cctcgaggag cgcgggttta 107940
ctgtcaaaat atgtatgaaa ggggatcgtg ccctcctttt catcacctgg aaaaaaatac 108000
aatccattga gataaacaaa aaagaagaat atctgcgcat gcacttcata caagacgaag 108060
agaaagcatt ttattgtaaa tttttagagt ctagatgagc ttttacgcaa tgttgtacag 108120
tgttgtatat atgtcttgta agcatttgtt gtagagtaat aagtaaaaga taaataaaaa 108180
tgactattaa aataaagccc aaaccattaa aaatattttt atctgttaga tttaatttaa 108240
taaatggctc atggaatgtg tggtgcgccg ctgcatgagg tgtggccgca tgggatgtgg 108300
tcgcataaga tgtagctaca tgggatgtgg catttgcttg catgtaagga tcatgatgtg 108360
ttgggtcttc atcccagcaa taatcgccat ctttatctag ctgaattgta taccccatta 108420
tatatcactt attatttttt tttaatgttt catgaatttc attataggcg gtgaaagggt 108480
cctcaggccc cttctgtaaa agattataga gatcttcgga cgctttatgt ttcgtgcgaa 108540
ttaaggcggg atataacaaa agagagggcc ccagttccaa acaaatttta cttagcgggc 108600
tcatattttg caccaagttt cccactactt gcgatgtttc ataacgcatt ttaaagagct 108660
ttatcataaa agtgttatgc aggccggtgt agtctggcct atagttaagg aaggggattt 108720
ctctggtacc gtcaaacacg atctcaagtc ctctagcaag cccgatcaaa atttcttcag 108780
caatggatga gtatctaatt cctacattac gaagcgtaag catttctata acatcatcta 108840
tttcctgcat agaggaatct attgtaggaa ttttaatatc atctgtgctg atttgttcat 108900
tcccaagata ggtaagcagc atattaattt tttctagctt tactagctta gtcttacgct 108960
cataatcatg atctttttta taaaaagagt tgggatcacc gttggaccgt agatgattaa 109020
taaggcggtc tacttgcttt gtactaggtt taatactttt ttcactatac tcgctttcag 109080
catagtggtt tttacgatct cttttagaaa tagctgtttt ttgagatgcc tcagactctg 109140
catatttttt tctatgcgta gaaagagaat aaccgcggtc attacgtgaa ctactgttgc 109200
atgcaaggcc tcggcgcgtc ttaccgctgc gcacactgcc attgcgtata ctgccatcgc 109260
gcacactgcc gctgcgtata ctgccattgc gtatactgcc gctgcgtatg ctgccgctgc 109320
gtatgctgcc gctacataca ctatcactac atatgctgtc agtacatacg ctatcgcggc 109380
gtatgccgcc gtgtacctta tcgccgcccc tacccgaggg ttttttagat ataatactgt 109440
gtggggagtc aagcgaaaat tcagggtcat taaagttaat gcccaatgac tttgccaatc 109500
cattaagctc ttcatcaaaa tgatcggtag gaaaactttg ttgcttgccc atgacctgtt 109560
tttcaagttc ctccaaattg gcttgctcat ttatatggag attattcata agcgtcgtaa 109620
ttccagcaag atttgctcct tctaaaaatg tggtgtcctc catcggatat actatactat 109680
ttaaaagctt ttaaataaaa atgtgtttgg aagaaatgct ctcttcaagc gtgtgtagct 109740
cagatataaa tgcctcctca gaaagctttc caccatactc ctttctcatc gtataggagg 109800
gcgccggttt aatgtaggaa atccactggg aggtaaaaaa ccggtacaac atatttagca 109860
gctcgcgggc ctcccacctt ttgggctccg tatagtgcac atcaacataa gaggcggcgc 109920
atgaaaagct gcaaaagttg ccgagaacgc ccatctcaat ctctcctcgc tcattttcac 109980
gcatataggt gggcacgaat tttgggacag tcttgaaata gagatgacat gtccagcatt 110040
taaagctaga atgggtaacc catttggaaa cagtggtgaa tacggagggt agcttttttt 110100
cgacctcggc ttcatcgtca ttcgtattta acgtatcggt ggcagttttt ttggattgca 110160
agcattcttc aatggtaatc ccggataagt ataaaatatt aggacaatta gtttccataa 110220
ttttgatagt tatttttata caacatggat ttaattaaag ataaatggag gacgaaacgg 110280
aactgtgttt tcggtcaaac aaggtgacga ggcttgaaat gtttgtctgc acatacgggg 110340
gaaaaattac cagccttgca tgttcgcata tggagttaat taaaatgttg caaattgctg 110400
agccggtgaa ggcattgaac tgcaactttg gccaccagtg cctaccgggc tacgaatctt 110460
taataaagac tccgaaaaaa actaaaaaca tgttgcgccg tccgcgcaaa acagaaggcg 110520
atgggacttg cttcaatagt gccattgaag cctccatttt gtttaaggac aagatgtata 110580
aattaaaatg ttttcctagt accggggaaa ttcaggtccc gggcgtcatt tttccggatt 110640
ttgaagacgg aaaaaacatt atacagcagt gggtagactt cttgcaacat caacccattg 110700
aaaaaaaaat ccagattatt gaatttaaaa cgattatgat taattttaag tttcaaataa 110760
acccagtgtc tccccgcgtc atcattcatt taaaaaaatt tgcagctttg ttggaacaca 110820
tccctactcc atatcccata cgtgaaataa agcctccatt agaagactca aaagtatccg 110880
caaaatttat ggtcagtccg ggaaaaaaag tacgcattaa tgtttttctt aaaggtaaga 110940
taaatatttt aggctgcaac acaaaggaat ccgcggagac catttatacg tttttgaaag 111000
atcttatcag cgtacattgg caagaaattt tgtgcgtgtt accggtaccc gattaaagaa 111060
tgttttcatt aataaggtaa tcgactatgc taaaaagaat aacaagaaaa ataccttgaa 111120
gaactatacc aaagtaggta ggttttctgc atgtcacggc atggttaaaa ttgctaataa 111180
tgtagtccac aaaagcattg ctcaatacga ctaaaaatag taaaaaaagg ataagtgctc 111240
tttttatatc catatacttt aaaacttatt ttttacacta ataatttcct gcggccgcaa 111300
tataaactgt aggtcatcta taacgcccag acctgttaaa agtagagtac tatgttttaa 111360
gggatttaaa atatccgccg caagaatgtg aatataattt tcaaagtggt ttacaggaat 111420
gcgtaagcgt tttttttgc actgcggttg gtttagggtc gaatactggc aggaggtata 111480
tatattaata agaccgcggt cgatggtttc aatatcttca tagaattcaa tgcgcggcgt 111540
caaaagtttt ttaagatgtt gacataactc atcatacgtg taggactgga ggggggaaag 111600
aagggtgtag tcaaagttaa aaatgttttt ttgaagaacc tttaaagcat gttccgcgtc 111660
cgtggtttcc aaaatatgtt ttatggtatg aatgtcattt aaatctacaa agtctgacag 111720
ctttgtgtag aactcggtga cggaggttat tttctggaaa tcggtttttt gaaaaagatt 111780
ttcaatgtgt ttgcgggttg agttgctttg cagtccatac aagacatcaa aaaattcaat 111840
cagcaaaaac ttatacaaat ggttaatata aaaagctttg ttggccttat tctgctgagg 111900
atatggttcc tctaggggat atagaatggc ttggtctata tccctaggat caatagtcaa 111960
tgttgcgatg ggaagctttt ccagcgtagc gggaagagtt tgggttggag cgtagtaaaa 112020

-continued

```
gtatagcccg gtttttccct ctgaaagaaa gcccacaaat tcttttttta tattttgcag 112080
caccgctgag ggtacgattt cgtactgttt atactgtttg ttgaaaaggg taataaattt 112140
ccaggtttct tcaaagcttg caatctgggt gggccgcaga tcaaagtcga tgggaatgtc 112200
gtcatgaatg taggatgata gtcttatagg aaaataaata gggcgatcgg tgtctgaatc 112260
gataagtaaa gcataacaaa agttatgcct gttgataagt tttttaccaa ccgtgtagcc 112320
gggaatgttt ttcacgtcat ggatatccca ccagttatcc ttgcacataa actcgctcat 112380
agactggatg acctccatca cagggtcatc ttcggtaaaa atatactggg cctcactgtt 112440
tttcagaaat ctttttgct gggtgatggc cattgggtag atcccttcgt ccgtgtcaaa 112500
gataatggct atcttcttcg atgggctaag aatttttgt attgtgctgg gggacacctc 112560
aaacccgatg tcgccctgtt tatctttaaa aaagacacag tgaaggtcgt agcatatggc 112620
aacaaggtcc agaaagatgt cctgccatgt ggtgtcccat tgaagcagtt ggtttttttg 112680
ttcaacaaag gtttgtaaga taaggtttgc cagctccgcg ccgctggaaa acatgttgcc 112740
ggccccattc cccaaaatat agtactgcgg tgtgttggcc gcctttgcaa tttcaatggc 112800
aagggccttg ggggcaagat ccaaaattcg agcaagggaa taaaaaagcc cggcattgct 112860
aattccaagc atggtttgct ccaccccac aatgcaaaaa atgtcgggct cttttatcgt 112920
atttaaaaac agttcatctg ctatctggtg gggtagaaag gcaatccggt tcaccggtat 112980
tttttttcca taggacaagg tatgacgcga tgtttgtgta ttaagatcct ccaggtcttg 113040
ttctacaaac gtgtgcttgg tgaggcaggt attgttaata tagaaccgct ttgtgcccag 113100
cagggccttc gtcttttggc agcacggcag acagtaattt agggggtggc ggccttctag 113160
taggcttaga tgagggtagt caggatgcgg gcagctatag taggcaggta ccccctccgt 113220
gaaattccaa tactttacta gctccttgcg cttggctggc ggcatggact tcacctcggc 113280
ctctgagtaa atgacgggtg gccgtgggtg ctggcatagg acggagtaaa ccgttgcctg 113340
cgtgtcgtac ttgcgcaggt catacaggtc ggggtcctgt tcttgaagcg cacgtagctg 113400
agaggctccc tttccttgtt gtttatcgtg cagttgagag agtttattaa ccaaaatttt 113460
gtcaggcccg gtgatcaagt tatctaaaaa cacaaatagg taaacccaaa gatagttaaa 113520
ctcttcctgg gtaatgttaa acatttctat tttgatatct gtaaccctat ggtagatgcg 113580
aatgttgcgg ccgccgtaga ttgtttccca ccgggccgca acatttgtgt caaagaggta 113640
cgcatacgtg ttttggagca acgcaacatt gatgtccatt ttgcgccccg gaccggagga 113700
aataatgatc atccgttcga tttcgtgggg atcatacgaa taaatcccct ttttaaataa 113760
aaaattgtag accccggttt gctggaggcc ccgcacggaa ataatccctg cttgctcgta 113820
ttcccgccaa cgacttttga gctcggtaaa tcccttgcta gaaagcgtat agggccaaaa 113880
ggtggacacc gacatggagc tgatagaaat ttggatgtcc tcgttggagg gaaggggcag 113940
actccctcca cgaggaaacg cggcaggccc catatcatta attgtatgaa taataggatt 114000
tatgaaatta tttagggtgg acaccacgga gttaaagtcg tggcgctcgt tttctgacca 114060
attgctttcg ataaagtagt gcccattatt ttgtatggta agaataaagg ccttttttatt 114120
gataaagcgt attaaaataa tagtgggtac acggaatgtt ttattgctga atttttcagg 114180
ctccgtggaa gttatgtggt gtttggaaac cacggtggga cctgttttac tataaaagaa 114240
caccaccagc tgaggaatat cgggagtagc tggaaatagg tcgaaaacat tgcgcacatt 114300
aatttgaata tttacgaggg gtgaaatttt aatcattgcc gaggtgacgg ccaacgtgcc 114360
gcgtgttagt ctattcccct cgtacttggc aatgacttgt tgtgctctgg catacgtaaa 114420
```

-continued gtttattagt ttttgctcta ggagaagcct ctttttaaga ctggtcaagg atggagaaag 114480
agcaggatac tgtttttcca tttgtaaggg agattgtacc aatagtttaa aggcatcggg 114540
ggaaagaaga ggccaatact tcataataag gccgtaatag agtaagtcaa attggtaatt 114600
atcctctatg gcaatggaga tttggcgccg catgggggcc actagcgtgt tgaggtctgc 114660
tacaaagatg tgatgaatgt tttttatgag ctggaagctg tcgagcgctt ccacatagag 114720
ctcatctttt tgactttcca tagatgcgtc gatgttcacc ccacccacct gttgaaactc 114780
ctttttgtag tcgcgaatgt ctaacgccac cccgctaccg cttaacaata ggcgatacgt 114840
tacctgaagc gcattgtttt gaaaaaagaa aatgtgttgt ctataagggg ggatccctgt 114900
ggcaacgtaa attttttctc gaatgtcttt aaaagtgtct tcagggaaaa tactatactc 114960
gctatacatc gtctcaattt ctggcatcat cacgtttgtc tcctcgccac gatcctccac 115020
aaaaagtttt tcaaactcat ctaaatcatc gctatctcca cccaccacgt attgggaaag 115080
ctttttctcc caatcctcgc cgtaaaaatt ttgtaaaatt tctttgtcct taggggttcg 115140
ctgcaggtct ttgcggcagg cctgtaacac gtttgcagga acggatccca aaaaaataaa 115200
cgtcttcgtg tactcatttt ccacaggatt ataaagagta actcgtagag gatttgttaa 115260
aaagtcattt tggaaatcca ttatacccgg tatagaaaat aaaatttaaa ataaaaacgg 115320
atgatatcta tcatggaccg ttctgagatt gttgcacggg agaacccggt gattacccaa 115380
cgagttacaa atctcctaca aaccaatgct cctctactat tcatgcccat tgatatccat 115440
gaagtacgat atggagccta cacacttttc atgtatggtt ccctcgaaaa cggttacaaa 115500
gcagaagtaa ggattgaaaa catcccagtt ttctttgacg tacagattga gttcaatgat 115560
acaaaccagc ttttttttaaa gtcgctactg acggctgaaa atattgtgta tgaacggctg 115620
gagacgctca cccagcgtcc tgtaatgggg taccgcgaga aggaaaaaga gtttgcacca 115680
tacattcgaa tattttttaa aagcctgtat gagcgacgaa aagccattac ttacttaaat 115740
aatatgggct acaacacggc cgcggacgac acaacctgtt attaccgaat ggtttcccga 115800
gaattaaaac tacctcttac aagttggata cagcttcagc actattccta cgagcctcgc 115860
ggcttggtac acaggttttc cgtaaccccc gaggatcttg tttcctatca gaatgatggc 115920
cccacagacc acagcatcgt tatggcctac gatatagaga cctatagccc tgttaaggga 115980
accgttccgg acccaaatca ggcaaacgac gtggtgttca tgatatgcat gcgcattttt 116040
tggattcact ccacagagcc tctagcgagc acgtgcatca ccatggcacc ctgcaaaaag 116100
tcctcagagt ggaccaccat tctatgctcc tctgaaaaaa atttgttgtt aagctttgct 116160
gaacagttta gccgctgggc tcctgatata tgcacagggt tcaatgattc tcggtacgac 116220
tggcccttta tcgttgaaaa atctatgcag cacggtattc tagaagaaat ctttaacaaa 116280
atgagccttt tctggcacca aaagctggat accattctaa aatgctatta cgtaaaggaa 116340
aagagagtca aaatctcggc cgaaaaatcg atcatttcct cctttttgca taccccctgga 116400
tgcctaccca ttgatgtccg caacatgtgt atgcagcttt accctaaagc cgaaaaaaca 116460
agcttgaaag cgtttttaga aaattgtggg ttagattcga aggtagacct gccgtaccat 116520
ctcatgtgga agtattatga aacacgagac agcgaaaaaa tagccgacgt ggcctattac 116580
tgcattatag atgcccagcg ctgtcaggac cttctggtgc gccacaatgt tatccccgat 116640
cgcagagagg taggaattct gtcatacacc tcgctgtatg actgtatcta ctacgcggga 116700
ggacacaagg tatgcaatat gctcattgcc tatgccatcc atgatgaata cggccgtatt 116760

-continued gcttgcagta ccattgcccg aggtaagcgg gaacacggaa aatatcccgg cgcctttgtg 116820
atagaccccg ttaaagggct tgaacaggat aaacccacca caggtctcga ctttgcgtcg 116880
ctgtacccct cactcatcat ggcctacaac ttttcgccag aaaaatttgt agcctctcgg 116940
gatgaggcaa atagcctcat ggccaagggt gaatctcttc actacgtctc ctttcacttt 117000
aacaatcgtc tcgtggaagg atggtttgtg cggcataata acgttcctga taaaatggga 117060
ttgtacccaa aagtactcat cgatctactt aacaaacgga ccgcccttaa acaagagctt 117120
aaaaaactag gtgagaaaaa agaatgtatc catgaatccc atcctgggtt taaggaacta 117180
cagtttcgcc atgccatggt agacgcgaag caaaaggcgt tgaaaatttt catgaacacg 117240
ttttacggcg aggcaggtaa caatttgtcg ccccttcttc tgcttcctct agccggagga 117300
gtcaccagtt cgggtcaata taatcttaaa cttgtctata actttgttat caataaaggt 117360
tacggcatca agtacggtga caccgactca ttatacatta catgcccaga tagtctttat 117420
acagaggtaa cagacgcata tttaaacagc caaaaaacga taaaacatta tgagcaactc 117480
tgccacgaaa aagtgcttct gtctatgaaa gccatgtcta cactatgcgc cgaggtgaat 117540
gaatacctgc gacaagataa tggcaccagt tacctacgta tggcctacga ggaagtactc 117600
tttcctgtgt gctttacagg caagaaaaag tattatggta ttgctcatgt aaacacaccc 117660
aattttaata caaaagaatt attcatccgc ggaatagata tcattaagca gggtcaaaca 117720
aaactcacca aaacgatagg aacgcgaatt atggaagaat ccatgaaact acgccgccct 117780
gaggaccatc gcccccctct tattgaaatc gttaaaacgg ttttgaagga tgctgtggtt 117840
aacatgaagc agtggaattt tgaagacttc atccaaacag atgcgtggag accggacaaa 117900
gacaacaaag cagtccaaat ctttatgtct cgcatgcacg ctcggcgtga gcaactaaaa 117960
aaacacggcg ctgcagcatc gcaatttgct gagcccgagc cgggagaacg cttctcctac 118020
gttatcgtgg aaaaacaggt acagtttgat atccagggcc accgcacaga ttcctccaga 118080
aagggggaca agatggaata cgtctctgaa gcaaaggcta aaaatcttcc tattgatata 118140
ttgttttata tcaacaacta tgttctaggc ttgtgcgcga gattcattaa tgaaaatgaa 118200
gaatttcaac cccctgacaa cgtcagcaat aaggatgaat acgctcagcg ccgagctaaa 118260
tcctacctac aaaaattcgt gcaatccatt caccctaaag acaagtctgt cattaagcaa 118320
ggcaatgttc atcgacagtg ctacaaatac attcaccaag aaattaaaaa aaaaataggc 118380
atctttgccg acctttataa ggaatttttt aacaacacca caaaccccat cgaaagcttt 118440
attcaaagca ctcagtttat gatacaatac tttgatggag aacaaaaagt aaaccattct 118500
atgaaaaaaa tggttgaaca gcatgctacg gctagtaatc gagctggtaa gcccgctggt 118560
aatccagccg gcaatgcgct gatgcgggct atatttacgc agctgattac ggaagaaaaa 118620
aaaattgtac aagccttata caataagggg gatgcaatac acgatcttct cacctatatc 118680
attaacaata taaattacaa aattgccacg tttcagacga aacagatgtt gacgttcgag 118740
ttttccagta ctcatgtaga actgctatta aagctgaata aaacgtggct tattttggct 118800
ggaattcatg tggcaaaaaa acatctgcaa gctttttttgg attcatataa caatgaatcg 118860
ccgtctagaa cattcattca gcaggctata gaggaagaat gtggcagtat taaaccatct 118920
tgctacgact ttatttccta atacttctta agaaactctt taaacaagga cttcgcatgg 118980
tcaaaggttc taaacccatg gcccttatga ttcgccaaaa aagcggtttc atcaagattt 119040
tctaaccctt tcacggatga agaaataagg tgttcggcct cgtttgccca ttttctatga 119100 tttttttca cctcgggttc tagatctgtt ttctccatat actcattgtg gtcatatttt 119160

-continued tttttgggag gaggcgtggg tggaggaatg ggtggaggaa gtacacccga ctttcccgct 119220
tcaaccgttt tataaaaaaa tagaagcata atacaaagaa taaggactat cgcaaatatg 119280
ataaccagtg tcccagtcga gggcattttg ttatataagt aacgtttttt ttatttttta 119340
taattcgaat gaagaaccat gttgaatagt cttctactca aagacatttt gttatacggt 119400
aaatgagaat ttataaaatc cgaatatcac tatcatactg tttatctgag aaggtctcac 119460
tgggtcctgt gatggagaac ccatactctg taatgctggg gtttataatg tggtcaggac 119520
tgacaagcac atttctgaac tgcgagagtt ctaggtttag acgcagtcgt aatagtcgct 119580
gtatatttgt aataaatatt agattgcgta tgaggcgagt gtcaaagcga tcctttccaa 119640
tttgtactaa ggtgggcttt tgtattccaa ctcccacttg tttaacgatg gaccagggtc 119700
cttcttcccg attttgttcc gtgatatagg tcagcacact attttctgta tatgaggtat 119760
gatgtcgcat attaatacct ggtgccattc caactggcgg ttgtgcaatt cgggctgtac 119820
cgggacccaa ccatcgtgga gttttataaa catatcgttc tagcgtattt aaaaattcct 119880
taaggttatt tacgagtagc atgaagggtg ctattaaaac aggtggatgg tttataacca 119940
ttgtcataaa ccattgcatt gcttcaatat catttttgtaa tgcttgacgg ggaggcgggg 120000
caggtaatcc acgtatgttg aataaagcgg ttaattgtgc accggctgtt tggggcgtaa 120060
tattttgtat taaatttatc atcgaattgg cttgcccggc atttcctata agatcgatta 120120
aattggttat ttgacctcga tattgttgta cccagttttg aatggcagcg atgatctcag 120180
gggttggatt gttttgaatt tcaggtgttt gtattagatt attcacttct cttcgtgtat 120240
cttcaagctg agtcctaaat gcatttaact cgcctataat ttggtttcta tcaataacat 120300
ttcttaaacc tcgaactgtt tcagccaatc gtatagtacg cacaatttca tgtaaggcct 120360
ggtttatgta tattgacatg ggatggcccc accgctcacg tccacgttga atacctgcgg 120420
ccaaactagg acctgcctcg tcataatcaa attgtgtagg ataaaggctt ccaaatagca 120480
ctttattgaa aatttggtca gaaagaaatt tagggcggcc catatttagc gcgttgtccc 120540
ctctaaagat gcgtgacatg tatccggcgt tgcctttgga tagtaactca ttcccatatt 120600
gagtaataga gaccgagaca taggggttta taagaagttt tagcataaat tctcgagtat 120660
ttatgggggg acgattcgga atgtttaata cctctgcaac atctggttga ggagccgtgg 120720
tgtccagaga tcgtactttt tcagccgaaa tgccgtacat aagacaagca atttcttcaa 120780
aactatagtc atagttgtaa atattggcaa gtggtataga tcgcatcagc gcatttacat 120840
tgataggtat aatattcata tcaaacaagt taaatatgcg ctcgcgctct ctattagagc 120900
caagagtgcg tgtttgacct ttcggcgaca ctattttgtg aatatgattg atttgctcct 120960
cttggtaaga gctttccacg aaggaaatta cgtcttgcaa tgttttacga agcgaataca 121020
ctgcattcat ccctattccc gctgttataa tgggtttatc gtctctgttc tcgctaataa 121080
gattaactcc accaaaagta ttttcattgt acatcatcac tgttttaaaa ctacggatat 121140
ttatgataaa tcggagagcc tgaatggcgt gggtataaaa gtgttcaaat cgcgtgggag 121200
taatttgttc gcgagcaact accgtttcat tatagttttt catgataagc tgtactccgg 121260
gcatatctga gagctgtacc ggatcatttc ccagtaattt tcttgtgccg tatagtagtt 121320
taaactcggg ggagccgctt tcaaggttcg ggtaaagaag aggatcatat acctcattat 121380
tttctattct taggtcatgt aaataataga gcgaaagtga aaatggcata agaggctcct 121440
tattgtaccg ggacatatag ttttgaatga agtgttcttc tgtttcaaga tagatgggat 121500

-continued gatcggtaag ctcgtgcagg acctccatgg cagaatctgc cagagtgtga gagcctctaa 121560
tgatcccgtc gatcactgcg accagtcgct ttcgcacaac atcgctcgta ttattttgtg 121620
cgtctcctag gggcataagc gtaacattgg gacgaaatac gccgccaatt ccccgcaggg 121680
ccgcctgacc gacggatagt cctgtcgcag gaacattgtt attattataa taaataacgg 121740
aatcattatt ggctcccaag agtgccgtca gattagggcg agctagttgg acatttgtgt 121800
attgtataaa ttgttttaga agctctccct ggctaataag aatattaaac attttgttaa 121860
atagtggaag attggctcta taattttctt taaggtaaat gggaatttct gttaaagtag 121920
aaataagatg ctgactcagg ccctggcgat tggtatcctt aataagccgc tgaagtataa 121980
gtcccaaaga cagaagaagc accgactgct ctgtggggtc gcctctatga ccaaagacgt 122040
tgttattgcg tgctaagtca gggtgagcat atcccatctc catcactgct tggctaaagt 122100
tcccattagc gaatgcatta ataagattta gatatatttt tccgctggga gcatcataaa 122160
atcgggtaat atatgaagct atgagctggt taaacaccat catcatacta cgattatttt 122220
gaataccata gtctgatccg tataggcgat aacgtcgaag gttgtttgcg gcatcattga 122280
cattggcata ggttctgagc gctatgttgt cccagtagct aagagtattt tcctcctggg 122340
cgttgttggt acgaataaga ttggagagtc taaagtctcc tagtgccacc tgctctacac 122400
gaagtccaga gttattctcc aaagcatcgt aaaatacgag tctactgaat actcttccgt 122460
attgttcaaa gcgttcagag gattggggat tgttatttat ttgaatatta gccgcgtccc 122520
ttctttgcgc cccacctcga agttgcagta cattataagg ctttgtaagc aaggtgtagg 122580
ttttattaat gatttggtta accccctcca ggcccaattc accgccagga agcggccttc 122640
ctccggcatc ggtaggtggt ttaataagtt tgtcaattaa atgttcttcc aaccagtaaa 122700
atgagccagg attagatcta ttttcatagt attgaataat gtttttatca atatgcgggc 122760
gtagaagatc aagaaaatac ttcgtgtcgg ccatcaaaga atcaattaag gaaataagac 122820
ctgtaaaatc taaatgcact tgagcggtgc tggtttcagg gaagcgaact tgaaccattt 122880
tgttaaaact ggaggtcatt tcgaagatat tggtcaacag gagctgcatg attcgctgat 122940
tatctactaa ataccttgcg gccaactctt gctccggacg aactcctcca ccagcaggaa 123000
tacccacata tggtacaatc caagcaaaaa gagtttctgt ggttaaattt cggtcttggg 123060
ctgctgcagc cgcttcggta gtgggatcag ggtacaccat agaaagccgc atattgattt 123120
ctttaatgac taatcctgga tttctaatct cagagatggc cccgtgtttt cttccgagcc 123180
agtcaataag attggcgcgg ttcacgttgg cagcttgtgt ctctcgtaac cattcgataa 123240
tgcttttttg aatcgtatct aggtctaaac ctttaatgtt attacgaaag ttattaagaa 123300
gtacgtaaat agcactcaat aagttaagac ctgtaataac ggtttcatga aacagaaata 123360
ttttgttaac atctgtatct gccagtgact cagagccttg aataagtttt gaaacgattt 123420
gaattttatc ggtatgctcc tttttgagtt cattgatagc ctggcgaatg agttcttggt 123480
aggaaatttt gcccaattct tgttgcagac tgggatcttc aaacatctca ctaagctgtt 123540
tcctaaattt ttgtaccaaa tcccactggg agttgggctg cagcattcct gtttggacat 123600
ccacagagtc tatattgtat agtgccgggc gccacttggg ggtaggctgg gttgaaggac 123660
taataaacct atcggaggga agtaattgtg aggattgtgt atagccatcc tcatcaggaa 123720
gaatggagta gttggtttga ttcatcattc caaaatcatt catagttcgc gcttcctgaa 123780
caatgcgttg aaatttttcc cattcggtgc gtgtaatgac accgaatctg cggtttattt 123840
catttacaaa atggataagc gctttttggg ttgcttcttg ttcaccatac tctaagttaa 123900

-continued

```
agtgttggta aatgacgttt atttctttga taagctgacg aatttcggtt tctgagtagt 123960
caccaatgtt aataagctca ataggacgca taaagataat gcgaataagt cctgagaaga 124020
ttccttccag ctcaggaagc atcgagatct gtacattttc atctctaaag gaaaacaact 124080
tttgataaaa ttcggcgagg cggggaaggc ggaagtaaag ctctgctgcc tcgggaatta 124140
cctcgggctc tagctcatcg gcaccccccca atatcatacg cgtgggtata agtttgtaca 124200
cgggctcagg ccgttcaaac atgtcgtaaa tccctaatac aataaaaatc ttggcggcca 124260
tacttttcag catgaaggtg aagaagacgt cctcggtttc ccagcgggtt gatagggcgt 124320
cgttaactct cacagtagag aggtagaccc gctgagccgc ttcctcggca gtctgtgcaa 124380
gcgccatcct ttgtcctcca atttctgatt gatttagatt tttaagtccc acggaaagcg 124440
cagaatgttg aagatattca agcaaggttt tatagatttg caggggcgac atgggcacca 124500
tttgccgcag ctcctctccc ccaagcatgt ccccaatccg ggcaaaggca ttgatgatat 124560
ttttaagcgc ctgaaagtta gaaagagagc gcccgataag gtcgcgaatg tttttagcct 124620
ggcttgctct gacgggacgg agggtaccaa cgcttcggcc ttgttggatt tcagccgcaa 124680
ctttttcgta gtagtggccc gcaggagcat tatccgtaaa gacgttggag tcgttgcctg 124740
tggaggtggg aaaactttca aagacttgtg caagcgtgtc ccctgttgtc tcggtgaacc 124800
atcgtcctat aatgcgcacg ccatccagca tctgttggac tgtttgaata gaatctatgt 124860
tgtttacaaa cgttttggta atgtttttaa gataaagatc tagcccttcc agagctcgat 124920
agaatcggcg ttttacatca tactccagct cgatggcgct tacggttgcc ttccagtcta 124980
cttcctgggc acctccagga tttgggccca cgtgtcctct ggcaagatct acagccggag 125040
aattaatgcg cgcatttttt tccgtatcca actgcatgag gcgtcccgca atagcatctc 125100
cgagaatagt ggcatagttt tcctcgtagg attgaaactc ctgtttgtta tgcgttaaat 125160
tggagtaaat ctgggccaca taatagtaat acataaaggt gttaattgcc tggttgaggt 125220
caacctgcga tcgcgcggcc ttgctgagcc caagctcttc aactgttagg gcagcaccgc 125280
ctacccttgt acactcgcag tcctcctcgc ctccatactt tttttgcaca atatcggtat 125340
aaaaatcaat aatctgtagc aagcgagagc aggagtcata aagattttta aaattagggt 125400
cggttttaga tatctcctcc aaaacatttt taacaagcgt aagctgtgtt aagaaggttt 125460
cgcgttcttc tcgtgcggcc gcattggtgt aaaagccgat aagacttaga tcaagtgcga 125520
tggtgcccat atcattaatg cgcgaaagag catctcgaag cctcgttatg ttcggcgtca 125580
aggcaatttc tttaacaagt ttgatgccta tttttttcac atttccaaa aagtcgttat 125640
aggcttgtgt gcttttattc aaaaattcca tgaggatgtg ctttctatcc agtctttgcg 125700
cttcaatcct cctatctagt ggcgttttct cctcatcgcc cccctttttg gcacaactgt 125760
tctcaaggat tttgtggcgt tcattaaagg tctgtcgcaa caggttcacg gctttttcaa 125820
actcagcaat gttttctgcg gagacaagac cactaaacct tttgaggtca agctccttgt 125880
caaactccgc ccagtttttg ctttgaaggt actgttcaac cttgagtcct actttctgga 125940
gagccttatt aattttattc gcaacagacg cagcaatacc tagattacaa agtgtgtacg 126000
aaagtacttt tccaaaattt ttggttccca agacactatt tgtatcattt aaaagtttaa 126060
taatatccac ctcatccgtc tgcagtttat caagttcctt ttgggtggga gttaaaatat 126120
tgtcaataaa attcgttaaa atgttgattt gcaggttttg ttcatttaaa agtcgacgat 126180
atactgcttc aatcatggtg actgcattaa tgacttcctc attgggggct gctttggtta 126240
```

-continued cctccgtcac catgcgctcg tgaagttgct taatggcgtc gtttaacagc ttgatatttt 126300
caagtgtatt ttctatactg ccgtgtacat caagatactc tgcgcgcagt ccatgagtta 126360
gggagttaat gtacagaact atttgtcgac atatactggc ggccccttcg gtggtatcta 126420
taagcttatc ctgacctaaa tcaataaatt cctggttaat ggcgtctgca atcattttac 126480
agacggtctc ctgtttttcc gcattttttta caaaggtgga accggctcga ggatcgggca 126540
gttgtttttt gatatcttta agaatatctt cgatgggctg ctttgtgtct actttgaacc 126600
ctattttggc aatcgccctg ataattcctt ctataatccg cagctttgct ttactcgata 126660
cggagtctat gtgataatct ttaatgtgtt gtacaggatt tttgtccccc ccgccattaa 126720
aatatcctcc ccctgaaaaa ggacgagttt gtctttgtat atgatcctgt aacttcgcat 126780
atatatttgc ttctgatgaa ggcagtggtc tactagaggt tgaagatcca cggttaccca 126840
ttataataaa aaaaataaag atttaaaact acaaatattt tgctgtttat aaacccaatc 126900
atataagact aactaaaaca ttaaatgtag gtgagataaa agcttatttt ttttaaaagt 126960
ttaataacca tgagtcttac cacctctttt tcttcttcct ttagaggggt tccataaatg 127020
gtttgaataa aattatgtgc tctaataacc ttgttaaaat caggtgcctt tccatattgt 127080
tcaatatgtt gcacagtctt ttgtgcaagc atatacagct tggagtcttt aggtacctcc 127140
gatgagggct cttgctcaaa caacgtttca aaggaggatg tgcattcatt ggtttcatta 127200
tcattttttt catgaatgtt ctccgaagat gctgaggatt ccgtctcctc ttcaaacagc 127260
acatgcagaa tcatattcca ttcttcttga gcctgatgtt cagtataccc ttgccctgca 127320
tatatacgag cagatttcac aatatcatac ttaacagtac taagcaatgt ttttatagcg 127380
gtcgtaacaa ttctaccgct attgataatc tcaacagaaa accaattata caggctaccc 127440
gcatgaaaca caacttgtga agatgatctt aaatccgttt tgaagatgac ctccattttc 127500
atggatatat ttaaaataaa atccattcaa ttttaaaatt ataaaataat aagaagatgc 127560
cctctaatat gaaacagttt tgcaagattt ctgtatggct acagcagcac gatccagatt 127620
tattagaaat tatcaacaac ttatgtatgc ttggcaattt atccgcggca aagtacaaac 127680
acggagttac cttcatttac cccaaacagg caaagatccg cgatgaaata aaaaaacatg 127740
cctactccaa tgacccttca caagccataa agaccttaga atcactcatc cttccatttt 127800
acattcccac tccagcggag ttcaccgggg aaatcggctc ctacaccgga gtgaaattag 127860
aggttgaaaa aacggaggcg aataaagtta ttttaaaaaa tggagaagcg gtcctagtac 127920
cggcggccga ttttaagccc tttcctgatc gccgactagc ggtctggatc atggagtcag 127980
gctctatgcc cctggagggt ccccccctata agcggaaaaa ggagggtggg gggaatgacc 128040
cgccggttcc taagcatatc tcgccgtata ctccgcgcac gcgtattgcc attgaggtgg 128100
aaaaggcctt tgatgactgt atgcgtcaaa actggtgtag tgtcaataat ccctatcttg 128160
ccaagtcggt ctccttgctg tctttcttgt cgctcaacca tcccaccgag tttattaagg 128220
tactgccgct tatagacttt gaccccttgg tgaccttttta tctacttctt gagccctata 128280
aaacgcatgg ggatgacttt ttaattccgg aaaccatttt attcggccct accggatgga 128340
atggtacaga tctgtatcaa agtgccatgc tggagtttaa aaagtttttt acccagatta 128400
ctcgccaaac ctttatggac atagccgatt cggctactaa ggaggtagat gttcccatat 128460
gttactcgga tcccgaaacc gtacattcct atgccaatca cgtgcgtact gaaattttgc 128520
atcacaatgc cgtcaataag gttacaacac ctaacctcgt cgtgcaggcc tataatgagc 128580
tcgagcaaac caataccata cgacattacg gccctatttt cccggaaagt accatcaacg 128640

-continued cactgcgttt ttggaaaaag ctgtggcagg atgaacagcg atttgttatc cacggcctgc 128700
accgcacgtt gatggatcaa cccacctatg aaacctctga gtttgcagag atcgttagaa 128760
atttacggtt ttcgcgtccc ggcaataact atataaacga gcttaatatt acaagtcccg 128820
ctatgtacgg cgacaagcat accaccggag atattgcgcc caatgataga tttgccatgt 128880
tggtggcctt tatcaacagt actgactttt tatacaccgc gattcccgag gaaaaggtag 128940
gggggaatga aacccaaacc agtagcctta cagacctagt tccaacacgg ctacactctt 129000
ttttaaatca taatctaagc aaacttaaaa tcttaaaccg cgcgcagcaa acggttagaa 129060
atattctttc aaatgattgt cttaatcaac tgaaacatta tgttaaacac acgggaaaaa 129120
atgaaatact aaagttactt caagaataag tatgttgata cctgtggtgt gttttacctg 129180
tgggtttcct attggaacct acgcggcaat ttttgacaag gctcgtaccg agtatattaa 129240
aaccaaaatg ggcggaacat tgccgcaaaa tatcccatta gatgcttctc tccagattga 129300
gttaaaagac ctcattacag ctctgggaat cccaatgcgg gtgtgttgtc gcactcattt 129360
aattactacg ttggattatc gtaaatatta ttaatatcta aaattgaaaa aatattttta 129420
atgttactag taaaaatgac tacacacatc tttcacgcag atgatctcct acaagcattg 129480
caacaagcaa aagcagaaaa aaatttttca tctgtatttt ctttagattg ggataaatta 129540
cgcacagcga agcgtaatac aacggttaaa tatgttacgg tcaatgtcat agtaaaaggc 129600
aaaaaagctc cgctaatgtt taactttcaa aatgaaaaac atgtaggaac cattcctccc 129660
agtaccgatg aagaggttat acggatgaat gctgaaaatc caaagttttt ggtgaaaaaa 129720
cgtgacaggg atccctgttt gcagttcaac aaatacaaaa tctcgccgcc attggaagat 129780
gatggtctca ctgttaaaaa gaatgagcag ggtgaagaaa tataccccgg cgacgaagaa 129840
aaatctaagt tgtttcaaat tattgaactg ttagaagaag cctttgaaga cgctgtgcaa 129900
aaaggtcctg aagccatgaa aacgaaacat gttataaaat taattcaaag aaaaatttct 129960
aatagcgcgg ttaaaaacgc agacaaacct ttgccgaatc ctatcgcacg cattcgtatt 130020
aaaatcaatc ccgctacaag tatactaaca ccaatattgc ttgataaaaa taagcccatt 130080
actttacaga atggtaaaac aagctttgaa gagttaaaag atgaagacgg cgttaaggcc 130140
aatccggata atattcataa gcttatagaa tcgcattcta tacatgatgg catcattaat 130200
gctagatcta tttgcatcag caatatgggc atttcatttc cgctttgctt ggaaatggga 130260
gttgtaaaag tttttgaaaa aaataatggg attgatgtga actccattta tggctcagac 130320
gatatttcaa ctcttgttaa tcagattgct attgcttaaa caatttgctc aaaacaagct 130380
tataaacgtt tcttaggtat gcgatacgta aatcctaatt ctttaataag ttctttttca 130440
gtagtgattt ttagaggtac taaagtttga tttttaaata atccatactg atttagctta 130500
taattctttt tttttaacgc agctcgaatt cttattaaat aagaaacggg acccgtaaaa 130560
tgaagtactg cgtatggctt ttcctcggct aaggccgtaa aaagatcaag ttgatatgtg 130620
ttttttttcc attcaataaa aagtacacac tttcgttctc cgcagacttt tacagaaaaa 130680
gaaagatcct ttatgcgaat gttgggcagg acgtgtttta aaagtttttt ttctggaaca 130740
ataataagaa gatccacgtc attaagcatt ttctcttcgc gtcttaagct accaacagca 130800
acgatgtttt ttgataaaat ttttataagt tgtccattat attcaaacgc aagtcgggag 130860
cgtaagtcat ttacaatttt ttttccttga ataagcgtta acattttata tttaatatta 130920
aaatcttttc attttatata ttatatacgc aaaatggcac ttgatggttc aagtggtgga 130980

-continued ggctctaatg tagaaacatt acttatagta gcaatcattg tggttattat ggcaatcatg 131040
ctttactatt tttggtggat gccccgccag caaaaaaaat gtagcaaggc tgaagaatgc 131100
acatgtaata acggaagctg ttccctaaaa acaagttaaa acatgcaatt atatgcatgc 131160
atataaacgc atgcatataa acgcatacat ataaaatgcg taaatactat ataaaaaact 131220
ataacatatc aatcaaggaa tcaacacttt tataattttc cgtaatatat ttttcatcca 131280
taatgatgtc agagtacatg gtccctatgc gaggaacaga gcccataagg gtaggcgcgg 131340
caataccgta aatgggattc acggcggagt caaccgcagc atctgtcaag acctggactg 131400
gagacgacaa ggccattcgc aacaacacgt tggaaggctc tcttgcatta agccctgcct 131460
tttctagaga ggtaacctgt cccgttcttg tcatgagatc tgcgtacatg agtaaatgac 131520
gatggttggg acccttgtcc cccataaccg ttctaatttc actaataatt ttttgccgtg 131580
ccgcttctat gccgtaaagc tccatggtgt ctcctataga ggacgatacg atggtgtatg 131640
ggtcgatgtt atcatcaagc attgcgccaa aaatattagt cccgtttgtt ttgatggcgt 131700
agatattgtc tagtcttacc agtttcccct gggcatccac acggtggcgc ataagcttaa 131760
caacattcgc atttttgatg cctggtattc ctctaatcgt gctatttaat agtttatcca 131820
ccacatttac ggcaattttt tcatccgtag ccattcgggt attggtactg cgtctaaagg 131880
cgctttcccg taggtatatg cgaataatga tgggaatccc tgaggccgtg ttttccacag 131940
aatgcatgat gtaggtgttg gggtgtttag ctcttagact attaataata ctttctagac 132000
taatgctttt taatatcatg gttgttttgt ttaattccaa gcggatacac cagtttgcaa 132060
tatcctctgg gggctgtagt agaggatggt tttccagaaa atccgtcatc cattccacat 132120
cacttgcaaa atcggggtac atcacatttt tttttgtgct tgaatacgtt tcgtacaata 132180
ggtgccactg caatatcaac cgttcgaacg ttataagctc tatgctgtta gcaatttctt 132240
gcgcatatgt tttatttgtt tccacttccg ggttctttag acgtaaaagc atttcagagg 132300
attgttcagc ctctacgggc ttcgcgctaa agatctcctg gggccgcaca attcccgact 132360
tgttggttcc cccggccacg gaccggtggt gggagtccag catatattgt gtcaagggct 132420
ctgatacgga ctgcgccgcc aggattccca ctgcctcacc gtagttaata agactttgag 132480
tatattgtag ccttatgagg tccaggatgg cactcatctg ctcgcaggta atgtttaatg 132540
ttttaacggt tgccagttcg atgcgaataa gcatgcgcat cagagaggca gcccgtttaa 132600
gataaacggg tatgggcgtt tgtagtcgtt cctgaatgtt gttaataaac acgtatggaa 132660
gatttttgca aaacgttttg accatcgcgt atttttgtag aatacttttt tcgtcgaagg 132720
gaagcacgcc actggtggag ctcagtagaa tgttttttac gatgctggcc acgtttaccg 132780
gcacctgtct aacatctgta agcagctgac tgaaattaaa attttcgacg tttaggaaga 132840
tctgtcgata tttatctcta tcctttttaa ggcgtgaaaa ttcttcttca aacaagggcg 132900
attgtatccc ggtgtacttg aatttgtctt caagttcctg gtccgacagc atgatggttt 132960
caaaccgtac ggtttcaagc tggcgcgcat caaggccgtc ctctccgtac aactgctgca 133020
caagacgcgt atcgatggaa acccgtcggt aataatccac aatacaggat tgaaggccaa 133080
agatggcttt acggttggca tagcctgtgg atgatgtcga taatgctttg ttgatcaagt 133140
cgaatcttcc attcatttcc ccaaagataa attcagggga ggtaaggccc gcaatatagc 133200
tgttgcagat gaacccgtag gcctgcgcct ccagggcaaa cctggggtag tacaccaggg 133260
tcctaccgaa ggaaaactgg ggttgaatgc gttgtgtatt aatttcaatt tggccgatgc 133320
ccgccatgat gtgaatcata ttggggtttg agcccttggc gccagtggcc accatctgaa 133380

-continued aaagcccatt ggtttccgga ttaatggaat tcataatcgg ctttaaaatt ctatcgggaa 133440
atttaagcgc attcagctgc aatttttcgt agaagtcatg cgttgtcagg cctataggcg 133500
gcatgatgtc tccatgaagc agccggttgt ttatttcctc cgactcaagc agcagttcat 133560
tgataatttc ttggacctcc tgatgtgcct ccggggttag gagcatgtcg gccgtggaca 133620
ctgtgaatcc ggcgttgcgc acgtagttta gggcgagctg ctgggtcgca aatatcattt 133680
tcaaggcctg ctgcggccca tacctacgcg aaataaggtg atagattcca ccggaggaac 133740
ccgctccgac ggccttttg tcaaggacgc cttcaatgag ttcgccgttg cgtatttgtg 133800
tagagatgtc ctgcttgtta taatgcatgt agggtgcata cacttctgag taccatgtgg 133860
gggctcgttg ataattgatg ggggtctgcc tcagtagcat agatacaacc gatttgccat 133920
ccagcaggtc agttggggag tagttggcaa aacaaggtgg gtcggtttgg gttgtttgaa 133980
acaaccccat ggcgtgcagc ttgttcatca catttttccc catgggggtg ttcgtgcgtg 134040
taagcaaaaa gcttcccacc gtggagtcct gcacctgccc attaacggga cccgagctct 134100
ttgtggaaat gaaccagttt cgcacagaac aaagtagttc ggcctcaacg cggctcatga 134160
cgctccaggg aacccagaga ttcatctgat ccccgtcaaa gtccgcatta taccaggcac 134220
atgcgctgac attcatttga aacgtagaaa tttttgggtt ttcaagaacg acaatccggt 134280
gaacccctat gctgcttcgt tcgagagaag gctggcgatt aaaaaacgcg acgtcgccag 134340
tgacgacgtc acggtaaagg atgtctccta cctccagcct aaagtcttgt ttgagaccct 134400
caatgtcgtg aacggattgt gttatttgct tatacactct tgaacaacca gggtactggc 134460
gctttccatt taaaaaatag ggcattaatc tattaatatt ataatgttgc actgtttccg 134520
caacttgcag cgttcgtgca aaggaaatgg gatagccaac ctcgtccagg tgaaggtctg 134580
agttcccgca gatggtggac cggctgatcg accatacctg gctgcccagt agggatttac 134640
gaattcttcc ctccttgcga ggaagtcttc gcatgatgga gggagcaggg cgtgcccccca 134700 tgacgatccc acgctttccc gtgcctccct gggttgcggt ggtggaaacg gaatccaaca 134760
aaaagttata gtaaagttgc tgtatggttt gcaaattgcg gtcaatattt aaaggtattt 134820
tttggccgcg cacgatttgt aggtccttcg ggatcagcag attctttcga accagatact 134880
gaatcacgtt gttaatgtcg tgaaagcttt gggggcctga cccgattccc aatctgatgc 134940
caggtcgtat gctgatgggg gggatctgaa tggccttaag cacaagtttt tcgggatggg 135000
agtttttact tcgccccagt tttacaacgg tgtcgtaggt tacgcgcgaa aaaatctctc 135060
tgatgatctg cgggtacagt ttgtcaatct tgccctgctg atccgcccaa aaggtaaaat 135120
aatcttccga gtccttaaca attttggggt gtactgcctt acagacgtag cactgctttc 135180
cttcggtttg gcttgaagcc gcttcaataa gacgcttagg cctaataagg tgctcgtacc 135240
tctttaggtc aacgatggga gccccgcagt tgagacatat aaccccttaac catcgtcgta 135300 tttcggcgat gaagagcggc tgaagcaccg gagcatgcat ctgcagtatc ccagggtgtc 135360
ccatacattg cttgcgctgg tgtgagcaag tgatgcattt ataatggtga tcggtggttc 135420
ccattcgcgc atcatagata ccccccttcgg cgggaagggt gccctcaaat aaattagaaa 135480
tggtaacctc cataacgcct tgcctcttat gatcattgtc accggcaata ttgaactgaa 135540
cggcggctat ttcggcatat ccagcctcca tatttttgct aaatacataa taaaacttca 135600
aatgttaaaa aaaataacat cggttggcat atttttttgt taaaaccaag tgttaaatga 135660
tttctaaaac atttatcggt tcacgaaaac ctaccgcacg ggcctgaaga ggaatgccag 135720 ttttgggga aagctcggca tattccacgg taagctcttt tccataaaga tgttttttaa 135780
ataaggcggg cgtgagtttt tgaaaaagag cataacgatc cgcgtacgtc aaatgcttag 135840
gagtgactac aaaccgcttt ttgtttggca attcgcaaac ccataaaatg gcgcctaagt 135900
cctttccctt ttttccctga gtatagtcca ctaaaataaa ttcagcgtct agcagcggtt 135960
tcagcttggc aagatgcgct gagtggtagt tgttgtatcc cggctcatag ggcccattgg 136020
cattgcgtac gatggctccc tcgtagccct ccttaataaa ctgcgcctta agcctaaggg 136080
cctcatccac attcttcacg ctaaaatttt caacttggtg gataaaggta agatcttcct 136140
tctgtttaaa aatatttgtt aatagctgtt gtctcttgtt ggaaggcatt tgaagctgat 136200
cactccaaaa acagtcaaac acgtaaaagt gcagctcgga ggaatctgtc ttcgcattcg 136260
cctgccccgc gatccattgc agaggtttgc ggtgtaaata aagctcacca tccaaatata 136320
ctctcacgtc tataaataaa taaagctgtt tgagctcttt tttaatattg tcaagaccta 136380
aaaattcctt tttcgtgcgc gaatacaaga gaatgctacc atcgccctgc tggcaggcca 136440
cagctcgaac gccattacgc ttgcgctgca cgatgggatc tgtttcttct tcaaaaaatg 136500
tcttaggaat tatattaaaa tattttacca gcataggggg gataattcct ctatttgtgt 136560
gggctccccg cttttgtctg gcatggcgat tatatttact aagggcgtcc ttgaatgcct 136620
gatggactac cgttgtggca ttttttttac ccaagttttt tccctcggta acacgtgtca 136680
tttttgatat ccgcaccgcc ccttcttcca caaaaaattt tgtgaaaatt tcagcaacgg 136740
cgtcttttac atctgtggaa aacatctcat ctgtgatggg aatgatcgtg ttgtgctgca 136800
ccacttgcac acaaataatc catgaggcct tttttccgct tttcgtttca gactcaatcg 136860
gaggaaaaca aaaaatgttg tttgaatatt gcccaggaaa ttgatttagc atggttttaa 136920
caataaaaata agcctatcaa tttttttata atttgaatag ttattccaaa ttcaatatgg 136980
cttctttaga taatttagtg gcacgatatc agaggtgctt taatgaccag tctcttaaaa 137040
atagtactat tgaacttgaa atacgttttc aacagataaa ttttttatta ttcaaaaccg 137100
tatatgaggc acttgtggca caagagatcc ctagcaccat ctcccacagc atccgctgca 137160
tcaaaaaagt tcaccatgaa aaccactgcc gggaaaaaat tttgccgtcg gaaaatcttt 137220
acttcaaaaa acagcctctc atgtttttta agttttcaga gcctgcatct ctgggctgta 137280
aggtctcgct ggccatcgag cagcccattc gtaaatttat cttggactcc tccattctcg 137340
ttcggctcaa aaatcgtacg acctttcggg tatctgaact ttggaaaata gagcttacca 137400
ttgtaaagca gctgatggga agcgaggtct ctgcaaaact tgccgctttc aaaacgcttc 137460
tgtttgacac cccagagcaa caaacgacaa aaaatatgat gacgttaata aacccagatg 137520
acgaatatct ttacgaaata gaaatagagt atacaggaaa gcccgaatcc ctaacggcgg 137580
cagatgttat aaaaattaaa aacacggtgt tgacacttat ttctccaaac catttaatgc 137640
taacagccta ccaccaggcc attgaattca ttgcctccca tatactgtcc tcagaaatcc 137700
ttcttgctcg tattaagagc gggaagtggg ggcttaaacg cctcctcccc caggtgaaat 137760
ccatgaccaa agcggattac atgaaatttt atccgcccgt tggctactat gtaacggaca 137820
aagcagatgg aattagaggc atcgccgtca ttcaggacac gcaaatttat gtggttgcag 137880
accagttata cagcctaggt accaccggca ttgaacccct taaaccaacc attttggacg 137940
gtgaatttat gcctgaaaaa aaagaatttt atgggtttga cgtcatcatg tatgagggca 138000
atctattgac gcaacagggg tttgaaacaa gaattgagtc tttaagcaag ggcattaaag 138060
tcttacaagc gtttaacata aaagcagaaa tgaagccctt tatttcgcta acaagtgcag 138120
atcccaacgt gctcctcaaa aactttgaaa gcatttttaa gaaaaaaact cgcccatatt 138180
ctattgatgg catcatttta gtagaacctg gcaattctta tctaaataca aacaccttta 138240
agtggaagcc cacctgggat aacacattag actttttggt gcgaaaatgt ccggagagtt 138300
taaacgtacc agagtacgcg cccaaaaaag ggttttccct gcatctacta tttgtaggca 138360
tctccggaga gctttttaaa aaattagcgc taaattggtg tccaggatat acgaaactat 138420
tccccgttac acagcgcaac caaaactact ttccagtaca gttccagcca tcggattttc 138480
cattggcatt tctttattac cacccagata cctcgtcatt ttctaatata gatggaaagg 138540
tccttgaaat gcgttgtctt aagagagaaa tcaatcacgt cagctgggaa attgtaaaaa 138600
tccgggagga taggcagcag gatcttaaaa ccggcgggta ttttggcaat gatttcaaaa 138660
cagccgaact cacatggctt aactatatgg atccctttc ctttgaggag ctggcaaagg 138720
gcccttctgg aatgtacttc gccggtgcca aaaccggcat ataccgcgct caaacagcac 138780
ttatttcctt tattaaacaa gaaatcatcc aaaaaataag tcaccaatcc tgggttatcg 138840
atcttggaat aggaaaaggg caggacctag gacgttacct ggacgcaggg ataaggcatc 138900
ttgttgggat cgataaggat caaaccgcgc ttgcggagct tgtttatcga aaattttcgc 138960
atgctacgac ccgacagcac aagcacgcta ccaacattta cgtgttgcat caagacctcg 139020
cagagcctgc gaaagaaatc agcgaaaagg tacaccaaat ttacgggttt cccaaggagg 139080
gagcttcttc cattgttagc aacctgttta ttcactatct tatgaaaaac acgcagcagg 139140
tggaaaacct ggccgttctg tgccataagc ttcttcagcc gggggggaatg gtgtggttta 139200 ccaccatgtt gggagaacag gtcttagaat tacttcatga aaatagaata gagctcaatg 139260
aagtatggga ggctcgtgaa aacgaagtgg tcaaatttgc tattaaacgt ctctttaaag 139320
aggatatatt acaggaaact gggcaagaaa ttggagtcct gttacccttc agcaatggcg 139380
acttctacaa tgaatatctt gtgaacacag cgtttttaat taaaatattt aaacatcacg 139440
gcttttccct agttcaaaag cagtccttta aggactggat tccagaattt caaaacttta 139500
gtaaaagttt gtataaaatt cttacagaag ccgataaaac ttggacaagc ctttttgggt 139560
ttatttgtct gcgcaaaaat taaatatttt ttcataagaa gtactaccca ggttttaaag 139620
aaatagctaa aaatatcata tggatactgc catgcagctt aaaacgtcta ttggtttaat 139680
tacatgtcgt atgaacaccc aaaataacca aatagaaact attctggttc aaaaacgtta 139740
cagccttgct ttttcagaat ttattcattg tcattactct ataaatgcta atcaaggtca 139800
tctgattaaa atgtttaata acatgacaat taatgaacga ctgcttgtca aaacactgga 139860
ttttgaccgc atgtggtatc atatttggat tgaaactcca gtctacgaac tataccacaa 139920
aaaataccaa aaatttagga aaaattggct tctcccggat aatgggaaaa agcttatttc 139980
attaatcaac caagcaaagg gctcaggaac acttctatgg gaaatcccta agggtaagcc 140040
gaaggaagac gagtcggacc ttacctgtgc catacgggag tttgaagaag aaaccgggat 140100
tacccgcgaa tattaccaga ttctcccaga gtttaaaaaa tctatgtcat actttgacgg 140160
taaaacagaa tataagcata tctacttcct tgcaatgtta tgtaagtcgt tggaggaacc 140220
caatatgaat ctttctttac aatacgaaaa ccgaattgcc gaaatttcta aaatttcttg 140280
gcaaaatatg gaggctgtac gttttattag caaacgccag tcattaaacc tggagcctat 140340
catcgggcct gcatttaatt ttattaaaaa ctatttacga tacaagcact aggatgccgc 140400
attaaaatgc cacataaggt aatacactag gaatgtcgca cacgcacaag aatacaacgt 140460
cgccggagat ttattatcta gtacacgttt tatgtatgta caatccgcct tcatttaata 140520
tattgagcgg atgtactatg tatttatttt aacaaaaaac attatttttt ttaatcttca 140580
tcatctgttt ttataaactc agtaatatca aaagtagctt gtggggtttc agagggttca 140640
ccttggttat cctccgtgag gataacatgt tcttcaggtt cgtcgtcact ggagaaccca 140700
tcatttaatt cctcttcact caacatctgt aaaaaatctt ccaagctttc gctatcgtta 140760
aaatcctcat catccataag aataatggta ccttcctcat cgtttcctcc ttgtttcgtg 140820
tctaaatagg cctgcatggc atttgcaaaa gtatcaaaat aggctgagtc agattgctgt 140880
tccaaaatat ggccttgcgt attaaatgtg gttgcatcgt tgttaaatgc ttgcaaatac 140940
agtaagggat ttatatccat tattattaag caaaaaaaat ttaaattatt tttcgaccga 141000
tgttaggtaa aattaaacaa ttgctatagg tgttaagcaa tgtttattga ttttaagtac 141060
tcaacaacca tgatgtaaat actatacagc acttttggat ttttaatcaa atccagatta 141120
atactaactt cttttgtgat acagttcgta ataatagtat cctgctcatc gttttgtaag 141180
atttctttta atatattttt ttttaccggg atactaagca attgattatt ttcttttaaa 141240
aactcctttt gatattcaat cgtcttattc attgaatatt tgtatataac tataattaca 141300
aatgttcaat gaattgttat tcatgtcggg agatggctat ttaaaaatca tgtcctattt 141360
ttctttgctc aataagcatc caaatatttt catggcgttt tattaattgt tcattattga 141420
acgtatcaca aagatcattt ataaattgca gatagtttat tatttctttc aagagagtaa 141480
caaacattac ttcagcagaa catataatag gtaattcagt ggcgttaaaa gaattttgat 141540
cttgttgata cgccaatggc gaggacttaa ggagatttgg gggtcttgcc caaaacccta 141600
ggctgctgtt cttgtttttt agggcgtcat aaagaaatga aagcacattg caaggcttaa 141660
gccgcgacat ctccttcccc ttgggccctt tccatatttt tagatctaag atctcatccg 141720
agcttataga gtaggtatag taaagttttt caaaaaagca tatctgcttg aagtcttttt 141780
tagaacgact ttcaagaagc atttctataa tgttaacaag ttttgttagg tttaaggcct 141840
gttcctgtgt aagctcctct tgcacgtgat agactgaaaa agtgtgctta ggaatgaaaa 141900
tactccccgt ggcactggcc tgttgtctgc caggtatata gtacacgctg ctgttagcaa 141960
gctgtaccgg cacaatttgc cccacttctg caacattatt ttgcgattcg gacgagggta 142020
tgacaatagt tacgggttca gtcaataggc tttcgccgag aataatatta ctgtcatttt 142080
taataatttt aacggccgct attaaatcaa aggcatttaa gtaagaaaca acagcagaaa 142140
atcttacatg catatatcct cttccgctat tattcgtacg cataataaaa caaggggagc 142200
gttgtataac gccagtaata ttaagaataa aactgttttt gaaacactta cccacataaa 142260
tgttttcaag ctccttcaaa agatgagcct ccacatttgt acaaaaaattg gtaggatcat 142320
caatattcaa cgttgtctca aaaatttttt ggtcgatcat atctataata tattctgtct 142380
atttcaattt aaataatata cgaataaaata acgagattat tttattaaat aagcaatggt 142440
gtatacactt tgtatttact ttgagatata ctttgtgtat cacaacgtgc cctaagatgt 142500
gtgcacaagt gacggcattt tgtcgttaaa aaggtaaaac cagcggattc catcctgcat 142560
tccatttggt tgattacgag cctccatttc tttttgcaaa aggttattgc gaatgagtaa 142620
gcagagcttg atggcactaa tctttgtaag gtttaaactt atgcccaatt ggtcagcaat 142680
tttttgttgc tcctcccgtc cgcgtgtttc gcatacggct ccccggttta gcatgcgaat 142740
atcagtaatc tcattctttt ttaaaacctg gataggtggg cggattttaa atttaagggc 142800
ctttcccttg ctttccatat agcctatgac gatgtcgttt tcttttcgtt taacattaat 142860
attaagcata taaagcggaa tttcatgcca ggttttatct tctcgcgagg taataagtcg 142920
cacggagtcc tccgtggcat agcccactag agtgttgtca tccccaggca cgtggcttat 142980
aattttaaaa atgtccggaa atggctgaat atcttttttt gaaaaagcga tgaaaaactt 143040
tttataaacc tcgacaaggg cccccatacc tgcaagatta tctataataa gtgcttctag 143100
catcgtatag tgaaatgaag cggggtagtg gatgagtacc tgctccattg gctcatcctg 143160
aaaatccttc tgaaactttt catacaatac ttgaaagggt tctttggtct gcgagtgttc 143220
gaggtatttg gtaatacgga tgctgtgcat cgcgggaggc tgaaaatccc gaatatatgt 143280
ttcaatatct aataccggtt cctttttatg gttaagcacc gcagcgacgt acaaatgctc 143340
aggctttgcc ggcacatgca taatggtgca aagacgattc tgtatccata attccttgca 143400
ctggtttttt gagtagcata gagaaatgag cgccagcgcg aagttgtcct ctgagaagag 143460
tttattatcg atggtaattc cctgtatgag cttgggagtg gaaacagcct tccatagctc 143520
ggagtacgtc cacacggggc gtgccataaa caaagatata ataatattag aaattgtttt 143580
tacctcttgc tccccgtatc cataggcctc aaaggtattg aggacggtgg ctccgacgtt 143640
tgccggcgtg atggatggac taaggggcag actttccaac ataggcttat caatcttaat 143700
ctggttggtg aacccatcaa tggcgtgctt tcgcagcgcc ttatccccct cctgtattaa 143760
aatgtattct tttaattttt gtgcgtactt agcgagctct ggccctccat cgggtgttgt 143820
cgatacgtac aaataaattg tcacgttgcg ctcactgggg gggagctcca tgtgtgaatt 143880
ttttcgcacc accctcccaa atacctgaat aagccgggga atatcaaggg gcaatgacat 143940
aatcatctcg taccgcacgg cctgaaagtt caaaccctcc acaatcacct tggacccgat 144000
gagaatacgc agctggtggc cttccaggtt ggacgaggcg ttaaaaagag ccaggcttcg 144060
ttcgcgtaca gcgggctcta tttcgctgtg cagaatggtg aaccgtactg gaataaactg 144120
atggtcgcta tgtgtgtgct catcgcgaat cgcggcgcag atggagcagc gggtcgttcc 144180
cacaggggac gaaacttcat ttaaaatgcc attactttgt aaaatttctt gcaagataag 144240
aacccccgac atgcggaccc gattgtggta aattaaaatt ttcccccggc cttgccgaat 144300
aatggaaaga atgtctttca tcatttgagt gtattttccg ctataaaagg ccaatcccga 144360
gatgtgcgtt ggtggctgca gcgacaaaaa gctgccactc acattaaagg gggctctacg 144420
cgaaggctca ataatctgta ccccgttttc cagaagccag tctgtgcttg ccatagaaag 144480
ggcggtgggg gtttccgtcg agttaaacag gccgtaagcc ttgggttccg tttgttttga 144540
aaattttggg ttgggaaaca ccatgtcata aatgctgtac gcattactcg agattttagg 144600
gtcagggccc agctgtttaa gcgtttcaag ctgatactca gacatggggc attcgatgaa 144660
atgtaagtac ggcaatgttt cgtctttata ggacaacatc tttccggcaa atattctttc 144720
ggggtaaaaa ttggtgttgg tatccaacaa aaaagatacc cttccggtgc tcagtctttc 144780
cacaagagct agggcgtcct ttttccattt aacggaatgc ccactgctgt caaacagttg 144840
ctggcgctgg aggggctggc cgttgggcag ctcatgccgc ggaaccaaaa ggtttaacag 144900
gtcgacgtat tccatgacac tcccggttac gggcgttgcc gacatgaaga cggccctggg 144960
ggcctggtga ggtggaaagg catccaggac atactgtaaa gcgatgccat aattatttcg 145020
ttcctggata ttgtacacgt tgtgtatttc atccgcaatg agcagtcctc ccctaagttg 145080
ctccatgatt ttttgattca cccggatgag gccgtttgtc tcggcctcgc taattttttg 145140
cacgaactga gatatatcgt tctcattcaa tgtatcttct gcttcgtcag aacgatgaaa 145200
cagagaaagc acatcaaagt ttttctcttc acccttactc gtaatattga aaagcttgga 145260
tgcaaattcc ttatagccgt aaaactgaaa aaagcctccg cggtttctat cggttaaacg 145320
gcgctttaac gtactaacga acccatttag atgccgtgat tcgaccgacg tggtgctgcc 145380
agactgcttt gcaatgtgaa gaagccggtg tagctcagcg acctccttgt aagaaacaaa 145440
tcccagctca ggacgtctta gcatttctgt ttgaatgatg gcgcgtgtaa agcctaccac 145500
aaaaatccag ggcgcatttt caataaaatt catgtagtgg ttcataaatt gacgcgcgat 145560
ggcaatcgcg gcaatgcttt ttcccgtccc ggtctgccag tttaataaaa gacgcgagta 145620
gggcgtgttg ggattttgaa agttttggac gaaaagctgg gcattatgca attggagacc 145680
cttgatggaa ggaaagggcg acgcgtaggg gtcacacgga aaaaacgctc gcccccccctt 145740 ctcgcagcca ggcccaccga tctggacaaa atgagcccgc agatcacgaa tgagctcttt 145800
ttggtcgaca ggaggggaaa tcaacgattt aaactccttt cttcgcgcca actgctgcaa 145860
aaagtctgcg gcatccaatt cgggatacgc catattatca taaaaaaata aacctttta 145920 tgaaaacttt tatgtgattc tgtattgcaa ttgtttttta tgaatactgt aaataagcgt 145980
atcaacttgt ttttctaacg aagaggcgtt attctttttt tctggatata aaataataat 146040
aagtataata attaagacta aacagcaggc aatcactatc aaactcatat tatacttact 146100
tttttataaa aagtattata tcttatgaat gcgcaagttc agctaattgt tcgtcgcttg 146160
gaatgtggga ctgcagggag gtggagtttt tcctttttct aaagaatacc gggaaatggt 146220
ggtgaggctc aggttgttgt acatagtagc taggaggagg tttaggtatg ctcgacttgc 146280
agtcaatagt ccggttatag taaacgatgg caacgatgat aagaataata atgagcaaaa 146340
tcaaaatgcc caggagaatc gcagttgttc cgggatattt ggcgattgta tgggctaaaa 146400
ggccttgggt gctttgttta attccctcgc gggttgacag gttatgagaa agcagtggag 146460
acgtttcagt gtccatttat tacaattgaa cagttatatt aatctcaaat aaaatataac 146520
acaaaattaa ttatggccat gcaaaagtta tttacgtata tttacgagtt tattgaatat 146580
cgtaagatgg tgctgttgga agaaaaggta ccatatgata agtttgttca aatggtactt 146640
aatacaggat tttttcgtat taacgcggag acgctgaatc acggaatcgt atccgtgttt 146700
atctttggag caaatggcaa gtacgttcac cacggaggcg acatgagaac gcttttaacg 146760
aatacgctta atgaaaaaaa acattatgaa gaattaattt taatcgttga taagcccgtt 146820
ttaagcaaaa aaaatatttt agatataatc gtcgagcagc gcgctgcaaa tcccacgatt 146880
gtaataaaca tatatcccta ccacctgttc tgcattaaca ttcccaaggt gagtgccatt 146940
cctaaacata aactaattac tcaggaggag gcgcaggagt ttttaggtcg cgaatatctg 147000
caaccgcagg acctcatgca aattagcgcg tcagaccccc cggtggtctg gctgggagga 147060
agaccgggag actttgtgca aattgagcgg ccctcagaga cagctatgca cgctgttgtt 147120
atccgcttta tcaccaagtc caaaatttga gtcccgtgtt taaagatgac agacagctaa 147180
gtaagcatat ctgtaaaatt gtcgatgtcc tctgtggata gagcgctttc ctctgagcag 147240
caaatttttt catacatctc catgggggat ggcgaggctt taatagtatg taggtcacgt 147300
aagaactgtt gtatgatggg atatttgtct tttaaaaact ggggatgttt cataactgga 147360
attatttgaa agataaagac cttccatcca aagtagccaa ccacatttgg catttcggga 147420
cacgcggttt cataaggcat agaatagtga atagtgtact gatctttttg atacagcgtt 147480
tcaagtagtt ggcgaaatgt ttccgcgtcg agcgtgccaa aatcttgagg agcctcggtg 147540
tgctcctgtg tagagcagat cgtgatgatt ccccaggcaa gcgggagcat ggactctgga 147600

-continued gggtggatat ccgtattggt ctcattattc gatcccagct gatgaatgcc gcacacgcga 147660
aacatggcct cgacgtagat gcccatagag ataggcggcg aaagggcaag accggattgt 147720
atttgcggca tatagtagga gggcaccgag ttttttattt ttcggttgaa tggggacttt 147780
atttctacca gcacggggat gcgtttcgtg gcctcatagc gtacgttgtt aaaaattgtt 147840
ttgatttccc aggactgttg agtgtatccc agcgttaggt gacaaaaccc atcggggcta 147900
ttactatgtc cggggtatcc caaataggtc ccatcaatat gaatattgtc acctatgacg 147960
gtggtttggc agaacaactc aagcagatct ttactaacac gctcaaaaag ggttccccag 148020
ctacaagcag cgcggttcaa attcttctta aaaagatttg ctttttccgc caaggttata 148080
taatagcttt tgtaagggtt taaacctaaa acgctggcaa ggtcagagcc acccacctga 148140
gtgcgacgaa tagcatgcca ggcatcggag cgctgctgag gagagtcttt aaacaggcgt 148200
acaaaggttt ccattatact tgttttaaca ggaattcaat ataaaaagtc aacacagttt 148260
gcaatttttc caatctcaag atatagccat acattttttt ttccaattgg cgaatatgtt 148320
taagctcatg tgtttcaata ttagcatccg gaaatttaaa tgcataaaga tgttcaaagg 148380
cctgatttat acacgtatca aaggatctgt ggtatgttat tagcttcagc atgtgtgcca 148440
gatcttcaag atggtctaaa tttatacggt tttccacgtg gtggatcatg tctgccacat 148500
cttgagcccc catccagggg atcacaaggt actcccccctt aaagatgatt cgtcgttttt 148560
ttaaaaaatc atgaaaacgt tttaaagctt caagaaaggg gcagttgggc tttgacccca 148620
aaatgctgac gacgatatcc tcgggcatga tgtattcgca gtgaggatag tagtttacgg 148680
actctaattc agcggcccgc cgttttattt cgtatcttgc ccagttattc agagagtact 148740
ccacgcctcc gaccacaaca gacatcctat ctattaaaaa ataacaataa aaaccttatg 148800
aaatctatgt atagtggccg ctaaaatgtc tatattagaa aaaattacgt caagtccctc 148860
tgaatgcgca gagcatctta caaacaaaga tagctgttta agtaaaaaaa tacaaaaaga 148920
gctcacctct tttttggaaa aaaaagagac actcggttgc gattcggagt cctgcgtaat 148980
tacccacccc gccgtgaagg cctatgcgca acaaaaggga ctggacctct ccaaagaact 149040
ggagactcgg tttaaagcgc caggacccag aaacaacacg ggtcttctta caaacttcaa 149100
tattgatgaa acgctgcaga ggtgggccat aaaatacacc aagtttttca actgtccttt 149160
ttccatgatg gactttgaga gggtccatta taaatttaat caagtggata tggtaaaggt 149220
atataaggga gaagagctac aatatgtaga aggcaaagtg gtcaagcgtc cttgtaacac 149280
cttcggatgc gttttaaaca cggacttttc aacgggcact ggaaaacact gggtagccat 149340
ctttgtggat atgcggggcg actgctggag catcgaatat tttaattcga cgggaaattc 149400
tcctccaggt cccgttattc gttggatgga acgggtcaaa cagcagctat taaaaataca 149460
ccacaccgtg aaaacgcttg cagttaccaa cattcgtcac caacggtcgc agaccgagtg 149520
cggcccctac agcctgtttt acatcagggc acgcctcgac aacgtgtcat acgcccattt 149580
tatatccgct aggattaccg acgaagacat gtataagttt agaacccatc tgtttcgcat 149640
cgcataaact aataaagttt gaattcttta taggaataaa aatggaagcg tttgaaatca 149700
gcgatttcaa agagcatgcg aagaaaaaaa gcatgtgggc tggcgccctc aacaaagtca 149760
ctatttcggg tcttatgggg gtctttaccg aagatgagga ccttatggcg ttacccattc 149820
acagagacca ctgccccgct ttgttaaaaa tttttgacga gatcatcgta aatgccacgg 149880
atcatgaaag agcttgccat aacaaaacaa aaaaggtaac ttacattaaa atttcgtttg 149940

```
ataaaggtgt gttttcttgc gaaaacgatg gcccgggaat ccccattgca aagcatgagc 150000
aagccagtct tatcgccaag cgcgatgtgt atgttcccga ggtggcttca tgtcactttt 150060
tagccggaac gaacatcaat aaggccaagg actgtatcaa ggggggaacc aacggcgtcg 150120
ggctgaagct cgccatggtg cattcgcagt gggccattct taccaccgcc gacggcgcgc 150180
aaaagtatgt tcaacatatc aaccaacgcc tagatatcat tgagcctcct accattacac 150240
cctccaggga aatgtttaca cgtatcgagc tcatgcccgt ataccaggaa ctagggtacg 150300
cggagcctct gtctgaaaca gagcaggcgg atctttccgc ctggatttac cttcgcgcct 150360
gccaatgcgc ggcctacgtg ggaaaaggca ccaccattta ttacaatgat aagccttgcc 150420
gcacgggctc tgtgatggcg ctagccaaaa tgtacaccct gttgagcgcg cctaatagca 150480
cgatacatac ggcgaccatt aaggccgacg caaagcccta tagcctgcac cccctgcagg 150540
ttgcggcggt cgtgtccccc aagtttaaaa aatttgaaca cgtgtccgtt atcaacgggg 150600
taaattgcgt aaaaggagaa catgtcacct ttttgaaaaa gactattaat gaaatggtcg 150660
ttaaaaaatt tcaacaaacg attaaagata aaaaccgcaa aacaacatta cgagacagct 150720
gttcaaacat ctttatcgtt atagtgggtt ccattccagg aatagaatgg accggccagc 150780
ggaaggatga acttagcatc gcggaaaatg tttttaaaac gcattactcc attccttcta 150840
gtttttttaac aagtatgaca aagtctatcg tggatattct tctgcaatcc atttctaaaa 150900
aagataacca taaacaggtc gacgtagaca aatatacgcg tgcccgcaat gcgggaggaa 150960
aaagggcgca ggactgcatg ctactcgcgg cggaagggga tagcgcactt tccctgctgc 151020
gcacgggact aaccctggga aagtccaacc caagcgggcc ctcctttgac ttctgcggca 151080
tgatctccct gggaggagtc atcatgaatg cctgcaaaaa ggtgacaaac attacaacgg 151140
actctggaga aaccattatg gtgcgcaacg aacagcttac caataataaa gtgttgcagg 151200
gaatcgtgca ggtattgggt ctagacttca actgccatta caaaacacag gaagagcgag 151260
caaagctgag atacggctgc attgttgcgt gcgttgatca agatctggat gggtgtggaa 151320
aaatccttgg actgctgctg gcctactttc acctgttttg gcctcagctt attatccatg 151380
gtttcgtaaa acgactgctt accccgctga tacgtgtgta tgaaaagggt aagaccatgc 151440
ccgtggaatt ttactatgaa caagagtttg atgcctgggc aaaaaagcag accagcttag 151500
ccaaccatac cgtaaaatat tacaagggat tggcggcgca tgacacccat gaagtaaaaa 151560
gcatgttcaa acattttgac aacatggtgt acacgtttac cctggatgac tcagcaaagg 151620
agttgtttca tatttatttt ggcggggagt cggagttgcg aaaaagagag ctttgcaccg 151680
gcgtggtgcc gctcaccgaa acccagacgc agtccattca tagtgtccga cgaattcctt 151740
gcagcctgca tctgcaagta gataccaagg cttacaagct ggatgccatc gagcggcaga 151800
ttcccaactt cttagacggg atgacgcggg cgcggcgcaa aattttagcc ggggggggtga 151860
aatgcttcgc ctccaacaac cgtgaacgaa aggtttttca gttcgggggc tacgttgcag 151920
atcacatgtt ttatcaccat ggcgacatgt cgttaaacac aagtattata aaagccgccc 151980
agtattaccc aggctcctcc cacctctatc cggtattcat aggcatagga agttttggct 152040
ccaggcacct gggaggaaag gatgcaggat ccccaagata catcagtgtg cagcttgcgt 152100
ctgaatttat taaaacaatg ttccccgcgg aggactcatg gcttctcccc tacgtctttg 152160
aggacggcca gcgggcggaa ccagagtact acgtgcctgt gttgccgctt gctattatgg 152220
agtacggcgc caacccatcg gagggctgga agtacaccac ttgggcccgg caactggaag 152280
acattttggc cttggtgagg gcctacgtcg acaaagacaa cccaaaacac gagctactgc 152340
```

actatgcaat aaaacataag attactatac tcccgctgcg gccctccaat tacaatttca 152400
agggccattt gaagcggttt ggccaatact actacagcta cggcacgtac gtcatctcag 152460
agcagcgaaa tataattact attacggagc ttcctctgcg tgttcctacg gttgcataca 152520
tcgaaagtat aaaaaaatcg agtaaccgca tgacatttat tgaagaaatc atcgactaca 152580
gtagttcaga aactattgaa attctggtga aattaaagcc aaatagtctt aaccgtatcg 152640
tggaagaatt taaggagact gaagagcaag attccataga aaattttctg cgcctgcgca 152700
attgtttaca ttcacatcta aactttgtaa aacctaaagg tggcattatc gagtttaaca 152760
cgtattatga aattttgtat gcgtggctac cttacaggcg tgagctttac caaaagcgtc 152820
ttatgcgtga gcacgcggtg cttaagctgc gcattatcat ggaaactgct attgtacgct 152880
acatcaatga gtctgcagag ctaaatcttt cccattatga ggatgaaaag gaggcaagcc 152940
gcattctaag cgagcatgga tttcccccgc tgaaccacac gctgatcatt tcccctgagt 153000
ttgcctctat agaggaactc aatcaaaaag cactgcaggg ctgttatacc tatatactat 153060
ctttgcaggc tcgagaattg cttatcgcag ccaaaactcg tcgggtggaa aaaataaaaa 153120
aaatgcaagc tcgtcttgat aaggttgagc agcttttgca agagtctccc tttcccggcg 153180
ccagcgtatg gctggaggaa attgatgcgg tggaaaaggc tattataaaa ggaagaaata 153240
ctcagtggaa atttcattaa acgctaccgg ttttatgatg tccaataggt gttaagcaat 153300
cagttcatca acattttttt caagaatttg aaaagtttgg ataatgttct gaatactttt 153360
ttctaaaaga gttatcaaat cttcttgtga ggccttatga ataattgtta ataccatttc 153420
ttgcttatgg ggaacacact gataccccac aaagctaata tcaggaatca tttcataaat 153480
atatgttttt agcagatttc cgatggtatg ggtttcatct tttatcgtga taatggcctt 153540
tgtttttttcc tcatccatgg aaaacagcac aagttccggc tgcggctctt caaagttttc 153600
ataaattttt tgaatgcttt ggattcggcc aataatgatc cggcaggcgt tttttaaata 153660
cgtgcgaacg gcctggttga tatgtggcag cggcaccgct ggaaagcaaa gccccaggcg 153720
gtggtgacgc gggtctgagg tcatagagct ttgcttgtaa ccgctaagcg ccatatattc 153780
ttttttatcc gttgggtact gttcaatgtc aaggtgggaa aaatgtgttt taacggcaag 153840
attaaaggcg gcatgctttc gtcctatgcc ctttttaata tagatatcct ctataatcaa 153900
cgattttccg ggttgtagga agccaatctc aaaggtagga ttaaaaatcg ggtatttaag 153960
cttagggcct gccacctgga tgagatcgcg gctatagatg gttttaacct cacagctatt 154020
gtttaaactc cgcagagcaa ataccagtgt ctcgtttttc gcataaatcg gaatgaaatt 154080
aatgcggttt ctaataaatt gttccgtcat aaacaggtcc gtggaatcct cgatcttata 154140
cccaccgggc ttaatatcta gcatataatt gggaatttca tcttgcaaga cccgcgacag 154200
gccgtggacc gcggctctgc taatgccctt aaagtccata acaacattga ccgggacgag 154260
gggcaactgc tcctcgagct gaaatagttt tttggccgca tttttaataa agaggttgga 154320
aaagtctatc aaaaacggtt tgatttccac gttttggaaa attttttcca tttgtattat 154380
aaatatatct atatatattc aaattatggt agtttatgac ttgctcgttt ctttaagtaa 154440
ggaatccata gatgtgctac ggtttgtaga ggcaaacctt gcggcgttta accagcagta 154500
tattttttttc aatatccaaa gaaaaaactc gatcacgaca ccccttctca ttacgccgca 154560
gcaggaaaaa atttcgcaaa ttgttgagtt tttaatggat gaatataata agaacaatag 154620
aaggccctcc gggccgccgc gtgagcagcc catgcaccca ttattgccgt atcaacaatc 154680
ctcggacgaa cagcccatga tgccgtatca acagcccccg gggaatgatg atcagccata 154740
tgagcaaata taccataaaa aacacgcgtc gcagcaagta aatactgaac tgaacgatta 154800
ttatcaacat attcttgcat taggcgatga agacaaaggt atggacagca tgttaaaact 154860
tccagaaaag gcaaaaaggg atagcgatga tgaggacgac atgttttcta taaaaaacta 154920
acgacgtaac aattaaacaa aaataaaaat cattataaaa tgaatcttga atacgtccaa 154980
gttgttcaaa aatttaatca agtactccta gaacttacca aaaaagtatg taccgttgtg 155040
ggcgggagca aacccaccta ttggtatcac cacattagaa gggtttgctc agaatgtcca 155100
tccatgccga tgagtatgat aggtccgtat ctgaatgtct ataaagccca aattctaaca 155160
agggacaaga attttttat gaatttcgat cccgcgcata atgagtacac ctttatcatt 155220
caaaaactaa aagaagcagc ccgaaatatg ccggaagacg aattagaaca gtactgggta 155280
aaacttttat ttttacttaa aagctacata aaatgtaagc cctttattaa ttaaagaatt 155340
gatgcataac taataaatgg ccggtcgtgt taaaataaaa cagaaagagc tcatagactc 155400
tactgtaaaa aacaaaaatg tgatgaatct gttccatgaa attataggct caaaaggcaa 155460
tattaatttt agcgttgtct ggcccaagtt taaaaaaatc aaacagagcg tttatgacta 155520
catttccact ctttctgtgc tggaaaaagc aaacgttatg caaaactttg aagctgataa 155580
gaaactgttg gaactttttg tacaaaagct gtgggctgcc tatgaaggct atttcaaata 155640
tcccgagatt gaaaaatatg aggtggaagg ccaggtaaat ttcaatctcg tacctcagtg 155700
cgtcctcgaa aagtttagcc agttgtatag gataagaatc aattcagagc ttgtcacact 155760
catcctaaac agctgtgcct ttatgagtaa atataacgat tatattctca aaaaagatcc 155820
ctacatacta accataaccc ccggcctatg cttttccccc attcccaact tcgaggacct 155880
aaattttaaa catctttaca acagtgataa aaattctcag catgacaaag agtttatcat 155940
gtttatatta tataagcttt atacggctgc cctaggagtg tacaatgcca tctcgattcc 156000
agacatcgac gtagaagacc ttgaaaatat catcctatcc tcggtgagcc agattaaaaa 156060
acaaattccg cgctgcaaag acgccttcaa caaaattgaa tcttcggtac acctgttgcg 156120
caaaaatttt aacacatatt acagtgacta tgtgggctca ggctacaacc caaccatcat 156180
tatggaacag tacattaaag acatatcaca ggattccaag aacatatcac cacgcatttc 156240
ctaccagttt agaaccatca tcaagtatta ccgcgacatg attgccacca ggcatcaaac 156300
gatggacccc caggtattaa acctcgtaaa gcacgtcgaa aagaaattag atatgcttga 156360
tagagaaaaa aattagtata tatagttatg gtgaatcttt ttcctgtttt taccttaatt 156420
gtgattatta caattttaat tacgactcga gaactatcca ccacgatgct tattgtttct 156480
cttgtaacag attatattat tattaataca cagtatacgg aacagcagca tgaaaacaat 156540
acatttttca tgccgcaaaa aaattctttt aacgaatctt ataataaaga caaaaaatct 156600
aatatacata ttccctacca gtggctggcg cctgaactga aggaagctga gagcaagtac 156660
tggtggggca attatgatcc tcatagcgag cccgttctcg ctggcgcatc ttgaatatct 156720
tcatacgtgg cacgtcacca tcaaaaacat tgcccaacag cacgggcttg atataaaggt 156780
ggccattgtg gtctcaacat cgcatttaaa taattttttg ccaatttccg gggcgcttaa 156840
catcgaatgt ataaccttcc ccagttgcgg catcaaggag atagacctcc tatgggcgcg 156900
cattaaacta tttcaacatt actgcgccat cggtgcccgt cttttatggc tggtaagtgc 156960
tgacatcagg ccccctgttt cagcgtggcc agccatcgcc gacagtctaa aaaagggagc 157020
agatgcggtc gttattccct acccctcccg atggaacaat cttataccta ccgtcatcaa 157080
agaaatagtt gtccaccaaa aaaaatgcct tgtggcggtg gatgcacgcc accttgatac 157140
agatacccag attgtagggg ccgggatggg ctgcatcgtc ctaaccctaa aggcccttat 157200
ggtgcgccta agtattggca aacagcccgt taagatactg tggcccgacc ttcacggcac 157260
tgccgagggc attcctctgg agggggtgga ggttggctgg tttttaaacg cttatgcgca 157320
taaattaaat atacgctgcc taggggctga tcatattgcg cagcacttaa cttaattctt 157380
tatttaaaaa gtccacgcat ccagtggcgg cctacattaa gggcctacgc acataaatat 157440
acactggcta gaagtacgcc ttcatttaaa ccattgaatt atttatataa tggctgcaaa 157500
cattattgca acaagagccg tgccaaagat ggccagcaaa aaagagcatc aatactgtct 157560
gctagactcc caggaaaagc gtcatgggca ttatcccttt tcatttgaat taaagcctta 157620
tgggcaaaca ggcgcaaata tcataggagt acagggctca cttacccatg ttatcaaaat 157680
gacagtattt ccatttatga ttccttttcc tttacaaaaa actcatatag atgattttat 157740
tggtggacgc atttatttat tttttaagga actggacatg caagcagttt ctgatgtaaa 157800
tggaatgcaa taccacttcg agttcaaggt tgttcctgta agccccaacc aagtagagct 157860
tcttcctgtg aataataaat ataaatttac atatgctata ccggtagtgc aataccttac 157920
cccaatcttt tatgatcttt cgggaccgct agatttccca ttagatactc tttcggtcca 157980
tgtggatatc ctctccaatc atatacagct tcctatccaa aaccataacc taacaacggg 158040
tgatcgtgtt tttatttctg gatataaaca cctgcaaacg attgaattat gtaaaaataa 158100
caagattttt atcaaaaata taccgccgct ttcatccgaa aaaataaaac tatatatact 158160
aaaaaatcga atcagaattc cgctatactt taaatcttta aaaacgtcta agtaataaca 158220
tttttatagt ctactcctag ttccgaaata ggctgaattt ctttttaag tcctttaaac 158280
caaggatgtg atacaagact cttaaaggaa agccgcttat tttcattaat tgttaaacat 158340
tccgtgataa actgttttcc cgtctctgaa atgttctcgg gaatataatt ttcccgtttc 158400
aggatatcat ttaaataaaa attttctgca cgaaatctaa aaagattaac cgcgaccata 158460
cctatcgtcc acacggttaa aggaagctgg tagtaataac cataataata aaattctgga 158520
cacacgtatt cccatgttcc aaacatatta tattggggac gggtttcgtc taatctaaca 158580
gcgcttccaa agtcaatgac cttaatgatc ttttgattta tgtctataat aaggttctca 158640
tccttaatat ccccatggat aaagcccttc tcataaatgt tttgtataat aagaataagc 158700
tggaatatta tttttttggc ttcggtttcc tcaagttttt taaagtaatg ataatgaagt 158760
agatcaacac tatttggaat atattctatg attagtatat gatacatagc attttcggta 158820
tattcgataa gcttaataac accgggagta tcttgcaggg ctttcaacac gatgacttca 158880
tttcctggaa tttcttttt agaaacgtac ttaaatataa tgggttgccc tacttgatga 158940
cccaaaaaga cgttatttct gccaccctca aacatgggtc tcgtcgcaat gaaatacatg 159000
tgctgcgttg tggagatcct ttccaccttt gctgtaggat aaaacgcata ttgtgcctgg 159060
ggattttta acattttttt aagctgttgt tccggcctgg acatgtttta ttagctttat 159120
atataaaggg ttagaaggtt taatttcaat atatgcctta atgatgggat tatattcgta 159180
aaaggtatag cctaatccta cgtctttgtt tttttggtaa aaaaactgtt tgccctcgta 159240
ggatatgcta taggctttta cttcggcttt tacaagcggt tggcagggat tgggcaaacg 159300
taaatcgcgt tcaaagtttt catgaaaaag caaagcattt gtgggctgac acatcagaca 159360
gccgctttcg ccattgaagg cacattcaat ggccgccctt tttagtaaat cgcggaaagc 159420
agaattaaga tggctctttt caagcccccct ttcgtgaaaa cgctcatcaa tcgttttttg 159480
ttcctgactg ccttcgggaa tactataaaa catttttga ttagccaccg cgatgtacaa 159540
aaaaggctgt acggttttct cctcgggcgg tagcgcatcg tggctaccaa tgcgtataat 159600
gcgcgccttc acttgatcct ctcgggcctt atcccagtac ggctctagga tatgaacctg 159660
ccgcccgtat ttgagatcca atccctcagc tcctgtttta gagacgagta aaattttaat 159720
aacctctccg tgtatattca gcggcgaatt ccaaagctgc tggatcatgt cgcgctcttt 159780
agataaaatt ttccctgtaa taagcgtaaa tcgtgttatt ttggaggaca ggactaacgt 159840
atgggtcggc ccatcttccg caaagttttt caccataaga tctttcccat ccttatgaag 159900
gaggatggtg ttgtgccctt cttccaatac ttttaggggc tgaaggcact ggtagccctc 159960
tatttctaaa aagcgggcca cgacgtgaag gcccaattcc acaaactgtg agtaaatgag 160020
cacagggccc ggagacgttt taatattttt tagcatgcgt actattttgg gactagaatt 160080
ttctgtgaag gcctctttgg gcagctgctg aacagcctct gataattttt catcctcctt 160140
tactgttagc atttcggacg cgaagatgct gatcatacgg gaacgcacat agtaggagga 160200
gcctgactct tgctccgatc ctggcaggca gagggcggcg gcatttattt tttcatacat 160260
tcctgagctg gcgtgctttt ccgcgttttc aacgtctcgg gccagcagat attgcctata 160320
ctgctcgggt gacatttcaa ccttttctat aataagagga agctctgtgg ggaatagctt 160380
gttgagctca ttctggtttc cagcgtagct tatcataccc actaggcggt ttagtagttt 160440
gtccgcgttt aaagggctat tcgttgtttt attgacataa gcggtgtaga atctttcata 160500
gtgaagaggt aataagattc gcccgcttag catattaaaa cagggcacca tttcaaaggg 160560
gtccttcgaa cacggggtgc ctgttaaaaa cagaatacga atatttttag cttgcataat 160620
attattgtac agctggcggg catttgtttt atcattggcg ctattgataa ttcctctaaa 160680
gaggttgtgt gcctcgtcaa cgatgagcag gcatccattt agggaccctc ccgcctttat 160740
gatctgctgc cccatgttgt aagcgtctag ggacacaaac ctgaagcgcc gcgagatttt 160800
ttgtagctct ttggagtgat ccgtcgtttc cggatataaa agtttaataa gctttaacaa 160860
agactgttgg aagtttgagt gcaacgactt gggtgcgatc agaatcgggt tgtaaatatg 160920
tgaaagtgag atggcaagcg acaggctcaa aatggttttc cccatgccca tctggtgata 160980
gatgaggagg ccccgtgtgt tttccccctg gcctatccca aatttaggat ccgaaaaggc 161040
ggtgtaaatt aaaaactggt agtatttcag ggctcgtgca aagcgggcag tgagtgaggt 161100
gtctttgctt tcctgaagct ctttatattt ttcatatacc tcttttaggt atgcttctat 161160
ttggacgggg aaggaggtgt tgttgtgcac gcaagacatg actcgttata aggatcccat 161220
attaaaactt cattagaaga atagggctgc tgatagctag cgctgcactt aaaaatgggg 161280
tagccctttt tcttgtaaat ccggtgcctg tcgtagacct ggctagaaag cgggcttagt 161340
gtatctttaa tgtccacaac gatgcgtacc ttttttcat ccgatccctg ccgggtaata 161400
cgtcccaaga tttgctccat gttgtttctg cggggcgttg ccatgatgat cgatgtcata 161460
tgcttgaagg aaatgcctct acgcccgtag ccataggtca gcaagataat ggaagcgctg 161520
tgtgcctgag aaagagcggt atttgaaacc ccgccgcata ggagcgccac ctccggaacg 161580
ataatttgaa catctttgaa ttctttggaa agcgcctgat aaaaaatttc taaaagtttg 161640
cgaaattcca cgaaaatgat gatgccatac ggctcatcgg tcccccattt gtgaggctca 161700
gcggtatgca gggagtaaag ccgctttgcc tcatttacga caagttgtat acgcgaagga 161760
tcttgaagta gtttatcaat ggtggcaatg gccgatacct tttcattaat atacacaggg 161820
ctaacgaagt caggatgtcc ctgatattcg atttccctca cgtacccgga aaaggttgtg 161880
gtgggactta cagtcctctg ggctgtcct agatggtgaa taataatctt gtccatacca 161940
tcgggccggt ccaggggtgt agcggacagt cctaatatcc gactaagttg tattttccaa 162000
aaaattttgt aattctccgg cgagtgtaat tcatgtgcct catctaacac gactagacca 162060
aagggctcaa agaactgctc aggcttcttg cgcagggtat taatgattcc cacgatgacg 162120
tcgtactctt tgctcgtcat gtcctttttc ttgcacgctg cattattgta agcagctaca 162180
cgtaggtggg gcaggagcaa tgttagctcg tcgatccact gtatttgaat cgccttggtg 162240
ggcacgatga ccagggtagg gtacaaaagt ttttgaataa tgctgatcgc aatacgcgtt 162300
ttccccaaac cggtatttag atgtaggtaa aagcgcccat agggggacag gagcttttta 162360
tgaatcttat cgaccatttc ttgctggtag ttaaatagtg gaaattctgt ttcaacgcat 162420
gggagggccc gcagcgacac ggggcgcgtc gtgtaaacca tgttaaacat ttcaaactgc 162480
ttttgcagca atatgggaaa ataaatgtat tccccctgca gcgtgaaggc agtttcctgt 162540
cttatggcta tgtgctttgg ctgcccgggt aatgcccgcg ccgtaacggt gagcgcctta 162600
agaacgcgcc cgaaatcatg ttgtaattta ctttgtagct tcttataatt tattcctatt 162660
ccagcaaagg atataatggc ctccattctc acgctggacg ggttatatgc agaggttcca 162720
aaattcttac cagaggcgtt acgagagggc tgtgctggca agaatcctct aagcttttat 162780
attcaacaaa ttttaaattt aatgggatgt gacggtaacg agtaccatgt tctttttacc 162840
agcagctccg aggaagcaaa tactcatatg atcatggccg ccgtgcgtcg ccatttgctg 162900
cggacgcagc aaaggcctca tgtcattatc ggagcagccg agccccctag cgtcaccgaa 162960
tgtgtgaagg cattggcgca ggaaaaacgc tgcgtataca ccatcatccc cctaaaaaat 163020
tttgaaatag atcctgttgc ggtatacgat gccatacaaa gcaatacctg cttagcgtgc 163080
atttcaggca ctaatgctgt tgtcaaaacg ttcaacaaac tccaggacat cagcaacgtg 163140
ttaaaaggta ttcccctgca ctcagaagtg agtgatcttg tttatcaagg atgtattcaa 163200
caaaatccgc ccgctgatag tttttcaata aatagtctct acggcttcct gggagtcggt 163260
gttttgggaa tgaagaaaaa ggtcatgcaa ggattggggc cgctcatttt tggaggaggg 163320
ctgagaggcg gaagccctaa tatacccgga attcatgcca tgtataaaac gctaacccag 163380
caaaggcctt ctatgaaaaa aaataaatac aatacatacg ctgttcatga aaactttaaa 163440
aaacatcagc atgtatatct acccataggg ggcgtgtctg cagaggacac gtctgcagaa 163500
aacatatcta caaaagacat gcctgttgaa ggcccgaagg gactcccggg ctatatttta 163560
tttagcgttg gccgtcgcgc cgaggagcta caaaaaaaaa ttttcactaa atttaatata 163620
aaggttggcc gtgttgttga cttacaagag atactgtttc gtatcaaaat accccaaaaa 163680
tactgggaga cattattgtt catccaatta agagataatt tgaccaaaga ggacataaaa 163740
agagttatgg ttgttttgat gcatttagat accatcactc ctcgtggctc tcttcctcct 163800
ccgagccact cttcttcttt ttcttaatcg tttttgtttg ttctataata agggaaaaga 163860
actccgtggg atcttgttcc ccgtacaggt tatctgcgac cataaggatg cttagaatgg 163920
taaacaggtg agaatacata agggtttgcg ttttaagaaa accctgacgt tgaatcataa 163980
ttgaaaacac cttgcaaagc cgactcatca gttgttctgt aatggcgtta agcattttct 164040
ggaatttttc ttggttttcg ggtgtgattt tatattcatg tagaaagtgt ttcacacctg 164100
aggagaagaa tctttcctcc ttcgagagcc catctttgat gatgggaagt tccttgatca 164160
gggcaaacca ttcctcctct tgggcttgcg gattctgaag atactgatgg cagatatggt 164220
ttagaatggt gcacacgtag ctaataagct ctgagctgat tctttggttg gttttcaaat 164280
gttggcgaaa gtagtttttc accgaagtgc atgtaataaa cgtcttcatt ttcttataat 164340
atacaacagt atgttgagtc tttaatttaa aattacaagg agttttctag gtctttatgc 164400
gtataggtgt ttctttgtcg taaattttca atagccgaca ttgtttgtga agcagtgttc 164460
tgagtagtga ctgtcgtgta aggctcagcc ggatgagcag gagcactcgc ggccgcaggt 164520
gcggccgccg gcccgccagt tgccatgact agtctgtccg taactgggtt gtccgtaact 164580
ggtttgtttg ttgctggtct gtttgttgcc ggtctgcccg tgactggctt gcctacactt 164640
gctgtagtcg ctccagctgg tttagaggta cctggttgtg gagtgacttc tacccactgc 164700
tgatcttgat aaggatttat aaactgtata tcttcctcct caatagcagc agctttttc 164760 tttcttgaag agaatagata gattagaacg atgataatga tgactaagac cacgatagca 164820
atgagaatag tatacatatg tgtggagaag aagcttggtg tagtgactgg tgacaaacac 164880
tcaccataat gccgcggata aaccggttga aaaaattcag aatccattta agatactatt 164940
ataaataata tataaaaatg ttgtggcgca atgaaattac agaatttatg gaccaacttt 165000
ccaagtattc tcaagaaatc ttaaaaacgt ttaagcaatt gcgtcctagt gaatataaac 165060
aatacaatga atttttaaca caagttacac cgttgctgca aaaaacccct gaaaaaattc 165120
cagagttggt tgaccatata ttcaattacc tagacaacgt tgaaaaaatt tgtgagctcc 165180
tcgtgaatgc tagctcaatt attattagtt caaaaatacg agaacaagta aaacacggaa 165240
tgagcttcag ctataaagcc gacctcgact ccttggcgga cattctctct caaaaacagt 165300
acgtgcttat gcatctttca aaaaatattg cggccgagta ttttaatacg tgtttaaacc 165360
aagggaaatc caagttagat ctcaaagctg cctctgtatt ttatagtagt cgttcccgaa 165420
cggcaagctc agcagaactc tatagaaaaa tgctatacgc ctatggttca ccgcaggaaa 165480
ttaattatta tactgaaaaa gcccgaaata agacgttgga tgtggaggag agcgacagca 165540
tggccatcat cgaacgaacg gcccgacaca acctttccct tatgcacccg ctagaagcca 165600
tggggcttac ctttggggca accaacacgg acgccgaccc ggaggatctg aaggacaaaa 165660
cggtgataaa tttaacgctc ccgcaggcaa cagaaagcat cacctaccat cttaaatccc 165720
taatgcagct aaaaaaagta agtacggctt caggactaaa tacaaacatt ttgaaagcat 165780
ttgataatat tatttccacc cctgtgaaaa aaaataaaat ggcctccaag ttggcgcccg 165840
ggatggatgt cgtgttcact agcgataacg gaaaaacatt ttttactaaa aacattttaa 165900
gcaaaaacat gctagcgggg cccaaagagc gggtgtttgc atataataat ctcattagta 165960
atttaaataa ctcctgtttc atacaaaatc acaacgattt tttaagacag caggactctt 166020
ggcccttcta tgacgcgcac aattttacca acaagttttt aatgcagcct attttttcgg 166080
ggcagacccg tcctcggctt cagggagcca tggaggcggc gcatgtggaa acgcatctca 166140
cggcattttt acaaagtatt cagccctcta ggccacaaga tccctctgtt ttggcttccc 166200
ccaagttatc tgctctaatc ttgaactaaa aacagccttt cttggactta aatgatggtc 166260
taccagtttt tgaaataact tagagaacta tgaagatttt catgaaattt aaattagaga 166320
tttgcaaagg ttacttgcgg tcattttctg ttgaattaaa taattattcg aatagtataa 166380
tgtctgaaga tattcgtcgt ggtcctggca gaccgccaaa gaaaagggtt gttcccaact 166440
ttgagcgcaa gggcattctg gaaaaaccag ttcggccaca aagccgtctc gagttttcct 166500
atgataaccc gctgatattt aaaaatcttt ttatttactt taaaaacctt aaaagtaaaa 166560

-continued atattttggt gcgatgtacc cccaccgaga ttaccttttt ttcacgtgac cagtcgcagg 166620
caagctttgt tattgccacc atcgacggaa aaaacgtgaa ccattattac gccagtgatg 166680
tcttttggct aggcatcaac agagagctcg ttgaaaaaat gtttaacagc attgatcgct 166740
ctttttttaaa aattaccatc gttcaccgct atgacaagcc tgaaaccctg tttttttatct 166800
ttacggattt tgacattgac aaggagtgca cgtatcagat tacggtctcg gagcccgagc 166860
tcgatatgga ccttatcgaa atggaaaaaa gcatcagtga agaaagactc aagaactatc 166920
ctctgcgctg ggagtttacc tccaagcagc tcaagaaaac atttagcgac ttatcaaact 166980
acaccgagct cgtgaccatt gaaaaactcg gcggcgatac gccgctgcac ctgtatttcc 167040
aaaagtttaa ctccatctca taccacgaga tgtataaatc ttccaacaag atcaacctga 167100
cctcgaccat tcctaagtcg caggtgttcc agataaatgt taaaattgct cacatcaagt 167160
cgctggcctc ggctatggtc accgacaaga tccgcattct gtgcgaagaa aatgggaacc 167220
taatctttca atcggaaatg gatgccctta tgttaaatac gattaccttg aacaccacga 167280
tatagttcgg taacattaga tgttctaata tttagcatct aaataatacg ctgtagtccg 167340
gtcagggttg cgtcacagtt ttcccatttt tttgcctcgt cggcggtggc caccgttgcc 167400
ctatcattta cgcccggtaa gacaaagcta aaggcgttca gcggggcttg gcaatgcccg 167460
cccagcgtga aggagctcgg aggattttgc gcatcccgaa atcccttagc catgttgttt 167520
aacacttcgg ttacgtcaat cgagtgaagg gatcccttgg gatccgtgaa tgtaaagacg 167580
cagtttctaa agcgcatgta tgcgatggac gattcatcgg gggttttgaa ggtaacagtg 167640
ttccccttgc tgtacttaaa gggggaccat ccggtaaaat tataccaaat gaaagcaata 167700
ataattaaaa taaccaacac aatagttata gacaacacaa agtctgtagt gccgcccatt 167760
attaaataaa aatattttag accgccggct taaaatttac ttattgctca tagcttaagt 167820
ctattttatt catagcttaa gtttattgct catggcttaa gtctattgct tatagcttaa 167880
gtctatttta ttcatagctt aagtctattg ttcatggctt aagtttgttg ctcatagctt 167940
aactccatta ctgatagctt actgatcatg acttaaataa aaatattttg cccgcttaaa 168000
aattgtttag gtttgaaaaa ataagagatg gagggggcaa cttatcgtca ttgtgtttac 168060
ccccactgga agacatcaaa cggtaaataa ttataagaat caaaatgatt aatataaggg 168120
ttaaaaaagg atgattcatc acattaatta aaaacgtatt tataacgctg ttgcagttga 168180
aattttggta taggtcggaa atattgcccg agcctccgta ttctgcaatg ttctgacata 168240
tggtgagtcc ggaggggcac tgcttgttgg tcaaaatatt tctttgctcc gttgttttat 168300
aggcattttt atttccatta cacggagcaa acgcacattc aggccatagg gtgccggagt 168360
tcacacaggc acaatactgg ctatacgcat actcatcctt tgagcacaat ccctgtttat 168420
cgcatatgct cccaataata ttgtcatcct ccgccgtttg ttgatttgta tgcgagcgta 168480
aaatagcggc ccaggccttg ggctcctttt tttgcagctc ggaaatcgaa gggcctgtac 168540
agctaaagtc gacccaaata tcattgcatt tcgtggaaac tggcatgcaa gacataattg 168600
aaataattaa taagtatata tcatggcaac aaattttttt attcaaccta tcaccgaaga 168660
agctgaagca tactacccac cttccgtgat aacgaataaa cggaaggacc tgggggtaga 168720
cgtatactgt tgctccgacc tagtgcttca acctggacta aatattgttc gcctgcatat 168780
taaagtagca tgcgaacaca tgggcaaaaa atgcggtttt aaaatcatgg cgagaagcag 168840
tatgtgcacc catgaacggc tgctcatcct tgcaaacgga attggtttaa tagacccggg 168900

-continued ttatgtgggc gagctcatgc tcaagatcat taatcttggc gacaccccgg tccaaatatg 168960
ggccaaagaa tgtttggtgc agttggtggc ccaaggtgac catgtgcctg accatatcaa 169020
catcctaaaa agaaaccaaa tatttccgct gtttgcgcct accccaagag gcgagggtag 169080
atttgggagc acgggcgagg ccgggattat gagaacttaa ttttattttt tttcttaaca 169140
taatgggagg ctctacaagc aaaaattcct ttaaaaatac gaccaacatt atcagcaatt 169200
ccattttcaa tcagatgcaa agttgtattt ccatgttgga tggcaaaaat tacataggcg 169260
tattcggtga tggaaatatt ttaaaccacg ttttccagga tttaaactta tcattaaaca 169320
caagttgcgt gcaaaagcac gtaaacgagg aaaatttcat tacaaatctt tcgaaccaaa 169380
ttactcaaaa tttaaaagac caagaagttg cgttaaccca atggatggac gcaggaactc 169440
acgatcagaa aacggatata gaagaaaata taaaggtaaa cttaacaacc acacttattc 169500
aaaactgcgt ttcatccctg tcgggtatga acgtgctggt ggtgaagggg aatggcaaca 169560
ttgttgaaaa cgcaactcag aagcagtcgc agcaaatcat ctctaactgc ttgcagggga 169620
gcaagcaggc catagacacc acaaccggca tcactaacac ggtaaatcag tactcacact 169680
acacctcaaa aaactttttt gacttcattg cagacgcaat ttcggctgtt tttaaaaaca 169740
tcatggtcgc ggctgtagtt atcgttctaa tcatcgtagg gtttatagcc gtcttttact 169800
ttttgcattc acggcaccgc catgaggagg aagaagaagc tgaaccactc ataagcaaca 169860
aggtattaaa aaatgctgcc gtttcgtaat aatttaatta aaagtaaaaa aaaaggtatt 169920
gttatagtga tggcagattt taattctcca atccagtatt tgaaagaaga ttcgagggac 169980
cggacctcta taggttctct agaatacgat gaaaatgccg acacgatgat accgagcttc 170040
gcagcaggct tggaagagtt tgaacccatt cccgactatg accctaccac atcaacttcc 170100
ctgtattcac aattgaccca caacatggaa aaaatcgcag aggaagagga tagtaatttt 170160
ctacacgata ctagggagtt tacttcactg gtccccgatg aggcagacaa taaaccggaa 170220
gatgacgaag aaagcggtgc aaaacctaaa aagaaaaaac atttgtttcc aaaattaagc 170280
tcgcataaat cgaagtaaaa attgaagcga aaaaaagtag aaaaaaaatg tttggagctt 170340
ttgtaagcca ccgtttgtgg tcagatagtg gttgtacgac cacctgcatc acaaacagca 170400
ttgctaatta tgtagccttc ggcgaacaaa ttggatttcc ctttaaatca gctcaggtat 170460
ttattgccgg ccctagaaag gctgtgataa atattcagga agatgataaa gttgagcttt 170520
taaagatgat tgttaagcac aatctttggg ttgttgctca tggaacctac ttagatgtgc 170580
cctggtcccg taagagtgcg tttgttacac attttataca acaagaacta cttatatgca 170640
aggaagtcgg tattaaaggg ttagttttac acctaggcgc tgtggagcct gaacttatta 170700
tggaaggact aaaaaaaatt aagccggttg agggggttgt catttacctg gaaaccccgc 170760
ataacaaaca tcatacatat aaatacagta caattgagca gatcaaagaa ttgtttttac 170820
ggatacgaaa taccaggttg aaacagattg gtttatgcat tgatacggct cacatctggt 170880
cttccggtgt caacatctcc agctataatg acgcggggca atggctgcgc tcgctggaaa 170940
acattcattc cgtgatccca ccaagccaca ttatgttcca cctaaatgat gccgccacag 171000
aatgcggaag cggtatagac cgacatgcaa gtctttttga aggaatgatt tggaaatcat 171060
atagccataa aataaagcaa agcggtttat attgttttgt tgaatacgtt acgcgacacc 171120
agtgtccggc tatattggag agaaacctcg ggtcttccat gcaattacaa accgctttaa 171180
ccgcagaatt tactacatta aaatcgttat taaaataagg atgagtttta gcgaatgtcc 171240
cttagttatt agtgcatgca aaaaatttct acaaaagcgt attacaatag agaatgaagc 171300
acttataaat gccttaataa ccgctttagc gcagaccagc acgttgaatg atctttgttt 171360
attacctatt caaacctatt tgcttagtta taaaaatgct tttgagtgga tacacttcgt 171420
atgtattgca atcaccacta ttttggataa taagtataac tggaaggact gtacggtaga 171480
tattaattat atttttctcc atgtaaccta tatttacaat attaaaacca aggaatacct 171540
agactactgt tcttaaactt tattttttct atatttacgc caaagagaat atttaaagtt 171600
tttttgaaaa aaataatata tgtagataaa attcagttac atgatatatg tgtaaacatg 171660
tgtggtaaac aacatatggt tatgctttat aagataaatg cgcataatat atgtaaacaa 171720
aatatggtta tgtgttaaat gcatataaat gtattttaac gtatatcttg tgataatgga 171780
tatatgcatt tattaaaaga ggctgtattt attataaatc ttgctaagga tgccattgtc 171840
aacatatatc ccatgttgga caaattgcgt tgcgatccag ttcttttttt ttgattttgt 171900
ttaatgctat cctttttgaa gggatggttg tccaccatat ttattcgatg ttcaatgaat 171960
aggtctgctt tttcgtaagg cagtgaaggt cgttccaaga ctccttgaac gatggacgtg 172020
ttttcttgga tccacttaaa aagcacgtgg cattcaaaaa caggacagtg attggatcct 172080
tggatatgct ttggacagcc aatgcttgaa gagatgtagt ccctttttctt taggacaagc 172140 ttctccacgc tggggcaaca gagatcgttc aagttctgga cggtcgcatt tggaatgttg 172200
aaacttcgta tccattcacc ctcgggtcct cccttatgaa gaaggagtat ttgctcatgg 172260
tccttagtaa tcttaaccaa atgttggaag atcatttttt tacctgcttt aaaggcctga 172320
agggtgtcag ttggcaaagc tattgaattc gggagtgggc tttcatcaag cgtgaaatgg 172380
tgaatgtgac gcgactggaa agaaaacgac cgttgattta ttttttcaaa gattgggtcg 172440
attccgccat gaaagaacag ctgcaagatt ttagaaggcg tatttttttc ccaataaaaa 172500
atgaccactt ctcgtgggat taaaatcgtc tgtgtcccat tttcattata taattggccc 172560
ataaagccat caacgtcaat caacaccaaa agcatggtat agagagcttt tagaaccgga 172620
gttcgttaaa aaaatacaaa gttcgtttaa aacgtgtaat gttactaaaa aaatgtaatg 172680
tttaaatgat aatgatacca catgcattaa tgaaaaaaac ttttaaattt ttgttttaat 172740
atttgcatga aaatggaaac atttttagtc tgtttatttc acaatgcaga tggtttacat 172800
caacagattc aggaaatttt gtatttattg cggatgcata tttacgaaac aaatctttac 172860
ttaaagcagg aactatcacg gcttatatat ccaaataggc aactttcttt tgtgttactt 172920
atgccccttt cccttctaag aaactgggat gacattgaat atttaacgga cgttgtagat 172980
gataagcaga ctctacatta cgcggcaaat ttgctgacaa actacgttct acatctatcc 173040
atgtttcaaa agctgacaaa accatacttc cttttagcgg tcaagcgggt cagcgaaaaa 173100
ctcaacaaaa agcagcgaca ttcattttac gaggtattgg taacctccga aaccttgaat 173160
aattatgaaa acctatctaa aaacatttta aatacgttga tgtttgccgt gcgctacgta 173220
tttaaaccta cgccgaacta ttcagaaatt ctcgcagagt tggaaaaaaa aaataaaatt 173280
caccatatta tttttaatat ggtaattacg gattttgcgc aaatccgtga acaacaaatg 173340
gataaacatc tgtgtgaaac aaataatgag cttcgtcagg aatgtaaaga aactattttt 173400
gatttaaagg tggtaggaaa tgtttagcca ataaactcat gcccgcattt tttacaggta 173460
caaaatatcg tggatggctc atcgagggcg cgtgtttgta cttctctgta ggtacacata 173520
cgctgcttgc agttgggaca cttataaagt tgtgacgtct tttcggcgac cttttgctgc 173580
gaacgtagag taatttctgt cttctccttt aaggcggcag aggggcaaag ctcggcgaac 173640

-continued

```
gtcatgctac caattgcctc cggttttagc tcgccagaaa ttagcttatt aagggcatcg 173700
ttatcctgtt gttggtgact tttttttcg cagttaataa tatgattgat cgtcccacaa 173760
cgggttgaat attcttctaa aaaggttttt tcttgttgct ggtacgtata atgataacac 173820
gaggcctcga tttttgcgc gtattcggtg cataaatcag tatgttcctt aaaaaacata 173880
tgtttttgaa gcgttctaaa aaacatcatt tggatgatat cacgcatttc caaaataata 173940
tagggttcta gtcttttgga atctttcata actagatcgg tggtaatatt cttagtcata 174000
caatttatta aaaatggttt aatatattgt aaatattttt taggcgtgtc agcctgtaaa 174060
aaacattctt gttcaatctt atttgtaagg atagtatttt gcaaatactt atttagcaaa 174120
aatacgatag aatcgcgggc tatatgcatt ttcatataat tttttttaa aatttaatac 174180
aaaaaaaaga agtatagact cttcttctag tccggttagt tcgttggttg cctcaacatg 174240
gagactcaga agttgatttc catggttaag gaagccttag aaaaatatca ataccctctt 174300
actgctaaaa atattaaagt agtgatacaa aaagagcaca atgtcgtctt acctacagga 174360
tctataaata gcatactgta cagtaactca gaactttttg agaagattga taagacaaat 174420
accatttatc cccgctttg gatacggaaa aactaattgt aaccagtagt acatttaagg 174480
atagtttaag cagtaaatgt agaataacac agttaagcaa taaataacaa gtatatagga 174540
atatatagga atatatagaa atatatagaa atagctaagc ttaatactaa ttcagctttt 174600
tttttaacta aaacctgaat agatgcgaag tagcggacat atacatacta aaataagcca 174660
tacatttact ttcttcttga acatgaaacc ttttttctt ctgttgttgg tatataaaca 174720
ataggactgt ttgctgaggt tgtatgatct tctacaactg ctgtctcagg atgacgatgt 174780
tttttaaac taaaagtgta ggatggaatg agtggaatat agttatggct cgacttatcc 174840
tgtttcgtac aggaatattt tttacaaata gaacgcaaca agcatatgaa taaaaacaga 174900
aatgatatac aggagcataa aatagatatg aacactaagg ggtagcagct tttataacgt 174960
tccgtatttt tcttagctat caattgattt accgtaatat ttatctcggg aaactttgtt 175020
ctacaatatt ttgtttggta ttccagaaac tcatgtcctg gcttattccc gcagcttaaa 175080
aaatgataca aaaatgtgtt attgttacta aaattaattc ttcttaagaa aaactgcgga 175140
agacgcttta ggtacgtctg ttcctgtttt agtaggaagt agtataaggg acaatttctt 175200
tttccacaca ttagattatt gtaatatagg taggttgggg tgttggagcg aataagtttt 175260
ctgagtatgt tataatctat gacttgtaaa tcgttatacc ttaggtccaa aaacttgagt 175320
tctttaccaa agccacctgc aatttcagaa atatttttca tcccgcagcg gataatacgg 175380
atgtcctgaa acgtctttaa aatacttgta ttgtagtgaa tacttatgtt attttttgt 175440
aaataatcta tgtcatgaca agtgcatgaa atgccagcag cattgcttgg tatagtatta 175500
tatgcaggaa gaactatact actattgaga atagtcacat tgtacttata ccatgtatta 175560
ttttctgata taaagtattt gcaggtgacc tgtggtttaa tcctacctgt taagccactt 175620
cctaaaaaaa caaaaaatat gaaaaccctt agcatcctgt atatactatt aaaaatttat 175680
aaaattttct gtttaaattt catttagaca aaaaaataat atatatacat cagcaagaaa 175740
ttatatacag attatataat tttctgattt tttttgcca caataagcat cattatatgc 175800
attaaaatct caatactaaa cactaaaatc taaattctaa gcattaaatt ctaagcatta 175860
aattctatgc actaaactgt aagcactaaa atctaagtaa ctaaaatcaa cactaaatgt 175920
atgcaaccta aaatgtaaag cattactcat catcctcctc ttcttcatcc tcatcatcat 175980
aggttaagat atatgtgtca tcctccattt cttcacattc atcttcataa gcatcactgg 176040
```

gtattggtgg aacattggat gcagcatttt taaaatattc tatgtcttct ggtgaacact 176100
catctaatga tttttgaca gtccttttaa cttccatggg atatgattcc aaatcctctt 176160
tatataagag tttacggtag cttttagctg catccacatt tgctggagaa tctggatttg 176220
gctcattgag cagtgaaatt acactaagaa gaatggtatc aatcttttga gccggagacc 176280
aagtcattcc ctgttcttca gcattgtctc cgtgtaagat agagatacat agttttccat 176340
cagagtaaat attaggatgc cacatttcag aggtgaatgt taatctgggt ggtgcatatg 176400
ggtattctgg aggaaaggcg atttttgcct tgaataagcc tccctcataa aaagtgtcag 176460
gtgggcccct taagatcaca tcccattcag tcatatcctt ctcattcacc gaaattttga 176520
aattctcaga gggattctct atcaggtgtc tgtactctgc tattaaaaac ctggaaacca 176580
tggttattta atattaatta aattccctgg tttattcctc cttaaaagta gatgaacctc 176640
ttttgttttt tattgggttc atttttacta aatttatgaa ctggaaaaaa ctttaacggc 176700
ataattatca aatgcgaagg gggatccgta taaaatccta gcttgccggt aatggctatt 176760
aagttaaatt tggtaccagt aacactaata tttaaaaagc cctgatcatt aactttccac 176820
attaaaagat tattatattc gaatgtttgt ccaatatgga caactttgtc accagatgtt 176880
acatttgatt tggttgttag tggctgaagc ttggcacaat caaaaataag cccattaaca 176940
ctaagatata gaggagtggg ttgatctatt ttctcatagt ttaatattcc atctttccac 177000
gtaatagctt gataattatc cgcagcaatg agttgaaatt ttataaatag tacaggggtt 177060
ttagttgtcg ttatacattt aaagggtgtt ttataaaaat aaaaataata attgttaaaa 177120
gtatgataat aatcgccaaa ataatttcat acatttttta taagaattat acatagtatg 177180
gtatttaaaa tattagctaa atttaaaaaa acttcatgat ttttaaaaca gggaaaaagg 177240
ggattaggtt gaataaaaaa ggtaagcact tgtctatata tttttttac aatgttgcct 177300
tgagtcgcat ttttaactgg ctggggagta tcagagtgga atatcactgt agtaggtcta 177360
taaggtcttg ttaaaatatg atcggtcatt gttttcgtac tagtgtcatt tagggtcgac 177420
ctgatagctc gatataaagt tataggggat aacctatcaa atacagtctt atctgtgctg 177480
aaatgtatat cgtcttcttt atcactaata atattaggaa tggctgtcat taaataatta 177540
ctacttgttg ttgtgggtga aatagttgta ctggtattat tggaaatggc tgtcattaaa 177600
taattactac ttgttgttgt gggtgaaata gttgtactag tattattaga aatggctgtc 177660
gttaaataat tactacctat tacaagtaaa ctaatgctaa ctacattttt aacctcaata 177720
aacctaaaaa gccatactaa atacctaaac aacatcctgt tataatatga gcagaaaaaa 177780
aaataagtat aattagggaa ttattcttat tcgcttacta ttaagaataa ttcagaatct 177840
tatttagtta gaaactatca taaagtgaat aggactcatc gtcggatgaa gattccgttt 177900
cagagatagt ttctttttct tcctcagaat aatctgttcc tacaatagaa tcggtgtcat 177960
cctcagaaag agaagtattt aaatatggac tatctatagc aatatcctct tctatctcgc 178020
aatcctcctc ctccatttcc atagtgtgta ggagaatatt tttatcatca tgctcacttc 178080
tttttttgtt gaaagatgaa ccgtcctcaa tacggttcat gttaagttcc ttcatcttat 178140
gtataatttc cgtaatccgt gatgtttttg acatgtaaga tggttttaag gttatatcca 178200
caataacagg agaatctcta tcattttcat ttgataaact ttgatctttg atttcttcgt 178260
ctaaaattct tgtctttttt tgggtactag atgaaataga ggaattcata ttctgaaacg 178320
atatatcaag gggagctgga cgcttttttc caattaaacc gtttttcgag atactatgat 178380
tagatgaatg atctttagcc aagctgtcct tggatatact atagttagat attttacctt 178440
taaataatat tcttctatac aagttattct taggtaaaga attagtatgg attcctatat 178500
ttttatctga aggagtgtcc atatcggaga acgtcctctt acgaatattt tgaccacgag 178560
ccatttcatc cactataggc agtattttgg ctggctatgg ttctttgttg tgacaattct 178620
atgagatttg attgcaaatc aatttttagt tttaaatata ttggtaccta ggacaaagaa 178680
agtatatata gccaataatt attccactaa attgatttcc agactgatgg gtatggagcc 178740
atgttgtctc tgcagacgat cgcaaaaatg gccgtagcaa caaacaccta ctccaagtat 178800
cactatccaa tactgaaggt ctttgggctg tggtggaaaa acaatacgct aaatggccct 178860
attaaaatat gtaaccattg caacaacata atggtaggag aatatcctat gtgttacaat 178920
catggaatga gtctggatat agctttgatt cgggcagtaa aggagcgtaa tatatcctta 178980
gtccagcttt tcaccgaatg ggggggaaat attgactatg gggcactttg tgctaacact 179040
ccatctatgc aaagattatg taaaagtttg ggagccaaac caccaaaggg ccgaatgtat 179100
atggatgctc ttatacatct ttcagatacc ttgaatgata atgatctgat tagggggtat 179160
gagattttg atgataatag cgtgttggat tgtgtcaatc tcatacgact caaaataatg 179220
cttaccttga aggcccgtat acctctcatg gaacaactag accaaattgc cttaaaacaa 179280
cttctgcagc gatactggta tgccatggct gtacaacaca acttaacaat cgctatccac 179340
tattttgata atcatattcc taatataaag ccatttagtc tgcgctgtgc tttgtatttt 179400
aatgatccct ttaaaatcca tgatgcttgc agaactgtaa atatggatcc taatgagatg 179460
atgaacattg cttgtcaaca ggatttaaac tttcaaagca tttactattg ttatctttta 179520
ggggctgata ttaatcaggc tatgctaatg tctttaaagt atggtcatct ttctaatatg 179580
tggttttgca tagatttggg ggcggatgcc tttaaagagg caggggcgct tgctgagaaa 179640
aaaataaaag agtgttacaa cacatattag gtcttaatat ctttaagcga gagttgattc 179700
ccccctgtaa agatcctgat ccttatcaaa tccaaattct gttaaaaaac tacattctaa 179760
aaaatgtctc aactgttttt acatattatt gccagtagcc attgtttata tcagaaaata 179820
acccatttgt ttatcttttt ttgtggggca accattaaga cccgacgcaa aaaaagatta 179880
atcttttatc agatacctaa aacgttctat aagggagtct atgagatgga tcatattttg 179940
atggtcatag taagaagcaa gctttttggc gaaaacaacg gagttaaaga atttaacccg 180000
ctcatgtttg gataggactt ttaacagcga gccaaaacag tatttaaaaa tttggcaata 180060
gttttttgg gatgcaataa acaaacactt gatcagtgcc cgcttcactt tctgatcaga 180120
catgtttgcc gcataacagg ccttttaaa cttagtaata taattatgtt ccgcaagcac 180180
cattaacaag ggaacgatgg gaagctgctt ttcttggtga aatttacgta aatattcgat 180240
ggccaccgct tggacgactg tgtaatttac taagttagaa atgatagctt tcatggttgt 180300
aaaaatatac ataggatttt ctttttctgt atacagtttg aaaagcttat gattacgtga 180360
aatgatggcc atttttaata caagatggta tagtgtatct ttaggtaaaa atgccttgca 180420
agccgcgatg atgtcgatgt tgtctccatg aacagcgata gaaactaatg tttccaatct 180480
aaatgttttt atctgcatta atagaagaat gcagtcaatg ttattatact taataatact 180540
gtaatacacc gaatcaatga ccgtcatctg agaatcaagc tgacttatta gtaaatttaa 180600
cgtttttttg gaggcatgac ctttgatcgc ggcactaagt gcacacagta tagcaaaatt 180660
gttaaataca ttttgattta ggagaaggag taatattttc cttcggttat agtacgcagc 180720
atctgtgatg attattggcc gataaatgtt aaaatgtgtt aacagctttt taaaaaaacg 180780

-continued gaagtaattt ttttggatcg ctgtttgcat catcgaaata atgagataat cagggtatat 180840
aatgggtagg tcacatgcta cctctaacaa agaatagtcg cccaatctaa aggctgtgtt 180900
gaaaagcgta ctatcatcat acgtatcgag taccccctgct gttacaaacc aagcgataag 180960
atgaatgtgc cgttccttgc aagctatcgc aaatagggag tttcctatgg aatgtcgaat 181020
aatgtactcc ctattttttt ccaaaatgtt tggaaaattg tatagcgttg cggcatacag 181080
tagacactcc attctggcgt tataattttt acttttacat atgaataggt ggaagaactc 181140
gaataattct tgagaacttg ttaaatgcat aatatggtga tattttggtg tcgttaaatg 181200
gtatgagaaa atgcattcta atacatcttt tcggttatgc tttagcgcct gagctaaggc 181260
atattcaggc tcgacccata ggactagtgt ttctataatt gagatattcg cctgctttgc 181320
cagggcatac tttaagacgc tccggttaga aaaaatgttg ttatgaagat ggataaccgt 181380
atccattttt acgatgggac cattccagta tagtcctaaa tgctgtagca gatcttttgt 181440
tagttgtgaa gcgttctcgg gtgtcatata aatatgttgc agggcttttt tctgtaagga 181500
gaacatttcg tcgtaatcgt acaaaaaaaa ttaaaatttg ggcatggatg attcaaacat 181560
aacaaaatca agattttata acagtttgca ttaacctata catatatgca agtaaatgag 181620
atattatcta tcataacgaa tcaagggata tttgtatata tcaggagttt ctgaaataaa 181680
gatatgaaga ttatcatagt agtatccatc aatcacaatg caacttcctt taaggcataa 181740
tttagtaaac tcagcactcc catcttctgg atgctttaca actaacatta aaaactcctc 181800
agtcatatta tctgtaataa aataagatcc tcctggagcc atttgtagca tgtctcttat 181860
tcctacaaaa tctttttttgg gatggtaaaa actcagcagt ttcaaactct tttttagttt 181920
tttttcctgg tatttaagcc atttgttata aaacagtttt cttatgaaaa tgcatttgaa 181980
aatattggga atgtttaacc atgcttcttc cgagcacatc tccagatact tactttcttt 182040
gtttcccatg tctaatttat tgctcactaa gttagtaatg aatctatttt aataatctac 182100
tttactaatc tatcttaata acctatctta taatctatct taataaccta attataacct 182160
atttataatt ggctaatgct gccggcattt catgcctatc taaacaactc ctactaagca 182220
atctactatt acatatatag attcactttt tatatttgta aatcatgaga attataaaat 182280
cattactcat ttttattgta aattagtggg tatttgtaaa aatcttcaaa cgttttaaga 182340
tagttttcta gagagaagta atctttgcca tcaatatata atgcttttcc tttaaactcc 182400
agttttgcta tgtttagtga gccgtttcta gatctttttg ggcaataaat agattttcat 182460
tggttgcatc gtccgtaagc agaaaggtac cactaggcac gttaaaaaac atacgttcta 182520
tttcatggtc ggatttttga gaatagaaaa aatctaattt tttaatccgc gttaactctt 182580
ttttatcaat ctttccagac tgttttatat atactttatt gcaaatctta caatcctcta 182640
tggcttcatt atacttattt tgcttatcct ctattgacat gtccgtattt gataggtaac 182700
ttccgttaag gcggttcccc atggttttag atagattttt aattcagttg tatactttta 182760
ttatgaggct aaaatataga agtttgatcc taaaaaaata aaaagatttt gtacatttat 182820
ttatggttta tagcggtata gaggccgata aaaggtatcc gggtagtctc ctatgatatc 182880
gtcaattttg gtataataac agttgttatg gtagtattgt ccaaaccgag tatgtatgcg 182940
ccggtgaagc gtccgcccgc taatggtaca gttccaggtt aagacaatca tatcacaccc 183000
aaaaagagag gaaacagcat aggtgcccaa aggttcatta tataacatac gccgcatata 183060
ttttagtttt ttttctccat ggtaataatc acaggttttc atgtcctgct taataggatg 183120
attccccatg tatgataata tataataaat ttagttttta gctttttcaa aaaattgggc 183180
gctcgaaact aaattttcct tatcacagcg tttggagaaa gcgtatttaa agatatatct 183240
tcttctaaca agactgcaaa aaaaatctta ccccttattt ttataatgtt catcatagcg 183300
tttgaagata tcagaaggtg ccaggtttta taaaaatatc ctttaggatt tataacgata 183360
caagggtcta taaaatatat gcgggtataa tcttataaaa tcatcgattt tttcataata 183420
ttctccgttt atacaataaa gatcataaca gatattgatg cgtagatgca ttattcgcgt 183480
gttcgttggg cagctaaagg atatcacaac gtagtttttt ttaagaaaag acgaaactac 183540
ataagtccct aagggttcat tgaatagtaa acgccatatt tgttttaaat tttgttgttc 183600
accatagtag tattcgcact ttttcaagtc ttttttaata agcctattcc ccatgtatgc 183660
ttataaataa aaatttagaa atgtgctata ttatttgttg atgaatcatg aacacgtctt 183720
atatgttgat atgttacttt aaaaacattt gtattttcaa cagacgcgtt ctattcttat 183780
taagaatgat gccgtcttta ttttaaacct tggtttaaaa tttaaagaag tatttataaa 183840
ctataatcat gggaactttt tcagtaactg cctctgcaaa aagtgacgat gctgtttgta 183900
agtatttaga agaaccaata gatgaaaatt acagaaacat attaagaaat gagcatgtta 183960
aaaaaaattt aaatgaggct ctgaatcgac atattactac ctataatcca gtagttgatt 184020
ggtgtaataa ctattcaaca ttttcatctc aggatttcga tgaatataaa atttatatac 184080
atagcgatct tatggatgga cgacctcgtc caaaaaaaac atggtgtgtc atcatgtaat 184140
gtttgttagt tttatataaa cgcaaaaata ttcttctagg agatgttgat atactaccta 184200
ttgaattcaa tatattaaag tacatttctg gctattccca ttacggtatt attattacta 184260
tttttaagag ctagatgtgg atttaagtaa taataacatt ctcccgttcc tcctagagac 184320
acctcatcaa attcccatcc tatgcaacct ttatgttgta aacataatga ttgacagcat 184380
tcatcttctt ttgaccaagt cgtccaaatc ctaccaagat ctatacgtgt ttttccaaat 184440
ggagattgaa gatcagcagt agtggcatta aacctataaa aaccaggtgc ataatcacat 184500
gaacggatcg taggatctaa tttaatatct tttatatctt gttttactgc ttctagacaa 184560
cttttatcag tacatgttcc acgtacacag tggtgtcctt tatccttaca atccgtatct 184620
gtcttacatt ttttttcgg cggtttatgt ttcagatggt aaaaacccag tattaaaata 184680
atcacaagaa taattcctat aagtacttga acaacaggat aaaacatttt aatattaaat 184740
atatttttta attaaatgaa tagatttaat ccaagtagta ttaaaatttt ttagaaatag 184800
tgttctacaa ataatgaaat gaatggtcca aaaaaaataa ggtgtacaat aatgtaatat 184860
attgttaggc taagtaaatt taatatttta aagtatttgg aaaaatattt tttaacatat 184920
gatgtctagg aatatttttt agacatttaa aaccatatag ttactttatt tattacactg 184980
aacttgaaaa gacttattac ctaaaatatt aatagatgaa gtaatattgt gtaattgagt 185040
ccataacatg ggtgggaaac aaaaatctcg taatatgaaa aataaacatc ctaaaaagag 185100
tgcaattgtt ataagtttat gtaactttat tttaaagtaa gaatataaaa atatgagtac 185160
aagaggaata ggggccatta ctaacattgg ctccaacatc ctgttgtcta caaaaaaaaa 185220 tattttttt agcaaaaaaa aatccatgga aggatattaa tacacataat tatttgacat 185280
cacattagtg tacttaccaa atagtaatat acaaccatcc taatattcac ctttatgaaa 185340
tgatcccaac ctatacggta aaatagtata ggttttaata aagaaaaaag atattctgtg 185400
gtttttattt ttgtatagtg tgtgaataca aaataaaatc ccaaatttta accttttctt 185460
ttttttctat acaggatgtt agaaatagta ttggcaacgc tgctaggcga cctgcagcgg 185520

-continued ctccgggttc ttacccctca gcagcgggca gttgccttct ttcgagccaa tactaaggag 185580
ctagaggact tcttatgctc agatgggcag tctgaggagg tactgtctgg ccccttctt 185640 aaccgtctac tagaaccctc aggccctctt gatattttaa ccggatatca cctatttcgt 185700
cagaatccca aggcaggtca gttgcgcggc cttgaggtca agatgcttga acggttatac 185760
gatgctaata tttacaatat actgtctcgg ctgcggcctg aaaaagttcg caacaaggct 185820
attgagctat actgggtttt ccgagctatc catatttgtc atgctccttt agttttagat 185880
attgtacgat atgaggaacc ggactttgct gaactggcct ttatttgtgc tgcttacttt 185940
ggtgaacctc aggtaatgta tttgctctac aaatatatgc ctctgacccg cgcagttctt 186000
acggatgcca tccggataag tcttgagagc aacaaccagg tagggatttg ctatgcttac 186060
ttgatgggag gcagcctcaa gggactagtc tccgccccac tgcgtaaacg tctgcgcgcc 186120
aaactacgct cgcagcgcaa aaagaaggac gttctttcac cccacgactt cttactgctg 186180
ctccagtagc ttttttgcc gcaggagcac cgcggatagg agctcctcca cgctcgcgat 186240
ccggcgctgg aagcggaacc gatcgaccgc cacctgctcc cagggaccct tgcgctcgat 186300
gtcgtcggct tcccacacct cgacggctgt ggcaaaatgg acatgcttcg cgtcgttcgt 186360 ccgtttttg cgccgcctcc ccattattct tcctgtaaga ttagtgttta atacctataa 186420
taacataatt ttaagattta atataccaaa acttaaacta tttttgtata gtaactatta 186480
gcatgtctac acatgattgt tctctaaaag agaaaccggt tgatatgaac gatatatctg 186540
agaaatcagt tgtcgtggat aatgcacccg agaaaccagc tggagcgaat catatacctg 186600
agaagtcggc ccgcgaaatg acatcatcag aatggattgc tgaatattgg aaaggtataa 186660
aacgtggaaa tgacgtgcca tgttgttgtc caagaaaaat gaccagtgca gacaaaaagt 186720
tttcagtatt tggtaaggga tccctaatgc gctccatcca gaagaataat taaaaaaaat 186780 attttttta gcaagttttt aaactattta aataaatgtg gtaaaaaaat tcacataata 186840
attaaagtga acgtgttaga attaatattt ttttataatc ggatataata tccattaaat 186900
caataaatga tagtgttgct accacactaa acaataacaa acagaaacgc acgatacctt 186960
tcctcatgat ttataatagc gtgttatcta aagatttttt tgaaaaaaat attaaatttt 187020
agttgattat ttttttcagt tacaacattg ctttagaaaa aatacctaat tactacatag 187080
caaataaagc gagcgcattg ttacaaacaa cattttttt gcgcctggat actcctatat 187140
atgagaacta taatacggta tattaatcct attaccaaca ttgtcaataa tagtatgtag 187200
gcaatgacat actttaaata ccaaatatcc atggttattt ctaaaaatct tgaaaaaacg 187260
ttaaatttta gatcggtcac ctacgacagt aatactaatt ttaataattg atgactgaaa 187320
tcataatata atgccgtgcg aaaaataatt atttttcggt taaagatacc attacataaa 187380
aaatatgcca tctactctac aagtgcttgc taaaaaggta ttggccttag gggagcataa 187440
agaaaatgaa catatatcta gagaatatta ttatcatata ttaaagtgtt gcggtttatg 187500
gtggcatgaa gctccgatta tactttgtta tgatgggagt gagcaaatga tgataaagac 187560
tccaatcttt gaagaaggca tattacttaa tactgcatta atgaaagctg tacaggagaa 187620
taattatgaa ttaataaagt tgtttactga atggggagca aacatcaatt atggattaat 187680
ttccattaat accgagcatg cccgggatct atgtcgaaaa ttaggagcta aagaaatgct 187740
tgaaggaaat gaatttatac aaattatatt caaaacatta gatgatacca ccagtagtaa 187800
tataatttta tgtcatgaat tattcaccaa caatcctctt ttagagaatg taaatatggg 187860
ggaaatgagg atgataattt attggaggat gaaaaattta acgaacctat tattaaataa 187920
tgactctatt agtgaaatat taactaaatt ctggtatggt atagcagtaa aatataatct 187980
taaggatgcg atccaatatt tttaccagag attcatggac ttcaacgagt ggcgagtaac 188040
atgtgctctt tcttttaata atgtgaatga tcttcataag atgtatataa cagagaaggt 188100
tcatatgaat aatgacgaaa tgatgaatct agcctgcagc attcaagaca gaaatttatc 188160
aaccatttac tattgttttc tattgggggg ctaacatcaa tcaagcaatg ttaacctcag 188220
tattaaatta taatattttt aacttattct tttgtataga cttaggggct gatgcctttg 188280
aagagggtaa gaccctggcg aaacaaaagg ggtataatga aatagtggaa atcttatcat 188340
tagatatcat ttatagtcca aatactgact tctcatcaaa aatagaacct gaacatatta 188400
gttctttgtt aaaaaacttt tatccaaaaa atctgttcgc ttttgatcgt tgcaaccccg 188460
gtttatatta ttcttagagg accgctacaa aaattatttt ttttcttgat caaagctcca 188520
aaataattat tagattaaag tcgcctatag cagcagccca ctccaaaaaa agtattttat 188580
agtacaaaaa acacgaaaaa tagtttgcgg ccggcggcaa actatttgtt gttgtctaaa 188640
acttaatgtt tttttaatat ttttaaatgc aaccatggat tgttggacta tcagggagaa 188700
gaactatagc tacatcatat tgtcaatact ggtaatacta ttaatatggt atcttatact 188760
taactattgt cgatcgaaaa aaaatgcagt tacaaacaac atgccgccac catacacggt 188820
gtcaagtagc tgttctcaat aatagggttg attgacgctc ttcgtaataa tatgttgatt 188880
gacgcatcat aaaatgctgt ggttgattaa tatgttgatt gtcgcctact ttattatata 188940
agtaatgatt tttgtataaa atacgggttt gtgagggctt tattttttct tattagaaca 189000
aagcatgcaa tttaaggcct acagcaagag taatttaaca cctacaacag taattttaag 189060
gtcagtaata atgtttaatt aaggcctgac cactaaaact taaacgattt tgtaaaaaaa 189120
aatgtctact ccactttctc tacagactct tgttaaaaaa gtgctggcca cacagcacat 189180
atctaaagaa cactacttta ttttgaaata ttgtggttta tggtggcatg aagcgccgat 189240
tacgatttgc attgatgagg atagccaaat attgataaaa tcggcaagct tcaaagaagg 189300
cttatcttta gatatcgcat taatgaaagt cgtgcaagaa aataaccatg atttaataga 189360
gttgtttacc aagtggggtg cagatatcaa ctctagctta gttactgtta atacggagta 189420
tacccggaac ctttgtcaga aattaggcgc aaaggaagct ttgaatgaaa gggatatttt 189480
acaaatattt tataaaacac gtcatcttaa aactagcagt aatattattt tatataatga 189540
attgttttct aataatctcc ttttccaaaa tatagagaga ttgagtttaa tagtttatag 189600
gggcttgaaa aacttatcaa tcaactttat attggatgat atttcattta gcgaaatgtt 189660
aactagatac tggtatagta tggcgatatt atataacctt actgaagcca tccaatattt 189720
ttatcaacga tataggcatt ttaaagattg gcggcttata tgtgggcttt cttttaacaa 189780
tttgtctgac cttcatgaag tatataactt agagaagacg gatatagaca ttgatgaaat 189840
gatgaagttg acctgtagta cgtatgatgg taattattcg actatttatt attgttttat 189900
gttgggggct gacatcaatc gggcaatgtt aacctcggta ataaactttc atattggtaa 189960
cttgttcctt tgtatagatt taggagctga tgctttcgaa gacagcatgg aactagcaaa 190020
acaaaagaat aataatatat tagtagaaat attatcattt aaaaattatt atagttcaaa 190080
tacctctctt ttatcaataa aaacgacaga tccggaaaaa attaatgcct tattagatga 190140
agaaaagtat gagtcaaaaa atatgttaat gtatgaagaa ttatctcatt gatacaaaat 190200
tattttttat aacagaactc tctgatggtg acaaatctcc gataggaata tatgacgtaa 190260
cataattatt tttttcgccc agaaaaaaat tataaatgtt attattgcca gcacttttat 190320
caactatacg tacaaaaagg tgttgaccaa aaaaataatt ttttttcttg atcaaagtat 190380
gtaaacgccc gcttacagca aggatcttaa gtgagagcca ttaaatttta ttgatagctg 190440
cttgccacca gtagaatacg gccaaaccac ctaacaggaa atacaaggcg gcccttcggc 190500
caataaggtg gataaaaatc acgcataaga cggttgtaac atagcacttt agtgcgaata 190560
tcaggaatgc caatagcatg tagataaggc accaaacatc gcagctatac atggctaaag 190620
atcaaccaga aaaggtttaa attttaacgc cggcccaaaa cttaaacttt ttttgatatt 190680
tttaagtgca gccatggatt ggtccggcca taggatgacc tatgcctacg tggcattctc 190740
attgatggca atagcaataa tatggtatat tctacttatc tattgccgat cgaaaaaaaa 190800
tgttgttaca agcggtaata cgctcgcttt agcgccaata tcgcatatgt gaaaaatgtt 190860
cgccgaaaaa aacattaaaa tttagaaccg ccgcggcatc tcaggggcgg caacattttt 190920
ttttatatgg atattgtcac acaccacctc atctatgacg caatatatta ctgctaatat 190980
caggttcccc aatagtatgt agagaaacca cacaagatag atattcatgg cgatttttga 191040
cgaaaaaaca ttaagtttta gcttctttga cgcctgtgta ctaataatgt ttaacgcctg 191100
tagtataata attgatacct acagcagtaa ttgataccta cggcgataat gtctctctgg 191160
ccgccccaaa aaaaagtatt tacggtaggg tttattaccg gcggcgtaac accagttatg 191220
gtcaattttg tctggcccgc cgcccagccg caaaaaaaaa tcaattacaa ccgcaaaaaa 191280
aaatatttcc ggccgcggcg tttcaaaaaa taatctttgc gaaataattc cgcatcttgt 191340
gaaatgaacg cctacagtaa taattttaat ctttgacacc tacagcagta gtaataattt 191400
taatctttaa cgcctgcagc agtactaata ttttaatctt taacgcctac agcagtagta 191460
ataattttaa tgtttaacgc ctacagcagt agtaat 191496

<210> SEQ ID NO 4
<211> LENGTH: 61
<212> TYPE: PRT
<213> ORGANISM: African swine fever virus

<400> SEQUENCE: 4

```
Met Leu His Trp Gly Pro Lys Tyr Trp Arg Gln Tyr Trp Thr Phe Ala
1               5                   10                  15

Phe His Asn Asn Val Asn Asn Arg Leu Asn Lys Lys Ile Ile Ser Trp
            20                  25                  30

Ser Glu Tyr Lys Asn Ile Tyr Glu Gln Ser Ile Leu Lys Thr Ile Glu
        35                  40                  45

Tyr Gly Lys Thr Asp Phe Ile Gly Ala Trp Ser Ser Leu
    50                  55                  60
```

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
tagagatgac caggctccaa 20

<210> SEQ ID NO 6
<211> LENGTH: 23
<212> TYPE: DNA

-continued

<213> ORGANISM: Artificial Sequence
<220> FEATURE:
<223> OTHER INFORMATION: Chemically Synthesized

<400> SEQUENCE: 6
gttgcattgg ggacctaaat act 23

<210> SEQ ID NO 7
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 7
gacggcctgt gggcatt 17

<210> SEQ ID NO 8
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 8
gcgatggatt ccggcat 17

<210> SEQ ID NO 9
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 9
gtcttattgc taacgatggg aag 23

<210> SEQ ID NO 10
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 10
ccaaaggtaa gcttgtttcc caa 23

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 11
gtaagatacg aaaaggcgtg 20

<210> SEQ ID NO 12
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 12
gacgctccta gctggaa 17

<210> SEQ ID NO 13
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 13
gttgttatgg aacgcgaag 19

<210> SEQ ID NO 14
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 14
gggtttctac aggacgtaac a 21

<210> SEQ ID NO 15
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 15
ctgttgaatt acgttaagca tg 22

<210> SEQ ID NO 16
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 16
cattggggac ctaaatactg 20

<210> SEQ ID NO 17
<211> LENGTH: 119
<212> TYPE: PRT
<213> ORGANISM: African swine fever virus

<400> SEQUENCE: 17

Met Leu His Trp Gly Pro Lys Phe Trp Arg Thr Leu His Leu Tyr Ala
1 5 10 15

Ile Phe Phe Ser Asp Thr Pro Gly Trp Lys Glu Lys Tyr Glu Ala Ile
20 25 30

Gln Trp Ile Leu Asn Phe Ile Glu Ser Leu Pro Cys Thr Met Cys Arg
35 40 45

His His Ala Phe Ser Tyr Leu Thr Lys Asn Pro Leu Thr Leu Asn Asn
50 55 60

Ser Glu Asp Phe Gln Tyr Trp Thr Phe Ala Phe His Asn Asn Val Asn
65 70 75 80

Lys Arg Leu Asn Lys Lys Ile Ile Ser Trp Ser Glu Tyr Lys Asn Ile
85 90 95

Tyr Glu Gln Ser Ile Leu Asn Thr Ile Glu Tyr Gly Lys Thr Asp Phe
100 105 110

Ile Gly Ala Trp Ser Ser Leu

115

<210> SEQ ID NO 18
<211> LENGTH: 119
<212> TYPE: PRT
<213> ORGANISM: African swine fever virus

<400> SEQUENCE: 18

```
Met Leu His Trp Gly Pro Lys Tyr Trp Arg Ala Leu His Leu Tyr Ala
1               5                   10                  15

Ile Phe Phe Ser Asp Ala Pro Gly Trp Lys Glu Lys Tyr Glu Ala Ile
            20                  25                  30

Gln Trp Ile Leu Asn Phe Ile Glu Ser Leu Pro Cys Thr Arg Cys Arg
        35                  40                  45

His His Ala Phe Ser Tyr Leu Thr Lys Asn Pro Leu Thr Leu Asn Asn
    50                  55                  60

Ser Glu Asp Phe Gln Tyr Trp Thr Phe Ala Phe His Asn Asn Val Asn
65                  70                  75                  80

Asn Arg Leu Asn Lys Lys Ile Ile Ser Trp Ser Glu Tyr Lys Asn Ile
                85                  90                  95

Tyr Glu Gln Ser Ile Leu Lys Thr Ile Glu Tyr Gly Lys Thr Asp Phe
            100                 105                 110

Ile Gly Ala Trp Ser Ser Leu
        115
```

<210> SEQ ID NO 19
<211> LENGTH: 119
<212> TYPE: PRT
<213> ORGANISM: African swine fever virus

<400> SEQUENCE: 19

```
Met Leu His Trp Gly Pro Lys Phe Trp Arg Ala Leu His Leu Tyr Ala
1               5                   10                  15

Ile Phe Phe Ser Asp Ala Pro Asn Trp Lys Glu Lys Tyr Glu Ala Ile
            20                  25                  30

Gln Trp Ile Leu Asn Phe Ile Glu Ser Leu Pro Cys Thr Met Cys Arg
        35                  40                  45

His His Ala Phe Ser Tyr Leu Thr Lys Asn Pro Leu Thr Leu Asn Asn
    50                  55                  60

Ser Glu Asp Phe Gln Tyr Trp Thr Phe Ala Phe His Asn Asn Val Asn
65                  70                  75                  80

Lys Arg Leu Asn Lys Lys Ile Ile Ser Trp Ser Glu Tyr Lys Asn Ile
                85                  90                  95

Tyr Glu Gln Ser Ile Leu Lys Thr Ile Glu Tyr Gly Lys Thr Asp Phe
            100                 105                 110

Ile Gly Ala Trp Ser Ser Leu
        115
```

<210> SEQ ID NO 20
<211> LENGTH: 119
<212> TYPE: PRT
<213> ORGANISM: African swine fever virus

<400> SEQUENCE: 20

```
Met Leu His Trp Gly Pro Lys Tyr Trp Arg Ala Leu His Leu Tyr Ala
1               5                   10                  15

Ile Phe Phe Ser Asp Thr Pro Gly Trp Lys Glu Lys Tyr Glu Ala Ile
            20                  25                  30
```

```
Gln Trp Ile Leu Asn Phe Ile Glu Ser Leu Pro Cys Thr Arg Cys Gln
        35                  40                  45

His His Ala Phe Ser Tyr Leu Thr Lys Asn Pro Leu Thr Leu Asn Asn
    50                  55                  60

Ser Glu Asp Phe Gln Tyr Trp Thr Phe Ala Phe His Asn Asn Val Asn
65                  70                  75                  80

Asn Arg Leu Asn Lys Lys Ile Ile Ser Trp Ser Glu Tyr Lys Asn Ile
                85                  90                  95

Tyr Glu Gln Ser Ile Leu Lys Thr Ile Glu Tyr Gly Lys Thr Asp Phe
            100                 105                 110

Ile Gly Ala Trp Ser Ser Leu
        115


<210> SEQ ID NO 21
<211> LENGTH: 119
<212> TYPE: PRT
<213> ORGANISM: African swine fever virus

<400> SEQUENCE: 21

Met Leu His Trp Gly Pro Lys Tyr Trp Arg Ala Leu His Leu Tyr Ala
1               5                   10                  15

Ile Phe Phe Ser Asp Ala Pro Gly Trp Lys Glu Lys Tyr Glu Ala Ile
            20                  25                  30

Gln Trp Ile Leu Asn Phe Ile Glu Ser Leu Pro Cys Thr Arg Cys Gln
        35                  40                  45

His His Ala Phe Ser Tyr Leu Thr Lys Asn Pro Leu Thr Leu Asn Asn
    50                  55                  60

Ser Glu Asp Phe Gln Tyr Trp Thr Phe Ala Phe His Asn Asn Val Asn
65                  70                  75                  80

Asn Arg Leu Asn Lys Lys Ile Ile Ser Trp Ser Glu Tyr Lys Asn Ile
                85                  90                  95

Tyr Glu Gln Ser Ile Leu Lys Thr Ile Glu Tyr Gly Lys Thr Asp Phe
            100                 105                 110

Ile Gly Ala Trp Ser Ser Leu
        115


<210> SEQ ID NO 22
<211> LENGTH: 119
<212> TYPE: PRT
<213> ORGANISM: African swine fever virus

<400> SEQUENCE: 22

Met Leu His Trp Gly Pro Lys Tyr Trp Arg Ser Leu His Leu Tyr Ala
1               5                   10                  15

Ile Phe Phe Ser Asp Ala Pro Ser Trp Lys Glu Lys Tyr Glu Ala Ile
            20                  25                  30

Gln Trp Ile Leu Asn Phe Ile Glu Ser Leu Pro Cys Thr Arg Cys Gln
        35                  40                  45

Arg His Ala Phe Ser Tyr Leu Thr Lys Asn Pro Leu Thr Leu Asn Asn
    50                  55                  60

Ser Glu Asp Phe Gln Tyr Trp Thr Phe Ala Phe His Asn Asn Val Asn
65                  70                  75                  80

Asn Arg Leu Asn Lys Lys Ile Ile Ser Trp Ser Glu Tyr Lys Asn Ile
                85                  90                  95

Tyr Glu Gln Ser Ile Leu Lys Thr Ile Glu Tyr Gly Lys Thr Asp Phe
            100                 105                 110
```

-continued

```
Ile Gly Ala Trp Ser Ser Leu
        115


<210> SEQ ID NO 23
<211> LENGTH: 119
<212> TYPE: PRT
<213> ORGANISM: African swine fever virus

<400> SEQUENCE: 23

Met Leu His Trp Gly Pro Lys Tyr Trp Arg Ser Leu His Leu Tyr Ala
1               5                   10                  15

Ile Phe Phe Ser Asp Ala Pro Ser Trp Lys Glu Lys Tyr Glu Ala Ile
            20                  25                  30

Gln Trp Ile Leu Ser Phe Ile Glu Ser Leu Pro Cys Thr Arg Cys Gln
        35                  40                  45

His His Ala Phe Ser Tyr Leu Thr Lys Asn Pro Leu Thr Leu Asn Asn
    50                  55                  60

Ser Glu Asp Phe Gln Tyr Trp Thr Phe Ala Phe His Asn Asn Val Asn
65                  70                  75                  80

Asn Arg Leu Asn Lys Lys Ile Ile Ser Trp Ser Glu Tyr Lys Asn Ile
                85                  90                  95

Tyr Glu Gln Ser Ile Leu Lys Thr Ile Glu Tyr Gly Lys Thr Asp Phe
            100                 105                 110

Ile Gly Ala Trp Ser Ser Leu
        115


<210> SEQ ID NO 24
<211> LENGTH: 58
<212> TYPE: PRT
<213> ORGANISM: African swine fever virus

<400> SEQUENCE: 24

Ser Leu His Leu Tyr Ala Ile Phe Phe Ser Asp Ala Pro Ser Trp Lys
1               5                   10                  15

Glu Lys Tyr Glu Ala Ile Gln Trp Ile Leu Asn Phe Ile Glu Ser Leu
            20                  25                  30

Pro Cys Thr Arg Cys Gln His His Ala Phe Ser Tyr Leu Thr Lys Asn
        35                  40                  45

Pro Leu Thr Leu Asn Asn Ser Glu Asp Phe
    50                  55
```